US012048818B2

(12) United States Patent
Gomez et al.

(10) Patent No.: US 12,048,818 B2
(45) Date of Patent: Jul. 30, 2024

(54) HANDHELD ELONGATE MEDICAL DEVICE ADVANCER AND RELATED SYSTEMS, DEVICES AND METHODS

(71) Applicant: New Wave Endo-Surgical Corp., Coconut Creek, FL (US)

(72) Inventors: Ricardo Gomez, Lighthouse Point, FL (US); Salvatore Castro, Coconut Creek, FL (US); Christian Abreu, Coconut Creek, FL (US); Juan Diaz, Coconut Creek, FL (US)

(73) Assignee: New Wave Endo-Surgical Corp., Coconut Creek, FL (US)

( * ) Notice: Subject to any disclaimer, the term of this patent is extended or adjusted under 35 U.S.C. 154(b) by 108 days.

(21) Appl. No.: 17/368,825

(22) Filed: Jul. 7, 2021

(65) Prior Publication Data

US 2022/0047847 A1   Feb. 17, 2022

Related U.S. Application Data

(60) Provisional application No. 63/167,918, filed on Mar. 30, 2021, provisional application No. 63/048,164, filed on Jul. 5, 2020.

(51) Int. Cl.
  *A61M 25/01*   (2006.01)
(52) U.S. Cl.
  CPC .... *A61M 25/0136* (2013.01); *A61M 25/0113* (2013.01); *A61M 2205/586* (2013.01)
(58) Field of Classification Search
  CPC ........ A61M 25/0113; A61M 25/09041; A61M 2025/09125; A61M 2205/586
  See application file for complete search history.

(56) References Cited

U.S. PATENT DOCUMENTS

| 2,176,977 A | 10/1939 | Nicolay |
| 4,634,042 A | 1/1987 | Smith |
| 4,676,249 A | 6/1987 | Arenas et al. |

(Continued)

FOREIGN PATENT DOCUMENTS

| EP | 0436303 A1 | 7/1991 |
| JP | 2005006868 A | 1/2005 |
| WO | 2016038677 A1 | 3/2016 |

*Primary Examiner* — Laura A Bouchelle
(74) *Attorney, Agent, or Firm* — Anthony Kandare; KandareIP, LLC

(57) ABSTRACT

A handheld advancer is provided for advancing an elongate device through a pathway defined in an advancer body and include a rotatable manual control partially embedded in the body to receive a user-exerted manual control movement from a thumb of a single hand that can hold and control the advancer and advancement. The advancer can include a manual drive arranged to convert torque applied by the thumb for a rotation arc distance into a translation drive force applied for translating the elongate device an advancement distance scaled at force factor and distance factor. The distance factor can be one or greater than one and translate the elongate device an amplified advancement distance compared with manual input. The advancer can include a nip having a pair of rollers extending into the pathway providing constant control and amplified translation via concave compressible surfaces forming continuous contact regions with the elongate device.

20 Claims, 81 Drawing Sheets

(56) References Cited

U.S. PATENT DOCUMENTS

| | | |
|---|---|---|
| 4,895,168 A | 1/1990 | Machek |
| 5,127,917 A | 7/1992 | Niederhauser et al. |
| 5,197,484 A | 3/1993 | Kornberg et al. |
| 5,199,310 A | 4/1993 | Yoshimura |
| 5,407,432 A | 4/1995 | Solar |
| 5,411,033 A | 5/1995 | Viera |
| 5,415,170 A | 5/1995 | Hammerslag et al. |
| 5,415,177 A | 5/1995 | Zadini et al. |
| 5,417,699 A | 5/1995 | Klein et al. |
| 5,443,078 A | 8/1995 | Uflacker |
| 5,527,322 A | 6/1996 | Klein et al. |
| 5,536,248 A | 7/1996 | Weaver et al. |
| 5,549,119 A | 8/1996 | Solar |
| 5,579,780 A | 12/1996 | Zadini et al. |
| 5,697,907 A | 12/1997 | Gaba |
| 5,749,371 A | 5/1998 | Zadini et al. |
| 5,810,012 A | 9/1998 | Lynch et al. |
| 5,843,091 A | 12/1998 | Holsinger et al. |
| 5,957,865 A | 9/1999 | Backman et al. |
| 5,971,963 A | 10/1999 | Choi |
| 6,139,540 A | 10/2000 | Rost et al. |
| 6,171,234 B1 | 1/2001 | White et al. |
| 6,197,001 B1 | 3/2001 | Wilson et al. |
| 6,589,157 B2 | 7/2003 | Fontayne et al. |
| 6,669,669 B2 | 12/2003 | Flaherty et al. |
| 6,743,241 B2 | 6/2004 | Kerr |
| 6,855,109 B2 | 2/2005 | Obata et al. |
| 6,878,136 B2 | 4/2005 | Fleury et al. |
| 6,918,894 B2 | 7/2005 | Fleury et al. |
| 6,972,027 B2 | 12/2005 | Fallin et al. |
| 7,060,033 B2 | 6/2006 | White et al. |
| 7,226,451 B2 | 6/2007 | Shluzas et al. |
| 7,455,664 B2 | 11/2008 | Fleury et al. |
| 7,550,001 B2 | 6/2009 | Dorn et al. |
| 7,935,141 B2 | 5/2011 | Randall et al. |
| 8,029,513 B2 | 10/2011 | Konno et al. |
| 8,062,312 B2 | 11/2011 | Gellman et al. |
| 8,118,061 B2 | 2/2012 | Hyun et al. |
| 8,128,644 B2 | 3/2012 | Carley et al. |
| 8,317,761 B2 | 11/2012 | Birk et al. |
| 8,439,050 B2 | 5/2013 | Tiphonnet |
| 8,579,913 B2 | 11/2013 | Nielsen |
| 8,636,760 B2 | 1/2014 | Garcia et al. |
| 8,647,324 B2 * | 2/2014 | DeLegge ............ A61M 25/0147 604/528 |
| 8,663,167 B2 | 3/2014 | Bartha |
| 8,672,953 B2 | 3/2014 | Reyes et al. |
| 8,764,683 B2 | 7/2014 | Meller et al. |
| 8,764,734 B2 | 7/2014 | Gobron et al. |
| 8,876,766 B2 | 11/2014 | Holmqvist et al. |
| 8,888,834 B2 | 11/2014 | Hansen et al. |
| 8,926,640 B2 | 1/2015 | Sauer et al. |
| 8,961,435 B2 | 2/2015 | DeMello |
| 8,986,363 B2 | 3/2015 | McHugo et al. |
| 8,992,487 B2 | 3/2015 | Eich et al. |
| 9,039,750 B2 | 5/2015 | Ryan |
| 9,061,097 B2 | 6/2015 | Holt et al. |
| 9,119,942 B1 | 9/2015 | Rollins et al. |
| 9,138,543 B2 | 9/2015 | Frantz et al. |
| 9,162,037 B2 | 10/2015 | Belson et al. |
| 9,180,244 B2 | 11/2015 | Anderson et al. |
| 9,351,722 B2 | 5/2016 | Koogle, Jr. et al. |
| 9,364,228 B2 | 6/2016 | Straehnz et al. |
| 9,408,742 B2 | 8/2016 | Dineen et al. |
| 9,451,950 B2 | 9/2016 | Patel et al. |
| 9,603,595 B2 | 3/2017 | Shelton, IV et al. |
| 9,610,185 B2 | 4/2017 | Capra et al. |
| 9,623,209 B2 | 4/2017 | Wenderow et al. |
| 9,707,327 B2 | 7/2017 | Heilman et al. |
| 9,822,551 B2 | 11/2017 | Ac et al. |
| 9,955,997 B2 | 5/2018 | Weisbrod et al. |
| 9,956,382 B2 | 5/2018 | Hwang |
| 9,999,443 B2 | 6/2018 | Heck et al. |
| 10,010,681 B2 | 7/2018 | Koch et al. |
| 10,098,618 B2 | 10/2018 | Thompson et al. |
| 10,143,826 B2 | 12/2018 | Castro et al. |
| 10,194,902 B2 | 2/2019 | Nobles et al. |
| 10,251,995 B2 | 4/2019 | Giambattista et al. |
| 10,279,118 B2 | 5/2019 | Oakley et al. |
| 10,299,781 B2 | 5/2019 | McGhie |
| 10,327,927 B2 | 6/2019 | Ryan et al. |
| 10,376,637 B2 | 8/2019 | Gymn et al. |
| 10,413,313 B2 | 9/2019 | Brown et al. |
| 10,449,073 B1 * | 10/2019 | Longo .................. A61F 2/95 |
| 10,507,307 B2 | 12/2019 | Gottlieb et al. |
| 10,518,029 B2 | 12/2019 | Giambattista et al. |
| 10,525,236 B2 | 1/2020 | Belson |
| 10,537,312 B2 | 1/2020 | Voss |
| 10,561,894 B2 | 2/2020 | Dalebout et al. |
| 10,588,622 B2 | 3/2020 | Cardinale et al. |
| 10,588,767 B2 | 3/2020 | Kaspar |
| 10,603,435 B2 | 3/2020 | Marsh et al. |
| 10,625,018 B2 | 4/2020 | Destefano et al. |
| 2009/0124934 A1 | 5/2009 | Rabbitte et al. |
| 2009/0209804 A1 | 8/2009 | Seiler et al. |
| 2011/0082484 A1 | 4/2011 | Saravia et al. |
| 2011/0106126 A1 | 5/2011 | Love et al. |
| 2011/0288533 A1 | 11/2011 | Koch et al. |
| 2012/0078231 A1 | 3/2012 | Hoshinouchi |
| 2013/0012964 A1 | 1/2013 | Warnock |
| 2014/0114291 A1 | 4/2014 | Defossez et al. |
| 2014/0309686 A1 | 10/2014 | Ginn et al. |
| 2016/0038677 A1 | 2/2016 | Kiilerich |
| 2016/0051765 A1 | 2/2016 | Morris et al. |
| 2016/0058949 A1 | 3/2016 | Bayer et al. |
| 2016/0151579 A1 | 6/2016 | Oakley et al. |
| 2016/0199206 A1 | 7/2016 | Lim et al. |
| 2016/0375223 A1 | 12/2016 | Avneri et al. |
| 2017/0189061 A1 | 7/2017 | Weisbrod et al. |
| 2017/0258507 A1 | 9/2017 | Hetherington |
| 2017/0296753 A1 | 10/2017 | Rowe et al. |
| 2017/0348019 A1 | 12/2017 | Nakano et al. |
| 2018/0056044 A1 | 3/2018 | Choi et al. |
| 2018/0116689 A1 | 5/2018 | Nakano |
| 2018/0193606 A1 | 7/2018 | Patel et al. |
| 2018/0368774 A1 | 12/2018 | Gray et al. |
| 2019/0015646 A1 | 1/2019 | Matlock et al. |
| 2019/0027905 A1 | 1/2019 | Sweeney |
| 2019/0038270 A1 | 2/2019 | Thompson et al. |
| 2019/0038301 A1 | 2/2019 | Algawi et al. |
| 2019/0069759 A1 | 3/2019 | Govari et al. |
| 2019/0076280 A1 | 3/2019 | Halbert et al. |
| 2019/0247050 A1 | 8/2019 | Goldsmith |
| 2019/0290314 A1 | 9/2019 | Gemer et al. |
| 2019/0374729 A1 | 12/2019 | Gomez et al. |
| 2020/0078566 A1 | 3/2020 | Mitchell et al. |
| 2020/0113718 A1 | 4/2020 | Westhoff et al. |
| 2020/0121357 A1 | 4/2020 | Gomez et al. |
| 2020/0129676 A1 | 4/2020 | Gomez et al. |

* cited by examiner

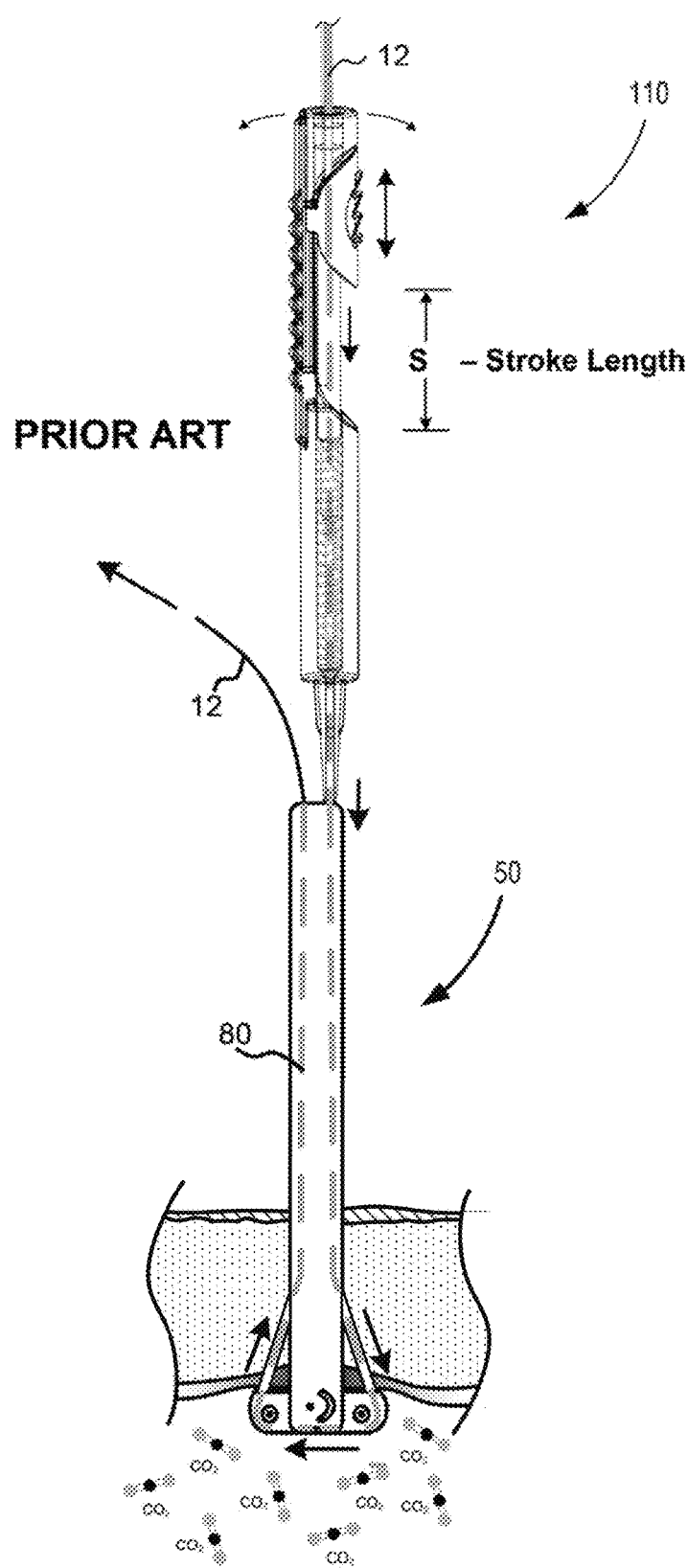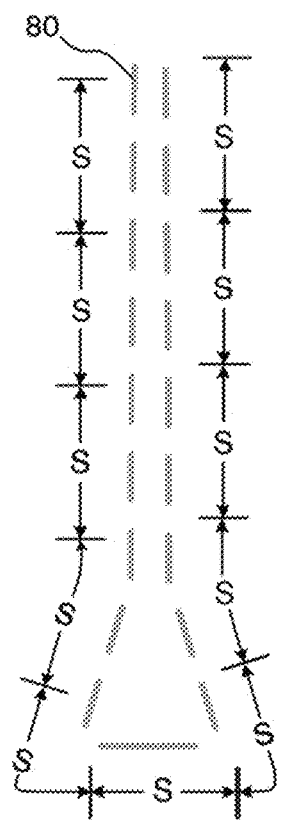
FIG. 4A FIG. 4B

PRIOR ART

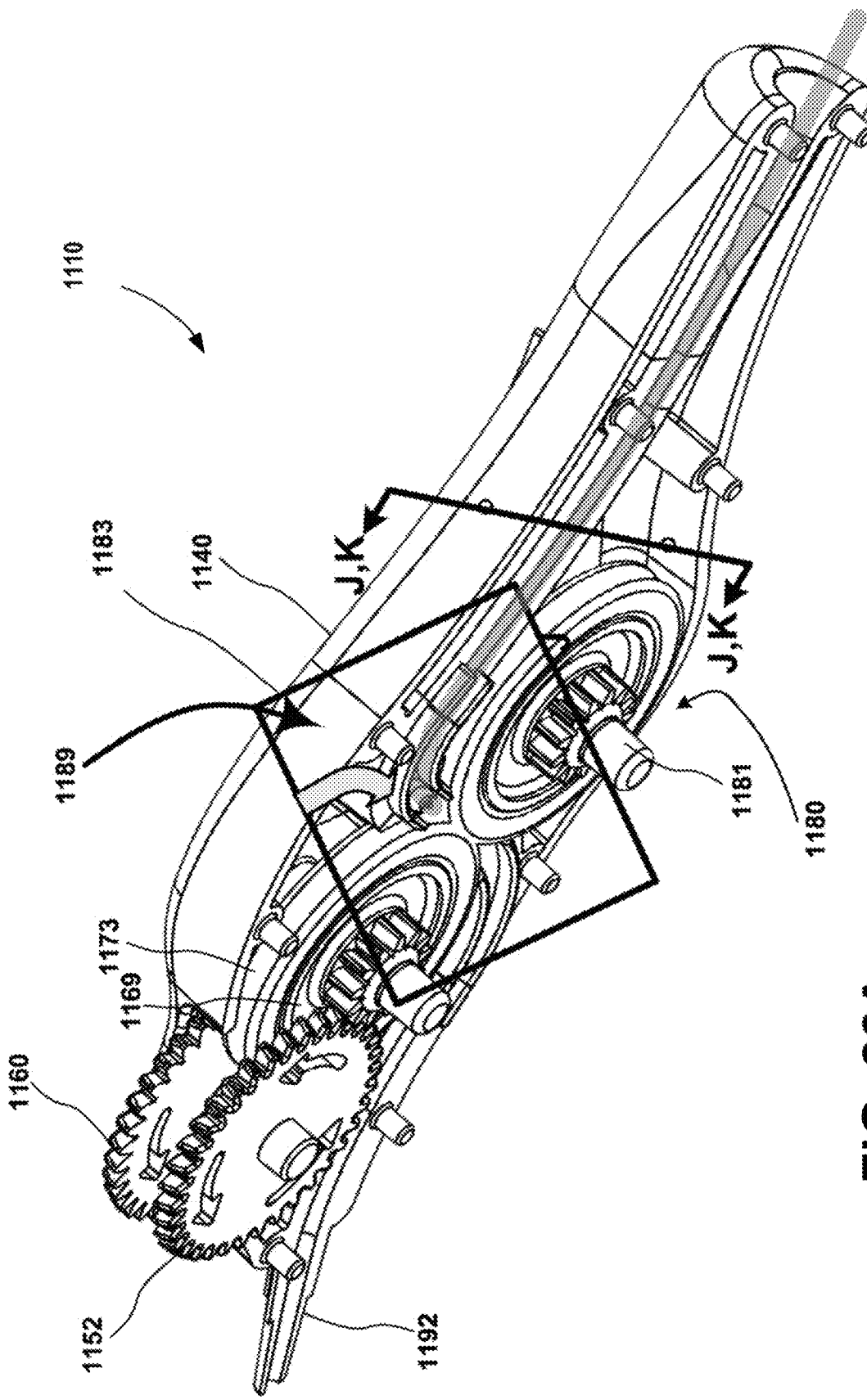

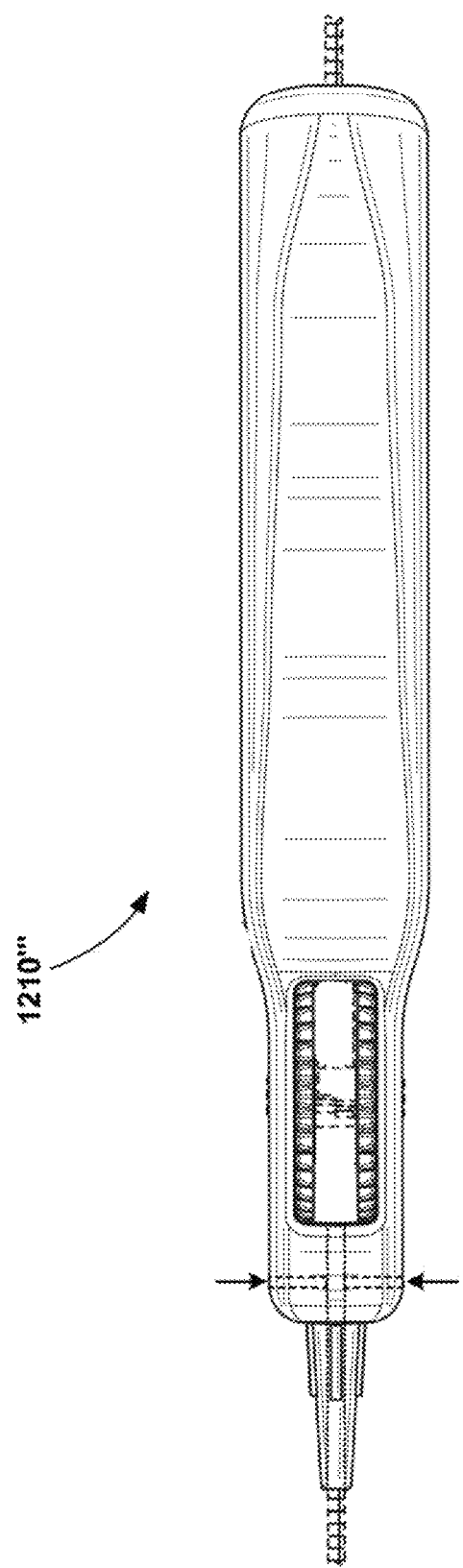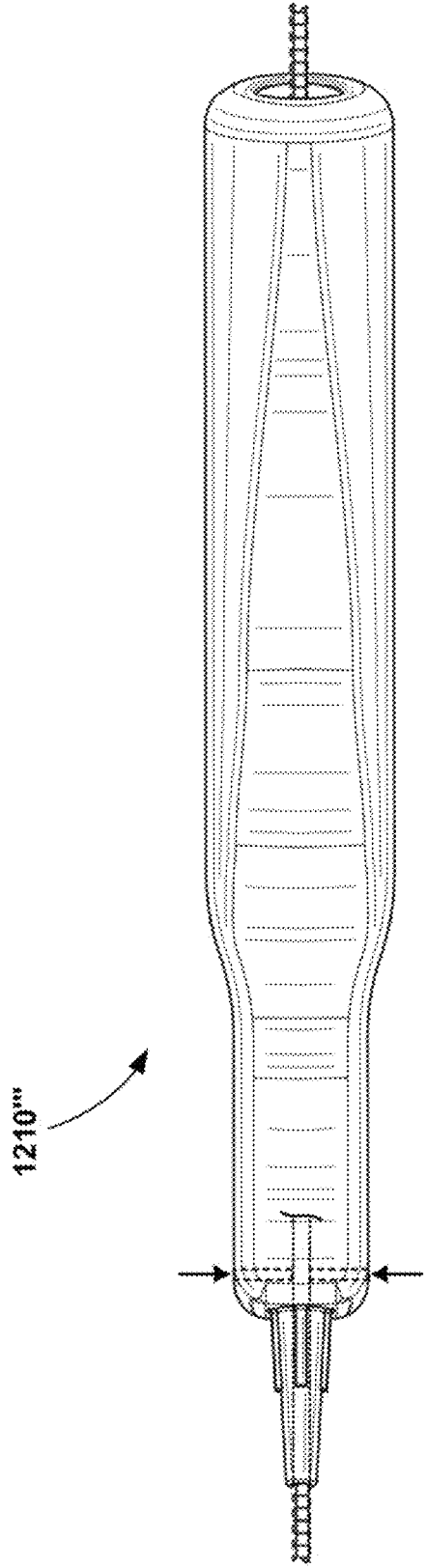

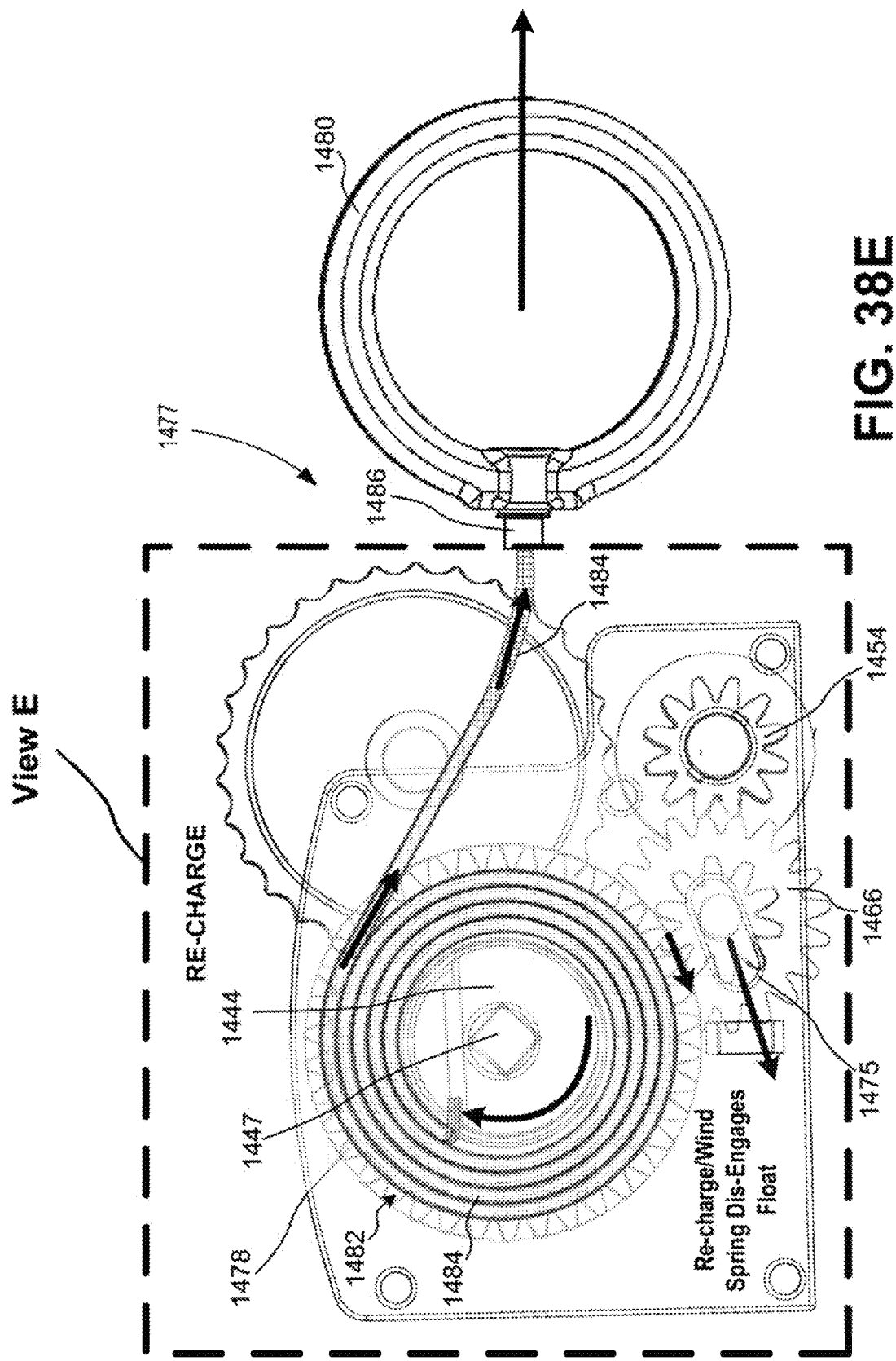

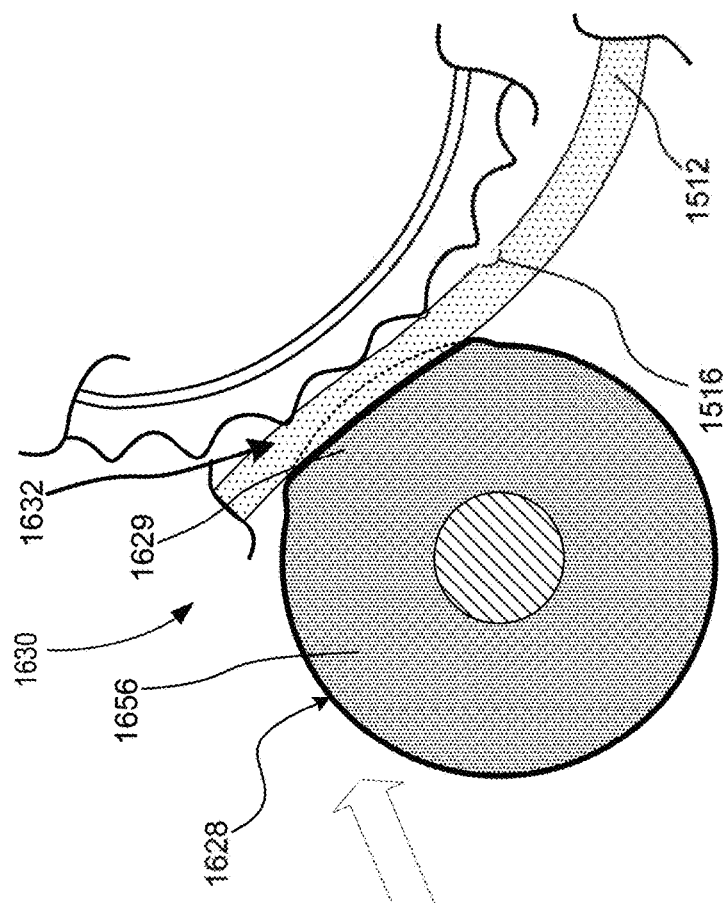
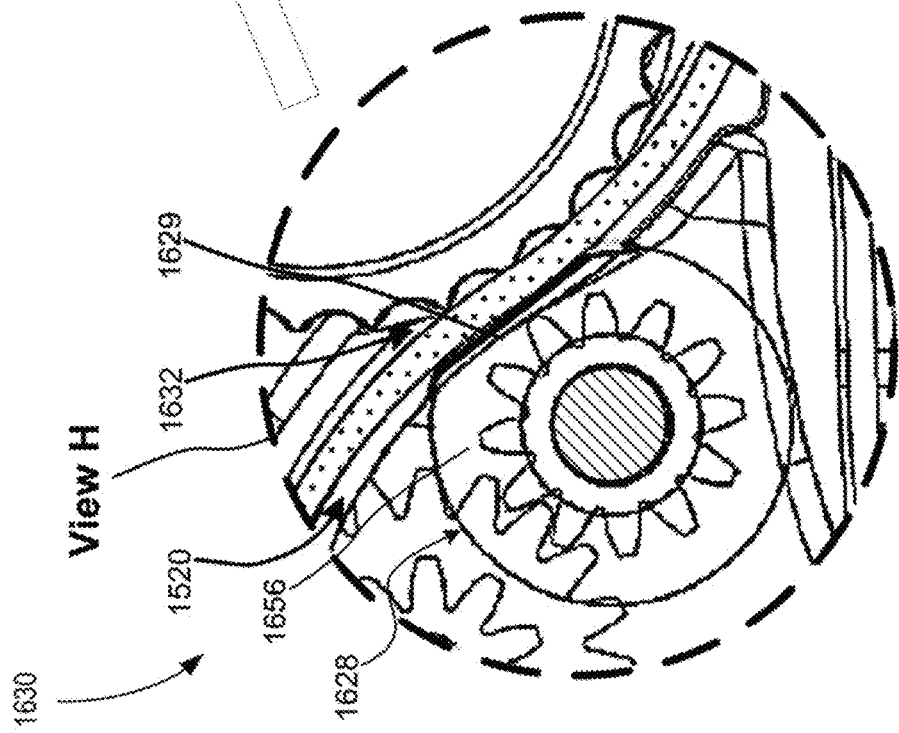
FIG. 58
FIG. 57

HANDHELD ELONGATE MEDICAL DEVICE ADVANCER AND RELATED SYSTEMS, DEVICES AND METHODS

CROSS-REFERENCE TO RELATED APPLICATIONS

This application is related to U.S. patent application Ser. No. 15/275,896 filed Sep. 26, 2016 at the U.S. Patent and Trademark Office (Now U.S. Pat. No. 9,986,987 to Patel et al. entitled "Apparatus and Method for Fascial Closure Device for Laparoscopic Trocar Port Site and Surgery"). In addition, this application claims priority to provisional U.S. Patent Application No. 63/048,164 filed on Jul. 5, 2020 at the U.S. Patent and Trademark Office entitled "Elongate device advancer For Use With A Surgical Instrument and Related Method"), and further claims priority to provisional U.S. Patent Application No. 63/167,918 filed on Mar. 31, 2021 at the U.S. Patent and Trademark Office entitled "Introducer/Advancer for Elongate Medical Devices and Related Systems, Devices and Methods"), the disclosures for all of which are incorporated herein by reference in their entirety.

BACKGROUND

The present application and related subject matter discussed herein relate to medical tools and particularly to surgical instruments, and more particularly relate to an elongate device introducer/advancer surgical support apparatus, such as an elongate device advancer, an introducer for a catheter or a feeding tube, and/or to an introducer/advancer for various elongate medical devices including elongate devices for use with endoscopic tools (generally referred to herein as elongate device advancers). Further, the embodiments described herein relate to an elongate device advancer configured to support laparoscopic surgical instruments with performance of minimally invasive surgery (MIS) functions. The laparoscopic surgical instruments can include a wide variety of MIS surgical devices. However, aspects, features and related concepts are discussed herein along with describing example medical devices and related techniques, such as for instance, procedures and device that can be used with intra-abdominal suturing devices, port closure devices, suture placement devices and the like configured for closing puncture wounds generated by surgical laparoscopic trocar ports and other puncturing devices.

For discussion purposes and example representations to assist with describing aspects, features and inventive concepts herein, reference is made to laparoscopic surgical instruments described in U.S. Pat. No. 9,986,987 to Patel et al. (herein "The Patel patent"). The Patel patent describes various configurations of an apparatus and related methods for treating tissue openings, such as an endoscopic trocar port opening created and used for a minimally invasive surgical procedure, including a suture placement device configured for rapidly, safely, efficiently and effectively closing tissue defects created to access the intra-abdominal cavity during laparoscopic surgical procedures. The device as generally described and schematically represented herein can obtain adequate tissue adjacent to the tissue defect for providing a strong closure along with maintaining the pneumoperitoneum during the closure process, which includes techniques involving removal of the trocar from the port opening prior to placement of a fascial suture therein.

Despite the demonstrated effectiveness, reliability and other significant advantages proven by the suture placement device of the Patel patent, concerns exist regarding potential leakage of gas around the cannula and loss of pneumoperitoneum during suture placement with the trocar removed along with loss of related gas sealing benefits. This concern can create challenges for performing suture placement and closing the wound while exercising extreme caution regarding movements of the suture placement device within the port that could exacerbate gas leakage and potential loss of pneumoperitoneum. Further, there are challenges with the use of suture loading devices described by The Patel patent for supporting the suture placement device to route a suture through the suture path and close the port. In addition, continual challenges persist with respect to the duration of surgeries and the likelihood of complications increasing with duration, for which effective time-saving improvements and aids for improving efficiencies are consistently desired and pursued.

Known improvements and solutions for supporting suture placement devices like the device of the Patel patent include guide wire advancement devices that advance a guide wire manually or advance it in a generally slow, stepwise automated manner—neither of which enhance efficiency, reduce suture timing, or improve suture and port closure procedures. Further, many conventional guide wire advancement devices used for orthoscopic and laparoscopic surgical procedures create challenges and introduce concerns that weigh against their usage with these types of surgical devices versus simple manual advancement devices. Due to their small size and precise maneuverability requirements, such devices have complex and sometimes tortious pathways for a guide wire to traverse quickly and easily, much less can easily be driven by an elongate device advancer, which can be especially true for port closure and fascial suture devices and procedures.

Many conventional elongate device advancers are commonly used with complex devices, surgical procedures and maneuvers, such as cardiac procedures like angioplasty or implant deployment, spinal surgery manipulations and procedures, complex routing for imaging functions, and even procedures for guiding catheters into blood vessels. These advancer devices are large, complex devices as necessitated by the complex functionality they are primarily configured to perform. Such conventional elongate device advancers are ineffective at supporting relatively small surgical devices and use with less invasive procedures including laparoscopic port closure procedures. The use of such suture placement devices can greatly enhance the effectiveness of the sutures and timing for implementing the sutures. However, guide wire routing and advancement struggles continue to impede the usage and full realization of their benefits. Similarly, the use of smaller, maneuverable elongate device advancers for introducing and/or advancing other elongate medical devices including tubes and catheters can enhance likewise enhance the effectiveness and timing for implementing related procedures. However, ineffective conventional elongate device advancers often increase risks and raise additional challenges when used for supporting other surgical devices, such as gas leakage or loss of the pneumoperitoneum associated with performing port closure functions.

Small, simple conventional elongate medical devices are known that are configured for manual operation including being operable with relative ease by a surgeon, such as by a single hand, which can be configured for use with port placement devices. However, there are drawbacks associated with using conventional elongate medical devices to support a suture placement device like the apparatus for port closure described in the Patel patent. For example, these conventional devices require the surgeon to perform repeated, time-consuming, manual drive actions or require the surgeon to make movements or perform actions that increase risks.

For instance, FIG. 1A shows a simple, conventional elongate device advancer 10 formed as a guide wire combined with a sheath coil 10. The sheath coil 10 includes an integrated manual advancement notch 12 formed through the sheath, which is described further in U.S. Pat. No. 581,012 to Lynch et al. entitled, "Guidewire Advancement System." As shown in FIG. 1B, advancement notch 12 requires the surgeon to manually push the guide wire using a thumb or finger through the sheath notch 12, which is difficult and cumbersome to use with a laparoscopic surgical device when installed in a patient, such as a suture placement device. Further, such conventional advancer devices necessitate numerous repetitive advancement movements that slows port closure procedures and thus provides little assistance, if any, compared with manually pushing bare guide wire through the suture placement device.

As further example, FIG. 2 shows another conventional manual advancement device that is representative of similar manual devices. Manual advancement device 110 is coupled with a guide wire within a sheath at a proximal end like advancement device 10, and includes a stylet guide at its distal end for improving alignment and coupling with a surgical device, such as a suture placement device. However, like advancement device 10, manual advancement device 110 requires the surgeon to perform numerous, repetitive advancement actions by repeatedly advancing and retracting shuttle 116. While advancement device 110 improves coupling of the advancement device with the suture placement device, it nonetheless is slow and cumbersome for efficient usage with such a surgical device—particularly for placing multiple sutures and closing multiple ports in a patient within a short period of time.

Referring now to FIGS. 3A-3E, a diagrammatic plan view of a minimally invasive surgical environment is shown that illustrates significant benefits and advantages that can be provided via the use of an effective suture placement device 50 for port closure procedures, as well as showing drawbacks associated with usage of conventional elongate device advancers in combination with the same. As shown in FIG. 3A, several small diameter ports are typically created through patient tissue for laparoscopic surgical procedures, such as intra-abdominal surgeries. These ports are often formed through the patient's skin 20 (i.e., abdominal skin), fat layer 22, through a fascial layer 24, and sometimes muscles, which are each kept open as a laparoscopic port via use of a trocar port device 85. The port depth A is determined and a trocar port device 85 is selected to maintain the port during surgery along with a corresponding suture placement device 50 for closing the same.

The trocar port device 85 permits access for surgical instruments, orthoscopic cameras, and the like during surgery while simultaneously sealing the port to prevent the loss of inert gas. Inert gas, such as carbon dioxide, is typically pumped in through one or more ports to create a pneumoperitoneum balloon or space below the skin and above the surgical area to provide vital viewability for surgical procedures and maneuver space for surgical instruments and performing procedures. At the conclusion of the surgical procedures, these ports require effective suturing to close the corresponding wound and prevent herniation, which is best performed while maintaining the pneumoperitoneum and starting with effective placement of sutures at the fascial layer to close the port from the inside out.

Suture placement device 50 greatly enhances the ability of a surgeon to effectively place sutures starting at the fascial layer 24. The approach of effectively placing fascial sutures first and moving outward has been shown to enhance healing, reduce pain, and greatly reduce the possibility that the port will reopen. An effective method for placing sutures using a suture placement device 50 is illustrated in FIGS. 3A-3E, which includes inserting 62 the distal end of an elongated cannula of the suture placement device 50 through the corresponding port such that its distal end extends beyond the distal end of the trocar port device 85, followed by withdrawing 64 the trocar port device 85 over the suture placement device 50 as illustrated in FIG. 3A. The surgeon will select a suture placement device 50 having a diameter slightly less than the inner diameter of the trocar port device 85, such that suture placement device 50 is able to maintain the port opening and prevent significant gas leakage until sutures are placed and the port is closed. The suture placement device 50 is selected for the port such that its elongate cannula has a longitudinal length B sufficient for extending internally beyond the distal end of the trocar port device 85, spanning the length of the port, and extending proximally an appropriate length for the surgeon to maintain control of the suture placement device and effectively use it for suture procedures.

The suture placement device 50 is used to position a suture for intra-abdominal suturing and suture puncture wounds generated by surgical laparoscopic trocar ports and other puncturing devices, and to do so without any exposed sharps, which is enabled due to the suture placement device creating the suture path within the device and the suture being loaded therethrough. This is accomplished, in part, via rotation 66 of a pivot bar or 'T-bar' disposed at the distal end of the suture placement device 50 about ninety degrees from its longitudinal orientation during insertion, such that the pivot bar is substantially parallel with the fascia layer 24 and skin 20, and extends across and beyond the width of the port as shown in FIG. 3B. Thereafter, the suture placement device 50 is withdrawn 68 externally until the top portions of the pivot bar are in contact with the fascia layer 24.

Referring to FIGS. 3C and 3D, stylet guides disposed on opposite lateral sides of the cannula of the suture placement device 50 are pushed downward 70 or extended distally 70 through the fascia (and muscle as appropriate) until each stylet guide connects with and extends into corresponding openings formed in the rotated pivot bar. The elongate cannula of the suture placement device, the pair of stylet guides, and the pivot bar each define channel segments therein. Upon connection of each stylet guide with and extending into the corresponding openings formed in the rotated pivot bar, the internal channel segments connect to form an uninterrupted internal channel pathway 80 within the suture placement device that extends through the fascia layer along a desired suture path.

As can be seen in FIG. 3D, the internal channel pathway defined through the suture placement device 50 extends from an entry port 81 formed at a proximal portion of the device longitudinally downward or distally within a first channel formed in the elongate cannula of the suture placement device to and through a first one of the stylet guides. The channel pathway 80 continues uninterrupted around and through the rotated pivot bar at the distal end of suture placement device turning into and upwardly or proximally through the second one of the stylet guides. The channel pathway continues proximally through a second channel formed in the elongate cannula to an exit port 83 formed at the proximal portion of the device. Thus, once suture placement device 50 has been placed or installed within a port to be closed, and has been prepared for placement of a fascial suture or other suture, the suture placement device 50 defines therethrough an uninterrupted channel pathway 80 along a desired suture path.

The use of a guide wire to traverse the channel pathway 80 can greatly enhance the placement and completion of sutures using the suture placement device 50. An appropriate guide wire efficiently and effectively advanced through the channel pathway can significantly shorten the time spent placing a suture using the device. In particular, this can be the case when a corresponding or matching guide wire is selected for the length Lee (see FIG. 3E) of the channel pathway 80, its internal diameter, and corresponding parameters of the guide wire, which can more effectively be advanced through the channel pathway according to the matching parameter. Such a guide wire can be advanced or threaded through the channel pathway from the entry port 81 to the exit port 83 and, thus be used to pull a suture thread attached to its proximal end through the channel pathway 80 for quick and efficient suturing. However, drawbacks continue to persist for effectively and efficiently advancing the guide wire through the suture placement device.

After the suture thread has been directed through the channel pathway and extends along the pathway, the suture thread is in place to form a highly effective suture through the fascia layer 24 for closing the port. Additional sutures can further be placed through the fascia layer as needed, such as for irregularly shaped or large ports by rotating suture placement device 50 along its longitudinal axis within the port and rotate the pivot bar a desired amount, such as ninety degrees, to place an additional suture in a similar manner. Once a suture thread is placed along the channel pathway, thin lateral slots along the stylet guides and pivot bar allow the suture thread to slide out of the channel pathway 80 and the suture placement device 50 while maintaining the desired placement through the fascia layer to establish the suture. The stylet guides can be withdrawn upward or proximally, and the pivot bar can be rotated back to its initial elongate position to facilitate the suture thread withdrawing from the device while maintaining its suture position, as well as partial or complete proximal withdrawal of the suture placement device 50 out of the port as appropriate for releasing and completing the suture. Thereafter, a suture can be tightened and tied off to close the port at the fascia layer.

It is understood that the same, related, or similar surgical devices including configurations of other suture placement devices could also be used for discussion and description purposes with respect to inventive features discussed herein, as well as for identifying disadvantages of conventional elongate device advancers discussed in the context of assisting the suture placement device 50. For example, various suture placement devices exist that include different structural elements, operate in differ manners, and employ different methods for creating suture path segments and/or even complete channel pathways. Nonetheless, disadvantages and/or shortcomings of conventional advancers likewise exist for assisting similar and different types of surgical devices, such as time-consuming, repetitive motion advancers and/or complex, cumbersome advancers configured for use with complex surgical devices and procedures, which are ineffective for use with relatively small laparoscopic surgical devices and the like.

In addition, aspects and features of example device arrangements described herein nonetheless apply to a wide variety of surgical devices including various suture placement devices, introducers and/or advancer devices for use with guide wires as well as with other elongate medical devices, such as percutaneous tubes, catheters including dual lumen balloon catheters and single lumen catheters, guide wires and other elongate tubes and devices, and are not limited to use with the example suture placement device or guide wires. For example, other suture placement devices may begin or end their channel pathways at different locations, such as at a middle portion of a cannula, or may require the use of two guide wires to be thread through a pair of partial channel pathways, as well as more significant variations. Many conventional elongate device advancers are designed for use with complex surgical devices and are some are even integrated therewith. Such devices are thereby overly cumbersome or difficult for use as an assist device for small, relatively simple surgical devices like with suture placement devices. Other conventional elongate device advancers that are designed for use with small and/or relatively simple surgical devices are slow, require repetitive manual controls, and/or tend to enhance risk or unduly complicate procedures such that benefits provided rarely the risks, ineffective operations, and/or other disadvantages—particularly for deployment of a guide wire along a non-interrupted pathway and/or having a determined or desired length for deployment of the guide wire.

Thus, although aspects and features described herein provide significant benefits and advantages for usage with a suture placement device and/or even the configuration of a suture placement device described as an example for discussion purposes including configurations of the Patel device, it is understood that the elongate device advancer device described herein is not so limited. FIGS. 4A, 4B and 5 further illustrate disadvantages of conventional elongate medical device advancers coupled with the example suture placement device and the like including the Patel device. FIG. 4A illustrates the use of conventional advancer 110 discussed above along with FIG. 2 coupled with the suture placement device 50 as described along with FIGS. 3A-3E. Although conventional elongate device advancer 110 may be able to advance a guide wire through the channel pathway 80 of suture placement device 50, advancer 110 requires many repetitive manual advancement actions by the surgeon to advance the guide wire through the length of the channel pathway 80.

Similarly, FIG. 5 shows usage of yet another conventional elongate device advancer 210 depicted in a usage arrangement with suture placement device 50 to advance an elongate device in the form of a guide wire along the channel pathway 80. Conventional advancer 210 not only requires multiple repetitive actions to be performed by the user, but advancer 210 further requires two hands to operate (or two users—one to maintain the suture placement device and another to advance the guide wire), such that its usage can induce significant movements capable of creating other challenges or enhancing risks to the patient or surgical environment.

Improvements have been proposed for more complex conventional elongate device advancers that attempt to address shortcomings of simple advancement devices, which primarily include complex, electrically powered advancement mechanisms specially designed for particular surgical procedures. While these devices can provide benefits associated with powered drives and customized functions, such devices can significantly increase surgical costs while having their applicability limited according to the customized designs. Proposed improvements also include more complex devices having combined functionality, which can reduce the need for swapping devices and/or introducing additional devices during surgical procedures. However, these devices suffer from design tradeoffs that limit potential features that can help overcome deficiencies and meet needs for versatile, highly effective and efficient introducers/advancers in favor of providing the combination device.

For instance, referring now to FIGS. 6A & 6B, a combination tool 21 is shown in FIG. 6A for performing sinuplasty related functions, which as shown in the cross-sectional side view of FIG. 6B, includes a guidewire and balloon insertion mechanism 150, which are shown and described in further detail in U.S. Patent Publication No. 2019/0038301 to Algawi et al. published Feb. 7, 2019 ("Algawi device"). The Algawi device includes a thumb-driven actuating gearwheel 164 and an intermediate gearwheel 166, which contacts a guidewire when downward pressure is applied on gearwheel 164 toward the guidewire and the thumbwheel is rotated by the user's thumb. Upon release of pressure on the gearwheel 164, the guidewire is freed from contact with intermediate gearwheel 166, such that the guidewire can freely translate with respect to mechanism 150 for enabling angioplasty-related functions of the tool. Thus, potential benefits for the conventional device when freed from integration with the overall tool, such as maintaining continued contact with the advancer for precise control of guidewire position and translation, can be lost between intermittent engagement of the guidewire as needed for combined tool functionality. Further, as can be seen in FIG. 6A, the guidewire and balloon insertion mechanism portion of tool 21 is fixedly retained as part of and in alignment with the overall sinuplasty tool, which further restricts maneuverability and related freedoms for use of the guidewire mechanism as integrated in the overall tool.

As another example, FIG. 6C shows an introducer apparatus 410 of a combination assembly for an Ultrasound-Guided IV Catheter, which is further shown and described in U.S. Pat. No. 10,143,826 to SanoStik, LLC that issued on Dec. 4, 2018 ("SanoStik device"). The SanoStik device includes a guide wheel assembly 610 having a pair of parallel guide wheels 611a and 611b rotatably mounted on a shared axis and spaced apart from each other by a spacer plate that defines a guidewire gap therebetween. A first one of the guide wheels 611a is arranged to rotatably engage a drive wheel attached to a rubber gasket 619, such that rotation of the pair of drive wheels 611a and 611b via a user's thumb in a forward or advancement direction rotatably drives the rubber gasket 619 in an opposite direction. An outer surface of the rubber gasket 619 contacts a side portion of the guidewire 412 and pushes the guide wire in the forward or advancement direction through the guidewire gap formed between the pair of guide wheels 611a and 611b.

Operations of introducer apparatus 410 for precisely controlling translation of the guidewire are limited to forward movements while under uninterrupted control of the user, so as to enable the IV catheter placement functionality and avoid related potential complications during such procedures that can occur with exposure to blood and fluid during reverse translation of the guide wire. As such, the introducer apparatus 410 includes a leaf spring 628 for providing tactile notification of forward movement to the user along with locking translation of the guidewire for only permits unidirectional translation in the forward/advancement direction. Further, similar to apparatus 310 described above, introducer apparatus 410 is constrained to an aligned orientation and position as integrated with the combined IV catheter placement apparatus, which limits potential operations and controls of the device.

Accordingly, there is a need for a simple elongate device advancer configured to be held in and easily operated by a single hand of a user as an assist device for usage with a small, relatively simple surgical device, such as a suture placement device including the Patel device, as an infusion catheter introducer/advancer, and/or an introducer/advancer usable for different types of elongate medical devices and for a wide variety of procedures. Further, there is a need for such a device that is easily operable by the user for imparting introducer/advancer operations without requiring significant control movements by the user or multiple manual advancement actions, and for providing precise continuous control over the position and translation of an elongate device being introduced into the body or advanced along a surgical path, as well as for an easy-to-manipulate & control, manually driven advancer capable of providing continuous direct control and translation of an elongate device, and/or amplified translation of an elongate device.

Further, a need exists for an elongate device advancer that can readily deploy a guide wire through a channel pathway having a determined length including deploying the guide wire through a substantial portion of the determined length. In addition, a need exists for an elongate device advancer configured for use with suture placement device 50 and other similar devices having known parameters, such as a known channel pathway length, diameter, shape, resistance or other matchable parameters, that can provide enhanced customized advancement or deployment along the pathway.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

One general aspect includes an advancer for advancing an elongate medical device including an advancer body arranged to be held in and controlled by a single hand. The advancer body defining a pathway between a proximal end portion and an opposite distal end portion for translating an elongate device therebetween. The advancer body can include: an inlet having an inlet longitudinal axis defined at the proximal end portion for receiving the elongate device into the pathway, and an introducer tip at the distal end portion defining an exit for the longitudinal device to exit the pathway, in which the exit has an introducer longitudinal axis. The advancer also includes a rotatable manual control partially embedded in the advancer body at the distal end portion arranged to receive a user-exerted manual control movement from a thumb of the hand including a torque applied by the thumb and a rotation arc distance rotated by the thumb as the torque is applied. The advancer also includes a manual drive having a gripper-driver for concurrently engaging opposite outer surface regions of the elongate device at a drive location along the pathway within the advancer body, in which the gripper-driver is arranged to maintain a constant drive connection with the elongate device and apply a translation drive force for translating the elongate device an advancement distance in response to the user-exerted manual control movement. The manual drive can convert the torque applied into the translation drive force and the rotation arc distance into the advancement distance. The translation drive force can be scaled by a force factor with respect to the torque applied by the thumb and the advancement distance can be scaled by a distance factor with respect to the rotation arc distance. In some arrangements, the advancer can be arranged such that the distance factor is 1 (one) or greater than 1 (one), and the elongate device is translated through the pathway an advancement distance equal to or greater than the rotation arc distance.

Implementations can include various features described herein and pertaining to concepts discussed along with example arrangements, which can be combined in various arrangements and combinations. In some arrangements, the manual drive can include a nip disposed along the pathway that defines a nip longitudinal axis at the gripper-driver. The nip longitudinal axis can have a transverse orientation from the inlet longitudinal axis, and the elongate device can be configured to translate through the nip in a translation orientation transverse from the inlet longitudinal axis. The pathway orientation and arrangement of the nip can be arranged to provide advance the elongate device along the pathway within a compact ergonomic arrangement of the advancer body arranged for being held and controlled in the single hand. In some arrangements, the distance factor can be greater than one, and the advancer can be arranged to amplify translation of the elongate device along and through the pathway for an amplified advancement distance greater than the rotation arc distance.

In some arrangements, the rotatable manual control can include a manual drive portion extending into the pathway configured to drivingly engage the elongate device at a distance factor of one (1), where the rotation arc distance and the torque applied by the thumb for the user-exerted manual control movement are configured to be equal to the translation drive force applied to the elongate device and the advancement distance. As such, the translation drive force and the advancement distance are a manual translation drive force and a manual advancement distance substantially the same as the user-exerted manual control movement.

In other arrangements, the manual drive can include a combination driver/driven roller rotatably coupled with the advancer body having an engagement surface rotatable with the combination driver/driven roller including a drive portion extending into the pathway, and the elongate device advancer can include an automated drive for translating the elongate device an automated primary distance when actuated that is greater than the manual advancement distance. The automated drive can include, for example, a power driver configured to store potential energy for driving translation of the elongate device the automated primary distance and transmitting a corresponding automated linear drive force, and an actuator configured to be actuated by the single hand to activate the power driver for transmitting the automated linear drive force to the drive portion of the combination driver/driven roller. A cooperative feed roller nip can be defined between the manual drive portion of the rotatable manual control extending into the pathway in an opposed arrangement with the drive portion of the combination driver/driven roller extending into the pathway. The opposing drive portions can be configured to engage opposite side regions of the elongate device and cooperate as a pair of feed rollers for translating the elongate device along the pathway toward the distal end portion responsive to one of the automated linear drive force or the manual translation drive force.

One general aspect includes a method for rapid advancement of an elongate medical device responsive to manual user input. The method can include defining an elongate device guided pathway through an advancer enclosure, and rotatably coupling a drive roller having a drive roller radius to the advancer enclosure in a drive arrangement with the guided pathway including projecting a rotary engagement surface of the drive roller into the pathway, in which the drive roller has a driven gear attached thereto such that the drive roller and the driven gear rotate together about a common axis. The driven gear can have a driven gear radius less than the drive roller radius, and the rotary engagement surface can be disposed at the drive roller radius. The method can also include rotatably coupling an idler roller to the advancer enclosure in a drive arrangement with the guided pathway opposite the drive roller including projecting an idler rotary engagement surface of the idler roller into the pathway opposing the drive roller engagement surface, such that the drive roller engagement surface and the idler roller engagement surface defining a nip for driving translation advancement of the elongate device along the guided pathway.

The method can also include rotatably coupling a manual input wheel to the advancer enclosure in an operative rotating connection with the driven gear including locating a radial portion of the manual input wheel outside of the advancer disclosure arranged to receive a user-exerted rotary control movement applied to the manual input wheel for rotating the input wheel according to rotatory inputs. The manual input wheel can have an input radius and engage the driven gear at the input radius for driving rotation of the driven gear in response to receiving user-exerted movement applied to the manual input wheel. The method can also include arranging the elongate medical device advancer to amplify advancement of an elongate medical device responsive to manual advancement inputs of a user while an elongate medical device extends through the pathway.

The method can further include performing actions in response to receiving a user-exerted movement applied to the manual input wheel rotating the manual input wheel a first input arc. The actions can include engaging the driven gear at the input radius including moving an engagement surface of the driven gear a first input arc length of the input wheel corresponding with the first input arc, and imparting rotation of the driven gear for an amplified arc based on movement of the engagement surface of the driven gear and the driven gear radius. The actions can further include rotating the engagement surface of the drive roller for the amplified expanded arc such that the engagement surface moves an amplified arc length based on the drive roller radius, and cooperatively driving translation of the elongate device disposed in the nip an amplified translation distance according to the amplified arc length, such that the amplified translation distance is greater than the input arc length of the user-exerted first input arc.

Other medical devices, support devices for medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIGS. 4A and 4B are plan views showing a conventional device and method for advancing an elongate device through the example suture placement device of FIG. 3D using the prior art advancer of FIG. 2.

FIG. 14 is a top plan view of the internal components of the manual driver shown removed from the advancer housing.

FIG. 26A is a top left perspective view of the elongate device advancer of FIG. 15 proximate the nip shown with the left housing removed for exposing the nip and interactions of the elongate device with the nip.

FIG. 28A is a rear perspective view of a lateral cross-section of the advancer of FIG. 15 at a location along the pathway as indicated in FIG. 26A for Views J & K, whereas

FIG. 29A is a rear perspective view of a lateral cross-section of the advancer of FIG. 15 at a different location along the pathway as indicated in FIG. 26B for Views L & M, whereas

FIGS. 32A and 32B are top (32A) and bottom (32B) plan views of yet another example elongate device advancer according to aspects and features described herein, which schematically depicts a lateral lock incorporated into the advancer body at the distal region that can engage lateral portions of the elongate medical device within the pathway for selectively restraining advancement and/or rotation of the elongate medical device routed through the advancer.

FIGS. 38C-38E are close views of the portions labelled as "Views C, D & F" in FIG. 38B, which illustrate example operations of the transmission switch including movements of the float gear.

FIG. 57 is a close side view of the nip portion of the drive mechanism for the elongate device advancer of FIG. 44A as identified in FIG. 54 (View H).

FIG. 58 is a schematic representation of the close view of the nip portion of the drive mechanism shown in FIG. 57, which illustrates additional options and features pertaining to the nip and drive components.

DETAILED DESCRIPTION

Figure 1A:
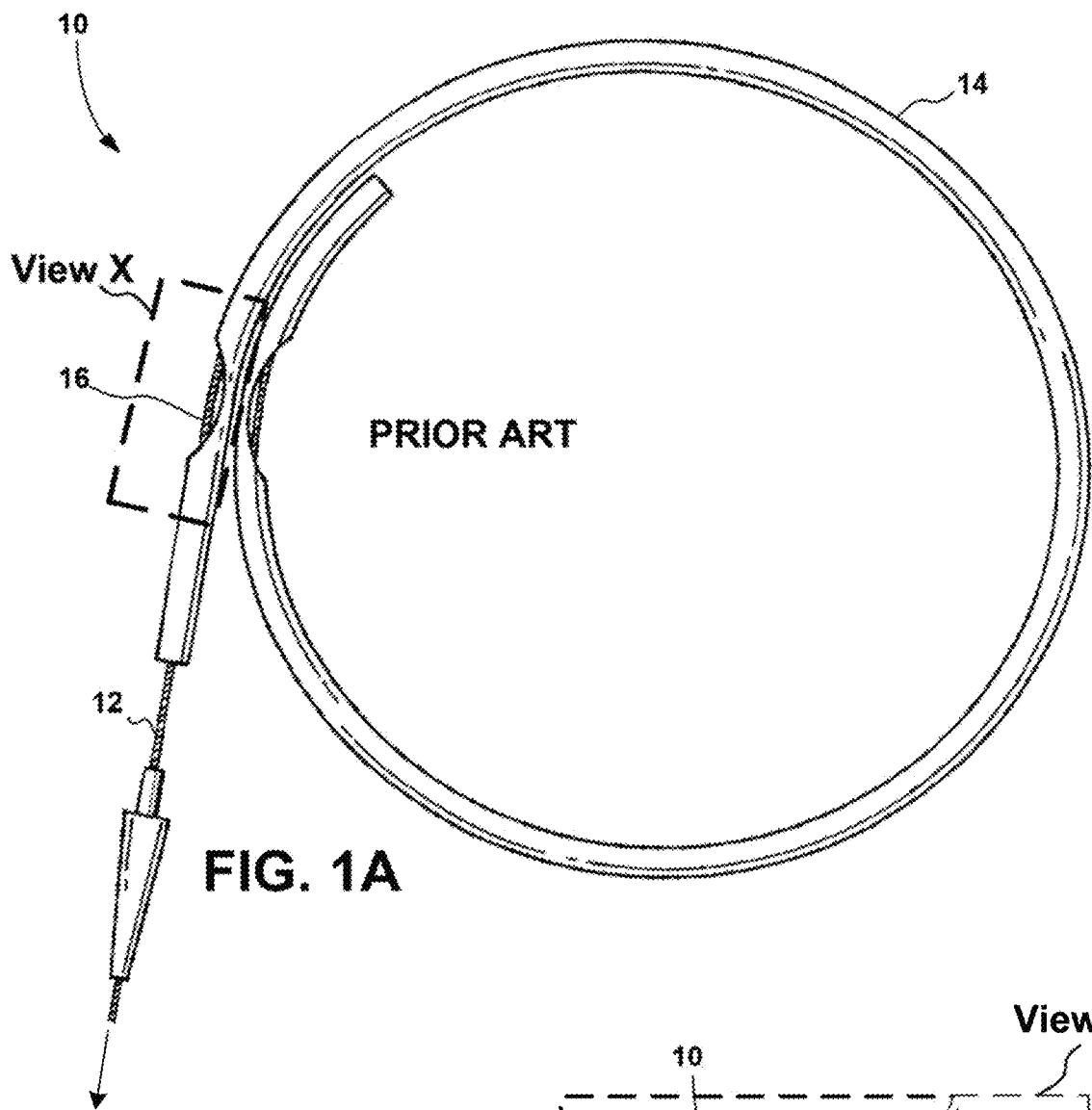
FIG. 1A is a plan view of a prior art elongate device advancer device.
Figure 1B:
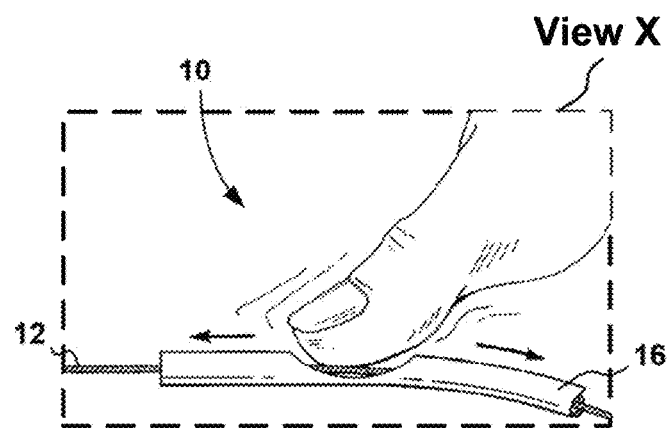
FIG. 1B is a close view of the manual advancement portion of the prior art elongate device advancer of FIG. 1A.
Figure 2:
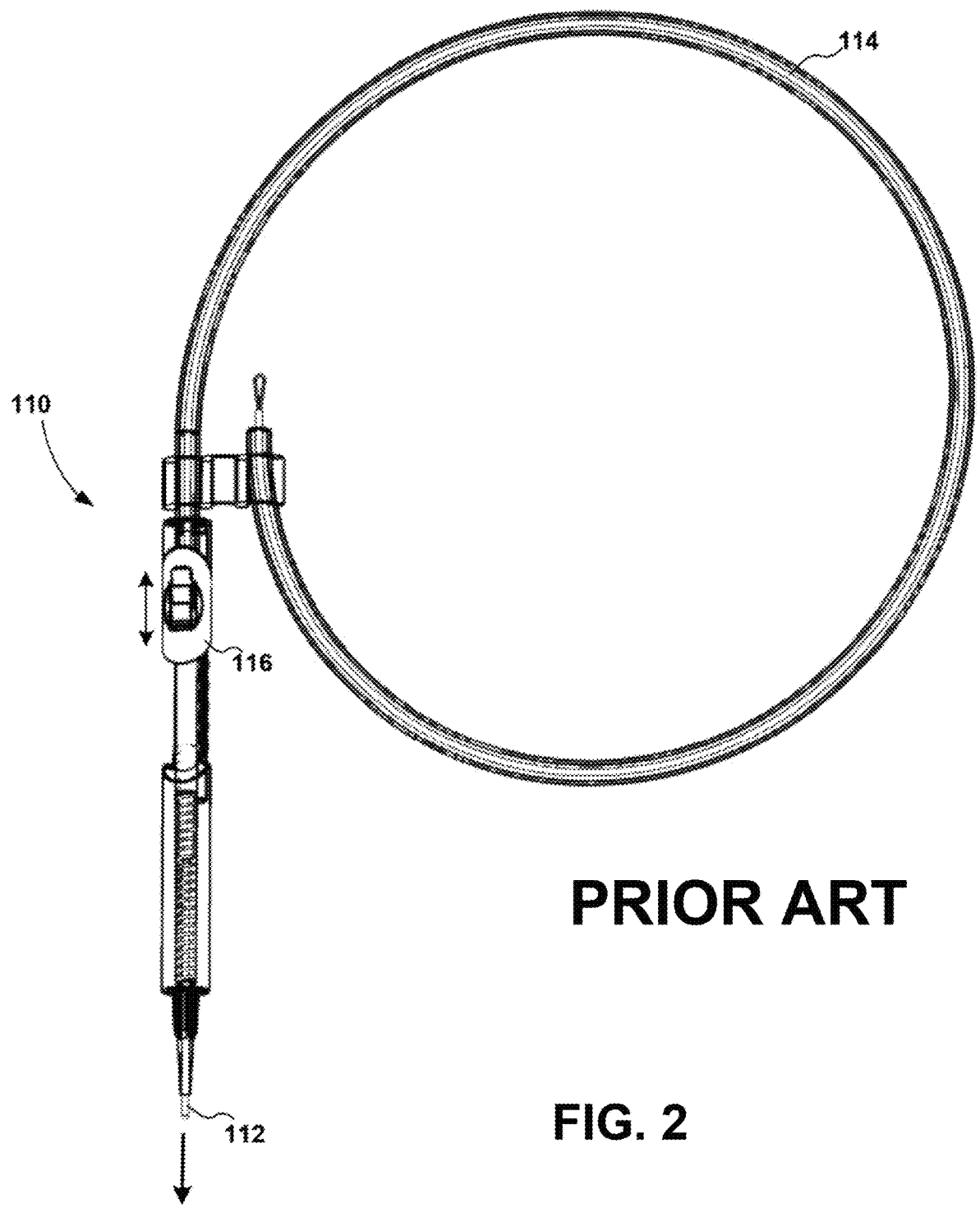
FIG. 2 is a plan view of another prior art elongate device advancer device.
Figure 3A:
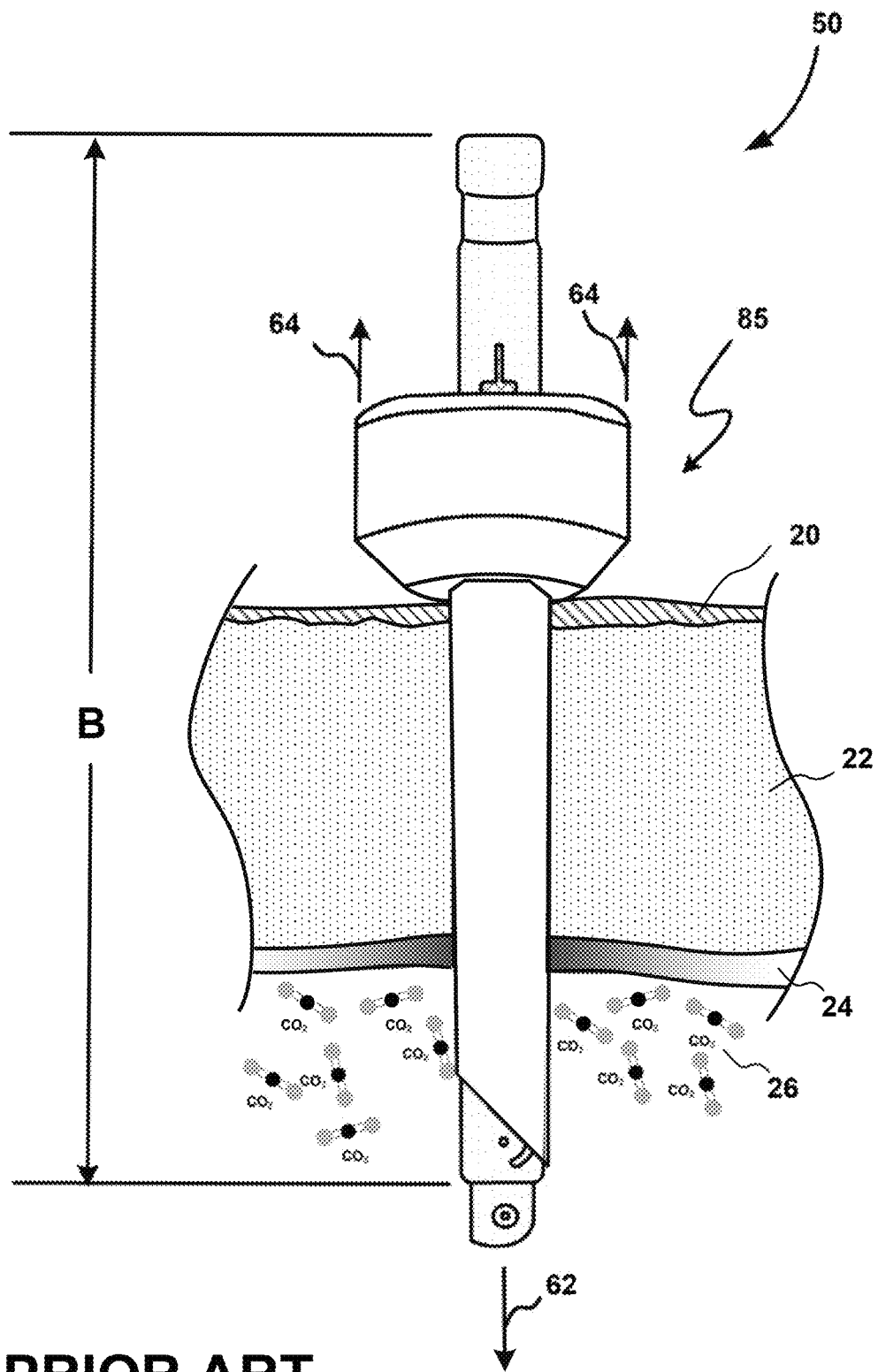
FIG. 3A is a diagrammatic plan view of a minimally invasive surgical environment configured to use an example prior art surgical device in the form of a suture placement device that can be supported by aspects and features of elongate device advancers discussed herein, for which the suture placement device and corresponding diagrammatic surgical environment are described and shown in FIGS. 3A-3D for discussion purposes to assist with describing aspects and features described herein; To Wit, the diagrammatic surgical environment shown includes a prior art trocar device installed through a laparoscopic surgery port formed through patient tissue along with the example prior art suture placement device inserted therethrough in preparation for port closure procedures.
Figure 3B:
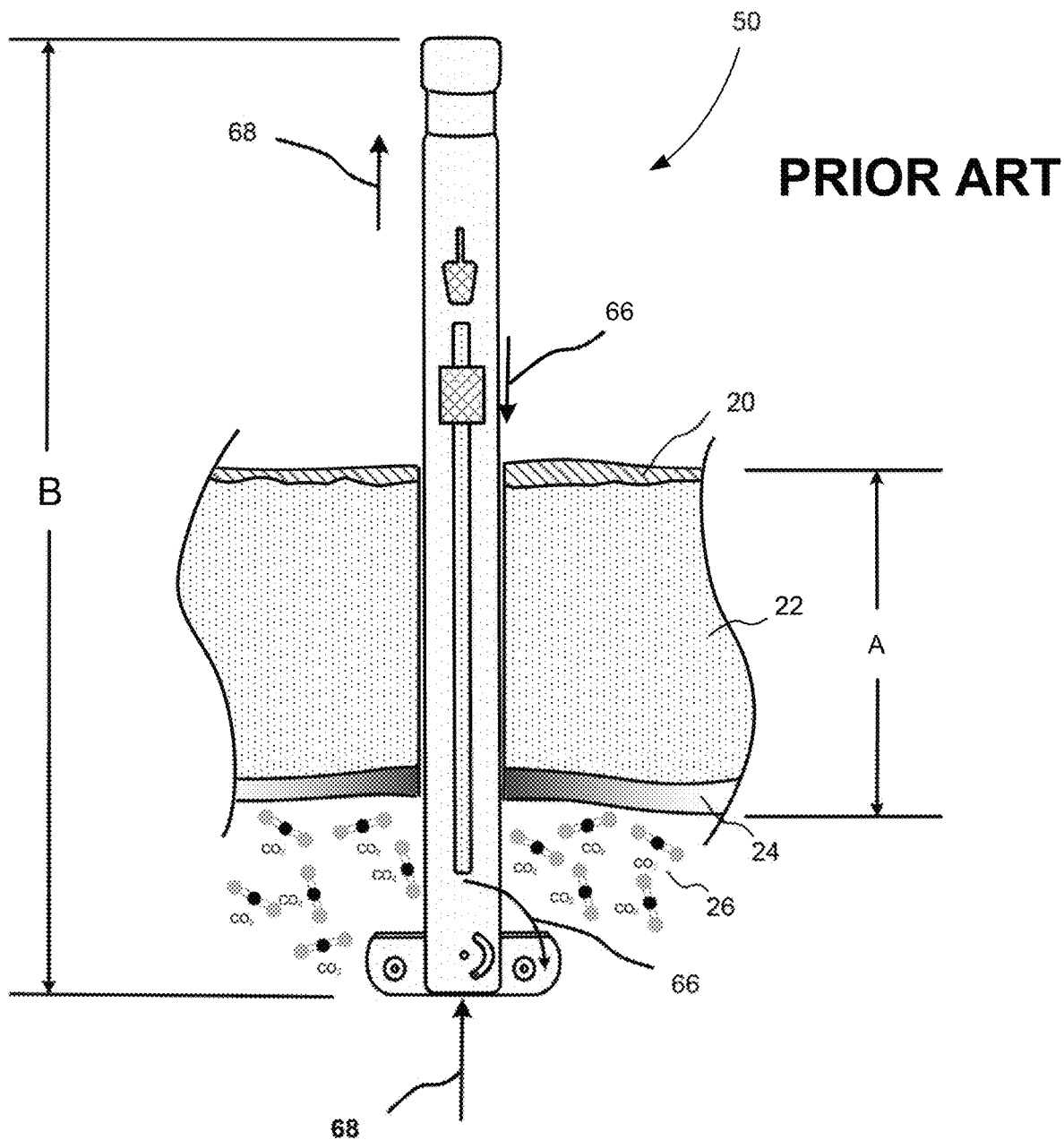
FIGS. 3B and 3C are plan views showing example actions pertaining to arranging the suture placement device of FIG. 3A for placement of a suture, for which aspects and features of the elongate device advancer and methods described hereafter can assist and provide benefits and advantages in comparison with conventional elongate device advancers.
Figure 3C:
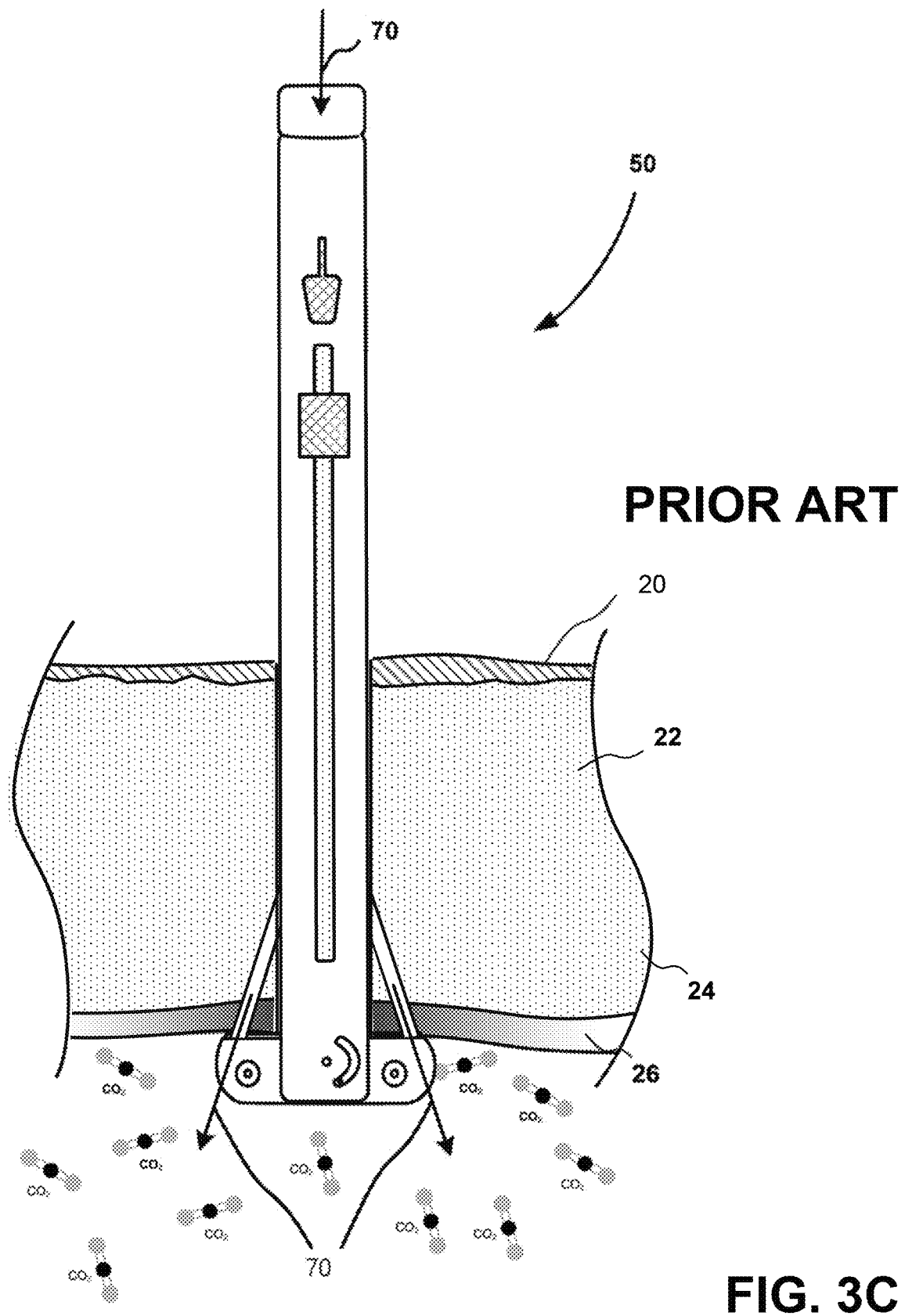
Figures 3D, 3E:
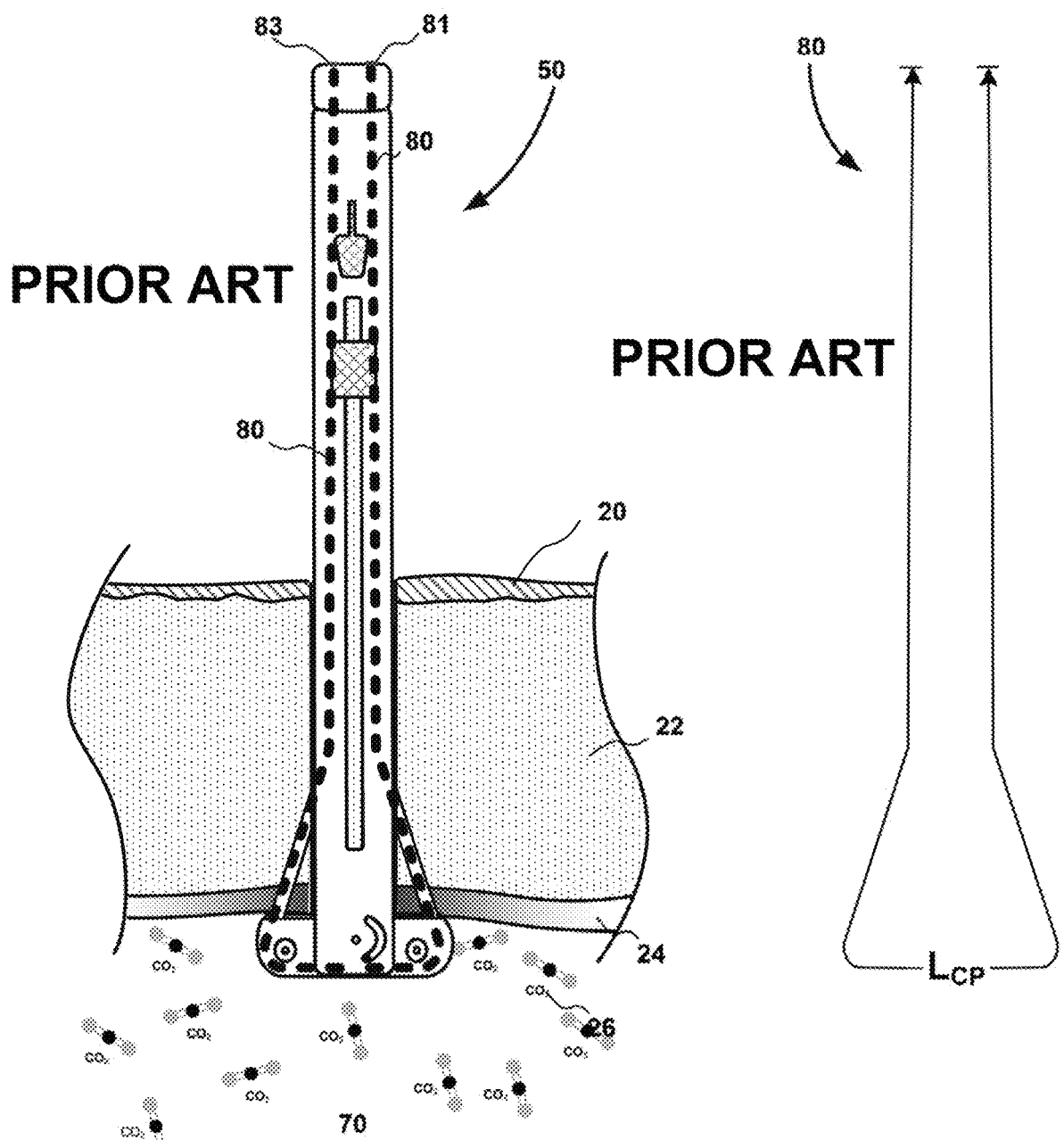
FIG. 3D is a plan view showing an arrangement of the suture placement device of FIG. 3A prepared for placement of a suture prior to introduction of an elongate device including having a channel pathway established through the device corresponding with a desired return loop pathway for the suture along with the elongate device in advance of suture material.
FIG. 3E shows an outline of the channel pathway for the arrangement of the example suture placement device illustrated in FIG. 3D along with identifying the length of the channel pathway through which an elongate device can be routed to assist with suture placement.
Figure 5:
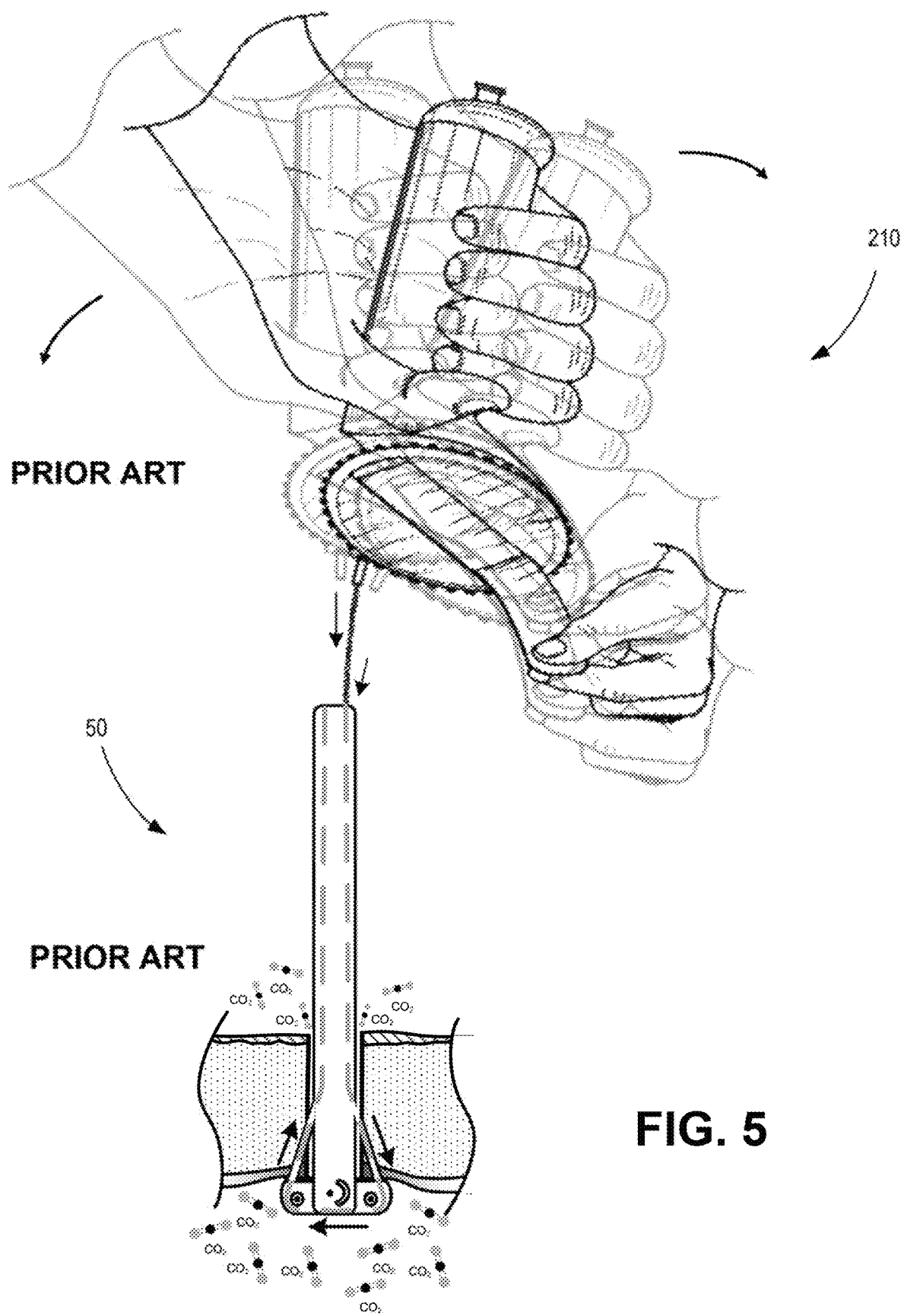
FIG. 5 is a plan view showing of another conventional device and method for advancing an elongate device in the form of a guide wire through the suture placement device of FIG. 3D.

The embodiments described herein can advantageously be used with a wide variety of surgical devices and procedures associated with minimally invasive surgery. In particular, the instruments described herein can be low-cost, disposable instruments that facilitate being used for only one procedure.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the term "target workspace" refers to anything within or pertaining to the endoscopic work cavity including the body of the patient, tissues and organs within the cavity, and tissue defining the cavity, and also to support structures for the MIS procedure including a cover and cannula supports, instruments and related attachments or medical implements including needles, suture materials, implants, meshes, etc. As used herein, the term "target tissue" refers to any tissue or organ that interacts with the target workspace including tissues and organs of the patient, natural tissues and organs introduced to the target workspace including natural transplant tissues and organs, artificial tissues and organs including mechanical or electro-mechanical organs, and tissue and organ assist devices such as pacemakers, mesh material, artificial skin and the like.

As used herein, a surgical device or tool or clinical instrument refers to a medical instrument having contact surfaces that are configured to engage organs, tissues and/or portions of a surgical cavity or wound to thereby move, hold, lift, retain, suture or otherwise engage, interface or make contact with the target tissue and perform clinical functions as appropriate for the surgical environment. The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to an actuation shaft) would be the proximal end of the tool.

Further, specific words chosen to describe one or more embodiments and optional elements, or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below", or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Referring generally to FIGS. 7-32B, example arrangements of compact, ergonomic, and manually driven elongate device advancers 1010, 1110 ???????????? are generally shown for precisely and quickly advancing an elongate device a manual distance, which can be coupled with an elongate device/sheath coil (not shown) for a usage arrangement with the elongate device of the coil. Although not necessarily shown for each example arrangement, it is understood that the example elongate device advancers can be operatively configured with a surgical instrument including the suture placement device 50 discussed above along with FIGS. 3A-3E while disposed within a port and prepared for suture placement procedures. Each of the example elongate device advancers 1010, ????????? are configured to be held within the single hand of a user and easily controlled to perform elongate device advancement actions to support a surgical device, such as the suture placement device 50 discussed above.

The elongate device advancer 1110 is advantageously configured for the user to impart translation of the elongate device 1112 through the elongate device advancer and into and/or through a support surgical device 50 or another desired path. The actuator is configured to provide amplified translation of the elongate device 1112 based on the user using the thumb of the single hand 1118 to simply engage a manual drive 1152 arranged as a thumbwheel of the device 1152 and apply a user-exerted rotary input to the thumbwheel for rotating it an input arc distance. Actuator 1110 is advantageously arranged and configured for amplifying a user-exerted input movement applied to the manual input or thumbwheel 1152 and, in response to the input, translating the elongate device 1112 an advancement distance that is greater than a length of user-exerted input arc length, and can be several times longer than the user-exerted input length. As such, the user can readily grip the advancer and easily control advancement operations without needing to apply numerous repeated advancement movements to impart significant translation of the elongate device.

Referring in particular to FIGS. 8-11 along with FIGS. 8 to 29B, an elongate device advancer 1110 is generally shown that includes an advancer body 1129 formed from a left housing 1130 and right housing 1140 attached to each other in an opposing relationship, a manual control 1184, and a manual drive 1150. The advancer body 1129 defines an elongate device pathway 1120 (FIGS. 10, 15 & 23) for advancing the elongate device 1112 therethrough from a first end portion 1123 to a second end portion 1125 of the advancer body, in which the advancer body is configured to be held in a grip of a single hand 1118 of a user and controllable by the single hand. The first end portion 1123 is configured to couple with the elongate device 1112 to receive a tip portion 1116 of the elongate device therein through an entrance 1122 of the pathway 1120 disposed at the first end portion 1123, and the elongate device 1112 is configured to advance through the pathway 1120 and out an exit 1124 of the pathway disposed at the second end portion 1125. The exit 1124 can include a stylet tip 118 or similar arrangement for coupling the elongate device advancer in a support arrangement with a surgical device, such as a suture placement device.

Figure 8A:
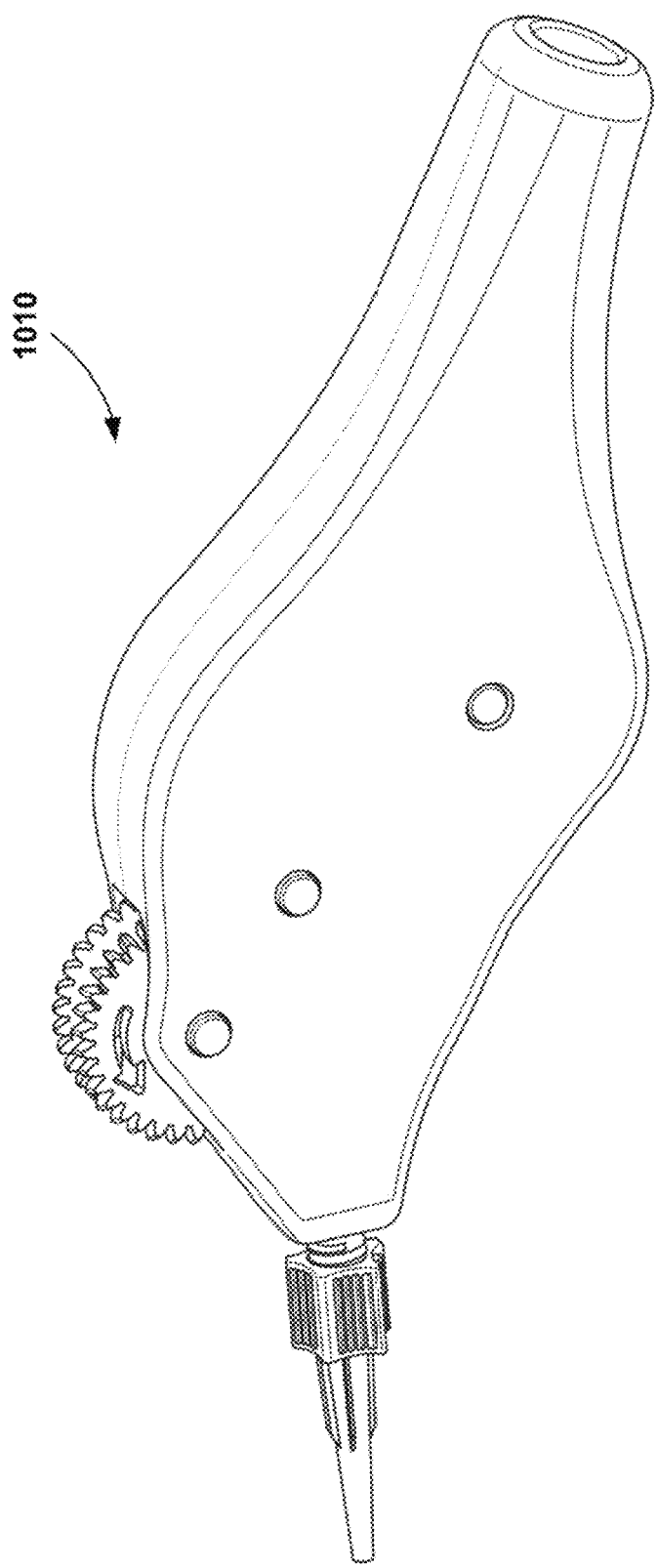
FIG. 8A is a proximal (rear) left side perspective view of the elongate device advancer of FIG. 7.
Figure 8B:
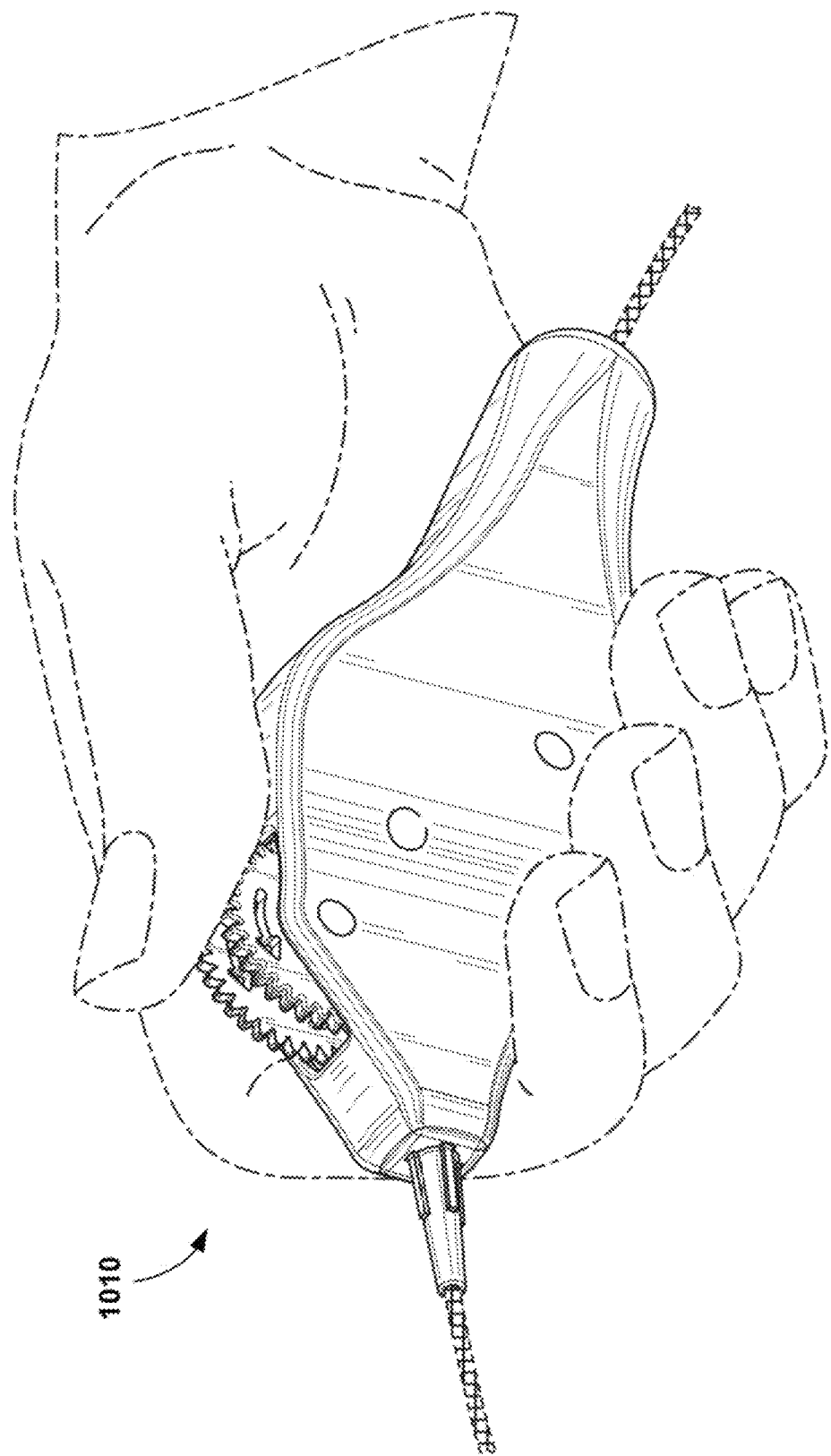
FIG. 8B is a distal (front) left side perspective view of the elongate device advancer of FIG. 7 depicted in a usage arrangement held and controlled in a single hand of a user.
Figure 8C:
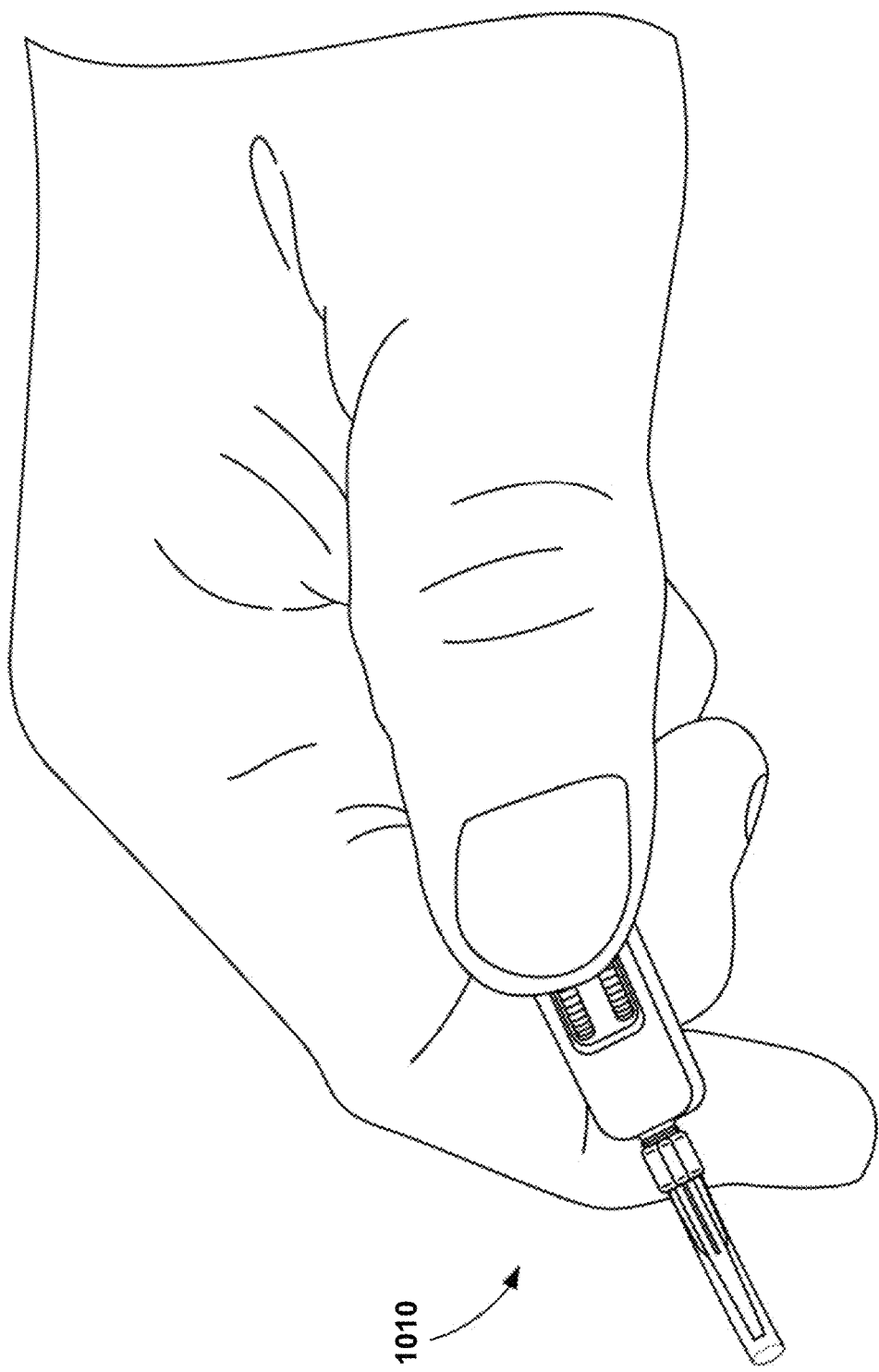
FIG. 8C is a top view thereof.
Figure 10A:
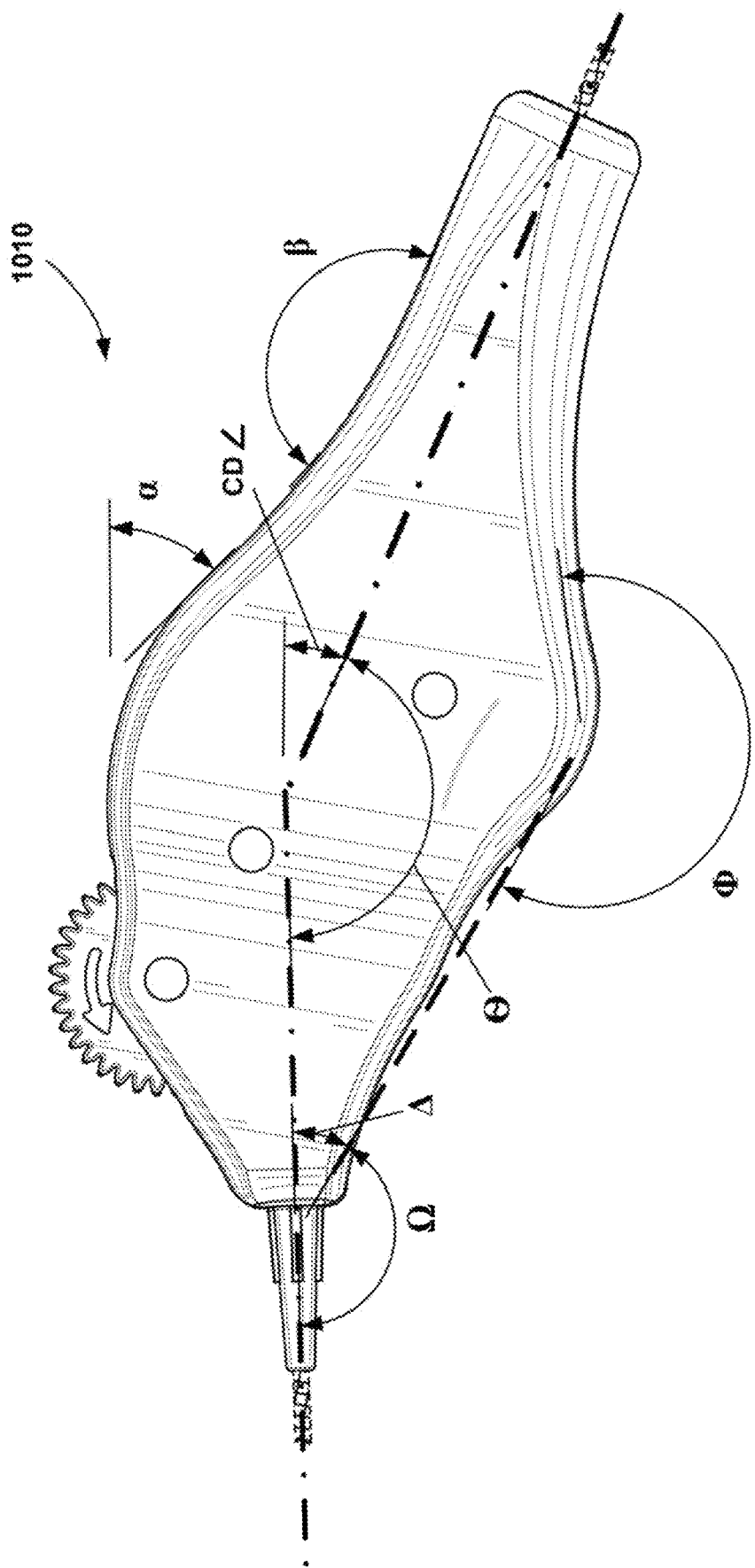
FIG. 10A is a left side plan view of the elongate device advancer of FIG. 7 schematically depicting example angular arrangements and orientations between edge regions of the advancer.
Figure 10B:
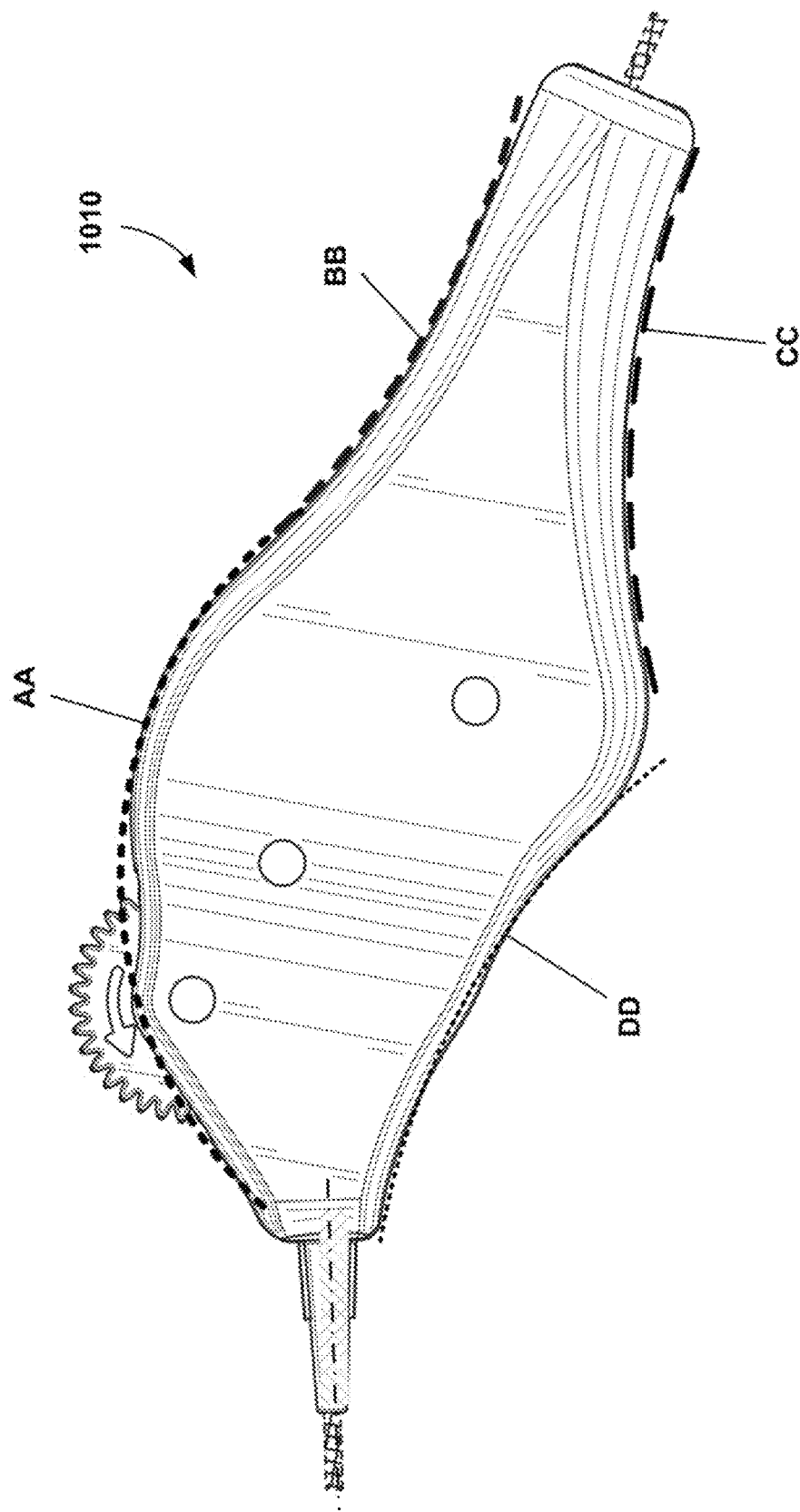
FIG. 10B is a left side plan view of the elongate device advancer of FIG. 7 schematically depicting example curvatures of edge regions of the advancer.

Ergonomic Shape & Intuitive, Comfortable Arrangement; Curved Pathway & Nip Angle As best seen in FIGS. 8 and 10, the arrangement of various features of advancer 1110 cooperate with each other to provide an advancer that is not only ergonomic and simple to use, but most users find it to be comfortable to hold, manipulate and control; intuitive to operate; and highly efficient in operation. As depicted in FIG. 8, the advancer body 1129 is shaped to provide an ergonomic grip such that the advancer body is readily cradled in the single hand 1118. The fingers are provided a lower edge portion for gripping around, which has a mild curvature matching natural contours of the fingers. In alternative arrangements [not shown] additional finger contours can be formed in the lower edge portion to further enhance grip. Further, an opposite upper edge portion has a slight convex curvature that provides a natural rest for the user's thumb, which leads directly to the manual control/thumbwheel 1184. A stylet tip 1192 extends from the distal end of advancer at a comfortable angle with grip portions provided by the upper and lower edge portions, which places the wrist at a comfortable, natural angle with a feed pathway into which the elongate device is being advanced. A proximal end portion 1123 is oriented toward the user and defines an entrance for the elongate device 1112 into the pathway through the advancer, which allows a coil or other supply for the elongate device 1112 to be located proximate the user for any required manipulations of the same during use.

As can be seen in FIG. 10, the advancer body 1129 defines a pathway within and through the advancer body 1129 that extends from a first proximal end 1123 to the stylet at the opposite distal end 1125. Although not readily apparent to the user, the pathway includes a significant bend or turn along a medial portion of the pathway, such that a longitudinal axis of the pathway along the bend portion is angled with respect to a longitudinal axis of the pathway at the stylet rather than being oriented generally parallel with the exit longitudinal axis as is common for conventional advancer devices. Rather, the medial portion longitudinal axis forms an acute angle, Q, with respect to the stylet longitudinal axis. The acute angle can be relatively small, such as about ten (10) degrees or more, as well as relatively large, such as about sixty (60) degrees or even close to about ninety (90) degrees. However, for most arrangements, the acute angle can be about twenty (20) to forty (40) degrees, and/or can be about thirty (30) degrees.

Such an arrangement of the advancer body 1129 having a pathway defined therein with a bend formed within the medial portion can provide various advantages and benefits for the advancer arrangement pertaining to ergonomics, operational benefits, and/or efficient and intuitive operability. For instance, such an arrangement and pathway cooperates well with ergonomic grip features and comfort for holding and manipulating the advancer (e.g., wrist angle) as discussed above. Further, such an arrangement enables arrangements that can provide beneficial operational benefits, such as amplified displacement of the elongate enclosure during use, powerful grip features, continual precise control over position and displacement of the elongate device, and/or force amplification for driving displacement, which are described in greater detail below. In addition, such an arrangement enables intuitive control and operations of the advancer including the orientation and location of the stylet at the distal end 1125, as well as forward thumb roll operation toward an advancement direction of the stylet for the manual input/thumbwheel 1184.

The advancer body can be formed via a mating pair of the left housing 1130 and the right housing 1140, which can be attached to each other along opposing, mating surfaces and joined to each other via an adhesive, ultrasonic weld and the like. Each of the left and right housing can be formed from a rigid medical grade thermoplastic or other appropriate material, and formed via known methods such as injection molding. As discussed in greater detail below along with FIGS. 28A to 29B, the housings can also include various mating features for providing enhanced structural stability along with other benefits. For instance, mating male protrusions and/or female recesses formed at opposing, corresponding or mating portions of the housings can provide benefits for the arrangement, such as reinforcing or enhancing the pathway defined through the advancer body, providing rotational supports and other support features for internal components, defining geometric features for providing structural stability or reinforcement, and/or providing aesthetic or visual features and cues indicating intuitive usage and operations of the advancer device.

Figure 23:
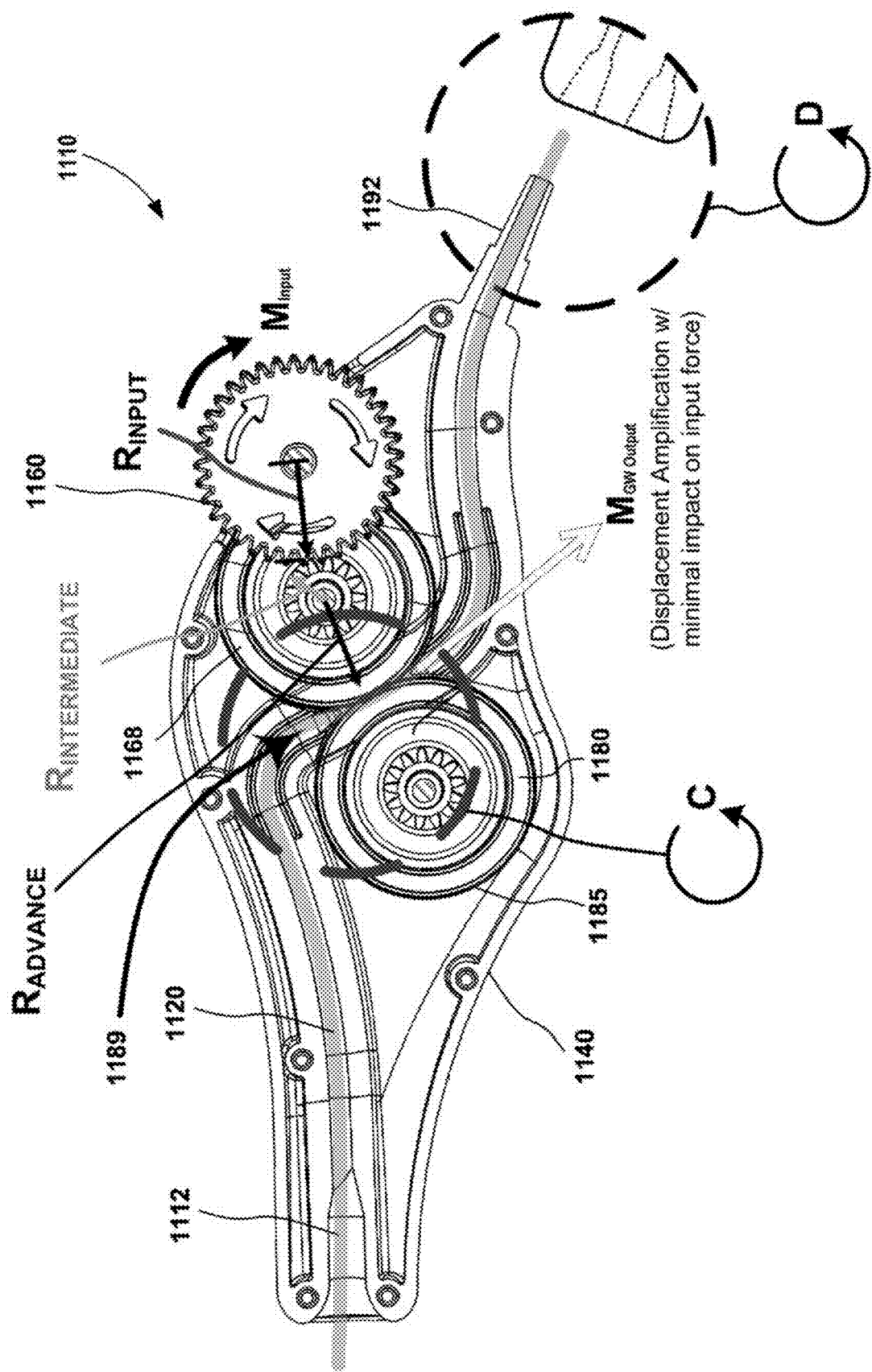
FIG. 23 is a right plan view of the elongate device advancer of FIG. 15 shown with the right housing removed to expose an example arrangement of internal components along with schematic representations pertaining to example operation of the drive rollers and outer roller assemblies of the example configuration of FIG. 15, which is shown with an elongate device arranged therewith.
Figure 24:
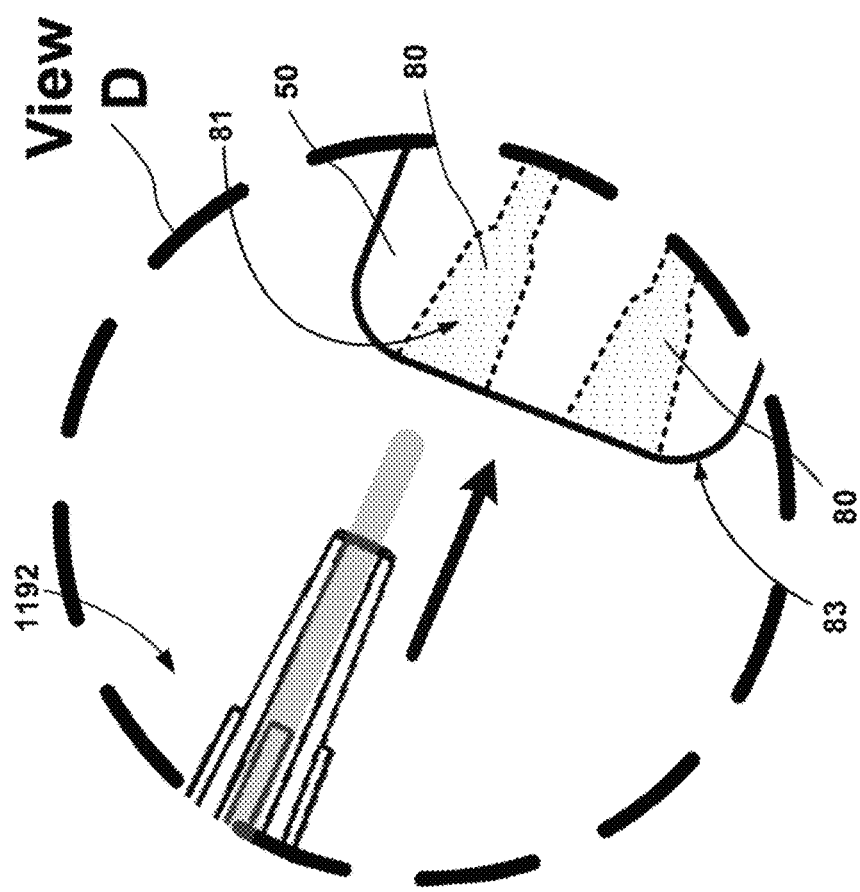
FIG. 24 is a close view the stylet tip of the elongate device advancer of FIG. 15 for the region identified showing a schematic representation for coupling with the example medical device shown configured as the suture placement device of FIG. 3D.
Figure 26B:
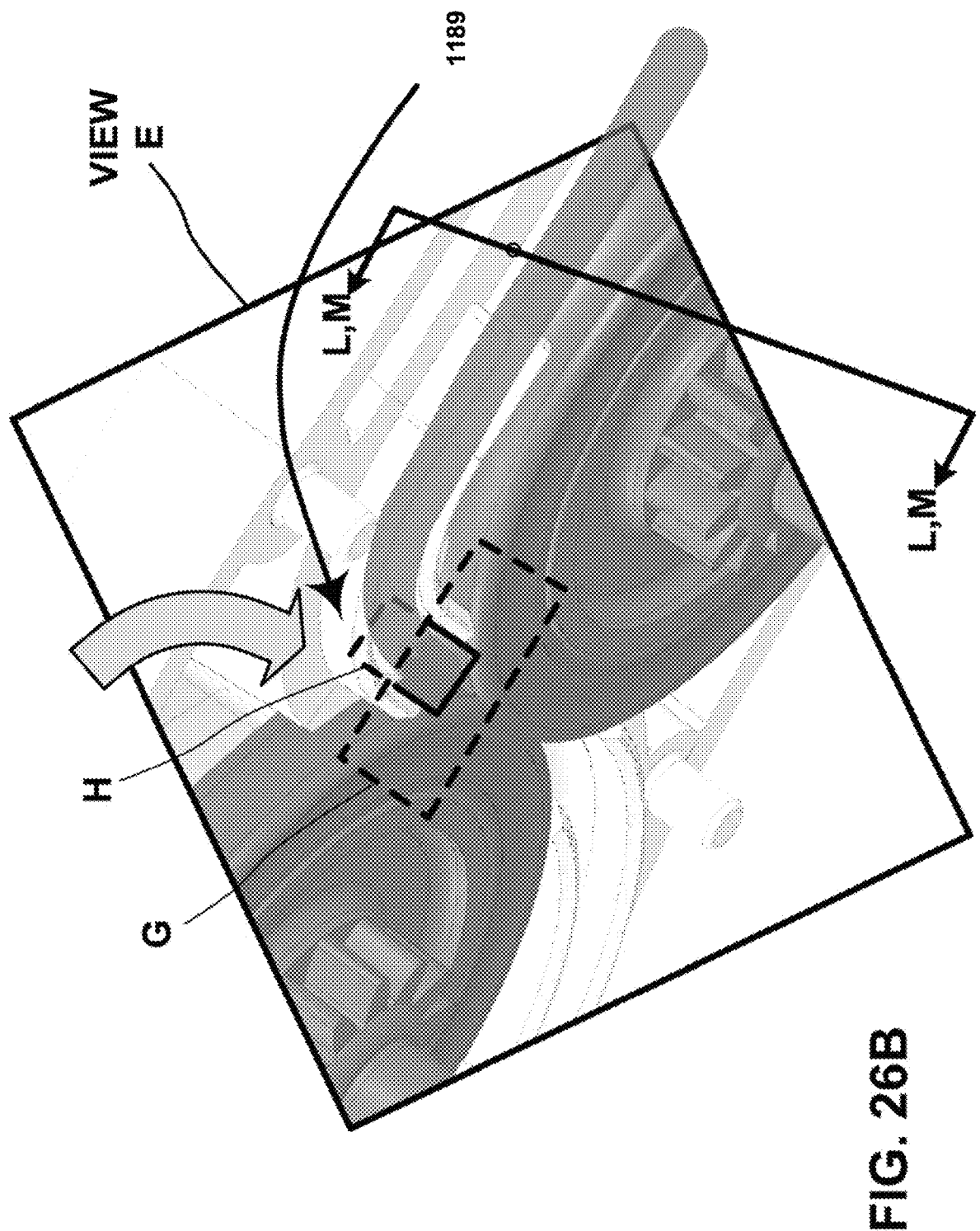
FIG. 26B is a close perspective view of the nip the advancer of FIG. 15 viewed as noted in FIG. 26A for View E, which is a close view from a top perspective generally corresponding with the orthographic side view of FIG. 23 and the close view of the nip of FIG. 25, which shows a portion of an elongate device that extends from a first, entry end of the pathway to an entry side of the nip without portions of the elongate device extending past the nip.

As best shown in FIGS. 23 and 24, a stylet tip 1192 can be provided at the distal tip of the advancer body for coupling with the suture device 80 discussed above along with FIG. 8 for advancing the elongate body into the suture device as it exits the advancer, which represent an example usage of the advancer. It is understood that attachments can be provided for connection with the stylet 1192 and/or the stylet can be replaced with another adaptor device for providing an appropriate coupling or connection with a different type of surgical device as desired.

Manual Drive/Thumbwheel Input and User Engagement

With particular reference now to FIGS. 12-15, as well as FIGS. 8-29B in general, the manual control 1184 is generally formed as a thumbwheel type mechanism disposed proximate the distal end portion and stylet tip 1192, which can be located along an upper portion of the advancer body that is arranged to support the user's thumb and thereby allow for natural operational control. The manual control can be arranged as shown and indicated for receiving rotary controls from the user including being arranged such that forward rotation toward the stylet tip imparts translation of the elongated device in a corresponding advancement direction for exiting the stylet tip. As show, visible indicia can be included on or proximate the manual input for guiding intuitive control movements of the user, which can be helpful and important during complex surgical procedures for properly operating the advancer. The manual control 1184 can be arranged for rotation and conveniently disposed along an upper portion of the advancer body configured for ready reception of user-exerted rotary input. Further, the manual control in a thumbwheel type arrangement can be partially embedded within the enclosure body in an arrangement for exposing a significant upper exterior portion of the rotary input outside of the advancer body, which can be accessible to the user and arranged for simple application of user-exerted control inputs thereto from the thumb of the single hand.

Figure 15:
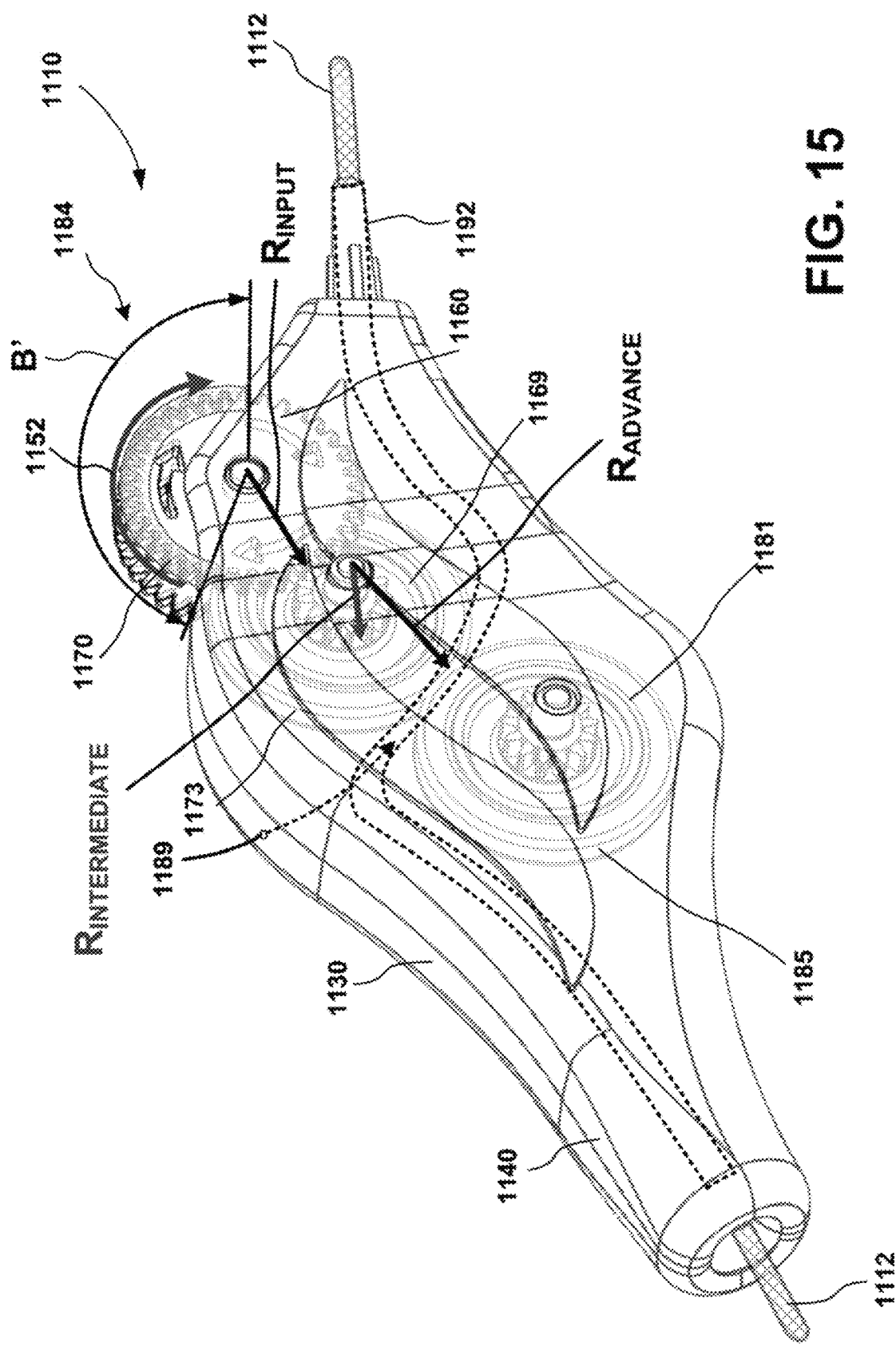
FIG. 15 is right rear perspective view of a schematic representation of another elongate device advancer in accordance with aspects, features and inventive concepts described herein shown with the housing partially transparent to expose an example arrangement of internal components.

As can be seen in FIG. 15, the manual control can receive a user input arc for movement of the manual control based on the exposed rotary angle, p, of the manual control exposed and accessible for user input and control, which can be about ninety (90) degrees to over one hundred eighty degrees (180), such as for an expanded input arc arrangement having a raised pivot for the manual control providing ready thumbwheel access for the user. In other arrangements, such as represented in the example of FIG. 15, the exposed rotary angle can be about one hundred twenty (120) to almost one hundred eighty (180) degrees. In other arrangements, the exposed rotary angle can be about one hundred thirty (130) to one hundred sixty (160) degrees. In such arrangements, an extended user-exerted control arc can be applied for the span of the exposed rotary angle. The exposed rotary angle can exceed one hundred eighty degrees. However, such arrangements can impair quick and easy access options for the user to impart control movement to the manual input.

Figure 14:
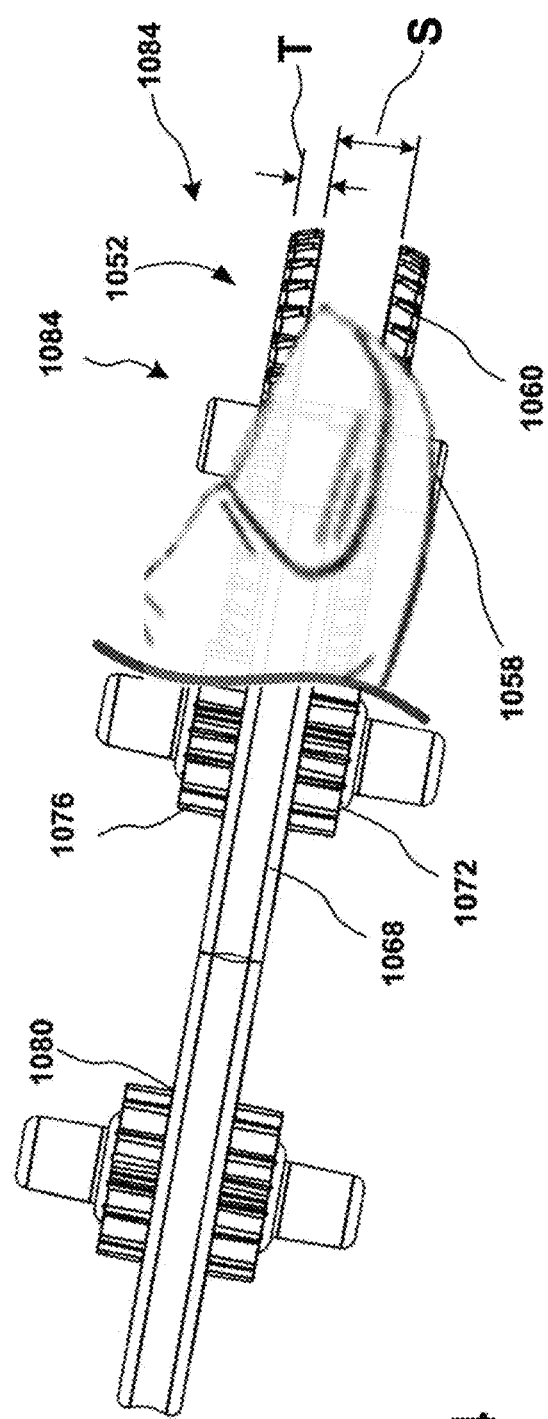

As best seen in FIG. 14, the manual control 1184 can include a left drive wheel 1152 and a right drive wheel 1160 disposed adjacent to each other and axially aligned along a thumbwheel shaft 1158 for joint rotation with each other about the thumbwheel shaft. The left and right drive wheels can be spaced apart or offset from each other by drive space, S. Further, one or both of the left and right drive wheels 1152, 1160 can be formed as a thin drive wheel having a thickness, T, that are each less than the drive space, S. Further, the thickness, T, of both drive wheels together can be less than the drive space, S, for providing enhanced engagement with the thumb. The combined thicknesses, T, and drive space, S, can be provided and arranged to be less than a typical thumb width.

Upon initial receipt of a user-exerted control movement, an engagement surface of the thumb of the single hand can encounter the manual control at an engagement angle that can be close to ninety degrees if the thumb rolls forward from the top edge portion of the advancer body. If the initial engagement angle is ninety degrees or close to ninety degrees, such as about sixty to ninety degrees, the engagement angle can provide a high frictional engagement according to the angle, as well as the force applied and the coefficient of friction for the engagement. It can be helpful when initiating translation of an elongate device from a rest position to have high engagement at the beginning of a manual control movement for assisting the elongate device to start translating from a rest position, which can be difficult for slippery surgical environments and for engagement with the thumb occurring though gloves.

An arrangement for the manual control having a pair of thin drive wheels spaced apart from each other by a drive space, S, and having a thickness, T, less than the drive space can enhance user engagement with the manual control. The pair of spaced apart drive wheels maintains and can even enhance a stable engagement region for the thumb of the single hand for avoiding slippage of the thumb to the left or right of the pair of drive wheels during engagement attempts, such that the thumb can bridge across the drive space and further partially fit within the drive space for effectively engaging the manual control and maintaining stable contact even for a low friction environment. Further, each of the pair of thin drive wheels is configured to concentrate engagement forces applied thereto by the thumb along with concentrating the reactionary engagement force applied to the thumb from each of the edge portions of the drive wheels. As such, the arrangement of a spaced apart, thin pair of drive wheels provides an enhanced engagement arrangement and stable engagement contact with the user's thumb for receiving the user-exerted input movement without slippage or similar losses.

As can further be seen in FIG. 15, a corresponding edge portion of each of the drive wheels can define a series of peaks and valleys, which can further enhance engagement with the user's thumb. Each of the peaks contacted by the user's thumb while applying the user-exerted control movement can concentrate the engagement forces and reactionary forces at the tips of the peaks contacting the user's thumb and further enhance the engagement contact. As such, engagement with the thumb of the single hand can be significantly enhanced to avoid input losses even for low-friction, slippery environments including engagement contact via wet gloves. The example arrangement of advancer 1110 for the manual control 1184 can provide high engagement contact as the user begins to exert a control movement, which input provided can include a user-exerted input art having an input arc length.

As discussed further below, beneficial features can be provided for the elongate device advancer based, in part, on the arrangement of the manual control 1184 including the arrangement of the pair of input wheels 1152, 1160. For example, the series of peaks and valleys for each input wheel can be formed as gear teeth, and each input wheel can form a drive gear having a radius, $R_{CONTROL}$. Further, each of the drive wheels 1152, 1160 can be arranged in a driving relationship with a lateral driven gear 1172, 1176 disposed at each side of the first drive roller and/or formed as part of the rotary axis for the first drive roller or attached with the input roller 1168 to rotate together about the rotary axis, such that the pair of drive gears 1160, 1152 each engage the first drive roller 1168 at outboard portions engaging the driven gears 1172, 1176 of the first drive roller in a stable bracketed or enveloped relationship. The gear teeth of each of the thin drive wheels can operatively engage corresponding teeth of the lateral intermediate driven gears attached to the first input roller, such that user-exerted movement imparted to the pair of drive wheels imparts movement at each of the driven intermediate gears of the first drive roller.

A matching rotation or movement distance for the mating gear teeth of the first and second input gears 1152, 1160 and movement they impart to the driven gear 1172, 1176 can be an arc length of the first and second input gears 1152, 1160 for a user-exerted movement applied to the first and second input gears. Although rotation of the first and second input gears for the input arc length and corresponding movement of the first and second input gears for the input art length can impart matching movement of the first roller driven gears 1172, 1176 for the input arc length. An intermediate rotary arc can be imparted to the first roller driven gears for the gear-connection movements of the first and second input wheels, which can be a function of the radius, $R_{INTERMEDIATE}$, for the driven gears. Thus, rotation of the intermediate input gears for an intermediate arc is applied to each intermediate gear in response to the input control wheels receiving a user-exerted control movement for an input arc 1170.

However, the span or rotation angle of the intermediate driven gears 1172,1176 can be a function of the radius, $R_{INTERMEDIATE}$, for the driven gears. The radius, $R_{INTERMEDIATE}$, for the driven gears is a smaller radius than the radius, $R_{INPUT}$, for the first and second input gears 1152, 1160 even though each of the intermediate driven gears rotated the distance of the input arc length. That said, the common rotation distance for the geared connection can identify the intermediate arc of the rotation imparted to the intermediate driven gears, which can be determined from the corresponding radii and a control input drive ratio of the corresponding radii ($R_{INPUT}/R_{INTERMEDIATE}$). As such, each of intermediate driven gears 1172, 1176 rotate an intermediate arc for the rotation imparted via the gear connections for moving the input arc length according to the control input drive ratio. Thus, each of the intermediate driven gears 1172, 1176 rotate an amplified imparted intermediate arc that is ($R_{INPUT}/R_{INTERMEDIATE}$) times the rotation of the first and second input gears for the user-exerted input arc 1170.

In some translation amplification arrangements between a drive gear rotating a user-exerted input arc, a control input drive ratio can range from about 2 to 4, such that the intermediate driven gear is rotated an amplified intermediate arc angle that is 2 to 4 times as large as the input arc 1170 exerted by the user. In many arrangements, the control input drive ratio for a translation amplification arrangement can be about 2.5 to 3, such that the intermediate driven gear rotates an intermediate arc angle that is 2.5 to 3 times the input arc angle, which can significantly enhance the utility, efficiency and effectiveness of such an elongate device advancer based on a first amplification of the user input occurring between the first and second input gears and the intermediate driven gears.

The initial amplification discussed above for an operative rotary engagement relationship between the first and second input gears and the intermediate driven gears can permitted and supported via a shape of the pathway through the advancer body 1129 as shown in FIG. 15 and discussed above along with shape and arrangement features of the advancer body. Namely, a bend or curve along a medial portion of the pathway defined within the advancer device can enable and enhance operations for a translation amplifying advancer arrangement, as well as for force amplifying arrangements as will be discussed in greater detail hereafter. Potential amplification and/or mechanical advantage options for advancer drive mechanisms can be enabled and enhanced in accordance with bend or configuration options for the pathway as described below along with operations of the drive rollers and nip.

Manual Input Translation Amplification and/or Force Amplification

Referring now to FIGS. 16, 17, 22, 23 and 25, components of the manual drive 1150 along with components of the manual control 1184 are generally shown for the elongated enclosure advancer 1110 showing operative arrangements between the components. The manual drive generally includes a first drive roller 1168, a second drive roller 1180, and a nip 1189. The first drive roller 1168 is rotatably coupled with the advancer body via a shaft 1171 and includes an outer engagement surface 1173 and a first driven gear 1172. The shaft 1171 is disposed through a central portion of the first drive roller and includes end portions that extend outward on both sides for rotatable attachment to the advancer body 1129. A first driven gear 1172 is attached to the shaft 1171 and is disposed through the central portion of the first drive roller with the shaft, such that the first driven gear extends laterally beyond the first drive roller and forms gear teeth disposed about the shaft on each lateral side of the first drive roller. The first driven gear 1172, the first drive roller 1168, and the outer engagement surface are attached to each other such that the first driven gear, the first drive roller and the outer engagement surface rotate together about the shaft. A drive portion of the first drive roller includes the engagement surface 1173, which is configured to extend into the pathway and engage side portions of the elongate device 1110 within the pathway for driving translation of the elongate device.

The second drive roller 1180 is rotatably coupled with the advancer body via a shaft 1183 and includes an outer engagement surface 1185. The shaft 1181 is disposed through a central portion of the second drive roller and includes end portions that extend outward on both sides for rotatable attachment to the advancer body 1129. The second drive roller 1168 and the outer engagement surface 1185 are attached to each other such that the first drive roller and the outer engagement surface rotate together about the shaft 1183. A drive portion of the second drive roller includes the engagement surface 1185, which is configured to extend into the pathway opposite the first drive roller engagement surface 1173 and engage side portions of the elongate device 1110 within the pathway opposite the first drive roller engagement surface and apply an advancement drive force to the elongate device.

The nip 1189 is defined between the engagement surfaces 1173, 1185 of the first and second drive rollers extending into the pathway in an opposed arrangement. The opposing engagement surfaces 1173 and 1185 are configured to grip the elongate device between the engagement surfaces and cooperate as a pair of drive rollers to translate the elongate device along the pathway between the first and second end portions. Further, the opposing engagement surfaces 1173 and 1185 are arranged and operatively connected to each other and with the manual control 1184 to impart amplified translation movement to the elongate device in response to the manual control receiving a user-exerted rotary movement as discussed above along with the manual control. A translation distance of the amplified translation movement is greater than an arc length of the manual user-exerted input arc applied to the manual control 1184.

Further to the discussion above of the previous section pertaining to the manual control 1184, the manual control converts the initial input force and input movement applied as the user-exerted input arc 1170 to the manual control 1184, such as movement applied to a thumbwheel-type mechanism like the pair of input wheels 1160 and 1162, and does so according to mechanical advantage principles, Newton's Second Law of Rotational Motion and/or conservation of angular momentum principles, as well as preservation of applied moments. Elongate device advancers arrangements according to such aspects and preferences discussed herein along with the present examples can makes beneficial, innovative use of these principles for providing elongate device advancement arrangements that can perform significantly improved, effective and efficient elongate device advancement operations—and do so for manually driven, user-exerted advancement.

The rotational moment exerted by the user for rotating manual control 1184 the input arc length 1170 is transmitted by input wheels 1152 & 1160 to the first roller driven gears, which rotates the same arc length distance as the input arc length via gear contact with the input wheels, but for the intermediate driven gears having a smaller radius and thereby having amplified rotation imparted to the intermediate driven gears 1172, 1176 to rotate an amplified arc angle that is greater than the user-exerted input arc. Because the first roller driven gear 1172 is rotatably attached to the first roller driven gear about the shaft 1171, the first roller driven gear further imparts rotation of the first drive roller 1172 about shaft 1171 for the amplified intermediate arc.

The corresponding amplified rotation of the first input roller 1172 rotates simultaneously with rotation imparted to the first driven gear 1172 (adjoined) for the amplified rotary angle, which permits the first input roller 1172 having a greater radius than its first driven gear 1172 to amplify further the amplified arc imparted to the intermediate driven gear, such that the translation distance applied to the elongate device can be enhanced further. In other words, the manual control 1184 operatively (rotationally) connected to the first input driven gear 1172 performs an initial output (imparted) rotary angle amplification, which the first input roller 1168 can further amplify along with applying the resulting final amplification to the elongate device at the nip. Note also that force amplification can be provided as well according to mechanical advantage principles, such as generally based on the ratio of the output radius of the drive roller 1168 ($R_{ADVANCE}$) with respect to the input radius of the manual control 1184 ($R_{INPUT}$) or ($R_{ADVANCE}/R_{INPUT}$).

Figure 16:
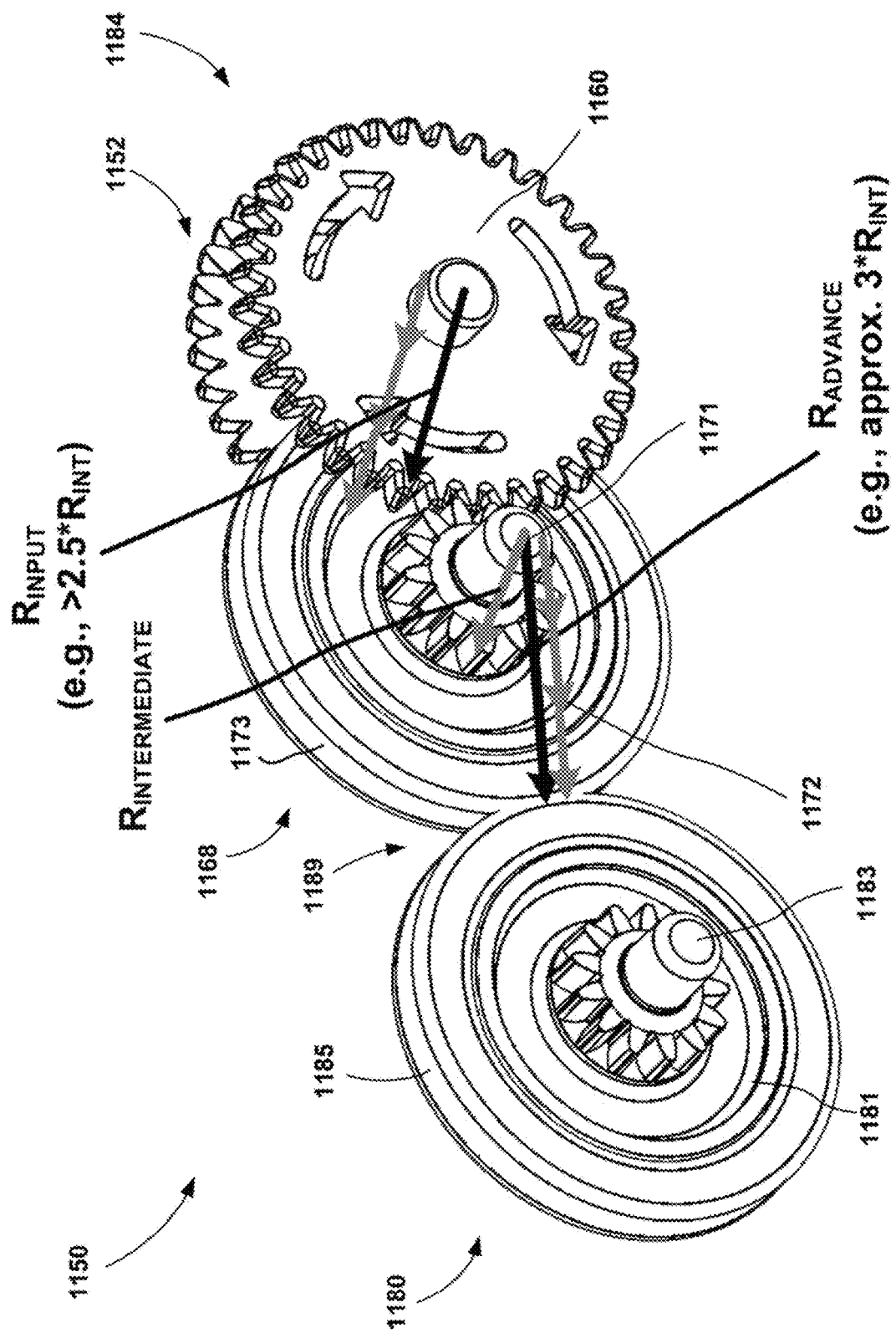
FIG. 16 is a right perspective view of drive rollers of the internal components for the elongate device advancer of FIG. 15.

For instance, FIG. 16 depicts as an example an arrangement in which the manual input 1184 for each of the pair of thin input wheels 1152 and 1160 have a radius, $R_{INPUT}$, about which an example user-exerted input arc of about ninety degrees can be applied. Rotation of input wheel 1160 as shown for an input arc of ninety degrees imparts rotation of the first driven gear 1172 according to movement at the gear interface for the input arc length. However, the radius, $R_{INPUT}$, of the input wheel 1160 is about 2.5 times the radius, $R_{INTERMEDIATE}$, of the first roller driven gear 1172. As such, the first driven gear 1172 rotates an amplified intermediate arc angle that is about 2.5 times the user-exerted input arc applied to the thumbwheels, which for the example would be about two hundred twenty-five degrees, AND the intermediate driven gear 1172 further rotates the attached first input roller 1168 along with the intermediate driven gear for the increased angular rotation of two hundred twenty-five degrees, but with an extended moment arm.

A radius of the first input roller 1168, $R_{ADVANCE}$, has a radial length from the common axis (shaft 1171) with the first roller intermediate driven gear, that is about 3 times as long as the radius, $R_{INTERMEDIATE}$, of the first roller intermediate driven gear 1172. As such, an arc length for the same rotation imparted to the first roller intermediate driven gear 1172 (e.g., two hundred twenty-five degrees) provides to the first input roller 1168 an arc length that is about three times greater than the arc length provided by the same rotation for the intermediate driven gear 1172, which when applied by the first input roller 1168 at a distal engagement end 1173 of the nip drives the elongate device an amplified translation distance for which the first drive roller drives the elongate device, and does so with a moderate to negligible mechanical advantage.

Thus, a length of a user-exerted input arc can be amplified, for example, to drive the elongate device for the present example a length that is about seven and a half times longer than the user-exerted input arc length, and does so via a mechanical advantage/force amplification factor of about 3/2.5 or 1.2 Such large amplifications of user inputs, such as via a thumbwheel, that effectively translate and advance an elongate device, such as a guide wire, during surgical operations can significantly enhance operability of the advancer, overcome many shortcomings and challenges of conventional manual advancer mechanisms, and ultimately enhance surgical procedures and operations involving the same—especially when operable based on about the same amount of input force or even slightly less input force than would be required to physically push translation of the elongate device or directly drive a thumbwheel 1184 of similar size to translate the elongate device via direct contact.

Figure 22:
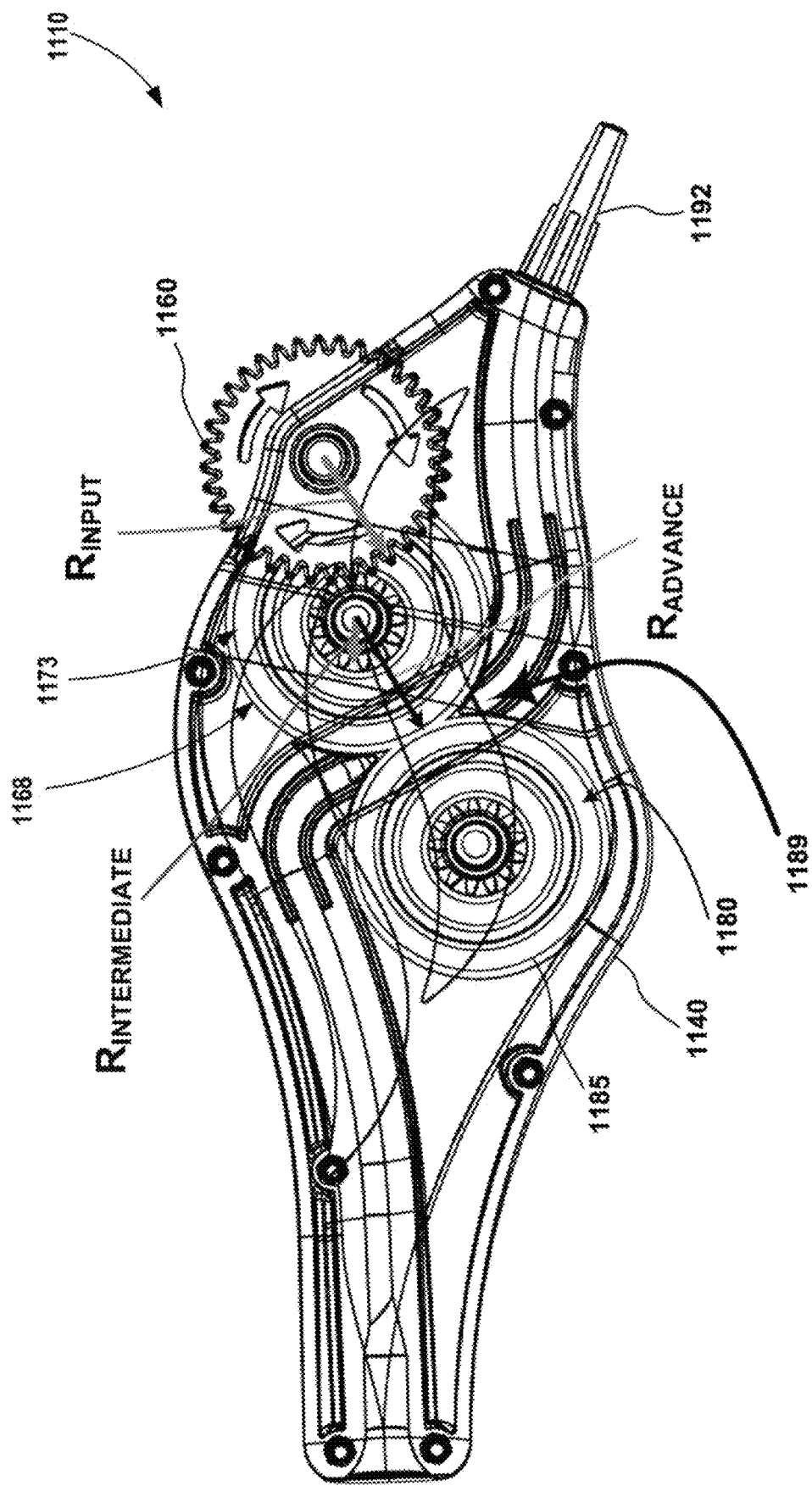
FIG. 22 is a right plan view of the elongate device advancer of FIG. 15 shown with the right housing partially transparent to expose an example arrangement of internal components along with example routing of an elongate device via an internal channel.
Figure 25:
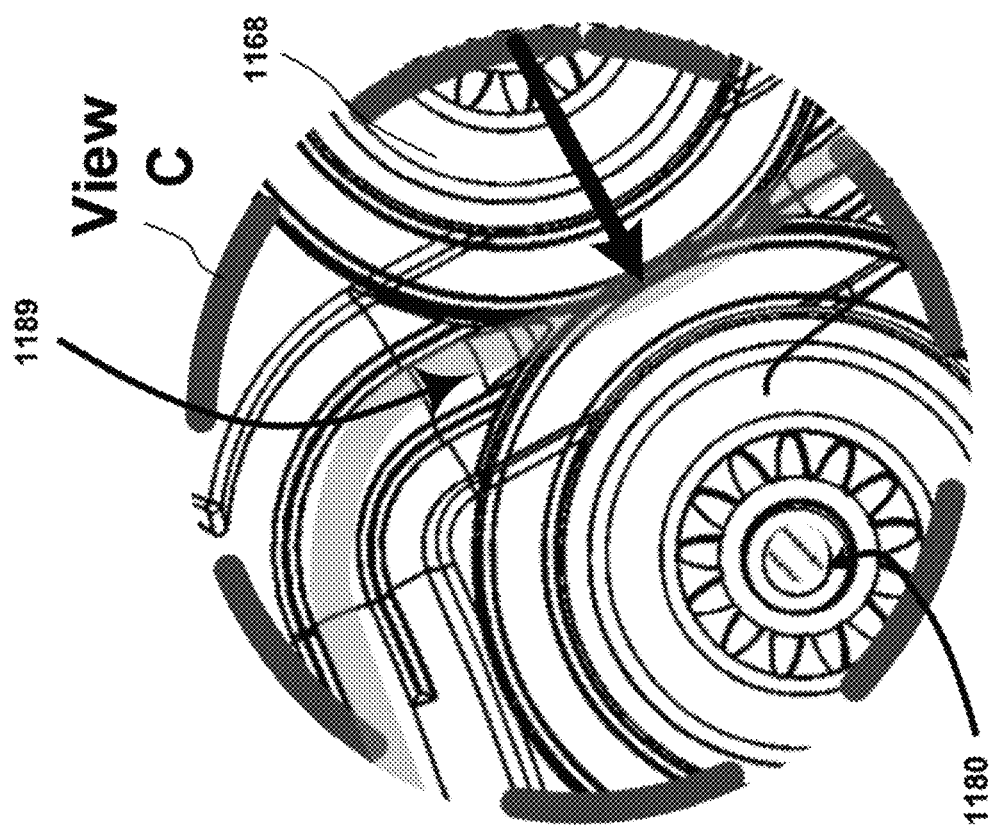
FIG. 25 shows View C identified in FIG. 23, which is a close view of an elongate device being advanced through by the outer roller assemblies of the elongate device advancer of FIG. 15.

However, drawbacks and challenges for conventional advancer mechanisms include conflicting interests between being able to provide an advancer having a lightweight, easy-to-hold and control, ergonomic advancer arrangement, vs. amplifying advancer or translation movements for significantly reducing required user-exerted inputs for operating known manual advancers. With reference again to FIGS. 22, 23 and 25, the applicants have researched, tested, and identified arrangements for manual elongate device advancers that significantly reduce manual inputs for driving the advancement and translation, as well as providing a wide range of beneficial features including providing compact ergonomic arrangements as discussed above that simple and comfortable to hold, control and use in a single hand. As can be seen in FIGS. 22, 23 and 25, relationships between features such as manual control/input mechanisms, drive and roller arrangements and connections, and other aspects and features discussed along with examples herein can be permitted and supported, at least in part, via innovative and creative pathway arrangements, as well as other inventive mechanisms, aspects and features including drive mechanisms as discussed in further detail below.

Enhanced Grip Envelope & Drive Contact Having Low Nip Resistance or Force Impact Referring now to FIGS. 19-27B, further aspects, features and related innovative and creative concepts pertaining to the example manual drive 1150 discussed herein are shown, which generally involve operations and features pertaining to the nip 1189 and engagement of elongate devices therein. Such features cooperate with various other beneficial aspects and features previously discussed herein, which overall describe well-developed, effective and efficient concepts for configurations of a manual introducer/advancer mechanism for elongate devices that can be used with many different surgical procedures and for various types of elongate devices. Various concepts, aspects and features illustrated along with the examples of the above-listed figures provide further insight and understanding regarding these mechanisms and options for the same Referring now to FIGS. 22, 23, 25 and 26B, various views of a nip 1189 are shown as formed from a corresponding set of rollers including first drive roller 1168 having an engagement portion extending into the pathway, and a second drive roller 1180 opposite the first drive roller also having an engagement portion extending into the pathway opposite the first drive roller engagement portion. Each of the engagement portions are configured to rotate with the respective drive roller for each engaging an elongate device therebetween to impart translation forces to the elongate device and translate the elongate device along the pathway. A nip 1189 is formed between the first and second drive rollers and the respective engagement portions. Although referred to as a drive roller, the second drive roller 1180 can be configured as an idler roller such that it does not receive any active drive forces for imparting advancement forces to the elongate device.

However, note that each of the first drive roller 1168 and the second drive roller 1180 generally have the same configuration, such that both rollers are about the same size and have the same support structure and arrangement with the same type of engagement portion disposed thereon as an outer portion of the drive roller. As such, unlike many conventional nips and drive roller arrangements, the elongate device is gripped between the two drive rollers in a matching bilateral arrangement having balanced forces applied to the elongate device at opposite sides of the elongate device. Further, although the second drive roller 1180 can be configured as an idler roller, the second drive roller 1180 is arranged to provide equal and opposite opposing forces or reactionary forces with respect to the first drive roller 1168 against an opposite side of the elongate device. Thus, the nip 1189 and arrangement of drive rollers 1168, 1180 can arranged as a bilateral, balanced opposing forces arrangement against opposite side regions of the elongate device, which can surround the elongate device in a firm, balanced grip about its circumference having a high contact area with the elongate device effectively and efficiently applying translation forces to the elongate device.

Figure 20:
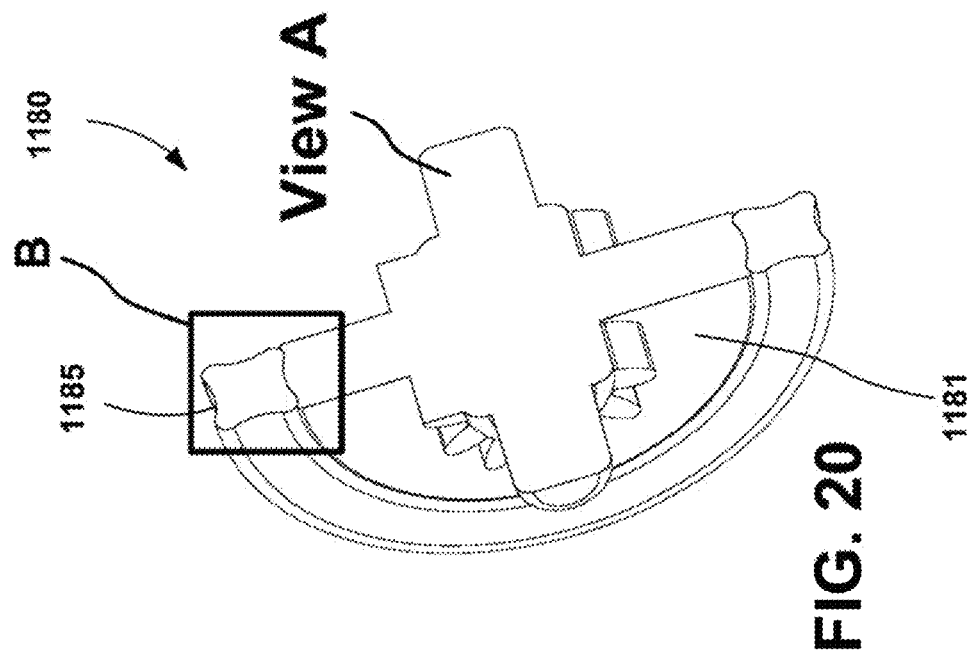
FIG. 20 is a cross-sectional perspective view of the roller assembly of FIG. 19 according to line A-A of FIG. 19.
Figure 21A:
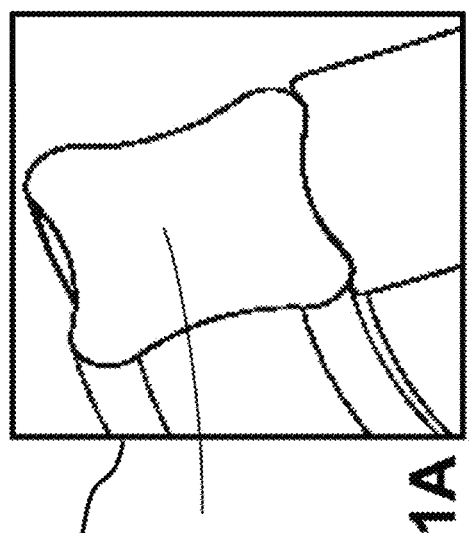
FIG. 21A is a close view of a cross-section of the double seal O-ring denoted as View B in FIG. 20.
Figure 21B:
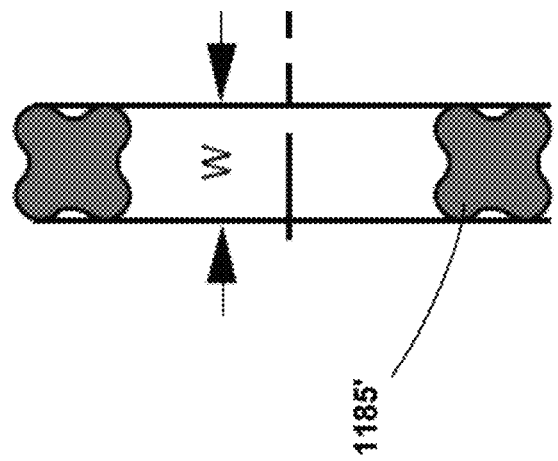
FIG. 21B is a cross-sectional view of an optional X-ring seal shown as an alternative for the double seal O-ring.

Referring now to FIGS. 19-21B, cross-sectional views of the second drive roller 1180 are shown as representative examples for either of the drive rollers. As shown, second drive roller 1180 includes an inner support frame 1181, which can be formed as a generally rigid support frame. The inner support frame 1181 includes an outer support surface defining either a groove or raised portion along the support surface. The second drive roller 1180 further includes an O-ring configured as a double seal O-ring. The double seal O-ring is one example of a newer family of O-rings that are also known as Quad-Rings or X-Rings, which are each arranged as circular O-rings configured to form a gripping, non-slip relationship with the outer support frame. Further each of the O-rings can be formed from an elastomeric material having a wide range of properties including high compressibility and high frictional contact properties as desired. Each of the O-rings include a four-lobed design such that each O-ring forms a four-pronged rectangular structure that forms a concave surface as it extends between each of the four prongs. Each of the O-rings are configured to make primary sealing contact at its lobes with an engagement surface, and compress, contour or expand as appropriate between the four lobes to form a full seal with an contact surface. FIG. 21B shows a cross-sectional view of an optional arrangement for the four-lobed O-rings have a more defined X-shape.

Figure 27A:
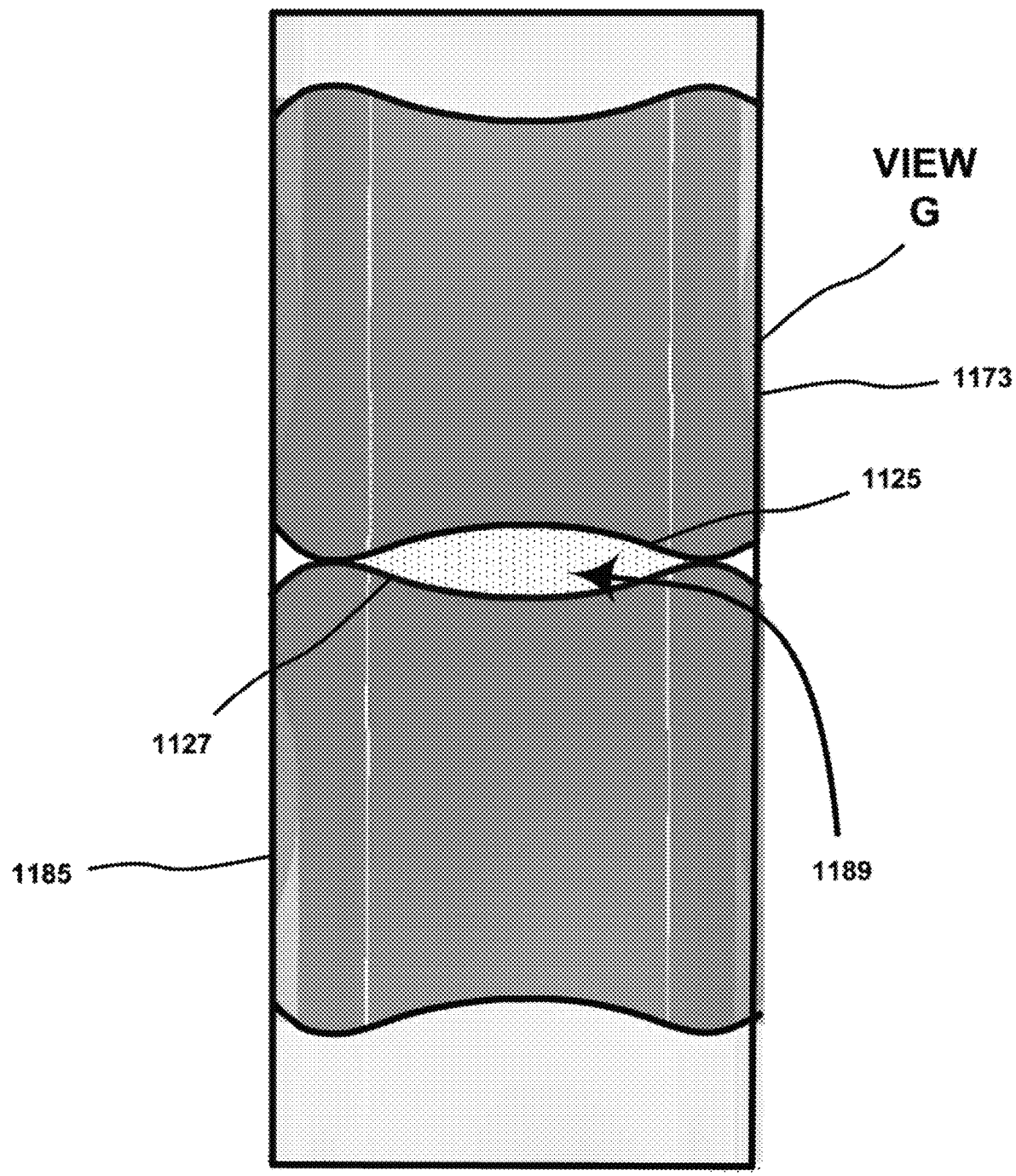
FIG. 27A shows a portion of the advancer of FIGS. 15 and 26B from a viewpoint proximate the nip as identified in FIG. 26B for region G, which is a Close View (G) of both front and rear double O-seal rings of the elongate device advancer of FIG. 15 proximate the nip and shown without having an elongate device within the pathway.
Figure 27B:
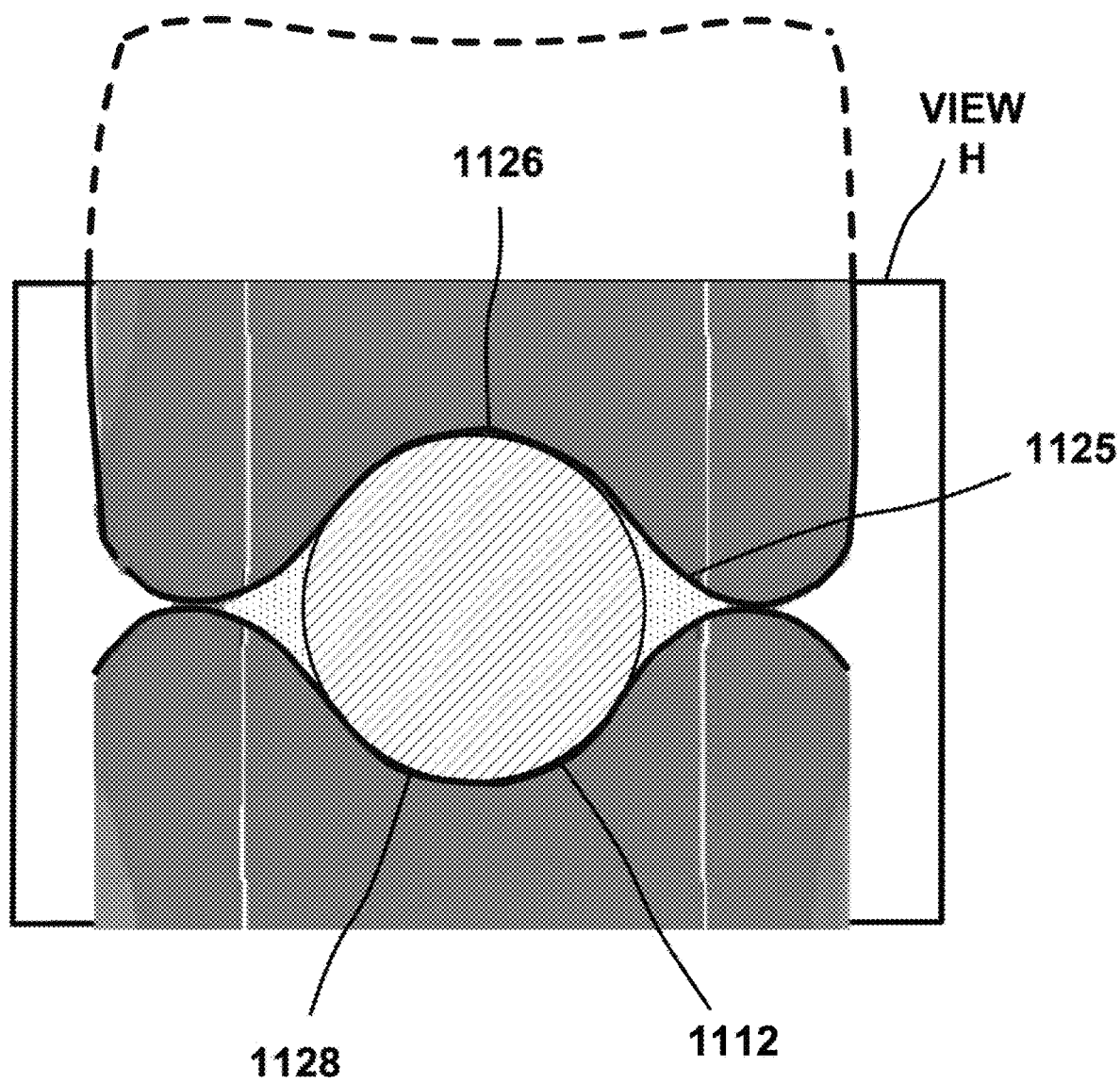
FIG. 27B shows a portion of the advancer of FIGS. 8 and 26B from a viewpoint proximate the nip as identified in FIG. 26B for region H, which is generally the same as FIG. 27A except with an elongate device shown disposed along the pathway and within the nip.
Figure 28A:
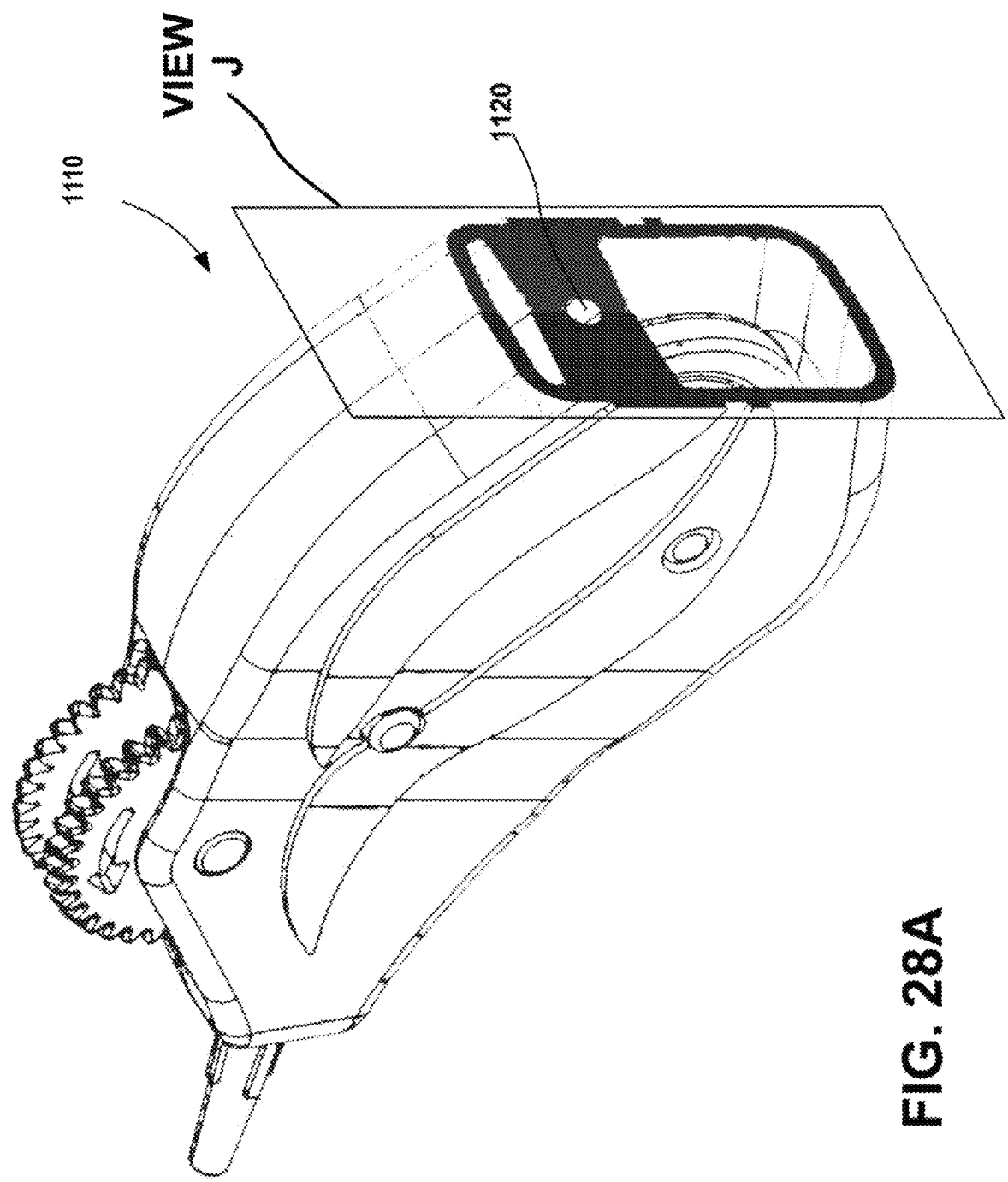
Figure 28B:
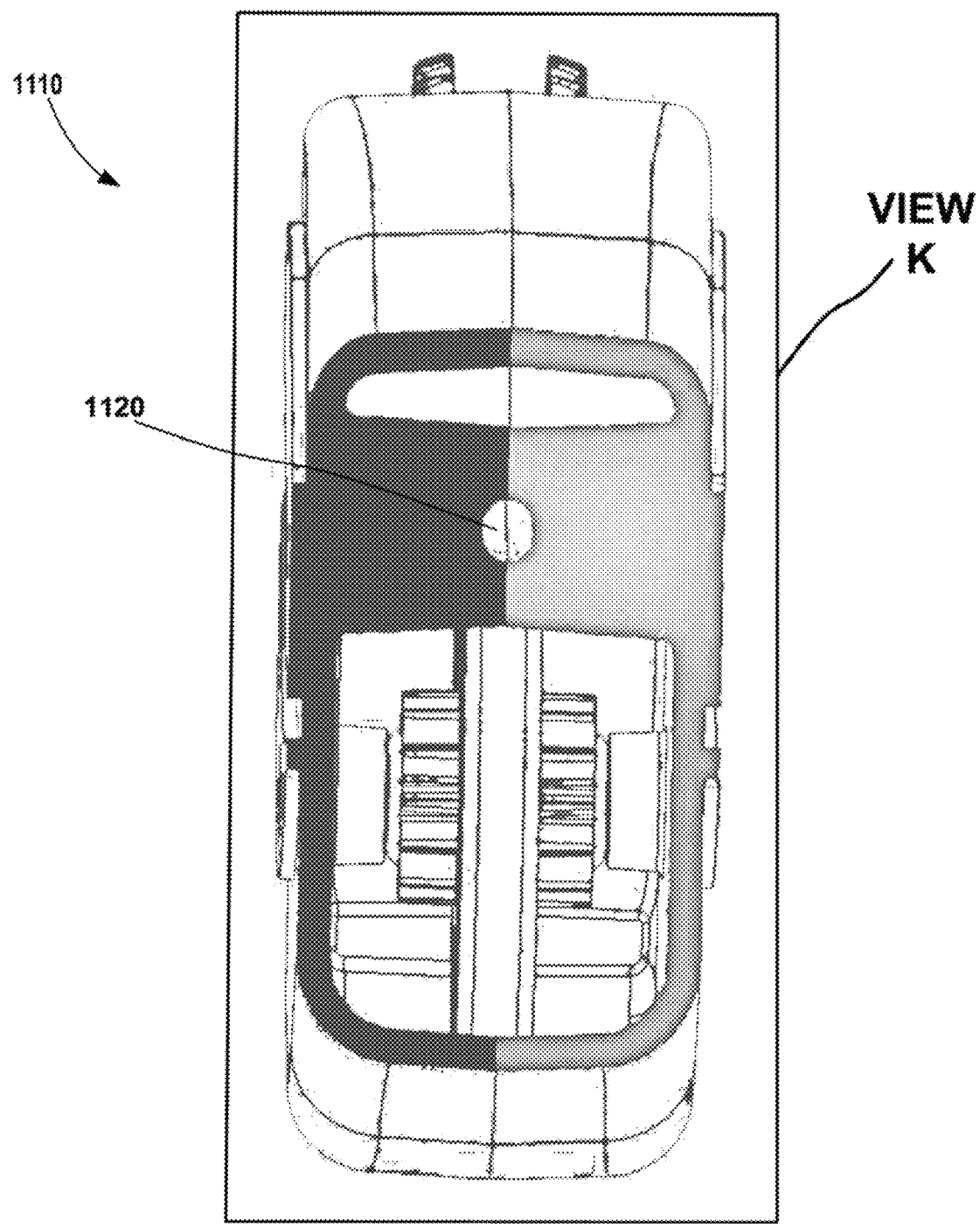
FIG. 28B shows a plan view of the lateral cross-section as View K.

Referring now to FIGS. 27A and 27B, a cross-sectional view of the nip is show with and without an elongate device being shown. As can be seen in FIG. 27A, the first O-ring 1173 for the first roller drive forms a generally concave engagement surface 1125 for contacting the elongate device in its natural non-contact states, as does the second O-ring 1185 for the second roller drive. As can be seen best in FIG. 27B, when an elongate device is fed through the nip, the quad-type O-ring arrangements of engagement members readily form about most of the outer surface of the elongate device to form a high contact area grip about a greater area of the elongate device than most roller engagement members. Further, each quad-type O-ring envelops and surrounds a corresponding lateral region of the elongate device without imparting significant compressive forces against the elongate device. As shown in FIG. 27B, the quad-type O-ring expands laterally and inward toward the outer support surface of the roller rather than firmly maintaining its cross-sectional shape and imparting high compressive forces against the elongate device. The high contact area of engagement provided by the quad-type O-rings offsets the engagement benefits provided by high compressive force arrangements for engaging the elongate device. Further, the elastomeric material of the quad-type O-ring provides enhanced frictional contact engagement with the elongate device. As such, enhanced engaging contact can be formed with the elongate device through the nip without applying high compressive forces against the elongate device. Further, such an arrangement can significantly reduce rotational forces regarding for driving the drive rollers simply for engaging the elongate device within the nip.

Figure 30A:
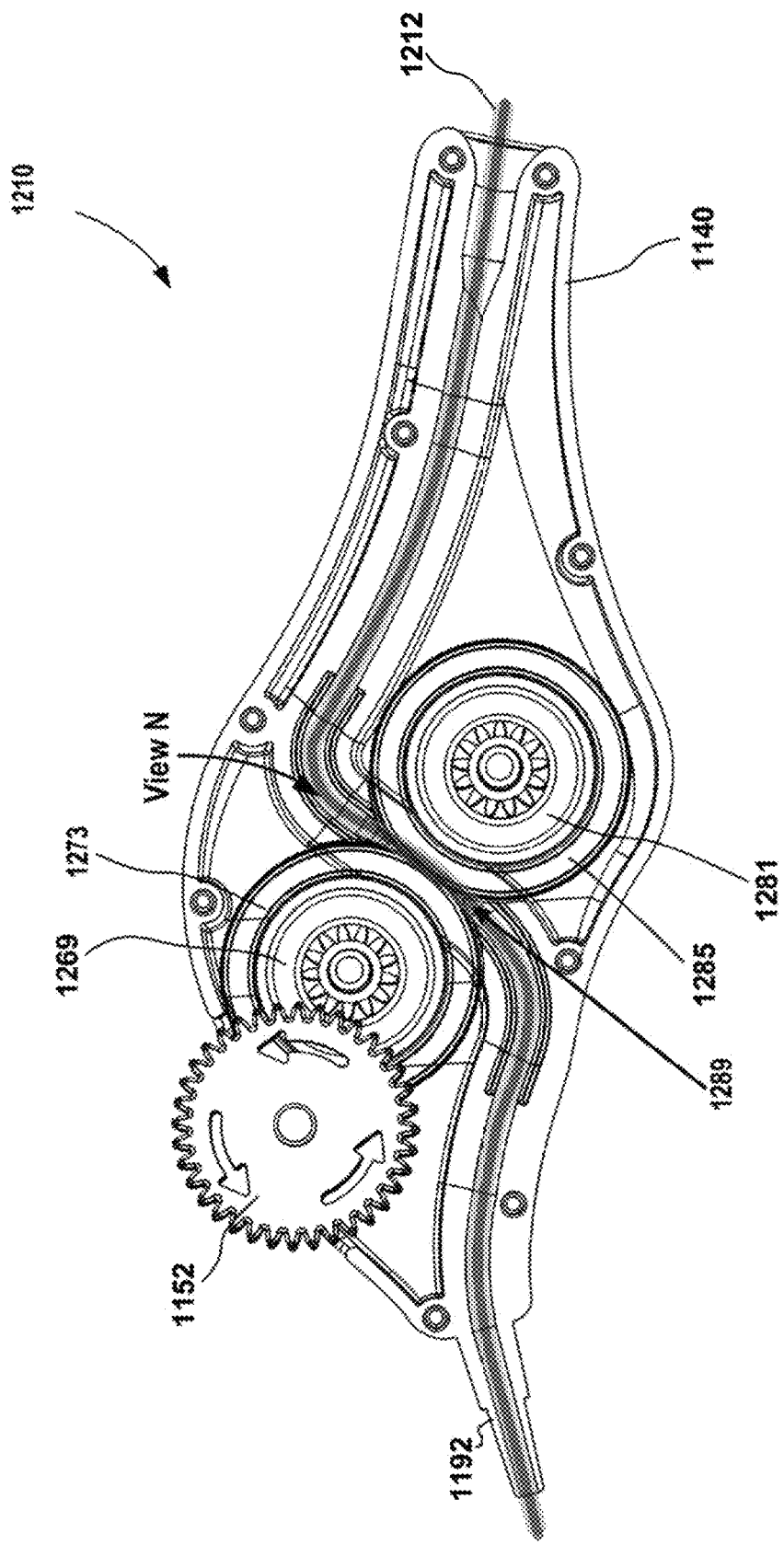
FIG. 30A is a left plan view depicting another example elongate device advancer according to aspects and features described herein including for an advancer configured to translate a catheter, which is shown with the left housing removed for clarity.
Figure 30B:
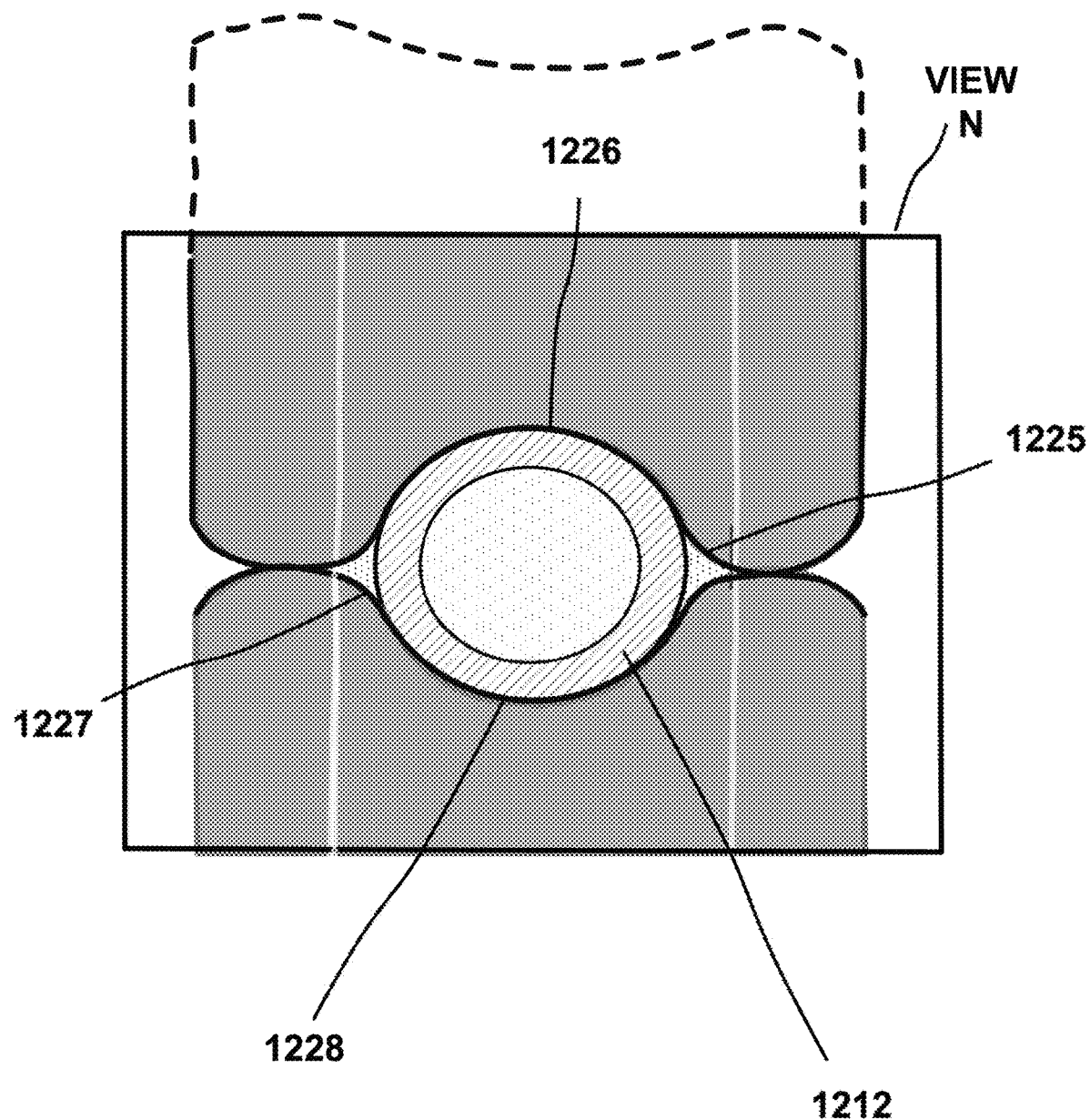
FIG. 30B is a close cross-sectional view of the nip at an entry into the nip of the advancer of FIG. 30A as indicated in FIG. 30A for View N, which shows portions of O-seal rings for the first and second drive rollers during engagement of a catheter or other tube as the elongate device.
Figure 30C:
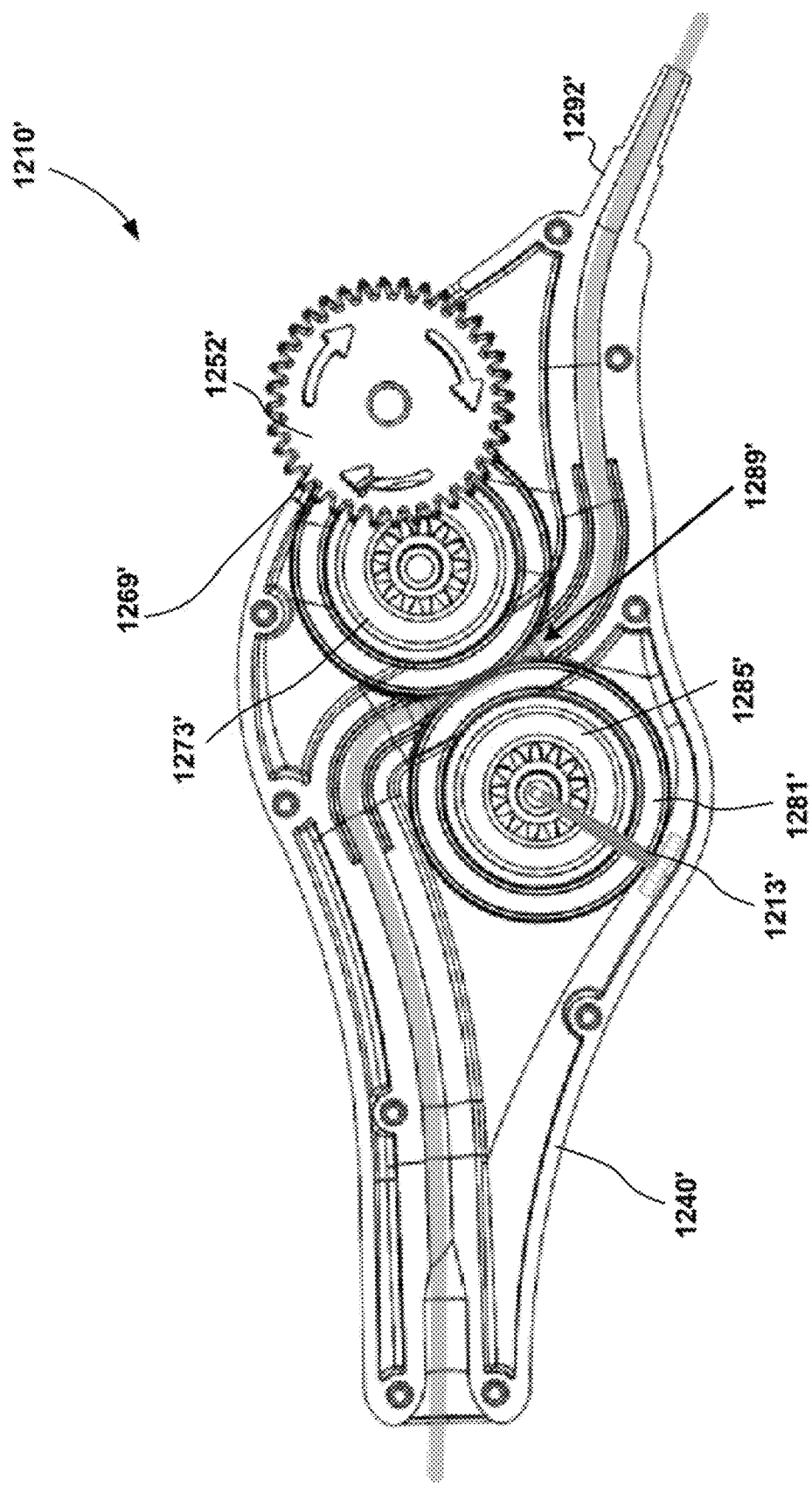
FIG. 30C is a schematic right-side plan view of a further example elongate device advancer according to aspects and features described herein, which shows an example conceptual arrangement of an advancer having an adjustment mechanism attached to the housing and the second drive roller for permitting adjustment of the advancer as appropriate for different types and properties of elongate devices.
Figure 31A:
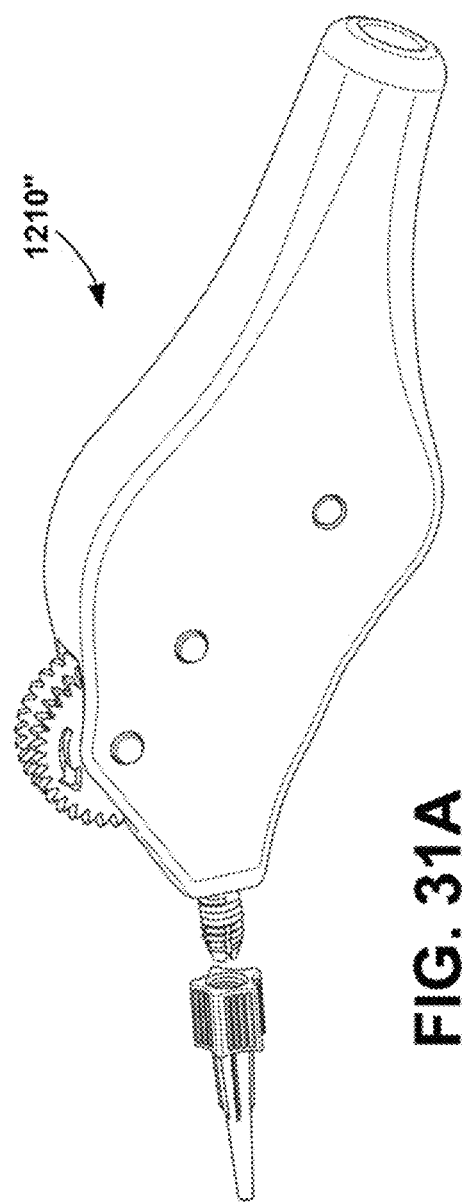
FIGS. 31A and 31B are left side perspective views of an additional example elongate device advancer according to aspects and features described herein, which schematically depicts a removable introducer tip that can optionally allow for the usage of customized tips and interfaces adapted for various types of procedures and medical devices.
Figure 31B:
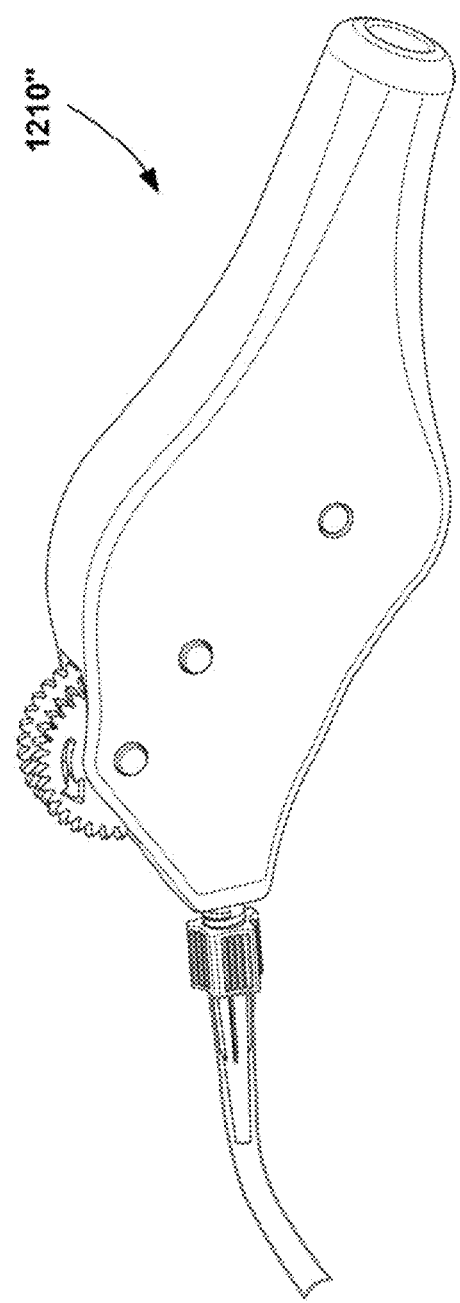
Figure 31C:
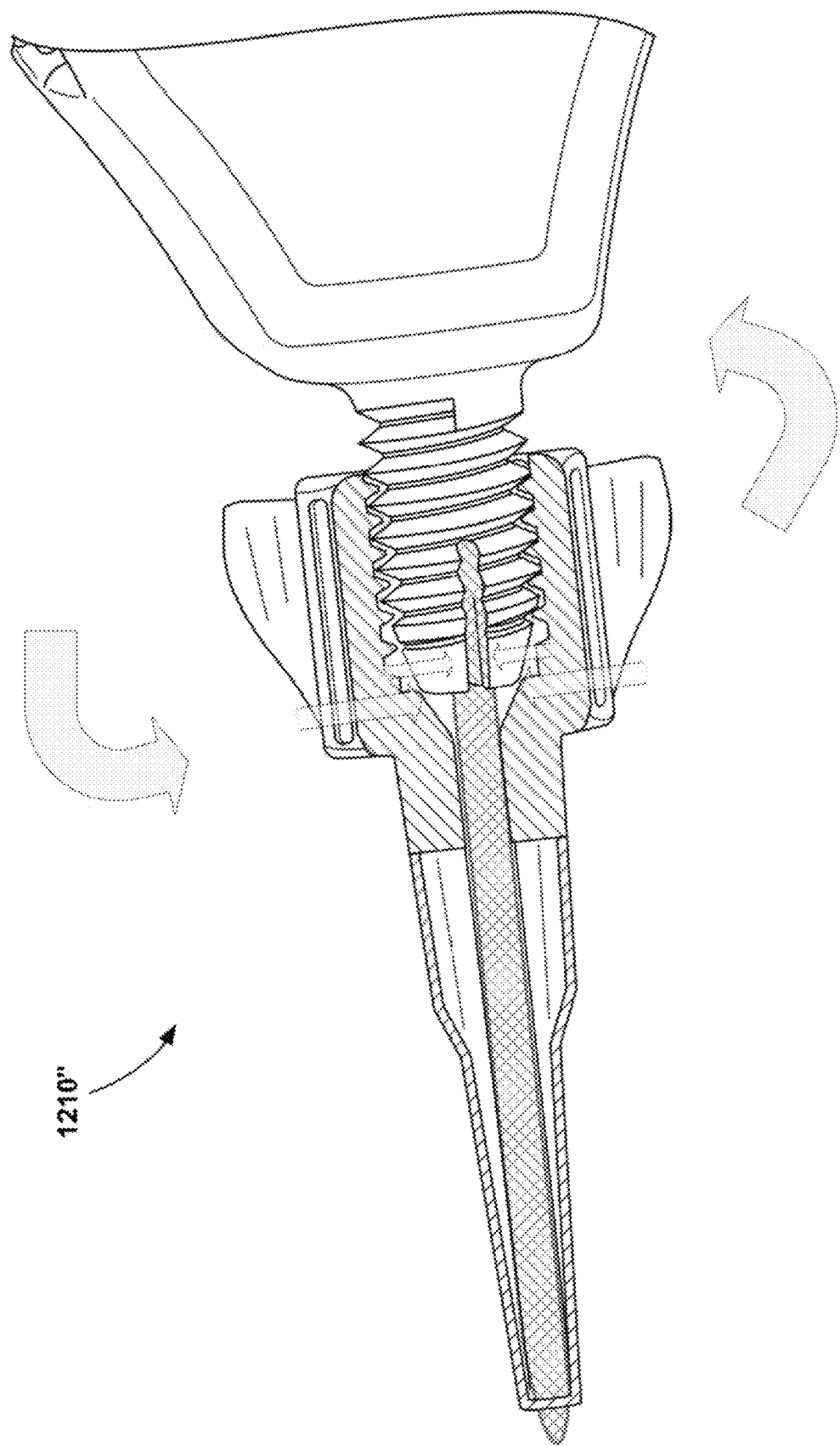
FIG. 31C is a left side perspective view of a further example elongate device advancer according to aspects and features described herein, which schematically depicts a twist lock incorporated into a threaded introducer tip attachment that can be over-twisted to selectively engage a lock at the tip for restraining advancement and/or rotation of the elongate medical device routed through the advancer.
Figure 33A:
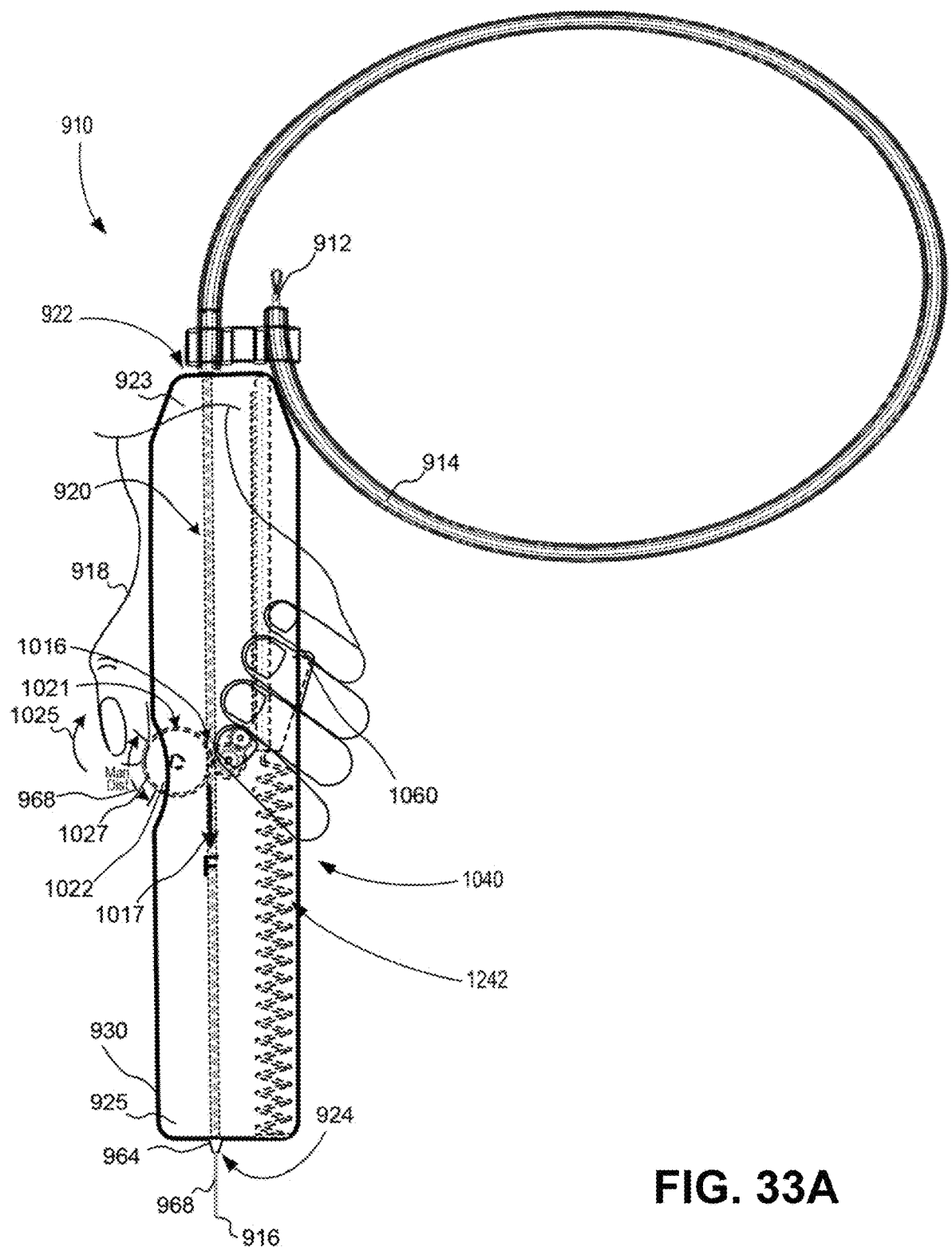
FIG. 33A is a plan view of a diagrammatic representation of an additional elongate device advancer according to inventive aspects and features described herein, which is shown coupled with an elongate medical device in the form of a guide wire coil in preparation for use with a medical device, such as with the suture placement device of FIGS. 3A-3D.
Figure 33B:
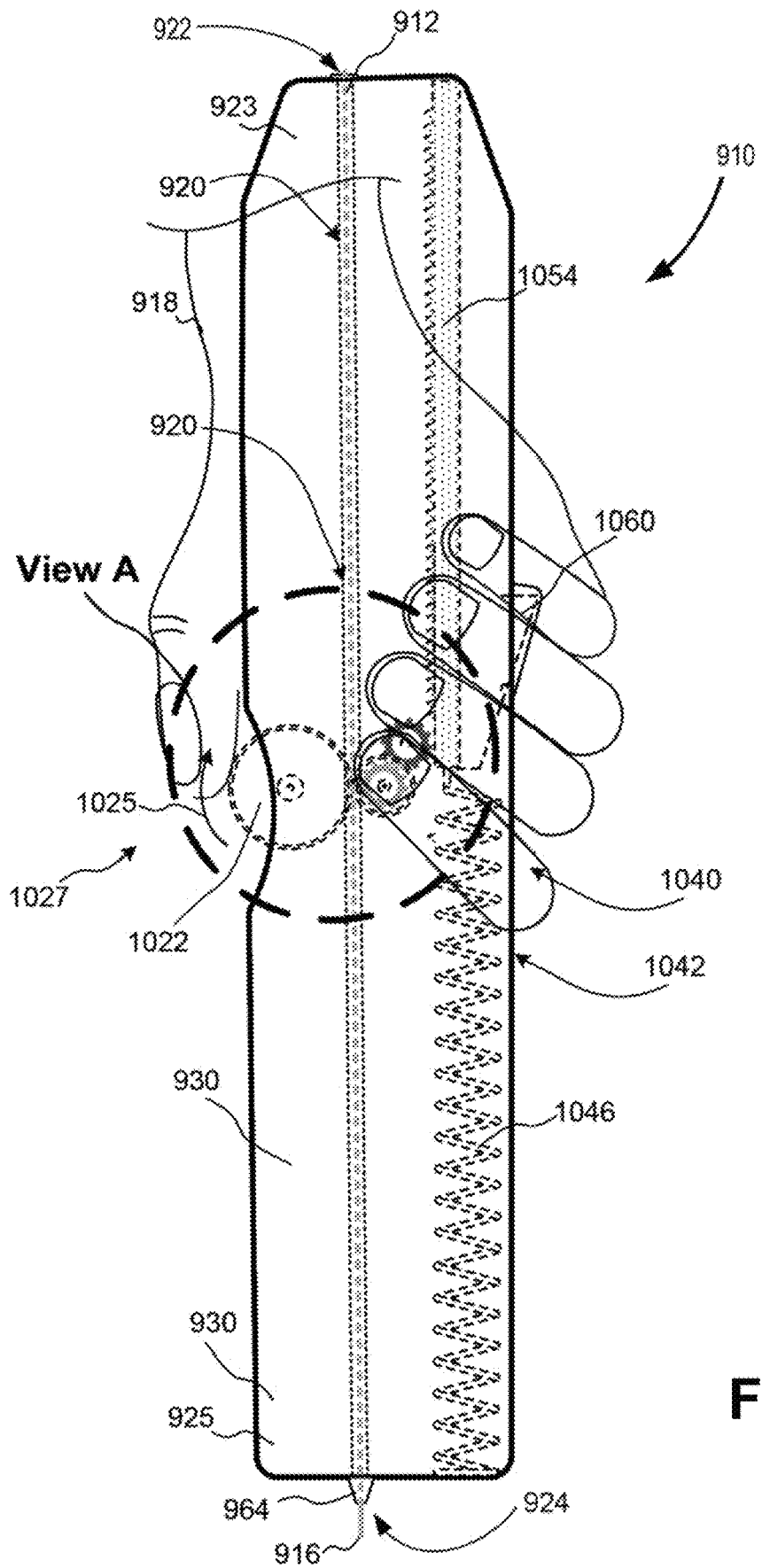
FIGS. 33B and 33C are diagrammatic plan views of the elongate device advancer representation of FIG. 33A shown prior to actuation of the actuator.
Figure 33C:
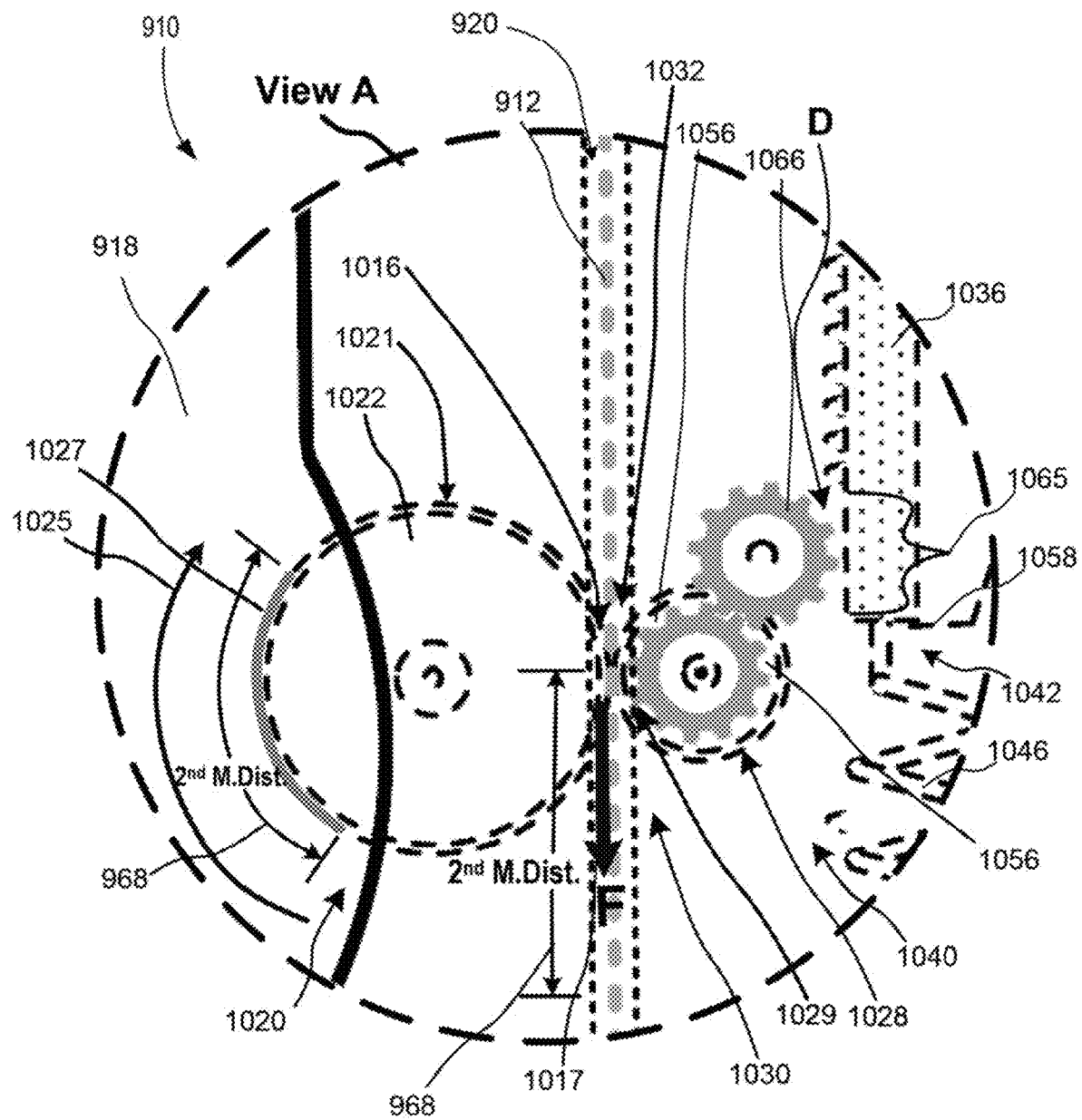
Figure 33D:
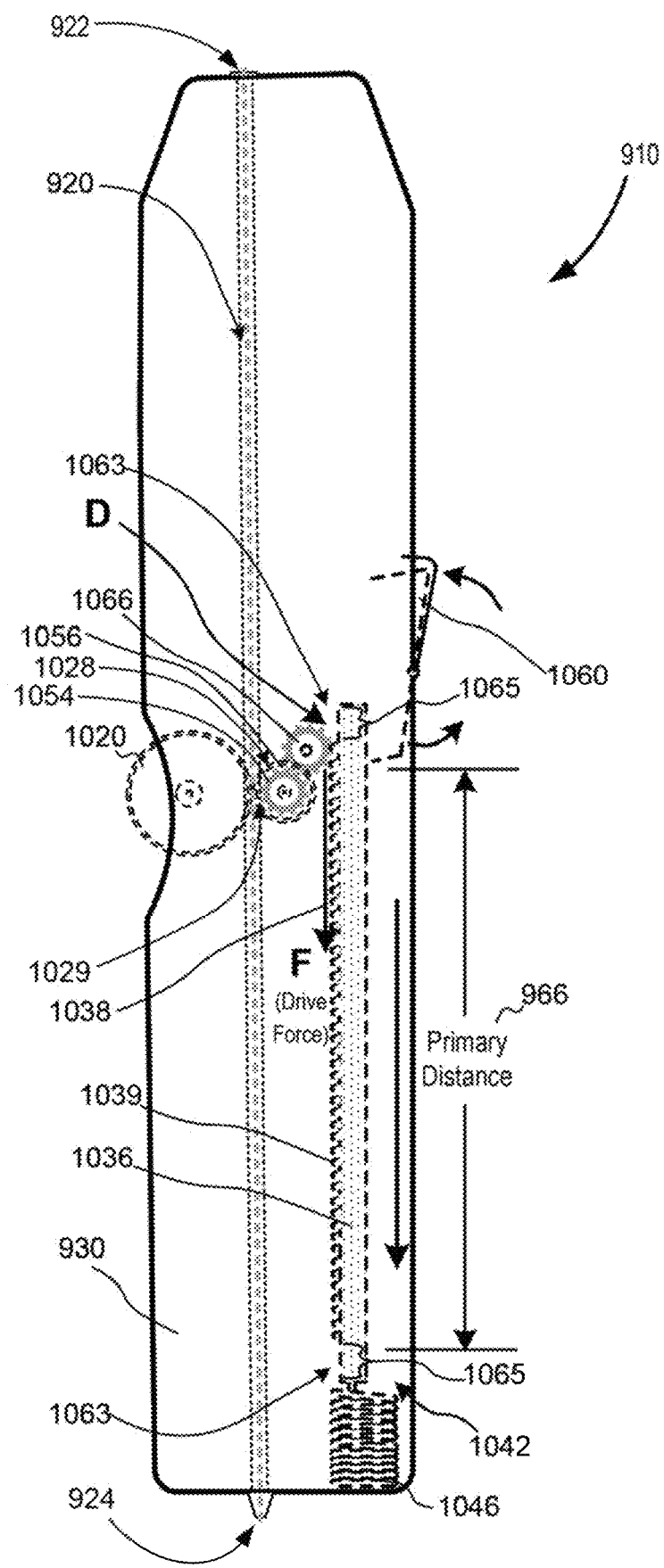
FIG. 33D is diagrammatic plan view of the elongate device advancer representation of FIG. 33A shown after actuation of the actuator.

Referring now to FIGS. 30 and 31, another arrangement of the advancer device is show along with an elongate device in the form of a catheter 1212 having a hollow center, which demonstrates the effectiveness for using a quad-type O-ring with the drive rollers and nip for engaging the elongate devices and translating the same through the advancer device. As shown in FIG. 31, an example advancer device according to aspects and features described herein can successfully translate and advance a tubular elongate device therethrough without collapsing the elongate device as would typically occur for conventional devices applying high compressive forces at nip or drive roller regions.

Figure 18:
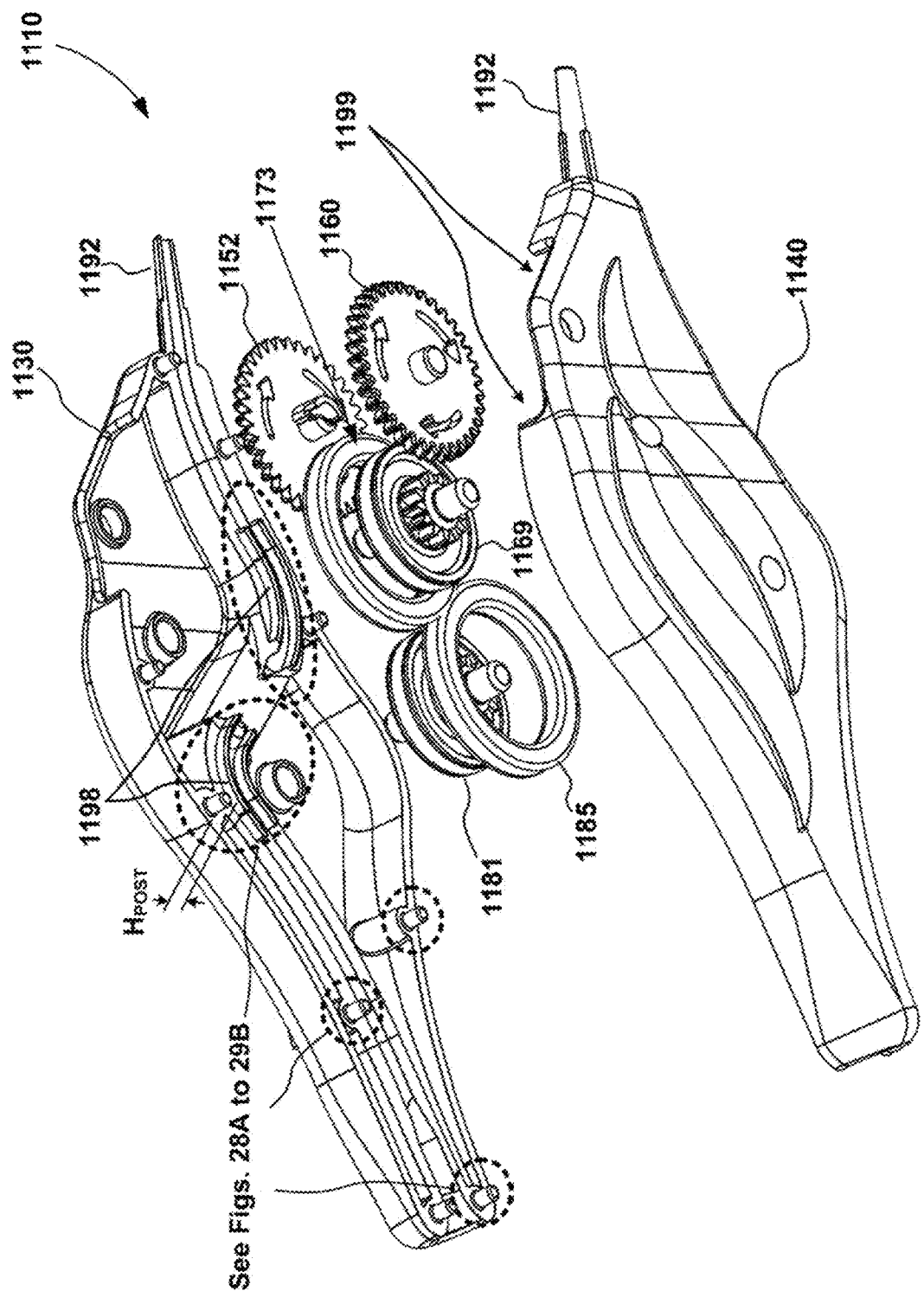
FIG. 18 is a top right exploded perspective view of the elongate device advancer of FIG. 15.

Referring now to FIGS. 28A to 29B, along with FIG. 18, cross-sectional views are shown through the enclosure along portions of the pathway 1120 for illustrating an offset male-female engagement arrangement of walls 1198 received in mating openings 1199 provided between the left and right housing along portions of the pathway at both sides of the pathway before and after the medial bend portion of the pathway. The male-female offset arrangement provides a barrier prior to the bend portion and the nip for blocking suture material or other fine materials that can be pulled by the elongate device from being caught within a seam or gap between left and right sides of the housing.

Referring now to FIG. 32, an optional cross-sectional concept view is shown for an advancer device similar to other examples shown and described herein, which includes an adjustment rod 1313 configured to provide fine tune adjustments for the nip to allow different size and types of elongate devices to be used with the advancer device.

Figure 6A:
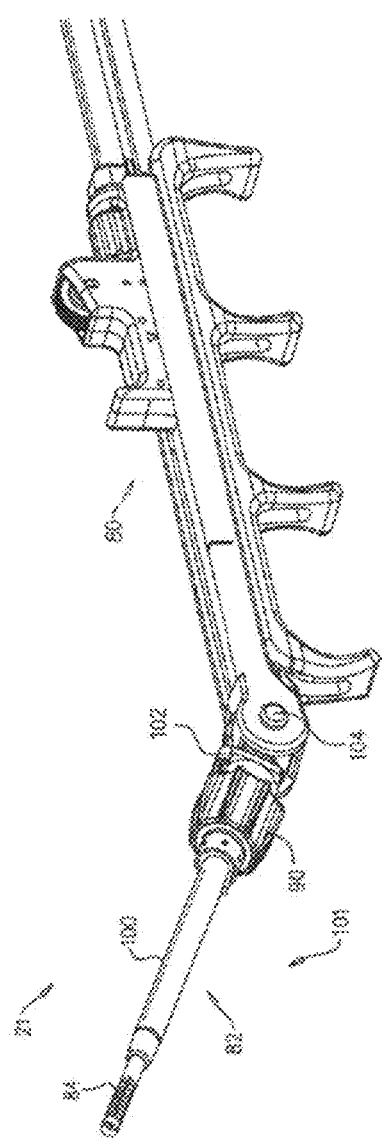
FIG. 6A is a perspective view of a combined functionality conventional sinuplasty apparatus including a guide wire introducer for use with sinuplasty procedures.
Figure 6B:
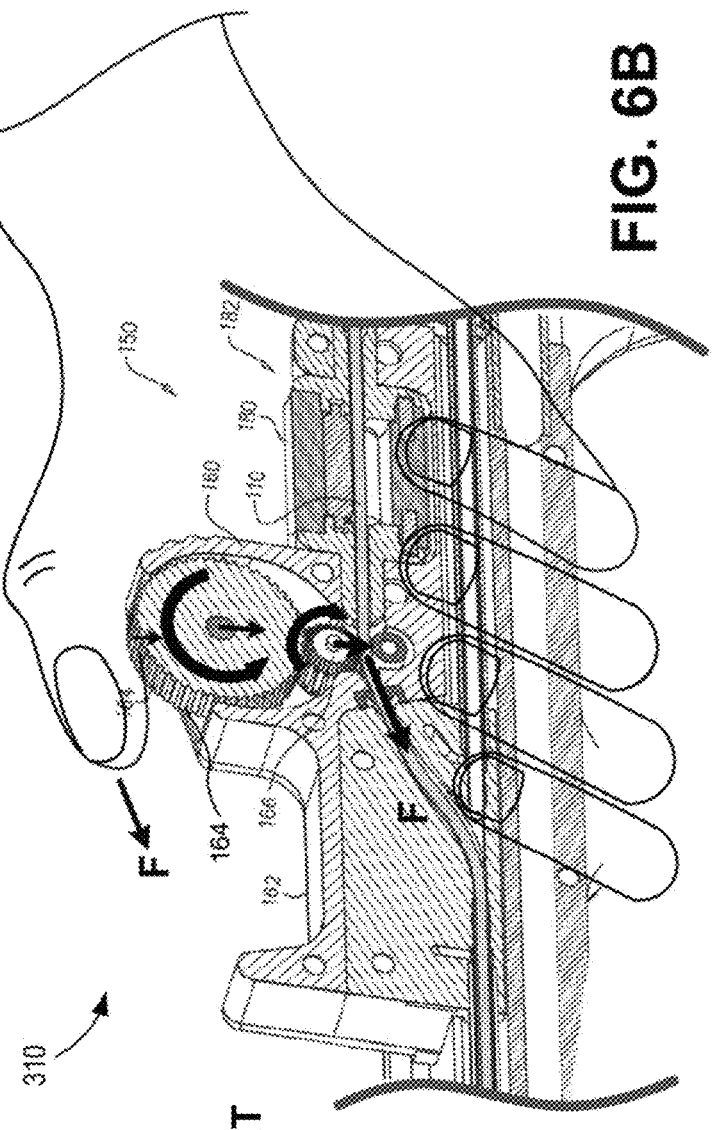
FIG. 6B is a cross-sectional view of a portion of the conventional guide wire introducer of the sinuplasty apparatus of FIG. 6A.
Figure 6C:
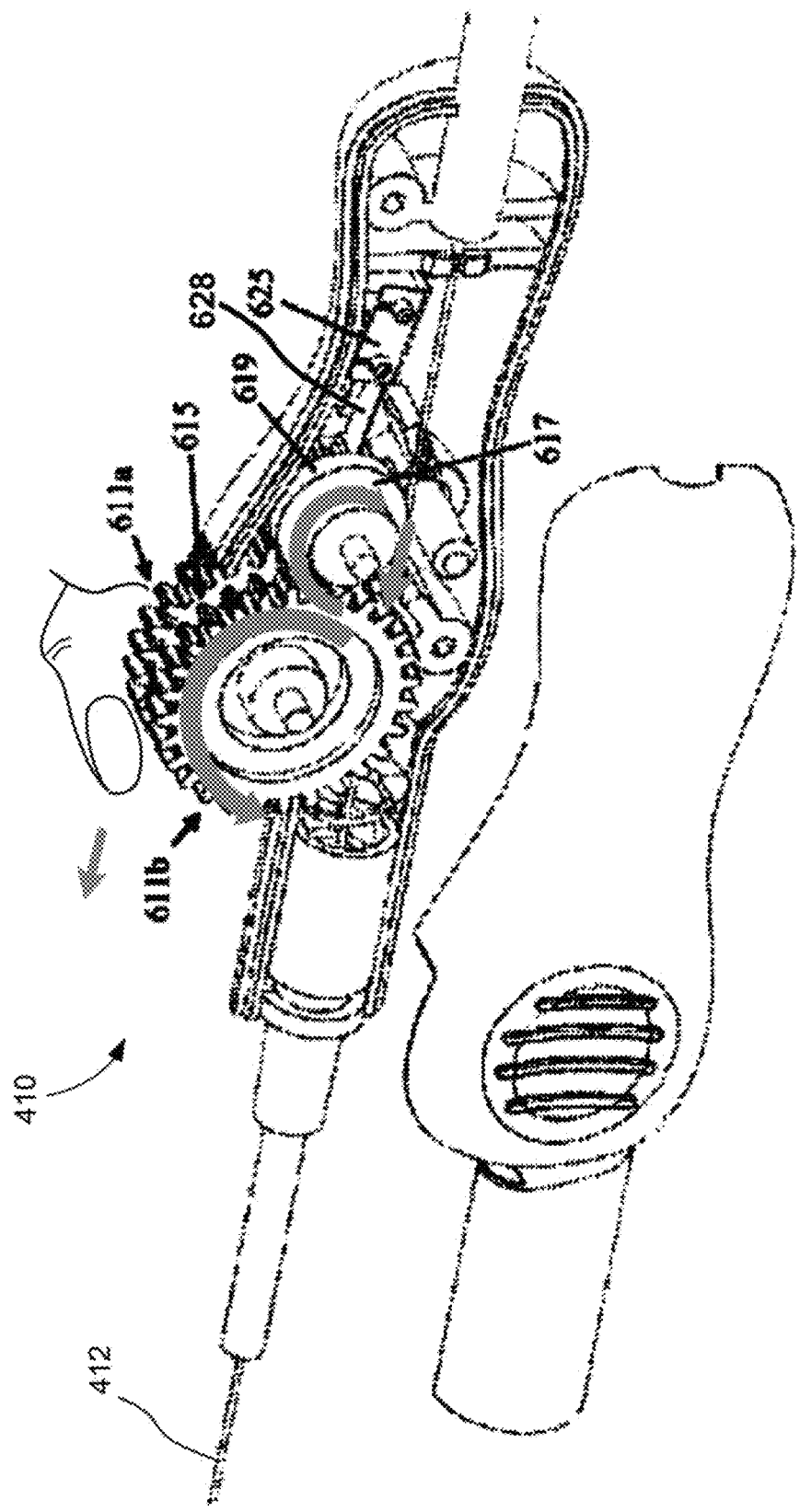
FIG. 6C is a partially exploded perspective view of another conventional elongate device advancer integrated as part of a combined function IV placement apparatus.
Figure 7:
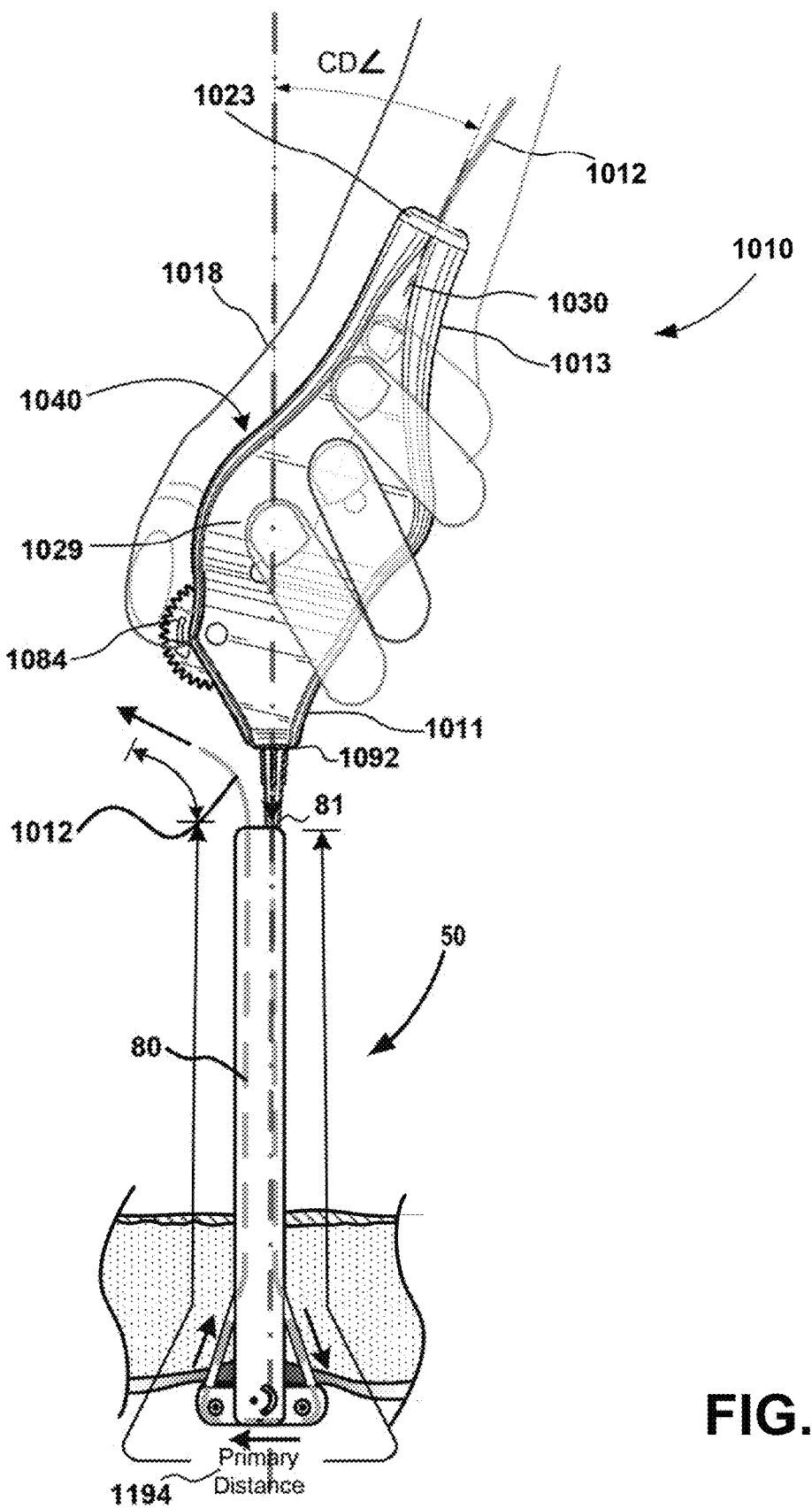
FIG. 7 is a left side plan view of an example arrangement of an elongate device advancer in accordance with aspects and features of inventive concepts described herein, in which the example elongate device advancer is schematically depicted in an arrangement with the example suture placement device of FIG. 3D.

Referring now to FIGS. 7-14, a combination automatically-manually driven elongate device advancer 910 is shown for advancing a guide wire an automated primary distance 966 and a secondary manual distance 968 that is less than the primary distance, which as shown in FIG. 6 can be coupled with a guide wire/sheath coil 914 in a usage arrangement with the guide wire 912 of the coil. Although not shown, it is understood that the combination elongate device advancer 910 can be operatively configured with a surgical instrument including the suture placement device 50 discussed above along with FIGS. 3A-3E while disposed within a port and prepared for suture placement procedures. The combination elongate device advancer 910 is configured to be held within the single hand 918 of a user and easily controlled to perform guide wire advancement actions to support a surgical device, such as the suture placement device 50 discussed above.

The combination elongate device advancer 910 is advantageously configured for the user to actuate an automatic drive and readily advance the guide wire a primary first distance 966 based on a powered drive force stored by the elongate device advancer including automatically advancing the guide wire through a pathway of a coupled surgical device being supported by the elongate device advancer, such as advancing the guide wire within the channel pathway formed within the suture placement device of FIGS. 3A-3E. The combination elongate device advancer 910 is configured for the user to readily actuate the automatic drive using the single handle gripping the elongate device advancer, such as via movement of one or more fingers to actuate the automatic drive as desired. Further, the combination elongate device advancer 910 is advantageously configured for the user to exert control movements as well as using the single handle gripping the elongate device advancer, such as via rolling thumb movements exerted on a manual control conveniently placed proximate the user's thumb. As such, the user can readily grip the advancer and easily control advancement operations including both an automated primary advancement of the guide wire and manual, fine-tune secondary advancement of the guide wire as desired.

Referring now to FIGS. 6 and 7A, the combination automatically-manually driven elongate device advancer 910 generally includes an advancer body 930, an automated drive 1040, a manual drive 1020, and an integrated advancement driver 1030. The advancer body 930 defines a guide wire pathway 920 for advancing the guide wire 912 therethrough from a first end portion 923 to a second end portion 925 of the advancer body, in which the advancer body is configured to be held in a grip of a single hand 918 of a user and controllable by the single hand. The first end portion 923 is configured to couple with the guide wire 912 to receive a tip portion 916 of the guide wire therein through an entrance 922 of the pathway 920 disposed at the first end portion 923, and the guide wire 912 is configured to advance through the pathway and out an exit 924 of the pathway disposed at the second end portion 925. The exit 924 can include a stylet tip 964 or similar arrangement for coupling the elongate device advancer in a support arrangement with a surgical device, such as a suture placement device.

As shown in FIGS. 7A, 7B and 8, the automated drive 1040 is configured to drive guide wire advancement for the primary distance 966 (FIG. 8) when actuated. The automated drive 1040 generally includes a power driver 1042, an automated drive roller 1056, and an actuator 1060. The power driver 1042 is configured to store potential energy for driving guide wire advancement for the primary distance 966 (FIG. 8) and transmit a corresponding automated drive force 1038 when actuated. The automated drive roller 1056 is rotatably coupled with the advancer body 1030 and has a resilient surface 1028 rotatable with the automated drive roller. The resilient surface 1028 includes a drive portion 1029 extending into the guide wire pathway 920 and configured to drivingly engage the guide wire 912. The actuator 1060 is configured to be actuated by the single hand 918 to activate the power driver 1042 to transmit the automated drive force 1038 to the automated drive roller drive portion 1029.

The power driver 1042 generally includes a spring 1046 coupled with a translatable rack 1036. In the deployable, stored energy condition shown in FIG. 7A, the spring 1046 is extended. A releasable lock 1058 (FIG. 7B) retains the translatable rack 1036 and spring 1046 in the deployable, stored energy condition until released by an actuator 1060 (FIG. 7A), which is readily accessible for the user to actuate via the single hand 918 when holding the elongate device advancer 910. When the actuator 1060 is actuated, it moves releasable lock 1058 to release the translatable rack 1036, which enables the rack to translate responsive to a drive force 1038 exerted on it by spring 1046. Drive teeth 1039 disposed along rack 1036 engage corresponding teeth on a pinion or floater gear 1066, which transfers the linear drive force 1038 as a rotary force to drive gear 1054 and drive roller 1056 attached thereto. Drive roller 1056 engages the guide wire 912 as described below via the nip 1029 to transfer linear drive force 1038 to the guide wire and drive its advancement for the primary distance 966.

As best seen in the close view of FIG. 7B, the manual drive 1020 is configured to drive guide wire advancement for the secondary distance 968 based on a user-exerted manual control movement 1025. The manual drive generally includes a manual drive roller 1022 and a manual control 1027, such as a thumbwheel or similar manually controllable device. The manual drive roller 1022 is rotatably coupled with the advancer body and has an engagement surface 1021 that is rotatable with the manual drive roller. The engagement surface 1021 includes a drive portion 1016 extending into the guide wire pathway 920 and configured to drivingly engage the guide wire 912. The manual control 1027 is configured to receive the user-exerted manual control movement 1025 from the single hand 918 and transmit a corresponding manual drive force 1217 to the manual drive roller drive portion 1016 for imparting guide wire advancement for the second distance 968.

For the relatively simple configuration of elongate device advancer 910, the range of movement for the single hand of the user with respect to the manual control 1027 generally corresponds with the greatest secondary distance 968 available for manual advancement, and the manual control movements act as a direct drive for manually advancing the guide wire. However, other configurations can provide greater manual control options, such as geared connections between the user-accessible manual control and one or more drive components that exert advancement force on the guide wire. Further, one or more mechanical advantage options or switchable arrangements can optionally be provided to enable enhanced manual controls and selectable or configurable manual advancement settings.

The integrated advancement driver 1030 generally includes a cooperative feed roller nip 1032 configured to advance the guide wire in response to transmission of the automated drive force or the manual drive force to a corresponding one of the drive portions. In other words, the integrated advancement driver 1030 is configured as a multi-source advancement driver that can readily advance the guide wire according to the user's control movements including responsive to user-exerted manual control or manual drive force 1017, and in response to user-actuation of automatic advancement to provide powered drive force 1038. As such, the cooperative feed roller nip 1032 includes a drive roller from both the manual drive 1020 and the automated drive 1040. Further, the cooperative feed roller nip 1032 is defined between the drive portion 1016 of the manual drive roller 1022 that extends into the guide wire pathway, which is configured in an opposed arrangement with the drive portion 1029 of the automated drive roller 1056 that likewise extends into the guide wire pathway. The opposing drive portions can be configured to engage opposite side regions of the guide wire and cooperate as a pair of feed rollers for advancing the guide wire 912 along the pathway 920 toward the second end portion. Further, the opposing drive portions can each be configured to function as both a drive roller and a driven roller based on drive roller is acting as the operative drive providing drive force.

Referring now to FIGS. 7A, 7B and 8, the elongate device advancer can include a transmission switch 1063 configured for automatic movement between a first position D and a second position E, in which the first position D (FIG. 7B) de-couples the power driver from the automated drive roller when the manual control receives the user-exerted manual control movement, and the second position E (FIG. 8) drivingly engages or connects the power driver to the powered drive roller 1056 when the actuator is actuated. The transmission switch 1063 in the example configuration for elongate device advancer 910 generally includes a floater gear 1066 and a pair of neutral portions 1065 that are each disposed at an opposite end portion of translatable rack 1036 extending beyond its drive teeth 1039. Floater gear 1066 acts as an intermediate gear between rack 1036 and powered drive gear 1054 as described above along with the power driver 1042 that engages rack 1036 with powered drive gear 1054 while in second position E during translation of the rack. The first position D includes one or more de-coupling positions with or without the power driver 1042 storing potential energy, such as before or after actuation of the power driver.

For instance, as shown in FIG. 7B, prior to actuation of the actuator 1060 (FIG. 7B), releasable lock 1058 retains rack 1036 such that the transmission switch 1063 is in the first position D de-coupled from engagement with power drive gear 1054 via disengagement from floater gear 1066. In particular, a distal one of the neutral portions 1065 disposed at end portion of rack 1036 is located proximate floater gear 1066, which de-couples the power driver 1042 from the automated or power drive roller 1056 due to non-engagement between the floater gear and the rack. As such, the user is free to exert manual control movements 1025 upon the manual control portion 1027 of thumbwheel 1022 and advance the guide wire 912 up to the second advancement distance one or more times as desired, such as for advancing the guide wire through the guide wire pathway 920, out of exit 924, and into entry port 81 of a suture placement device 50 described above along with FIGS. 3A-3D.

In addition, after actuation of the actuator 1060 completes, the transmission switch 1063 is again disposed in the first position D de-coupled from engagement with power drive gear 1054 via disengagement from floater gear 1066. In particular, as can best be seen in FIG. 8, a proximal one of the neutral portions 1065 disposed at end portion of rack 1036 is located proximate floater gear 1066 upon completion of deployment of the power driver 1042, which de-couples the power driver from the automated or power drive roller 1056 due to non-engagement between the floater gear and the rack. As such, the user is again free to exert manual control movements 1025 upon the manual control portion 1027 of thumbwheel 1022 and advance the guide wire 912 up to the second advancement distance one or more times as desired, such as for advancing the guide wire through the remainder of channel pathway 80 of a suture placement device 50 described above along with FIGS. 3A-3D.

Referring now to FIG. 10 along with FIGS. 6-9, a method 1270 for advancing a guide wire using elongate device advancer 910 coupled with suture placement device 50 discussed above is generally shown. The method 1270 generally includes step 1272 of holding the elongate device advancer 910 in a single hand 918 of the user, and step 1274 of coupling the elongate device advancer 910 in an advancement arrangement with a suture placement device 50 including placing a tip portion or stylet tip 964 of the elongate device advancer in the cannular housing entry portion proximate the entry port 81 of the suture placement device, which is inserted through a port defined in a patient and arranged for placement of a suture. The method can optionally include step 1275 (not shown) of advancing the guide wire one or more secondary advancement distances 968 less than an automated second advancement distance to advance the guide wire 912 through the entry port 81.

Method 1270 further includes the step 1276 of actuating via one of the user's fingers of the hand 918 the actuator 1260 to deploy a deployment drive force 1038 to the guide wire 912 to advance a tip portion 916 through a first advancement or primary distance 966 of the suture placement device channel pathway 80. The method 1270 continues with step 1278 of exerting a manual advancement or drive force 917 via the user's thumb of the single hand 918 to advance the tip portion a secondary distance 968 that is less than the primary distance 966, and optionally step 1280 of repeatedly applying the manual advancement force 917 as desired, such as to advance the tip portion of the guide wire through and out of exit port 83 of the suture placement device 50.

Figures 9A, 9B:
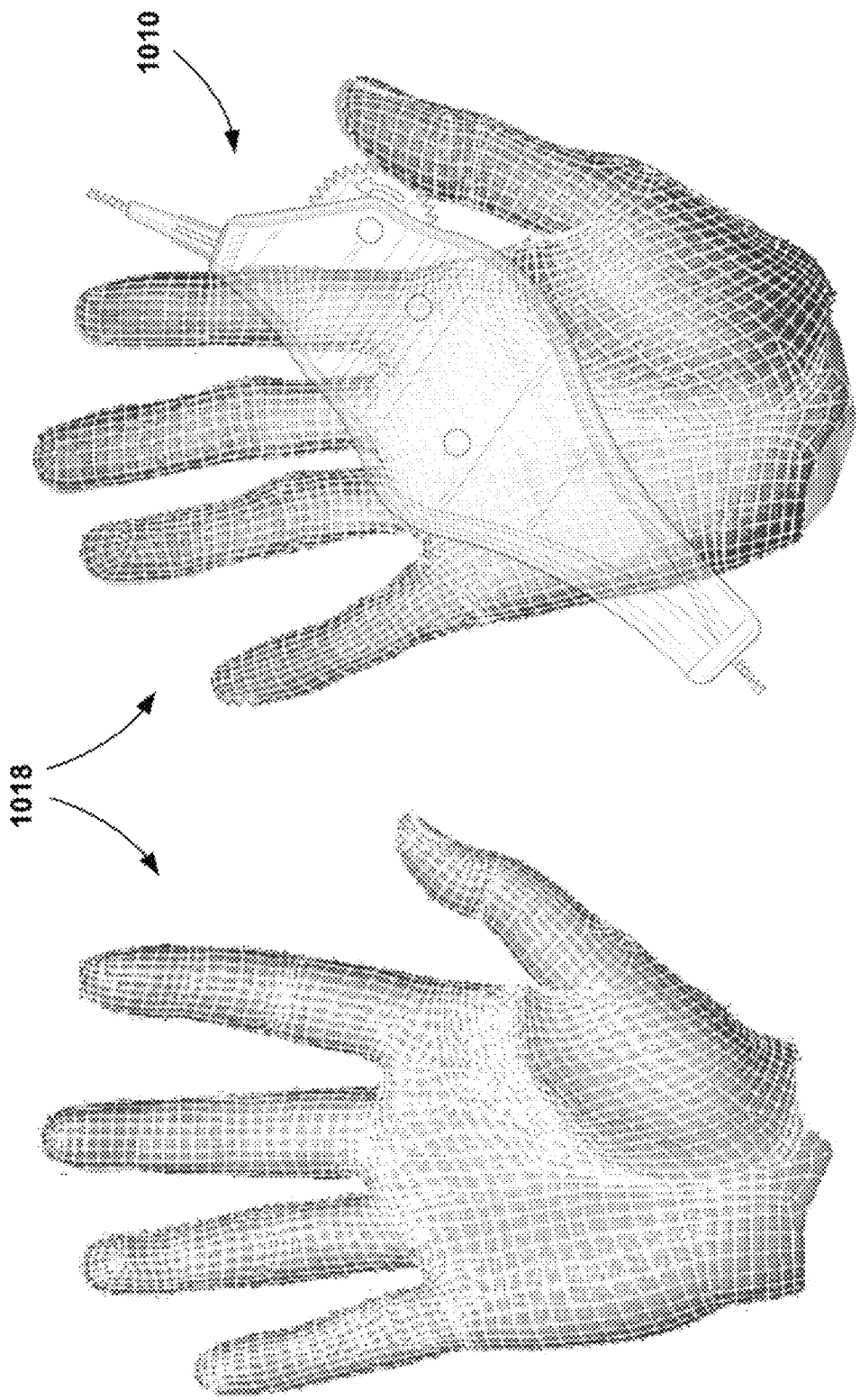
FIG. 9A schematically depicts a shape and contours from a plan view of the palm for an adult female hand, and FIG. 9B schematically depicts the same for an adult male hand, which is illustrated in combination with a left side plan view of the elongate device advancer of FIG. 7 over the palm region of the male hand.
Figure 9C:
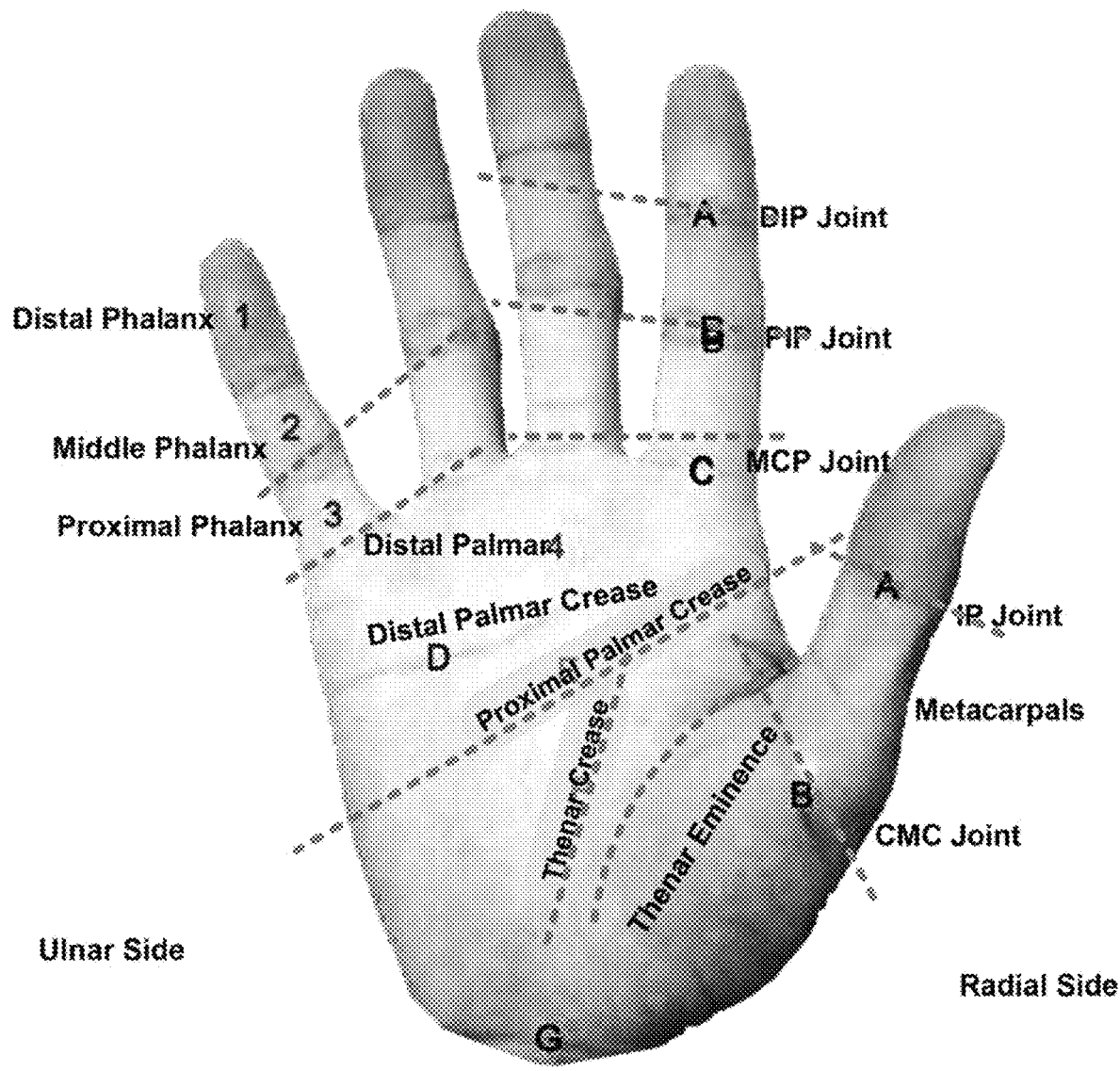
FIG. 9C schematically depicts a plan view representation of a palm of an adult hand along with corresponding anatomical medical labels for clarity and reference for features described herein.

Referring now to FIG. 9, a combination automatically-manually driven elongate device advancer 1110 is shown for advancing a guide wire an automated primary distance 1166 and a secondary manual distance 1168 that is less than the primary distance, which as shown in FIG. 9 can be coupled with a guide wire/sheath coil 1114 in a usage arrangement with the guide wire 1112 of the coil. Elongate device advancer 1110 generally includes the same or similar aspects and features as elongate device advancer 910 except as shown or discussed herein. Accordingly, like numbers general refer to like features. Similar to elongate device advancer 910, it is understood that the combination elongate device advancer 1110 can be operatively configured with a surgical instrument including the suture placement device 50 discussed above along with FIGS. 3A-3E and as shown in FIG. 9, which can be while suture placement device 50 is disposed within a port through a patient's body (not shown) and prepared for suture placement procedures. The combination elongate device advancer 1110 is likewise configured to be held within the single hand 1118 of a user and easily controlled to perform guide wire advancement actions to support a surgical device, such as the suture placement device 50 discussed above.

Similar to elongate device advancer 910, the combination elongate device advancer 110 is advantageously configured for the user to actuate an automatic drive and readily advance the guide wire a primary first distance 1166 based on a powered drive force stored by the elongate device advancer including automatically advancing the guide wire through a pathway of a coupled surgical device being supported by the elongate device advancer, such as advancing the guide wire within the channel pathway formed within the suture placement device 50. The combination elongate device advancer 1110 is configured for the user to readily actuate the automatic drive using the single handle gripping the elongate device advancer, such as via movement of one or more fingers to actuate the automatic drive as desired. Further, the combination elongate device advancer 1110 is advantageously configured for the user to exert control movements as well as using the single handle gripping the elongate device advancer, such as via rolling thumb movements exerted on a manual control conveniently placed proximate the user's thumb. As such, the user can readily grip the advancer and easily control advancement operations including both an automated primary advancement of the guide wire and manual, fine-tune secondary advancement of the guide wire as desired.

The combination automatically-manually driven elongate device advancer 1110 generally includes an advancer body 1130, an automated drive 1240, a manual drive 1220, and an integrated advancement driver 1230, which can be configured similar to corresponding aspects and features described along with elongate device advancer 910 with the exception of the automated drive 1240. Further, elongate device advancer 1110 can include a similar transmission switch 1263 to transmission switch 963 including a neutral portion 1265 that is configured to disengage the automated drive 1240 from a drive roller of the integrated advancement driver 1230 except during operation of the automated drive 1240 to advance the guide wire 1112 for the primary distance 1166.

However, the automated drive 1240 differs from automated drive 1040 of elongate device advancer 910 in that automated drive 1240 is configured as an electrically powered, motor-driven automated drive. Automated drive 1040 generally includes an electric motor 1206 that is electrically connected to a power supply 1208, such as an arrangement of capacitors or a battery 1208, a logic control unit 1202, such as a processor 1202, and memory 1204 that can be configured separately or as part of logic control unit/processor 1202, such as firmware or read-only memory (ROM). The electric motor further includes a drive shat 1247 drivingly connected with the motor 1206, and a worm gear 1249 attached to the drive shaft. It should be understood that the operating environment and the various components of the automated drive 1240 have been greatly simplified for purposes of discussion. Accordingly, additional or alternative components can be made available without departing from the embodiments described herein.

The battery 1208 provides power to motor 1206, which operates to provide a drive force when actuated to advance the guide wire 1212 the primary distance 1166. The use of a motor 1206 and power supply can provide several advantages including allowing the user to quickly and easily repeatedly advance the guide wire for the primary distance as needed for use with a particular procedure and surgical device, such as suture placement device 50, or for usage with additional suture placement devices for closing multiple ports near the end of a surgical operation or for usage with other surgical devices during a surgical operation. Further, usage of an electrically powered motor can permit elongate device advancer 1210 to be configured as a smaller, more compact and ergonomic device compared with a mechanically powered device.

In addition, usage of an electric motor in combination with control logic and modifiable control options, such as an including a processor 1202 and memory 1204 configured to control operations of powered drive 1240 when actuated can provide a wide range of options, customizations, user preferences, procedure-specific parameters and the like to entered or applied as parameters for operations of the automated drive. For example, the elongate device advancer 1110 can permit customization for use with a variety of surgical devices, types of procedures, and various parameters of the same such as guide wire gauge, pushability, length of the channel pathway, etc., as well as for user preferences, such as options for using multiple primary distances of differing lengths. The processor 1202 and memory 1204 are in electrical communication with the battery 1208 and motor 1206. The memory stores computer-readable instructions, which are processed by the processor to control operations of the motor 1206 and/or supply operating power to the motor from the battery 1208, such as controlling the current and/or voltage applied to the motor upon actuation of the actuator 1260 and the duration of power supply to provide for advancing the guide wire 1112 the primary distance 1166.

Figure 11A:
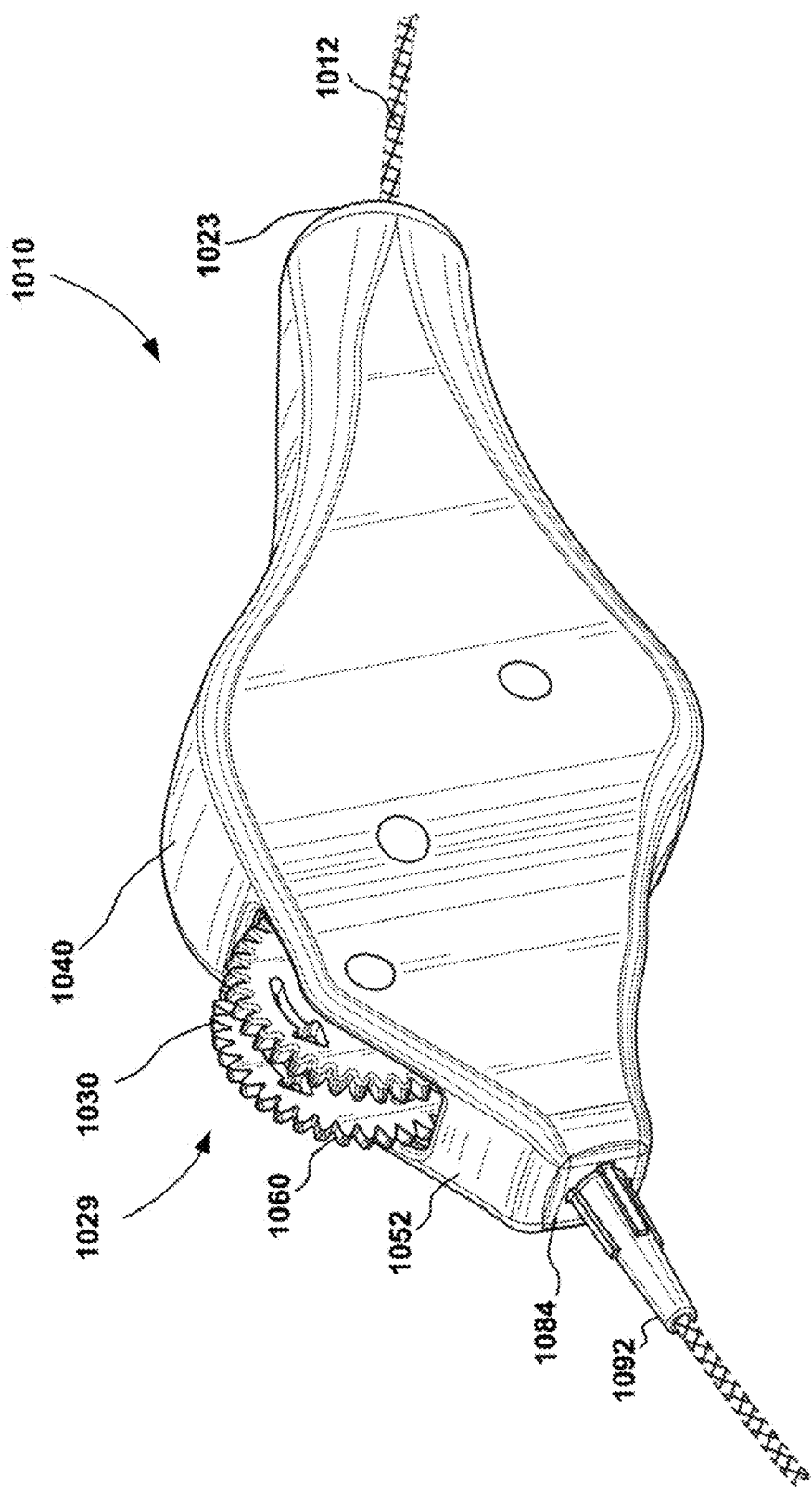
FIG. 11A is a distal (front) left perspective view of the elongate device advancer of FIG. 7.
Figure 11B:
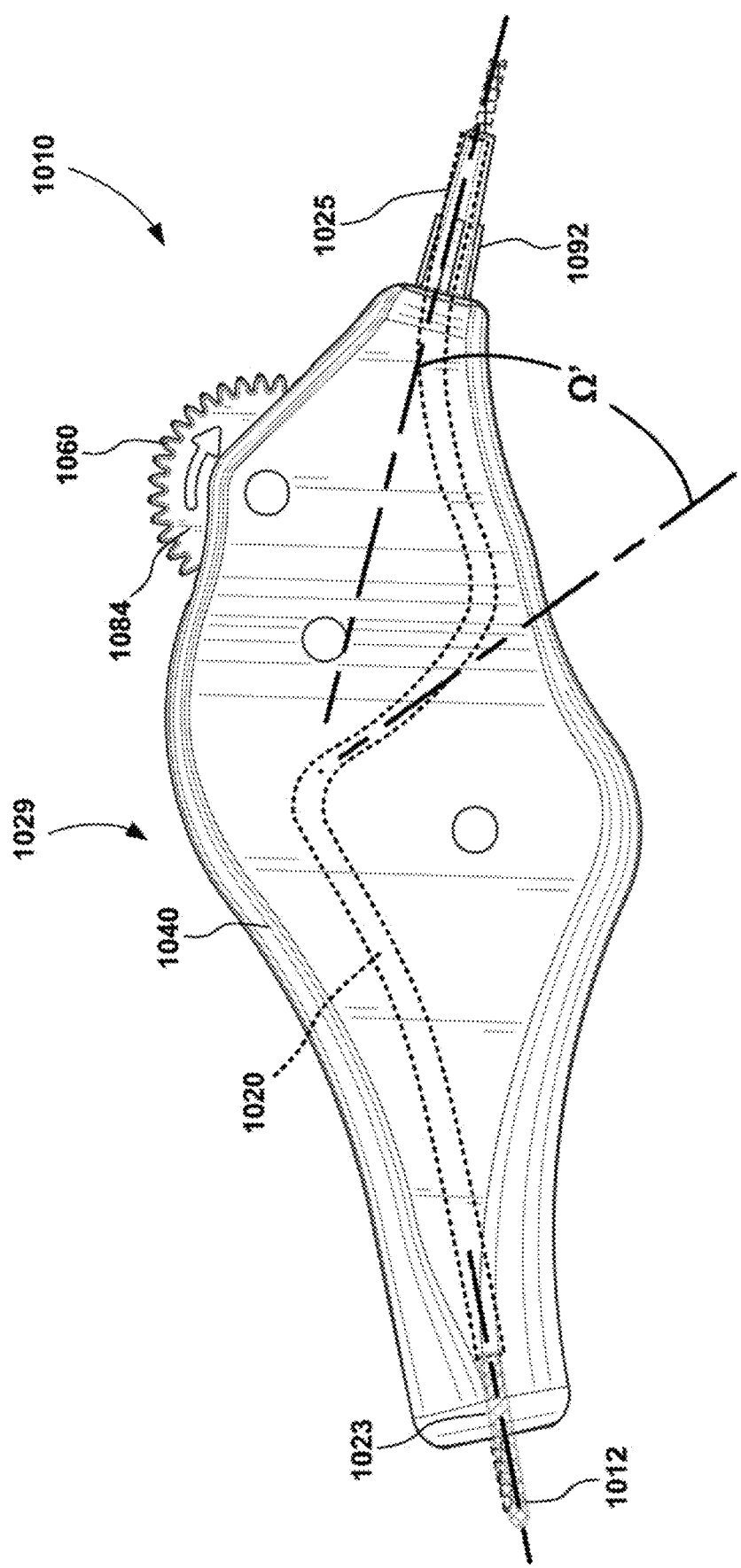
FIG. 11B is a right plan view of the elongate device advancer of FIG. 7.
Figure 11C:
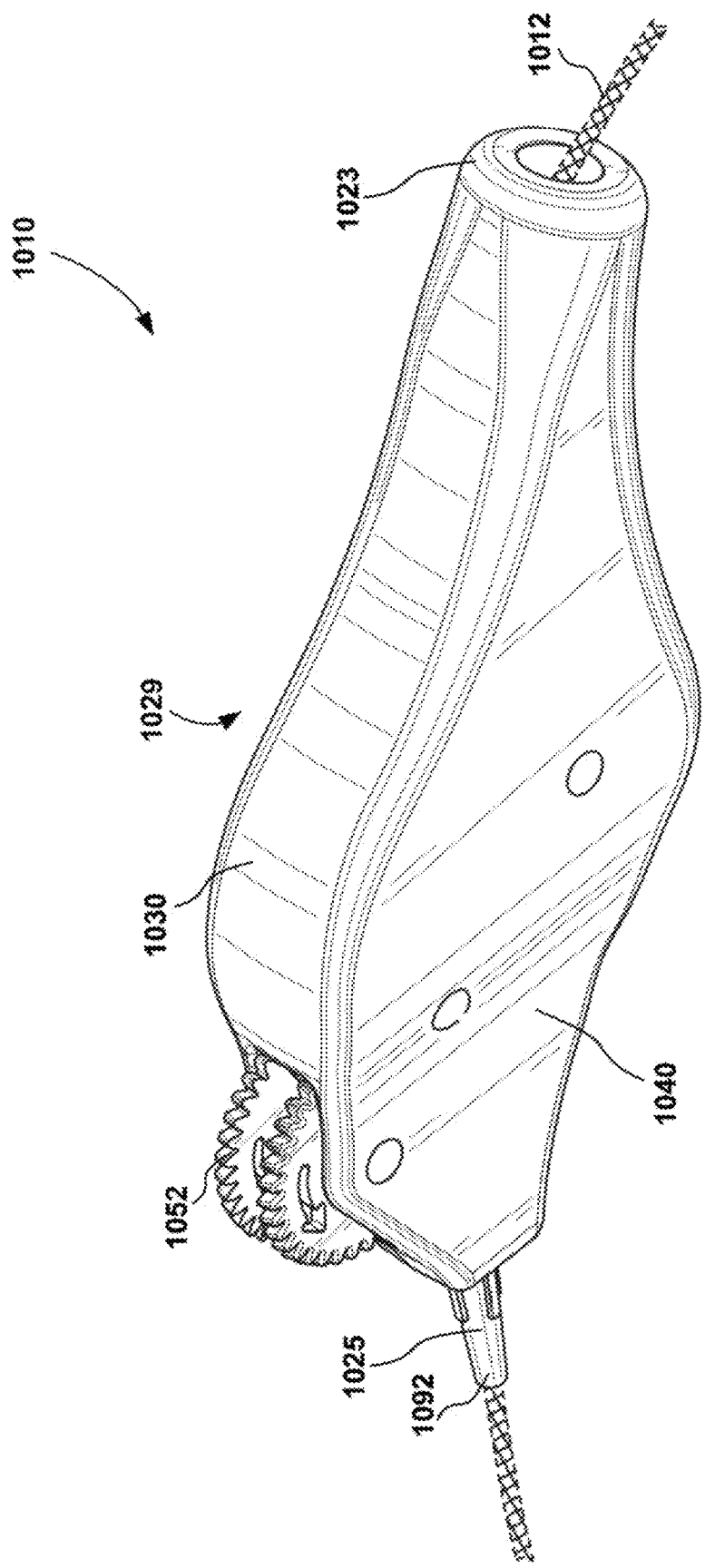
FIG. 11C is proximal (rear) top left perspective view of the elongate device advancer of FIG. 7.
Figure 12A:
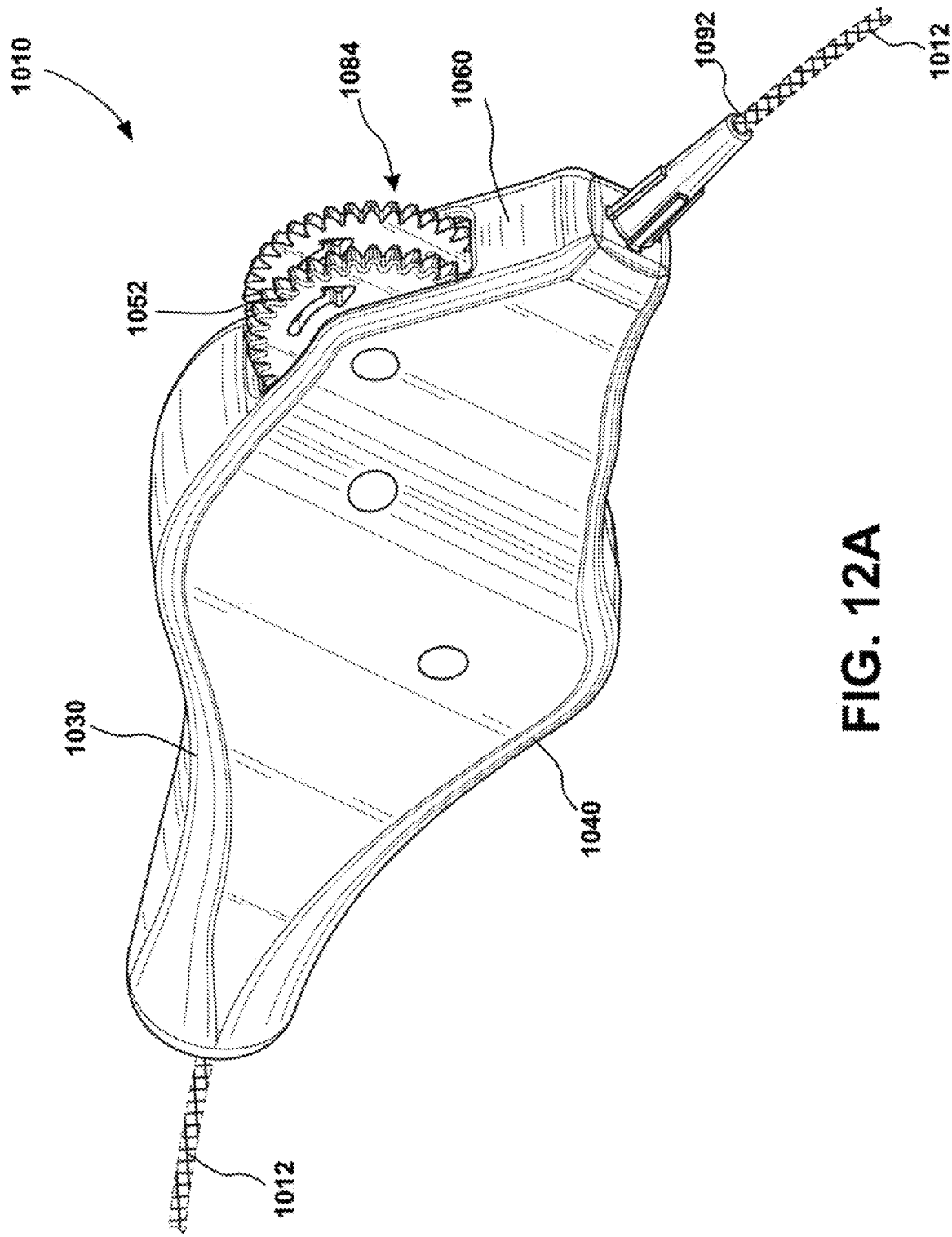
FIG. 12A is a distal (front) right perspective view of the elongate device advancer of FIG. 7.
Figure 12C:
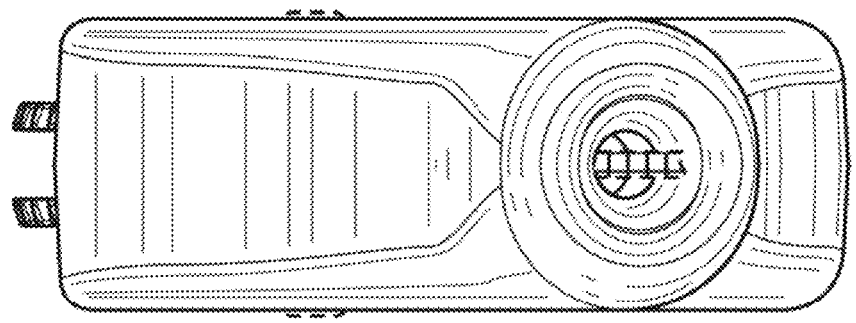
FIG. 12C is a proximal (rear) view thereof.
Figure 12B:
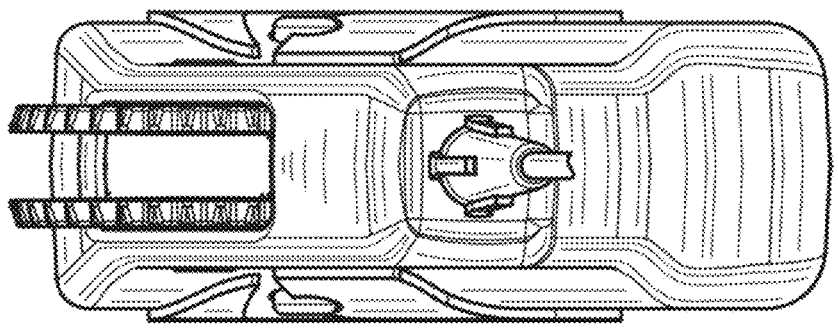
FIG. 12B is a distal (front) view of the elongate device advancer of FIG. 7.
Figure 13:
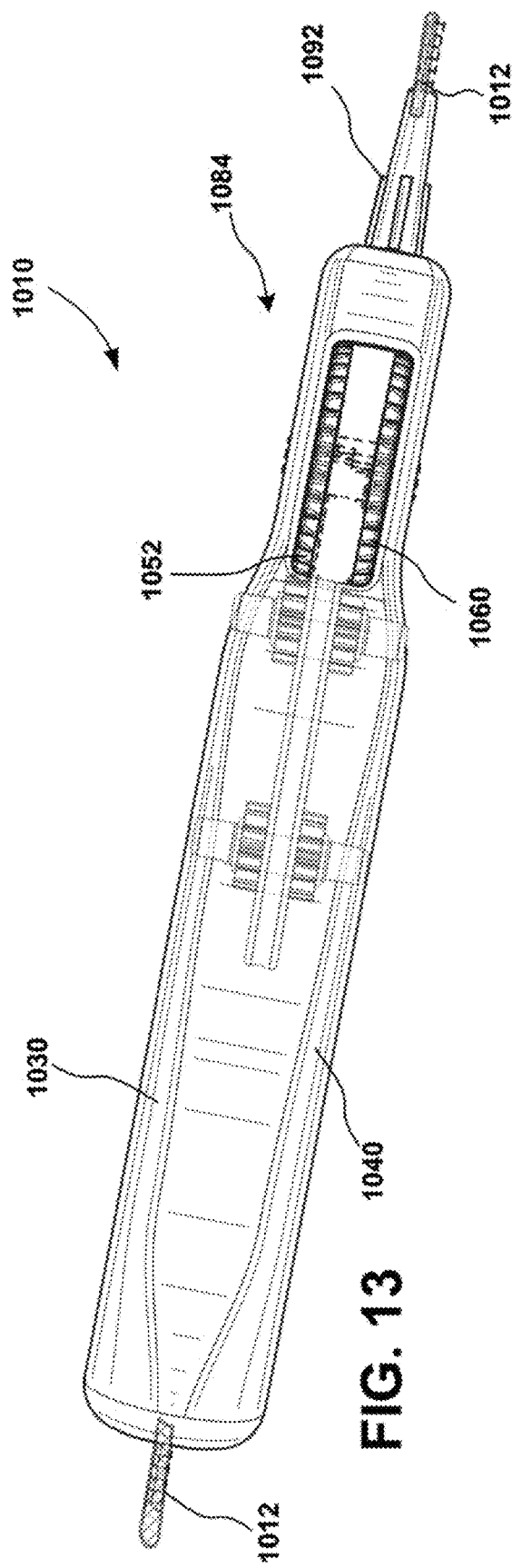
FIGS. 13 and 14 are top plan views of the elongate device advancer of FIG. 7 showing internal components of a manual driver thereof contained within an advancer housing thereof (FIG. 13)

Referring now to FIGS. 11-20 and in particular to FIG. 11, a combination automatically-manually driven elongate device advancer 1310 is shown for advancing a guide wire an automated primary distance 1366 and a secondary manual distance 1368 that is less than the primary distance, which can be coupled with a guide wire/sheath coil (not shown) in a usage arrangement with the guide wire 1312 of the coil. It is understood that the combination elongate device advancer 1310 can be operatively configured with a surgical instrument including the suture placement device 50 discussed above along with FIGS. 3A-3E and shown in FIG. 11 while the surgical instrument is disposed within a port and prepared for suture placement procedures, as well as with other similar and non-similar types of surgical instruments (not shown). The combination elongate device advancer 1310 is configured to be held within the single hand 1318 of a user and easily controlled to perform guide wire advancement actions to support the surgical instrument, such as suture placement device 50 discussed.

The combination elongate device advancer 1310 includes many aspects and features that are the same as or similar to those discussed above with elongate device advancers 910 and 1110. Accordingly, like numbers refer to like features. However, elongate device advancer 1310 further includes aspects and features not discussed along with elongate device advancers 910 and 1110 or that differ therefrom, which are discussed below and/or shown in FIGS. 11-20. Combination elongate device advancer 1310 is advantageously configured for the user to actuate an automatic drive and readily advance the guide wire a primary first distance 1366 based on potential energy stored therein. Such a configuration can provide a powered drive force to automatically advance the guide wire through a pathway of a coupled surgical device being supported by the elongate device advancer, like advancing the guide wire within a channel pathway 80 formed within the suture placement device 50. The combination elongate device advancer 1310 is further configured as a compact, ergonomic, high-power advancement device arranged for the user to readily actuate the automatic drive using a single hand 1318 gripping the elongate device advancer. For example, as shown in FIG. 11, movement of one or more fingers of the gripping hand 1318 can readily actuate the automatic drive by depressing an actuator 1460. Further, the combination elongate device advancer 1310 is advantageously configured for the user to exert control movements via the same gripping hand 1318 while gripping the elongate device advancer, such as via rolling thumb movements exerted on a manual control 1427 conveniently placed proximate the user's thumb. As such, the user can readily grip the advancer and easily control advancement operations including both an automated primary advancement of the guide wire and manual, fine-tune secondary advancement of the guide wire.

Further, combination elongate device advancer 1310 includes a compact, high-power mechanical power source, which can readily be re-charged or re-set by pulling a pull tab to enable repeated powered advancements of the guide wire. Further, combination elongate device advancer 1310 is configured in a general straight-through advancement arrangement, which minimizes the amount of friction or resistance for advancing the guide wire related to the elongate device advancer along with efficiently transferring advancement forces from the advancer to the guide wire with minimal losses. Thus, maximal portions of applied powered and manual drive forces can be transferred to the guide wire 1312 for its advancement through the corresponding surgical device.

Referring now to FIGS. 12-15B, the combination automatically-manually driven elongate device advancer 1310 generally includes an advancer body 1330, an automated or power drive 1440, a manual drive 1420, and an integrated advancement driver 1430. The advancer body 1330 defines a guide wire pathway 1320 (FIG. 14A) for advancing the guide wire 1312 therethrough from a first end portion 1323 to a second end portion 1325 of the advancer body, in which the advancer body is configured to be held in a grip of a single hand 1318 of a user and controllable by the single hand. The first end portion 1323 is configured to couple with the guide wire 1312 to receive a tip portion 1316 of the guide wire therein through an entrance 1322 of the pathway 1320 disposed at the first end portion 1323, and the guide wire 1312 is configured to advance through the pathway and out an exit 1324 of the pathway disposed at the second end portion 1325. The exit 1324 can include a stylet tip 1364 or similar arrangement for coupling the elongate device advancer in a support arrangement with a surgical device, such as suture placement device 50.

The advancer body 1330 includes a left housing 1332, a right housing 1350, and an introducer or stylet 1360 integrally formed with the right housing 1350 on the right side of the advancer body 1330. The guide wire pathway 1320 is formed through the stylet 1360 portion of the body as a generally straight-line channel through the centerline t of the stylet 1360. The guide wire pathway entrance 1322 (FIGS. 14A&B) is formed at the first end portion 1323 along the centerline ℓ of the stylet and guide wire pathway 1320, and the exit 1324 is formed at the second end portion 1325 along the centerline ℓ of the stylet and guide wire pathway. The integrated advancement driver 1430 is disposed along the guide wire pathway 1320 (FIG. 14A) within the stylet 1360, which as discussed further below is configured to apply drive forces in the advancement direction aligned with the centerline ℓ of the guide wire pathway 1320. As such, the elongate device advancer 1310 is configured to efficiently push or 'shoot' the guide wire through a low-friction, straight path lacking bends or features providing resistance, out of the stylet tip 1354 and exit 1324, and directly into an entry port of the corresponding surgical device (e.g., entry port of suture placement device 50). The elongate device advancer 1310 is configured to do so while closely supporting the guide wire within the guide wire pathway 1320 to prevent the guide wire from bending, kinking or folding over on itself. As such, elongate device advancer 1310 provides high efficiency, low loss, advancement of the guide wire 1312 directly into and along a channel pathway 80 of a corresponding surgical device 50.

As best seen in FIG. 11, upon actuation of actuator 1460, the automated power drive 1440 is configured to drive guide wire advancement for the primary distance 1366, which can be configured to correspond with substantially the entire length of the channel pathway 80 through the corresponding surgical device 50. The manual drive 1420 is configured to drive guide wire advancement for the secondary distance 1368 based on a user-exerted manual control movement on control 1427 that is configured as an exposed portion of a thumbwheel 1422. The exposed control 1427 of thumbwheel 1422 is configured to receive a user-exerted manual control movement (not shown) from the single hand 1318, such as rolling thumbwheel 1422, to transmit a corresponding manual drive force to the guide wire 1312 via the manual drive 1420 as discussed further below along for advancement of the guide wire 1312 the second distance 1368. One or more user-exerted manual control movements (not shown) can be applied by rolling the exposed control portion 1427 of thumbwheel 1422 repeatedly, which can beneficially be applied after actuation of the power drive to advance the guide wire the primary distance 1366, such as for manually advancing the guide wire tip portion 1316 to extend a desired length out of the surgical device. Manual control movements (not shown) can also be applied prior to actuation of the power drive, such as for manually advancing the guide wire tip portion 1316 through the length of the guide wire pathway and extend from the exit 1324 a desired length, such as for ensuring proper alignment and mating with a surgical device including extending into guide wire entry port 81 of suture placement device 50.

Thus, the combination of manual drive 1420 and automated power drive 1440 provides the user with significant control for advancing the guide wire as desired when aligning and mating the elongate device advancer 1310 with a surgical device, for quick and efficient deployment of the guide wire to advance through the pathway of the surgical device, and for arranging the guide wire for surgical procedures after deployment through the surgical device pathway. In addition, elongate device advancer 1310 is configured to effectively and efficiently advance the guide wire through and out of the advancer with minimal drive losses or opportunity for the guide wire to bend, kink or fold over. These advantages are provided in compact device configured to be held and controlled via the single hand 1318 of a user, which can further be re-set or re-charged as discussed further below to provide multiple actuations of the power drive as appropriate for use, for instance, with surgical devices having extended channel pathways, and for multiple uses with the same or similar surgical devices including multiple suture placement devices for performing multiple port closure procedures. Many of these advantages and other benefits provided by elongate device advancer 1310 are related to the advantageous integration and combination of drives within the elongate device advancer including manual drive 1420, automated power drive 1440, and integrated combination drive 1430.

Referring now to FIGS. 14A, 14C, and 15B, manual drive 1420 generally includes a manual drive roller or thumbwheel 1422 and a manual control 1427 configured as a user-exposed user-controllable portion of the thumbwheel. The manual drive roller 1422 is rotatably coupled with the advancer body and has an engagement surface 1421 that is rotatable with the manual drive roller. The engagement surface 1421 includes a drive portion 1416 extending into the guide wire pathway 1320 and configured to drivingly engage the guide wire 1312. The drive portion 1416 is configured to transmit a manual control force (not shown) applied by the user to manual control 1427 (e.g., rolling force applied by the thumb of hand 1318 to the thumbwheel) as corresponding manual drive force 1217 imparted by manual drive roller drive portion 1416 to the guide wire 1312 via the integrated combination drive 1418 discussed below to advance the second distance 1368.

The automated drive 1440 generally includes a power driver 1442, a powered or automated drive roller 1456, and an actuator 1460. The power driver 1442 is configured to store potential energy for driving guide wire advancement of guide wire 1312 for the primary distance 1366 (FIG. 11) and transmit a corresponding automated drive force (not shown) to the guide wire via automated drive roller 1456 when actuated. The automated drive roller 1456 is rotatably coupled with the advancer body 1430 and has a resilient surface 1428 (FIG. 14C) rotatable with the automated drive roller. The resilient surface 1428 includes a drive portion 1429 extending into the guide wire pathway 1320 and configured to drivingly engage the guide wire 1312 to advance when driven by power driver 1442. The actuator 1460 is configured to be actuated by the single hand 1318 (FIG. 11 along with FIG. 15B) to activate the power driver 1442 and transmit the automated drive force (not shown) to the automated drive roller drive portion 1429.

Figure 17:
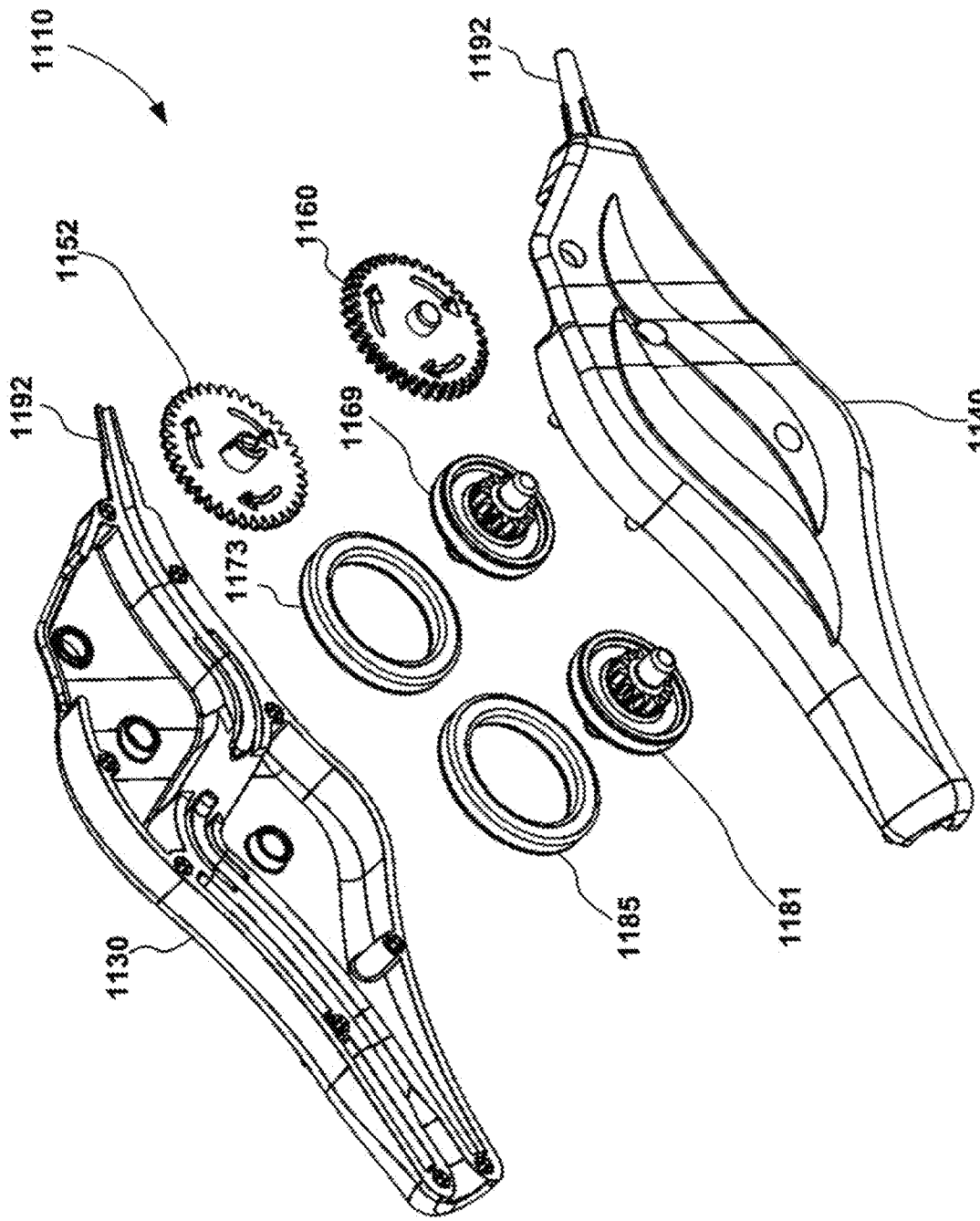
FIG. 17 is a right rear exploded perspective view of the elongate device advancer of FIG. 15.

Referring now to FIGS. 15A, 15B and 16-19, the power driver 1442 generally includes a flat coil spring 1446, a spring hub 1444, a spring shaft 1448, a pulley gear 1478 and a gearbox 1468. As shown in FIG. 17, the gearbox 1468 includes a gearbox body 1470, a gearbox cover 1472, and a gearbox front 1474. The gearbox body 1470 forms a generally rectangular case that retains the flat coil spring 1446, the spring hub 1444, the spring shaft 1448, and the pulley gear 1478 in an operative arrangement for providing an automated drive force F (FIG. 16) for advancing the guide wire 1312 the primary distance 1366 when the actuator 1460 is actuator by the single hand 1318. The gearbox cover 1472 is a removable cover providing access to components retained therein, which extends across a left face of the gearbox and supports operative arrangements of the components in combination with the gearbox box body and front. For instance, gearbox cover 1472 defines an opening that supports a left end of the spring shaft 1448 and permits rotation of the same, and also supports a left end of drive shaft 1452 discussed further below along with the power driver 1442. Gearbox cover 1472 further supports a left end of a floater gear shaft 1464 within a floater guide slot 1475, which is discussed below along with the transmission switch 1463 and FIGS. 15C, D and E. The gearbox is attached to the elongate device advancer housing 1330 and oriented such that the gearbox front 1474 is disposed toward the front or distal end of the housing, and the gearbox cover is disposed on the left side of the advancer covered by left housing 1332. In this orientation within the guide wire housing 1330, the spring shaft 1448 is supported laterally across the gearbox 1468 in a generally left-to-right widthwise orientation of the elongate device advancer 1310 and is rotatably supported via an opening formed on the left side within gearbox cover 1472 and similarly supported on the right side by a corresponding opening within the gearbox body 1470.

Gearbox front 1474 defines a spring end retention opening therein, which retains the outer end of the coiled spring 1446 and thereby affixes one end of the flat coil spring to the guide wire body 1330. Referring to FIG. 16 along with FIG. 17, the flat coil spring 1446 is wound as a flat coil around spring hub 1444, which is disposed on the spring shaft 1448 that is rotatably supported across the inside of the gearbox 1468. The spring hub 1444 is interlocked with the spring shaft 1448, such that the spring shaft and spring hub rotate together about a longitudinal axis of the spring shaft. The second end of the flat coil spring 1446 disposed inside the coil is attached to the spring hub, whereas the opposite first end at the beginning of the coil and located outside the coil is attached to the gearbox front 1470, which is attached to the guide wire body 1330 as discussed above. Thus, any rotational forces generated via potential energy stored in flat coil spring 1446 are configured to induce rotation about the rotational axis of spring hub 1448 and spring shaft 1448 with respect to the gearbox 1468.

As shown in FIG. 18 along with FIGS. 16 and 17, pulley gear 1478 is also rotatably disposed on spring shaft 1448 adjacent to spring hub 1444 with the spring shaft extending through a central axis of the pulley gear and interlocked therewith, such that the pulley gear rotates about the axis of the spring shaft and along with rotation of the spring shaft. Thus, any rotational forces or moments applied by flat coil spring 1446 inducing rotation of spring hub 1444 about its central axis along with rotation of spring shaft 1448 also induce rotation of pulley gear 1478 therewith. When flat coil spring 1446 is wound tightly about spring hub 1444 such that it retains potential energy for driving the automated drive 1440 when actuated, spring 1446 applies a drive moment M in the rotational direction shown in FIG. 16 about spring shaft 1448 via spring hub 1444, which likewise applies moment M in the same direction upon pulley gear 1478 about the axis of the spring shaft. However, actuator 1460 is operatively coupled with a lock 1458 that engages pulley gear teeth 1479 located along a perimeter portion of the pulley gear 1478, which blocks or stops rotation of the pulley gear along with rotation of spring shaft 1448 connected thereto and prevents operation of the automated drive 1240 until lock 1458 is disengaged from the pulley gear teeth.

As shown in FIG. 17, actuator 1460 is pivotably connected with lock 1458 such that movement of actuator 1460 via a finger of the single hand 1318 moves lock 1458 in an opposite direction and simultaneously disengages the lock from engagement with pulley gear teeth 1479. Accordingly, absent engagement of lock 1458 with pulley gear 1478, pulley gear can freely rotate with pulley hub 1444 and pulley shaft 1448 about the axis of the pulley shaft according to the drive moment M transmitted to the pulley gear from flat coil spring 1446. Gear teeth 1479 are configured to engage corresponding gear teeth on floater gear 1466 when actuated to drive rotation of the floater gear along with forcing the floater gear into a rotational, driving engagement with drive gear 1454 as discussed below along with FIGS. 15C, D and E.

It is understood that the pitch radii of meshing gear teeth 1479, the sets of gear teeth disposed along floater gear 1466, and the gear teeth disposed along drive gear 1454 can vary with respect to each other according to various parameters and preferences, such as the rotational spring force provided by flat coil spring 1446 and duration of drive force when actuated, the desired primary advancement length 1366 for use of the elongate device advancer 1310 with a particular surgical device or types of devices, and/or pushability and related parameters for the particular guide wire and its usage. Drive chain and related modifications can fine tune operational characteristics of the automated drive 1440, such as mechanical advantage features, drive duration that can be provided by the stored potential energy and spring parameters, and drive forces applied to the guide wire 1312 for automated advancement.

For example, in the configuration shown in FIG. 16, pulley gear 1478 has a large pitch radius for its mesh teeth 1479 with respect to the comparatively small pitch radius of mesh teeth on floater gear 1466 engaged by mesh teeth 1479. As such, a single rotation of pulley gear 1478 drives multiple rotations of floater gear 1466 with a lesser force applied than if the pitch radius of mesh teeth 1479 were smaller. However, floater gear 1466 applies mechanical advantage benefits via transmitting moment applied to it by pulley gear 1478 to drive gear 1454 using an attached gear having a large pitch radius to mesh with the drive gear and increase the force applied to the gear teeth of drive gear 1454 by a corresponding mechanical advantage factor. In other words, the rate at which drive force can be applied via the flat coil spring for the amount of potential energy its stores and the force ultimately applied to the guide wire as drive force F can be modified and fine-tuned as appropriate for usage of the elongate device advancer 1310 with different types and configurations of surgical devices according to mechanical advantage, gear ratios and related drive train principles.

Referring to FIG. 16, the integrated advancement driver 1430 generally includes a cooperative feed roller nip 1432 configured to advance the guide wire in response to transmission of the automated drive force $F_D$ or a manual drive force $F_M$ applied by the user via thumbwheel 1422. In other words, the integrated advancement driver 1430 is configured as a multi-source advancement driver that can readily advance the guide wire according to the user's control movements including responsive to a user-exerted manual control or manual drive force on thumbwheel 1422, and in response to user-actuation of the automated driver 1440. As such, the cooperative feed roller nip 1432 includes a drive roller from both the manual drive 1420 and the automated drive 1440. Further, the cooperative feed roller nip 1432 is defined between the drive portion 1416 of the manual drive roller 1422 that extends into the guide wire pathway, which is configured in an opposed arrangement with the drive portion 1429 of the automated drive roller 1456 that likewise extends into the guide wire pathway. The opposing drive portions can be configured to engage opposite side regions of the guide wire and cooperate as a pair of feed rollers for advancing the guide wire 1312 along the pathway 1320 toward the second end portion 1325. Further, the opposing drive portions can each be configured to act as both a drive roller and a driven roller based on the drive roller that is acting as the operative drive providing drive force to the guide wire.

Referring now to FIGS. 15C and 15D, further details of the manual drive 1620 and the power drive 1640 as drive components of the integrated advancement drive 1430 are shown, as well as aspects and features pertaining to a transmission switch 1463 configured to automatically move between a first position D and a second position E. The transmission switch is configured to automatically move to the first position D when the user exerts manual control via thumbwheel 1422. The first position D de-couples the power drive 1440 from its driving connection with the automated or powered drive roller 1454 to prevent drive force inadvertently being applied by the power drive 1440 on the guide wire 1312 while the user applying fine-tuning user-controlled advancement of the guide wire. The transmission switch is further configured to automatically engage or connect the power driver 1440 to the powered drive roller 1454 when the user actuates the actuator to transmit powered drive force to the guide wire 1312. The transmission switch 1463 generally includes a floater gear 1466, a floater gear shaft 1464, and a pair of guide slots 1475 configured to support opposite ends of the floater gear shaft. The pair of corresponding guide slots 1475 are formed through the gearbox 1468 with one formed through the cover 1472 on the left side of the gearbox, and the other on the opposite right side through the gearbox body 1470. The opposing slots support opposite end portions of floater gear shaft 1464 such that the floater gear shaft extends laterally between left and right sides of the gearbox across the width of the elongate device advancer 1310. The floater gear shaft is supported within the opposing guide slots 1475 to allow rotation of floater gear shaft 1464 and sliding translation of the shaft along the slot.

Referring now to FIG. 15C, operation of transmission switch 1463 is shown while the manual drive 1420 of the integrated combination drive 1418 is operative, as well as operations of the manual drive. Elongate device advancer 1310 is configured such that the user applies control movements 1425 to the manual control 1427 of the thumbwheel 1422 using the thumb of single hand 1318 via thumb movements rearward or in a proximal direction, which rotates the exposed control portion rearward or in a proximal direction. An outer surface portion 1421 of thumbwheel 1422 can be configured to have with a knurled, abrasive, tactile, contoured or other type of surface texture or features providing high frictional engagement, such as with the user's thumb of single hand 1318 and/or for driving engagement of the guide wire 1312. A manual drive portion 1416 of outer surface portion 1421 extends into the guide wire channel 1320 and drivingly engages a side portion of the guide wire 1312 disposed within the nip 1432 to transmit a manual drive force $F_M$ applied by the user to the guide wire. When the manual drive portion 1416 is applying manual force $F_M$ to the guide wire, automated drive roller 1456 acts as a driven roller and correspondingly rotates in an opposite direction as thumbwheel 1422. Drive gear 1454 is attached to drive roller 1456 and, thus, correspondingly rotates along with the drive roller as shown in FIG. 15C. Mesh gear teeth disposed along drive gear 1454 engage corresponding mesh gear teeth of floater gear 1466 when the floater gear is proximate to or in engagement with the drive gear 1454 and push the floater gear 1466 along guide slots 1475 while rotating as shown responsive to application of a manual drive force. As such, floater gear 1466 automatically slides into the disengagement position D, which de-couples the pulley gear 1478 from engagement with drive gear 1454.

Referring now to FIG. 15D, operation of transmission switch 1463 is shown while the power drive 1440 of the integrated combination drive 1418 is operative, as well as further operations of the power drive. Elongate device advancer 1310 is configured such that the user can actuate actuator 1460 as discussed above to release potential energy stored by flat coil spring 1446 such that moment M applied to pulley gear 1478 rotates the pulley gear in the direction shown. As discussed above along with FIG. 16, gear teeth disposed along the pulley gear engage corresponding mesh teeth of floater gear 1466, which applies rotational force to rotate and translate the floater gear along guide slot 1475 into an engagement position E, in which the mesh gear teeth of the floater gear drivingly engage mesh gear teeth of drive gear 1454 to drive rotation of the drive gear in the drive direction shown. Rotation of drive gear 1454 as shown correspondingly rotates drive roller 1456 that is attached to the drive gear and exerts power drive force $F_D$ upon guide wire 1312 disposed within the nip as discussed above along with FIG. 16. Thus, floater gear 1466 automatically slides into the engagement position E, which couples pulley gear 1478 into driving engagement with drive gear 1454 when the power drive is actuated. After potential energy stored in flat coil spring 1446 has been expended, the user can apply manual control via the thumbwheel and again disengage the floater as described above in FIG. 15C.

Figure 19:
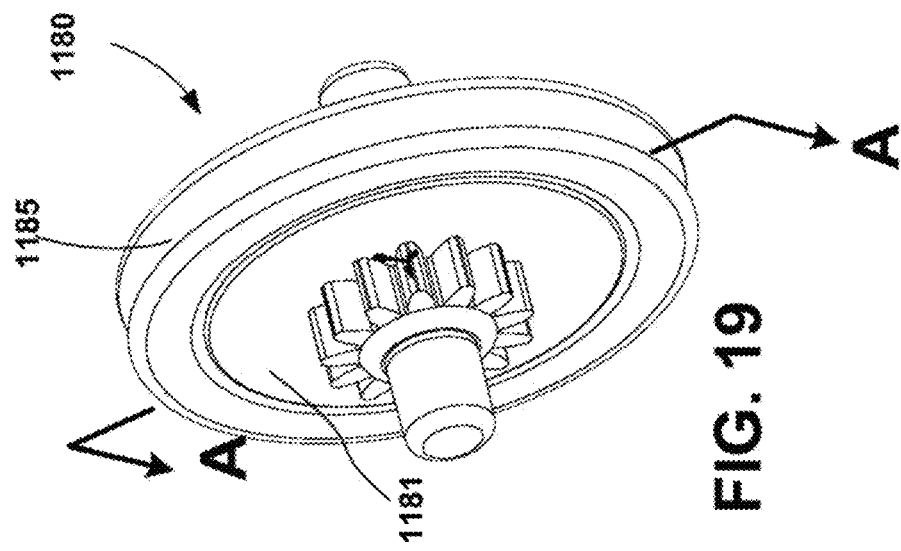
FIG. 19 is a perspective view of a roller assembly of the elongate device advancer of FIG. 15.

Referring now to FIG. 15E along with FIG. 19, elongate device advancer 1310 further includes a recharge assembly 1477 that allows the automated power drive 1440 to be reset or recharged along with rewinding the flat coil spring 1446, such that potential energy is restored for further actuations of the power drive. This option can allow elongate device advancer 1310 to be advantageously be used repeatedly for various circumstances, such as for usage with surgical devices having extended length channel pathways that exceed primary distance 1366, for re-advancing improperly executed guide wire advancement procedures or to switch guide wires, for using guide advancer to perform multiple procedures, or other reasons. Recharge assembly 1477 generally includes a pull tab 1480, a coil cavity 1482, a pull line 1484, and a pull line eyelet 1486. The coil cavity 1482 can be configured with pulley gear 1478 as a disk-shaped cavity adjacent to pulley gear 1478 bounded on one side by a side surface of the pulley gear and on the other side by a coil cavity wall (FIG. 19) configured as an additional disk shaped surface that is laterally offset from the pulley gear such that a generally disk shaped cavity is formed in which a pull line can be wrapped or coiled around spring shaft 1447 in a similar manner as flat coil spring 1446. A pull line 1484 is attached at a first end to spring hub 1444 similar to flat coil spring 1446, and is coiled around the spring hub in an opposite direction from the coil direction of the flat coil spring. An opposite second end of the pull line 1484 is thread through an eyelet 1486 as it exits a rearward or proximal portion of the guide wire housing 1330 and attached to a pull tab 1480 disposed outside of the guide wire housing at a distal end thereof.

As shown in FIG. 15E, pull tab 1480 is configured to be pulled in a proximal direction away from the elongate device advancer housing 1330, such as by the user via a second hand or by another person. As the pull tab is pulled proximally, the pull line 1484 uncoils and rotates the spring hub 1444 along with pulley gear 1478 and spring shaft 1447 in an opposite rotation direction from the direction of rotation imparted upon pulley gear 1478 when the actuator 1460 is actuated and the power drive 1440 becomes operative as discussed along with FIG. 16. Rotation of the spring hub 1444 in this opposite direction acts to rewind flat coil spring 1446 around the spring hub and restore its potential energy. Further, as indicated in FIG. 15E, while the pull tab is being extended and the spring rewound, pulley gear 1478 engages mesh teeth of the floater gear 1466 to disengage from driver gear 1454 and avoid inadvertently applying any drive forces. Once recharged, actuator 1460 can be moved outward in a reverse direction from actuation to rotate lock 1458 into engagement with pulley gear teeth 1479 and retain the rewound, stored potential energy arrangement of flat coil spring 1446 and power drive 1440 until actuation is desired.

Referring now to FIG. 20 along with FIGS. 11-19, a method 1370 for advancing a guide wire using elongate device advancer 1310 with a guide wire 1312 and a surgical device, such as suture placement device 50 and/or other surgical device(s) is generally shown. The method 1370 generally includes step 1372 of holding the elongate device advancer 1310 in a single hand 1318 of a user and step 1374 of coupling the elongate device advancer 1310 in an advancement arrangement with a surgical device including placing a tip portion of the elongate device advancer in an entry portion of a channel pathway of the surgical device. The method 1370 optionally includes the step 1376 of applying one or more manual control movements to the manual control via a thumb of the single hand 1318 to advance a guide wire 1312 into the entry portion of the surgical device. The method 1370 further includes step 1378 of actuating the actuator 1460 via one or more of the user's fingers to advance the guide wire 1312 a primary distance through the channel pathway, and the optional step 1380 of recharging the automated power drive 1440 and re-actuating the power drive one or more additional times to repeatedly advance the guide wire 1312 repeated primary distances. The method 1370 also includes the step 1382 of exerting one or more manual control movements to the manual control via the thumb of the single hand to advance the guide wire one or more secondary distances less than the primary distance.

Referring now to FIGS. 21-41 and in particular to FIG. 11, a combination automatically-manually driven elongate device advancer 1510 is shown for advancing a guide wire an automated primary distance 1566 and a secondary manual distance 1568 that is less than the primary distance, which can be coupled with a guide wire/sheath coil (not shown) in a usage arrangement with the guide wire 1512 of the coil. It is understood that the combination elongate device advancer 1510 can be operatively configured with a surgical instrument including the suture placement device 50 discussed above along with FIGS. 3A-3E and shown in FIG. 21 while the surgical instrument is disposed within a port and prepared for suture placement procedures, as well as with other similar and non-similar types of surgical instruments (not shown). The combination elongate device advancer 1510 is configured to be held within the single hand 1518 of a user and easily controlled to perform guide wire advancement actions to support the surgical instrument, such as suture placement device 50 discussed.

The combination elongate device advancer 1510 includes many aspects and features that are the same as or similar to those discussed above with elongate device advancers 910, 1110, and 1310. Accordingly, like numbers refer to like features. However, elongate device advancer 1510 further includes aspects and features not discussed along with elongate device advancers 910, 1110, and 1310 or that differ therefrom, which are discussed below and/or shown in FIGS. 21-40. Combination elongate device advancer 1510 is advantageously configured for the user to actuate an automatic drive and readily advance the guide wire a primary first distance 1566 based on potential energy stored therein. Such a configuration can provide a powered drive force to automatically advance the guide wire through a pathway of a coupled surgical device being supported by the elongate device advancer, like advancing the guide wire within a channel pathway 80 formed within the suture placement device 50. The combination elongate device advancer 1510 is further configured as a compact, ergonomic, high-power advancement device arranged for the user to readily actuate the automatic drive using a single hand 1518 gripping the elongate device advancer. For example, as shown in FIG. 21, movement of one or more fingers of the gripping hand 1518 can readily actuate the automatic drive by depressing an actuator 1660. Further, the combination elongate device advancer 1510 is advantageously configured for the user to exert control movements via the same gripping hand 1518 while gripping the elongate device advancer, such as via rolling thumb movements exerted on a manual control 1627 conveniently placed proximate the user's thumb. As such, the user can readily grip the advancer and easily control advancement operations including both an automated primary advancement of the guide wire and manual, fine-tune secondary advancement of the guide wire.

Further, combination elongate device advancer 1510 is configured as an ambidextrous device that can perform and be used equally well via a user's left or right. In addition, elongate device advancer 1510 is configured for ergonomic handling and extended usage such that it can be easily held and controlled in a single left or right hand of user, and maintains a generally neutral wrist angle during use along with having a comfortable form-fitting pistol type grip that can be held comfortably during extended usage. Combination elongate device advancer 1510 includes an angled connection for coupling with a guide wire supply and a flexible stylet tip connector for coupling with a surgical device, which increases the range of flexibility for comfortably using the elongate device advancer and coupling with related devices. In addition, elongate device advancer 1510 is configured to include a highly compact, yet high-power mechanical power source disposed within a small, lightweight envelope that provides enhanced flexibility and comfort for holding and using the advancer device with various devices, environments and uses. Moreover, elongate device advancer 1510 is configured for quick and easy recharging to enable multiple, repeated power drive actuations.

Referring now to FIGS. 22-27, the combination automatically-manually driven elongate device advancer 1510 generally includes an advancer body 1530, an automated power drive 1640, a manual drive 1620, and an integrated advancement driver 1630. The advancer body 1530 defines a guide wire pathway 1520 (FIG. 27) for advancing the guide wire 1512 therethrough from a first end portion 1523 to a second end portion 1525 of the advancer body, in which the advancer body is configured to be held in a grip of a single hand 1518 of a user and controllable by the single hand, for which elongate device advancer 1510 is configured to be held and used equally well by a left or right hand. The first end portion 1523 is configured to couple with the guide wire 1512 to receive a tip portion of the guide wire therein through an entrance of the pathway 1520 disposed at the first end portion 1523, and the guide wire 1512 is configured to advance through the pathway and out an exit of the pathway disposed at the second end portion 1525. The exit 1524 can include a stylet tip 1564 or similar arrangement for coupling the elongate device advancer in a support arrangement with a surgical device, such as suture placement device 50.

The advancer body 1530 includes a left housing 1532, a right housing 1550, and an introducer or stylet 1560 integrally formed within portions of both the left and right housings. As such, the left and right housing are generally mirror images of each other, controls are generally centered, and couplings or connections with other devices such as a guide wire 1512 or surgical device are arranged for ambidextrous usage such that elongate device advancer 1512 can be used equally well via a left or right hand. The guide wire pathway 1520 is formed through the stylet 1560 portion of the body disposed near the second end portion or distal portion of the device. However, the guide wire pathway 1520 follows a curved pathway as shown in FIG. 27, which provides significant benefits to user related ease of handling and controlling, compact size, and comfortable, ergonomic usage, as well as benefits for enhanced control and advancement of the guide wire.

The integrated advancement driver 1630 (FIGS. 26 & 27) is disposed within a front portion of the body 1530 proximate thumbwheel 1622 and along the guide wire pathway 1520 prior to traversing through the stylet 1560. As such, the elongate device advancer 1510 is configured to apply drive forces to the guide wire 1512 as it enters the stylet portion and enters the corresponding surgical device. The elongate device advancer 1510 is configured to closely support and guide the guide wire within the guide wire pathway 1520 along a curved pathway that prevents the guide wire from bending, kinking or folding over on itself along with enabling a compact, comfortable, high-power drive advancer arrangement.

As best seen in FIG. 21, upon actuation of actuator 1660, the automated power drive 1640 is configured to drive guide wire advancement for the primary distance 1566, which can be configured to correspond with substantially the entire length of the channel pathway 80 through the corresponding surgical device 50. The manual drive 1620 is configured to drive guide wire advancement for the secondary distance 1568 based on a user-exerted manual control movement on control 1627 that is configured as an exposed portion of a thumbwheel 1622. The exposed control 1627 of thumbwheel 1622 is configured to receive a user-exerted manual control movement (not shown) from the single hand 1518, such as rolling thumbwheel 1622, to transmit a corresponding manual drive force to the guide wire 1512 via the manual drive 1620 as discussed further below along with advancement of the guide wire 1512 the second distance 1568. One or more user-exerted manual control movements (not shown) can be applied by rolling the exposed control portion 1627 of thumbwheel 1622 repeatedly, which can beneficially be applied after actuation of the power drive to advance the guide wire the primary distance 1566, such as for manually advancing the guide wire tip portion 1516 to extend a desired length out of the surgical device. Manual control movements (not shown) can also be applied prior to actuation of the power drive, such as for manually advancing the guide wire tip portion 1516 through the length of the guide wire pathway and extend from the exit 1524 a desired length, such as for ensuring proper alignment and mating with a surgical device including extending into guide wire entry port 81 of suture placement device 50.

Thus, the combination of manual drive 1620 and automated power drive 1640 provides the user with significant control for advancing the guide wire as desired when aligning and mating the elongate device advancer 1510 with a surgical device, for quick and efficient deployment of the guide wire to advance through the pathway of the surgical device, and for arranging the guide wire for surgical procedures after deployment through the surgical device pathway. In addition, elongate device advancer 1510 is configured to effectively and efficiently advance the guide wire through and out of the advancer with minimal opportunities for the guide wire to bend, kink or fold over. These advantages are provided in compact device configured to be held and controlled via the single hand 1518 of a user that works well with either left or right hands, which can further be re-set or re-charged as discussed further below to provide multiple actuations of the power drive as appropriate for use, for instance, with surgical devices having extended channel pathways, and for multiple uses with the same or similar surgical devices including multiple suture placement devices for performing multiple port closure procedures. Many of these advantages and other benefits provided by elongate device advancer 1510 are related to the advantageous integration and combination of drives within the elongate device advancer including manual drive 1620, automated power drive 1640, and integrated combination drive 1630.

Referring now to FIG. 30A, manual drive 1620 generally includes a manual drive roller or thumbwheel 1622 and a manual control 1627 configured as a user-exposed user-controllable portion of the thumbwheel. The manual drive roller 1622 is rotatably coupled with the elongate device advancer body and has an engagement surface 1621 that is rotatable with the manual drive roller. The engagement surface 1621 includes a drive portion 1616 extending into the guide wire pathway 1520 and configured to drivingly engage the guide wire 1512 (not shown in FIG. 30A). The drive portion 1616 is configured to transmit a manual control force (not shown) applied by the user to manual control 1627 (e.g., rolling force applied by the thumb of hand 1518 to the thumbwheel) as a corresponding manual drive force imparted by manual drive roller drive portion 1616 to the guide wire 1512 via the integrated combination drive 1618 as discussed below along with the integrated combination drive to advance the guide wire the second distance 1568.

The automated drive 1640 generally includes a power driver 1642, a powered or automated drive roller 1656, and an actuator 1660. The power driver 1642 is configured to store potential energy for driving guide wire advancement of guide wire 1512 for the primary distance 1566 (FIG. 21) and transmit a corresponding automated drive force to the guide wire via automated drive roller 1656 when actuated. The automated drive roller 1656 is rotatably coupled with the advancer body 1630 and has a resilient surface 1628 (FIGS. 34 & 35) rotatable with the automated drive roller. The resilient surface 1628 includes a drive portion 1629 extending into the guide wire pathway 1520 and configured to drivingly engage the guide wire 1512 to advance when driven by power driver 1642. The actuator 1660 is configured to be actuated by the single hand 1518 (FIG. 11 along with FIG. 15B) to activate the power driver 1642 and transmit the automated drive force (not shown) to the automated drive roller drive portion 1629.

Figure 29A:
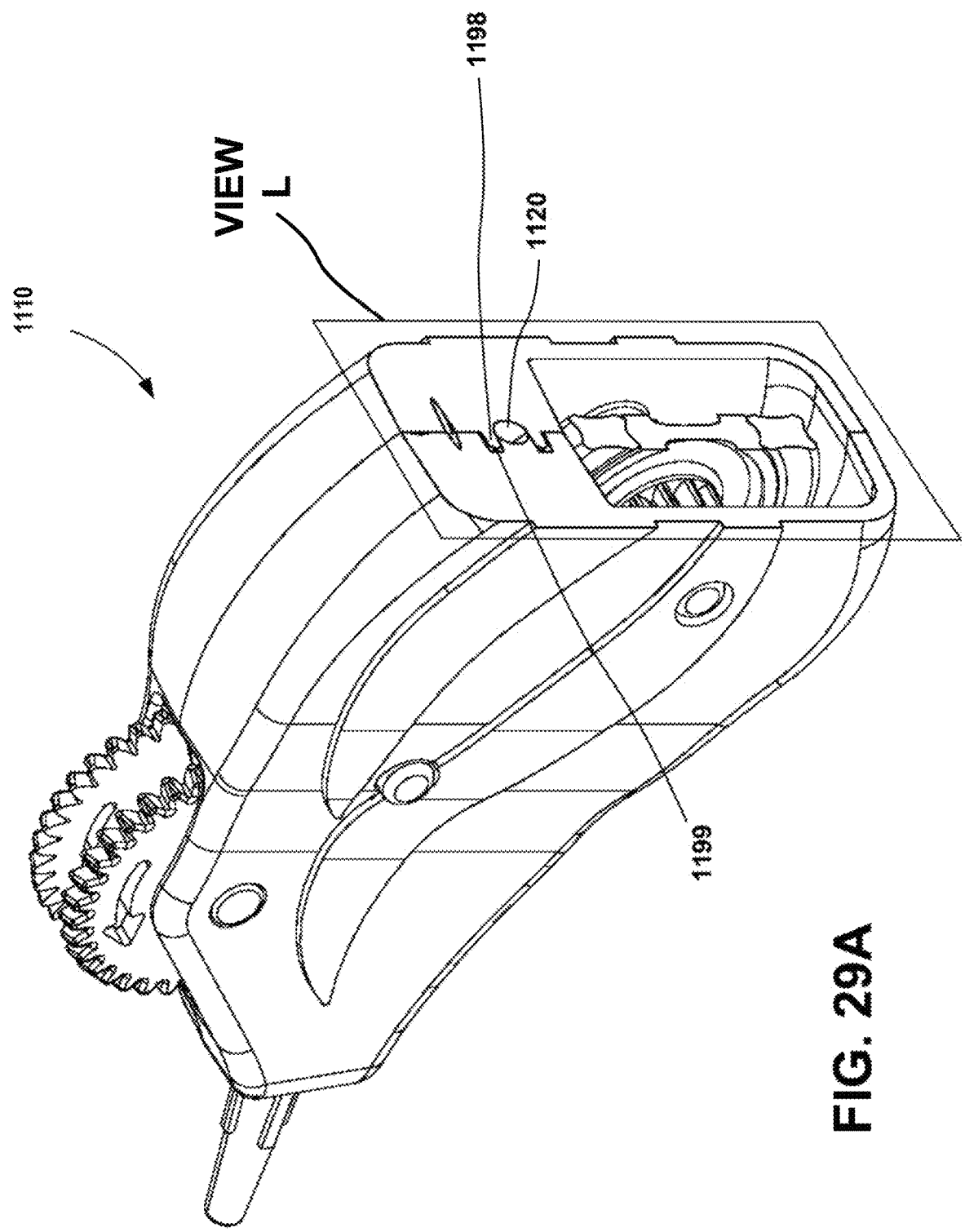
Figure 29B:
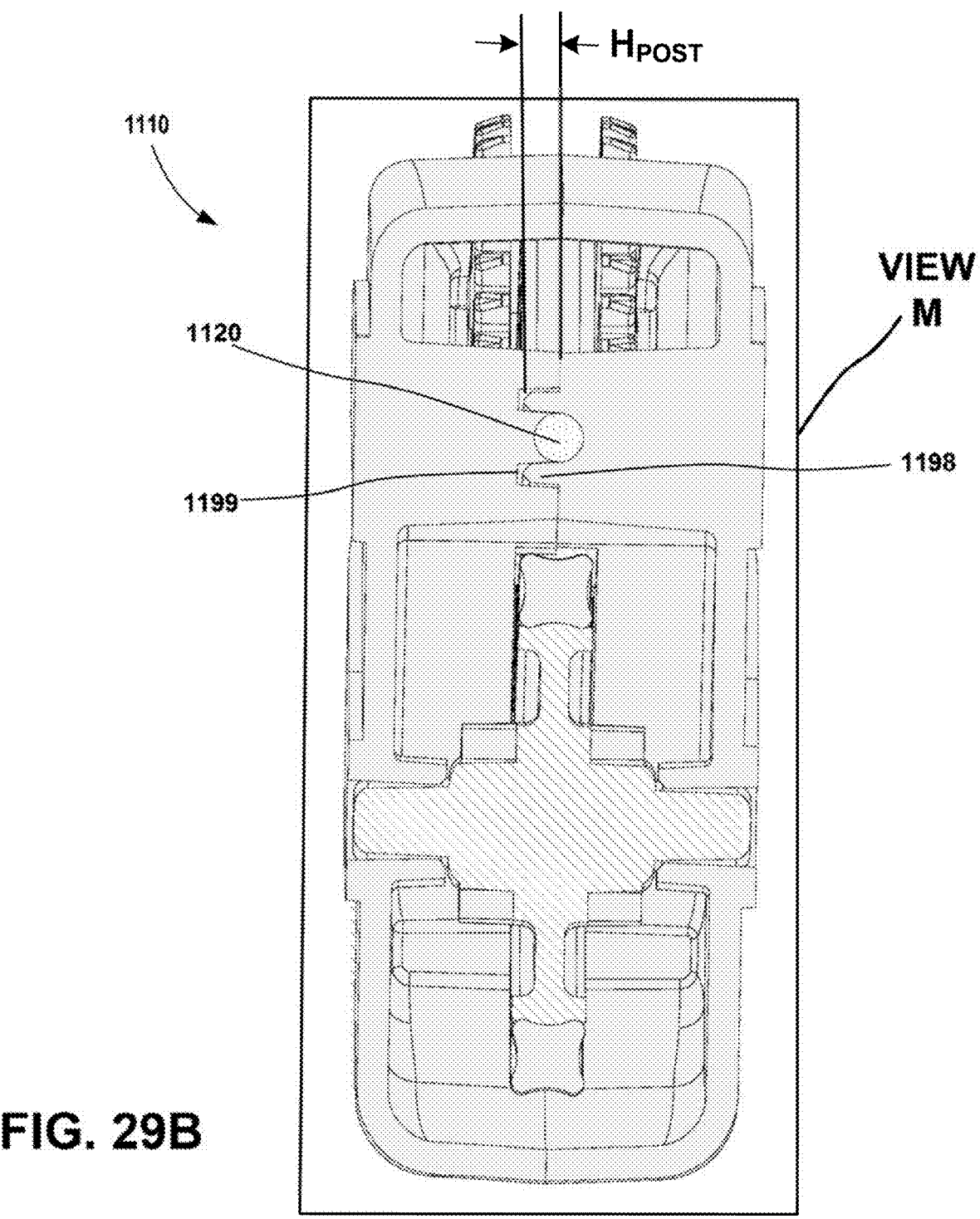
FIG. 29B shows a plan view of the lateral cross-section as View M.

Referring now to FIGS. 26-30B, the power driver 1642 generally includes a flat coil spring 1646, a spring hub 1644, a spring shaft 1648, and a pulley gear 1678 and a gearbox 1668. Inner portions of the left cover 1532 and the right cover 1550 include support features defined therein or therethrough for retaining drive components in their operative arrangement when the left and right cover 1532 and 1550 are attached to each with drive components arranged therein, which is generally shown in FIG. 26. The flat coil spring 1646, the spring hub 1644, the spring shaft 1648, and the pulley gear 1678 when configured in their operative arrangement such as shown in FIGS. 26, 29 and 30B can provide an automated drive force for advancing the guide wire 1512 the primary distance 1566 when the actuator 1660 is actuator by the single hand 1518.

Left cover 1532 and right cover 1550 define a spring end retainer (FIG. 30A), which retains the outer end of the coiled spring 1646 and thereby affixes one end of the flat coil spring to the guide wire body 1530. The flat coil spring 1646 is wound as a flat coil around spring hub 1644, which is disposed on the spring shaft 1648 that is rotatably supported across the inside width of the elongate device advancer by support features formed on inner portions of left cover 1532 and right cover 1550. The spring hub 1644 is interlocked with the spring shaft 1648, such that the spring shaft and spring hub rotate together about a longitudinal axis of the spring shaft. The second end of the flat coil spring 1646 disposed inside the coil is attached to the spring hub, whereas the opposite first end at the beginning of the coil and located outside the coil is attached to the housing 1530 via spring end retainer 1643 (FIG. 30A) as discussed above. Thus, any rotational forces generated via potential energy stored in flat coil spring 1646 are configured to induce rotation about the rotational axis of spring hub 1648 and spring shaft 1648.

As shown in FIGS. 29 and 30A, pulley gear 1678 is also rotatably disposed on spring shaft 1648 adjacent to spring hub 1644 with the spring shaft extending through a central axis of the pulley gear and interlocked therewith, such that the pulley gear rotates about the axis of the spring shaft and along with rotation of the spring shaft. Thus, any rotational forces or moments applied by flat coil spring 1646 inducing rotation of spring hub 1644 about its central axis along with rotation of spring shaft 1648 also induce rotation of pulley gear 1678 therewith. When flat coil spring 1646 is wound tightly about spring hub 1644 such that it retains potential energy for driving the automated drive 1640 when actuated, spring 1646 applies a drive moment about spring shaft 1648 via spring hub 1644, which likewise applies the drive moment M to pulley gear 1678 about the axis of the spring shaft. However, as shown in FIGS. 30A and 308, actuator 1660 is operatively coupled with a lock 1658 that engages pulley gear teeth 1679 located along a perimeter portion of the pulley gear 1678, which blocks or stops rotation of the pulley gear along with rotation of spring shaft 1648 connected thereto and prevents operation of the automated drive 1240 until lock 1658 is disengaged from the pulley gear teeth.

As shown in FIG. 30B, actuator 1660 is pivotably connected with lock 1658 such that movement of actuator 1660 via a finger of the single hand 1518 moves lock 1658 in an opposite direction and simultaneously disengages the lock from engagement with pulley gear teeth 1679. Accordingly, absent engagement of lock 1658 with pulley gear 1678, pulley gear can freely rotate with pulley hub 1644 and pulley shaft 1648 about the axis of the pulley shaft according to the drive moment M transmitted to the pulley gear from flat coil spring 1646. Gear teeth 1679 are configured to engage corresponding gear teeth on floater gear 1666 when actuated to drive rotation of the floater gear along with forcing the floater gear into a rotational, driving engagement with drive gear 1654 as discussed below along with FIGS. 38 and 39.

It is understood that the pitch radii of meshing gear teeth 1679, the sets of gear teeth disposed along floater gear 1666, and the gear teeth disposed along drive gear 1654 can vary with respect to each other according to various parameters and preferences, such as the rotational spring force provided by flat coil spring 1646 and duration of drive force when actuated, the desired primary advancement length 1566 for use of the elongate device advancer 1510 with a particular surgical device or types of devices, and/or pushability and related parameters for the particular guide wire and its usage. Drive chain and related modifications can fine tune operational characteristics of the automated drive 1640, such as mechanical advantage features, drive duration that can be provided by the stored potential energy and spring parameters, and drive forces applied to the guide wire 1512 for automated advancement.

Figure 39:
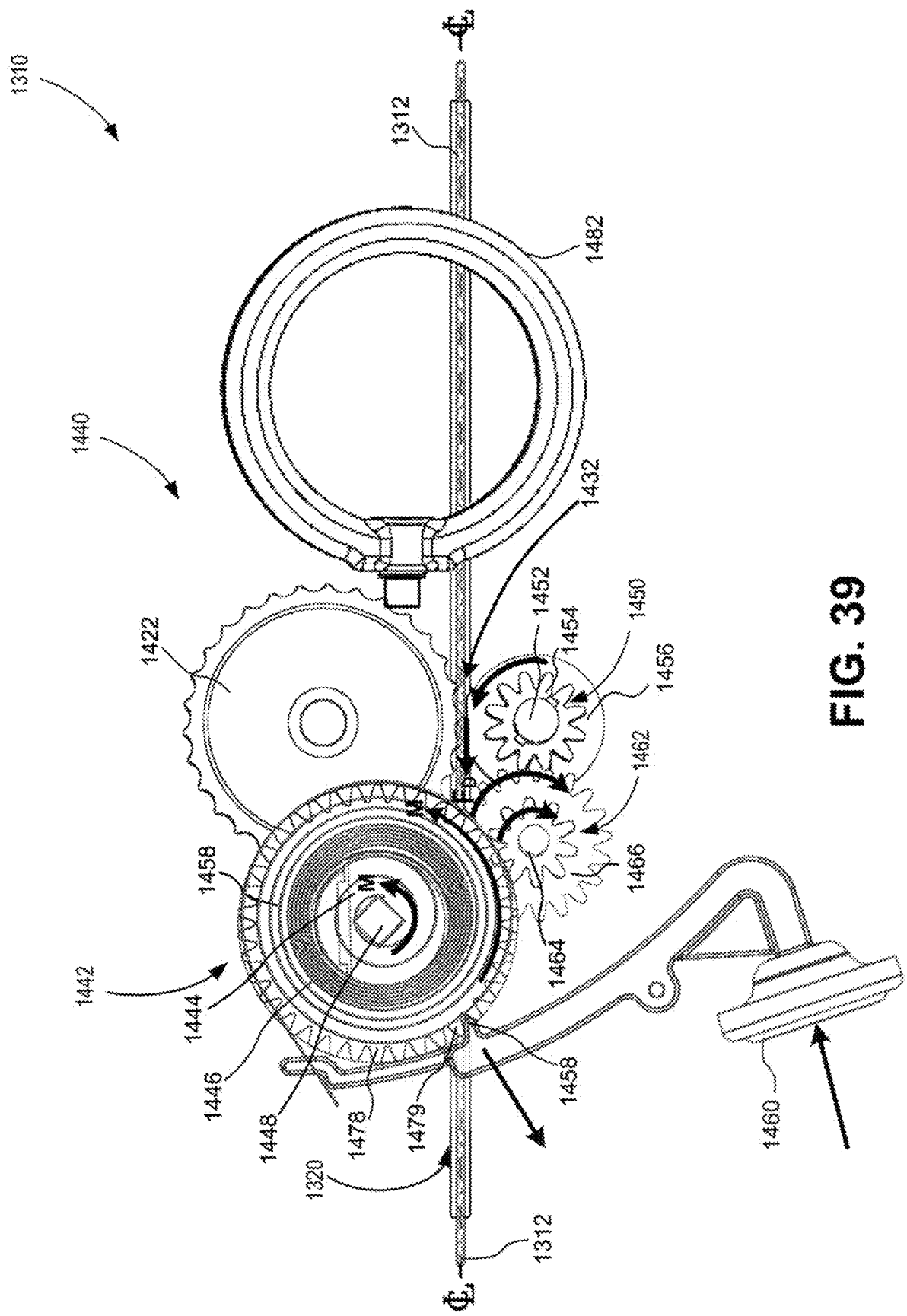
FIG. 39 is a left plan view similar to FIGS. 37A and 37B, but without showing housing components including gearbox plates, covers or the stylet body to expose more clearly the example arrangement and interactions of drive components of the elongate device advancer of FIG. 37A.
Figure 41:
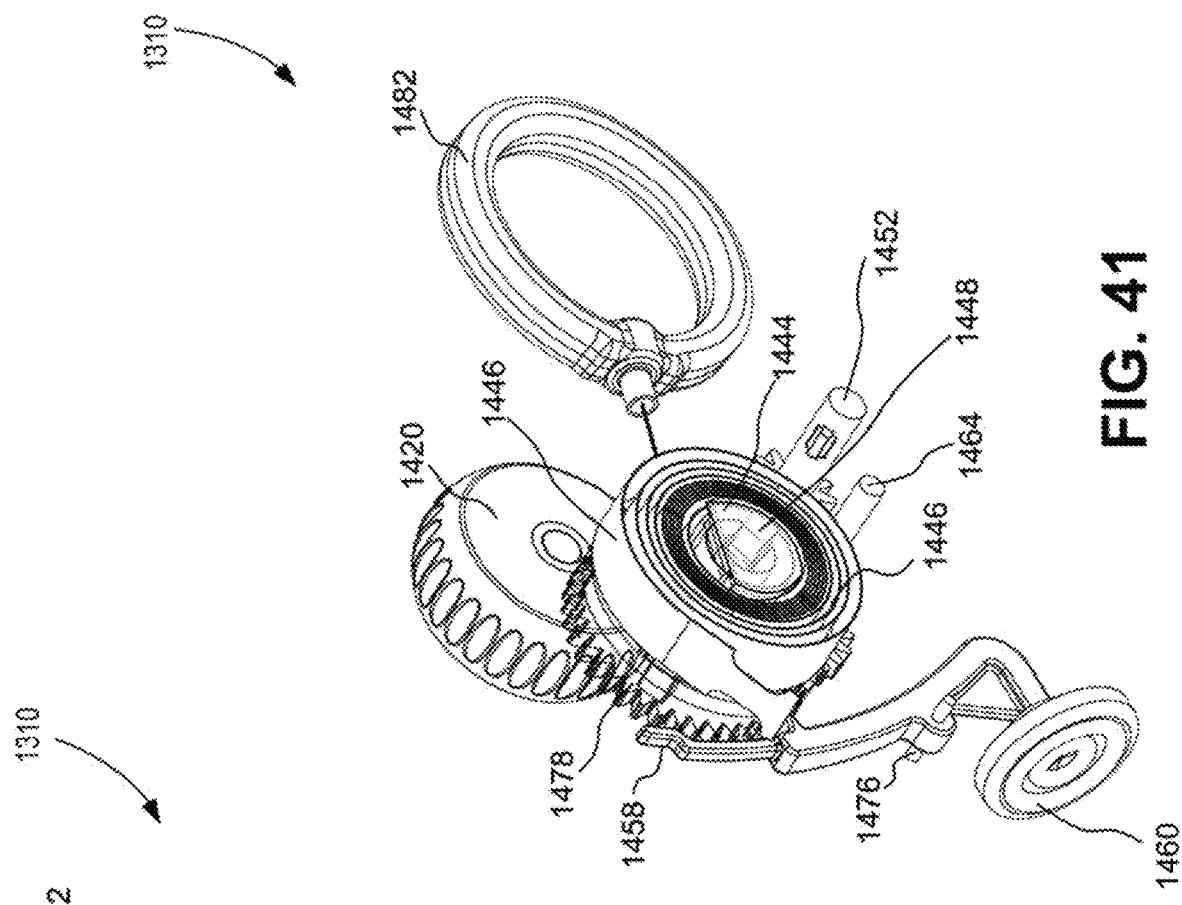
FIGS. 40 and 41 show assembled drive components with and without the gearbox housing components of the elongate device advancer of FIG. 37A.
Figure 40:
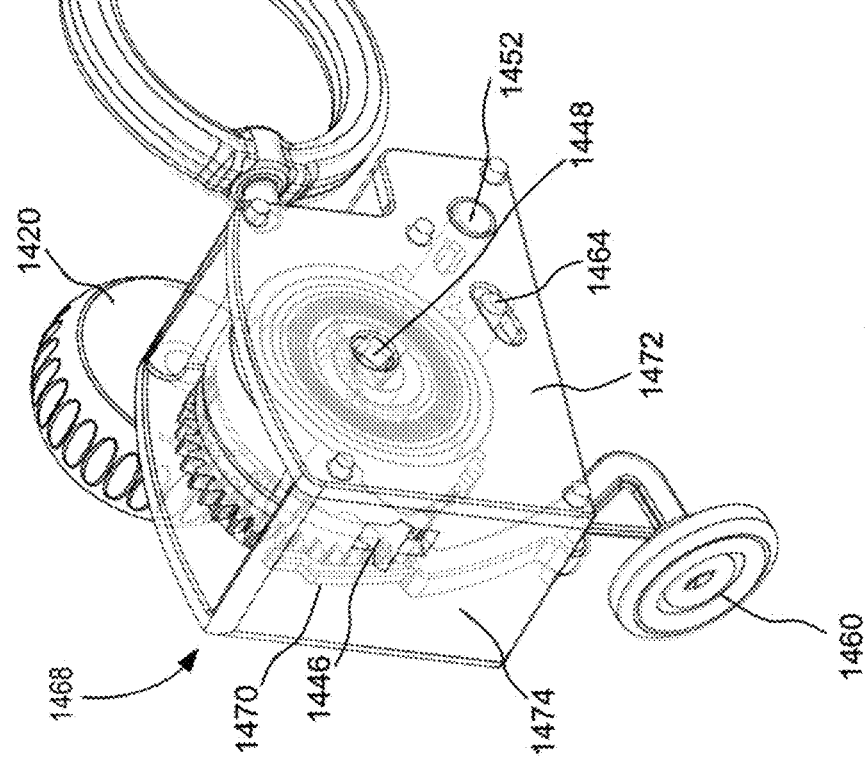
Figure 42:
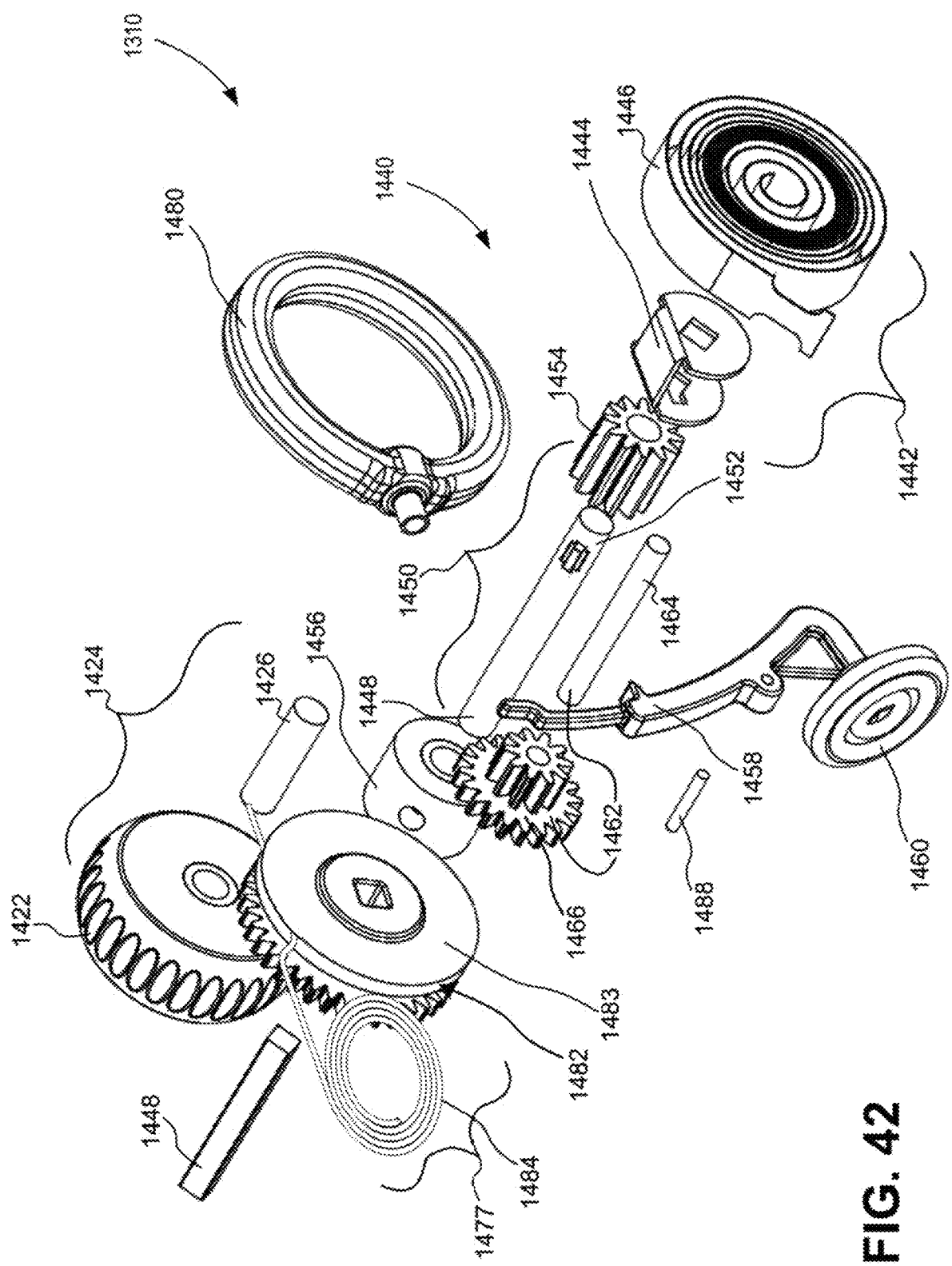
FIG. 42 is an exploded view of drive components of the elongate device advancer of FIG. 37A.
Figure 43:
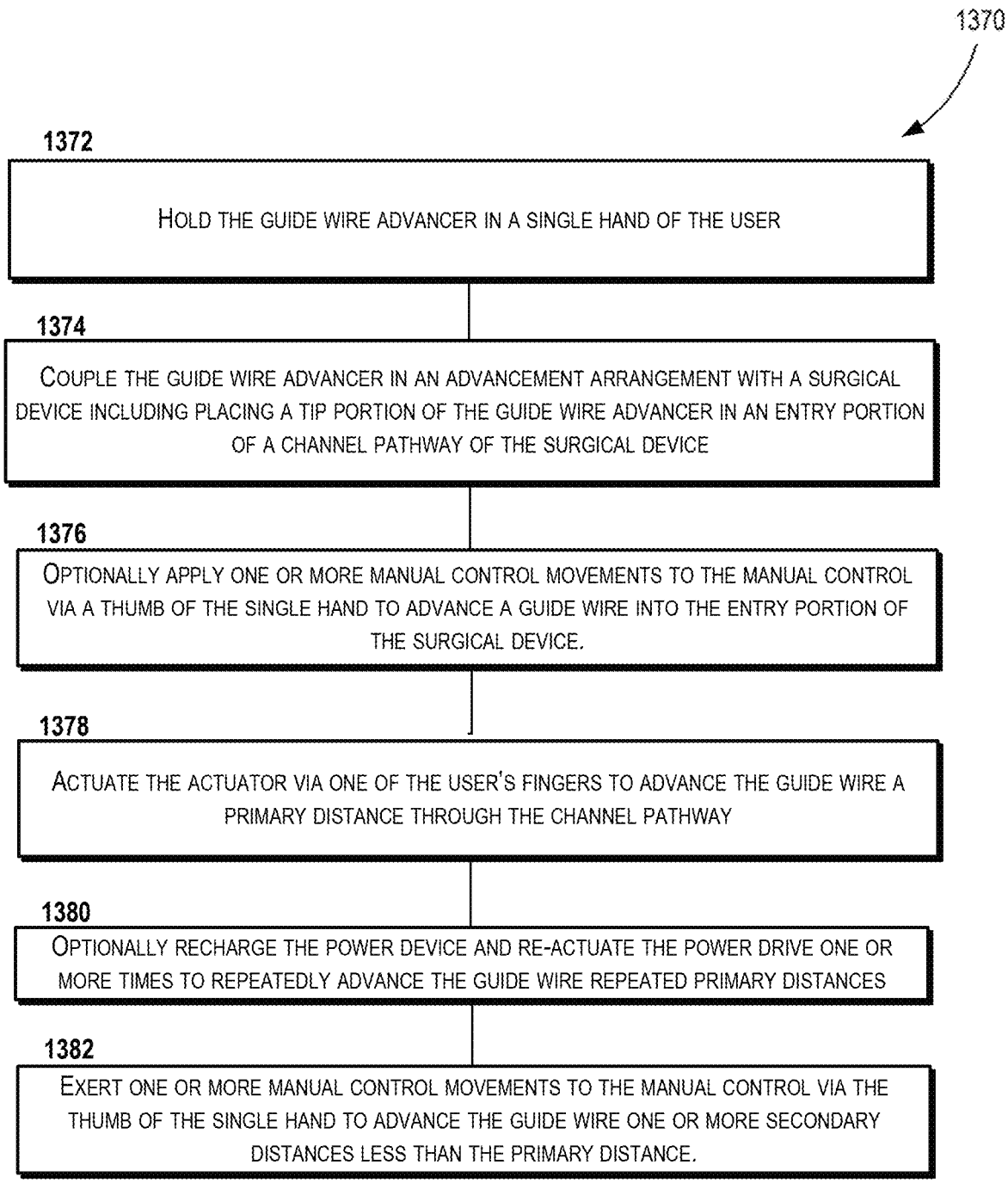
FIG. 43 is a schematic representation of a method for advancing an elongate medical device, such as a guide wire, through the channel pathway of a medical device using the suture placement device of FIG. 3D as an illustrative example along with aspects and features of elongate device advancers discussed herein, such as the elongate device advancer of FIGS. 36A & 37A.
Figure 44:
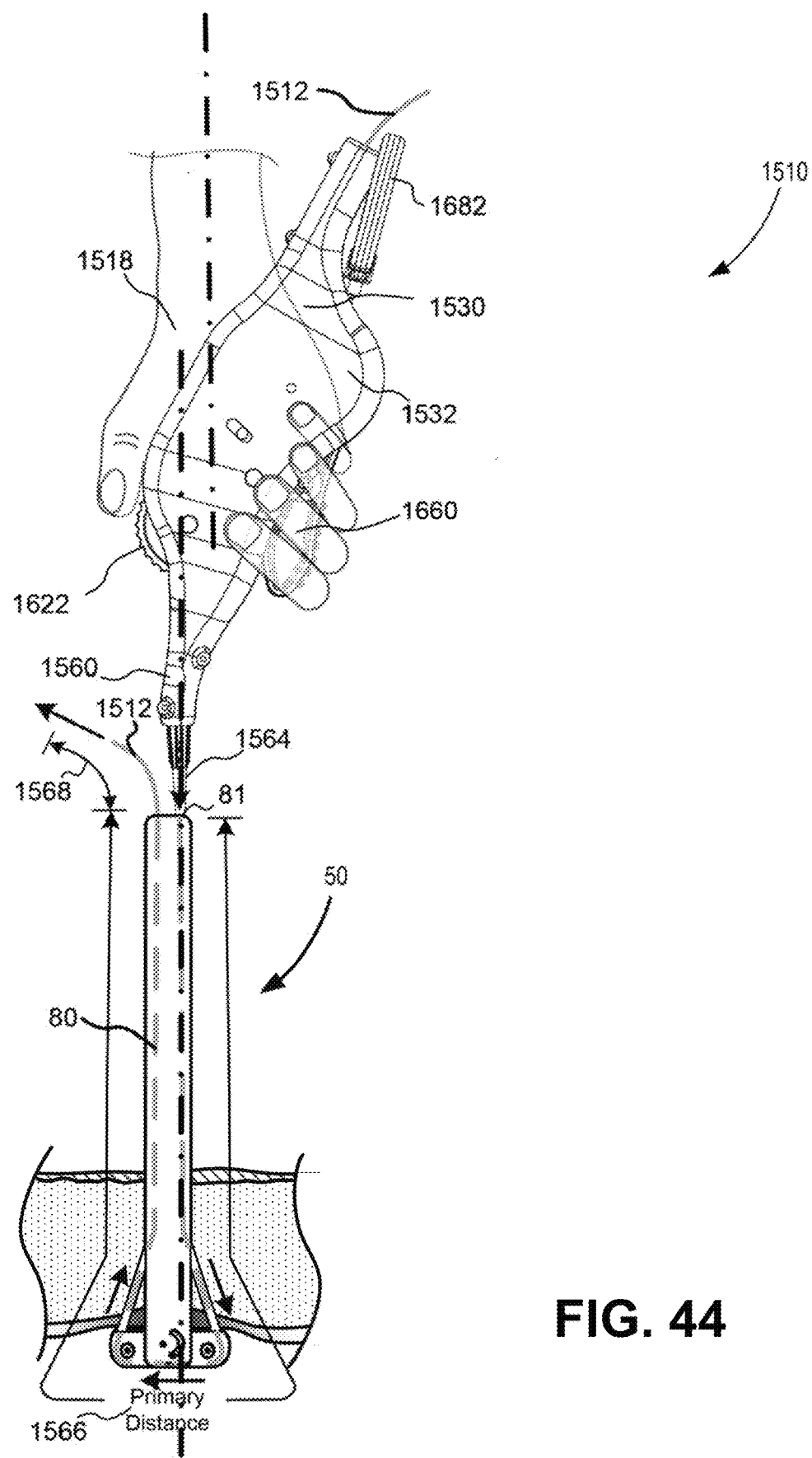
FIG. 44 is a plan view of another example embodiment of an elongate device advancer according to aspects, features and inventive concepts described herein illustrating advancement of a guide wire through the example suture placement device of FIG. 3D.
Figure 45:
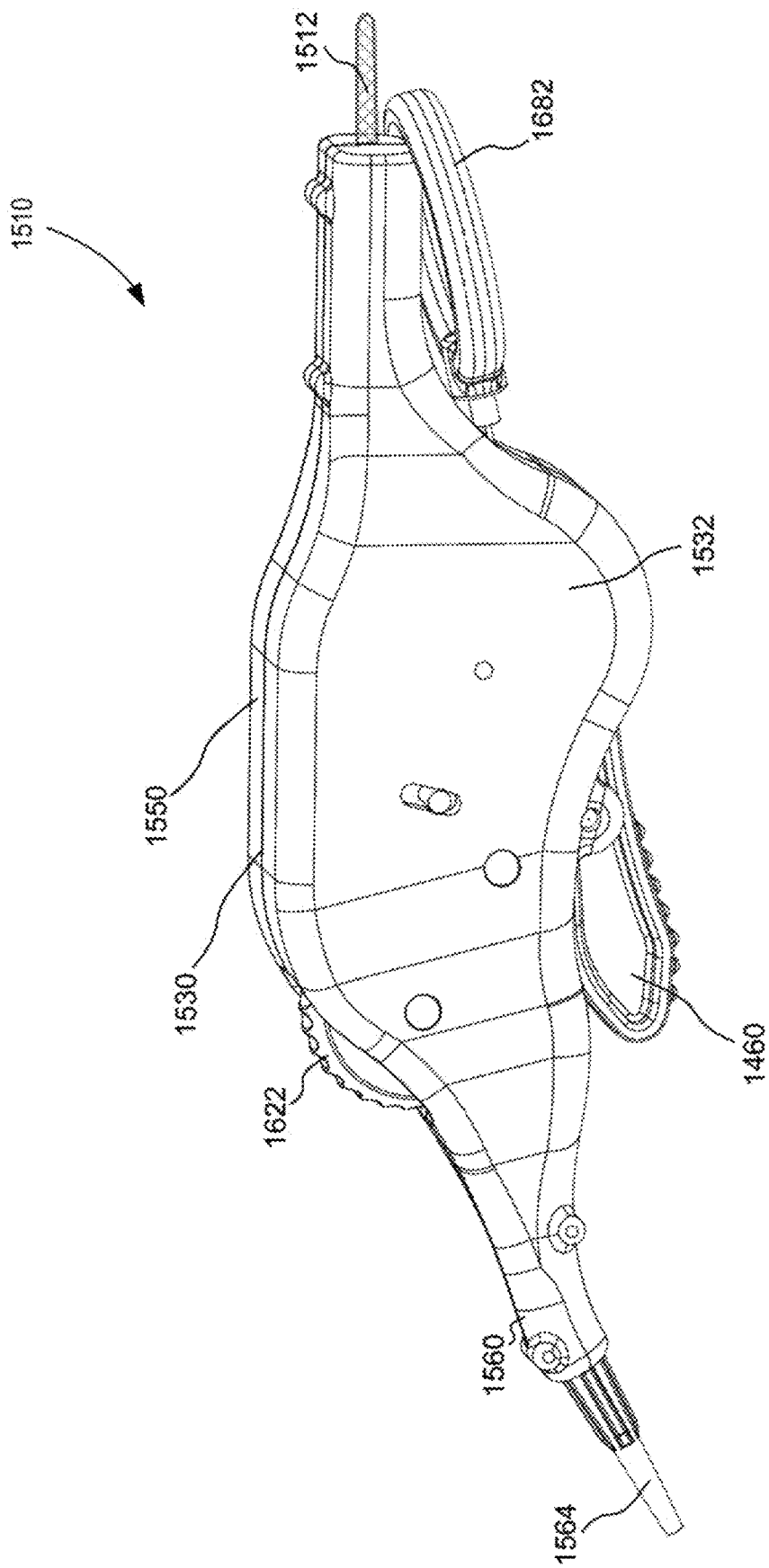
FIG. 45 is a left perspective view of the elongate device advancer of FIG. 44A.
Figure 46:
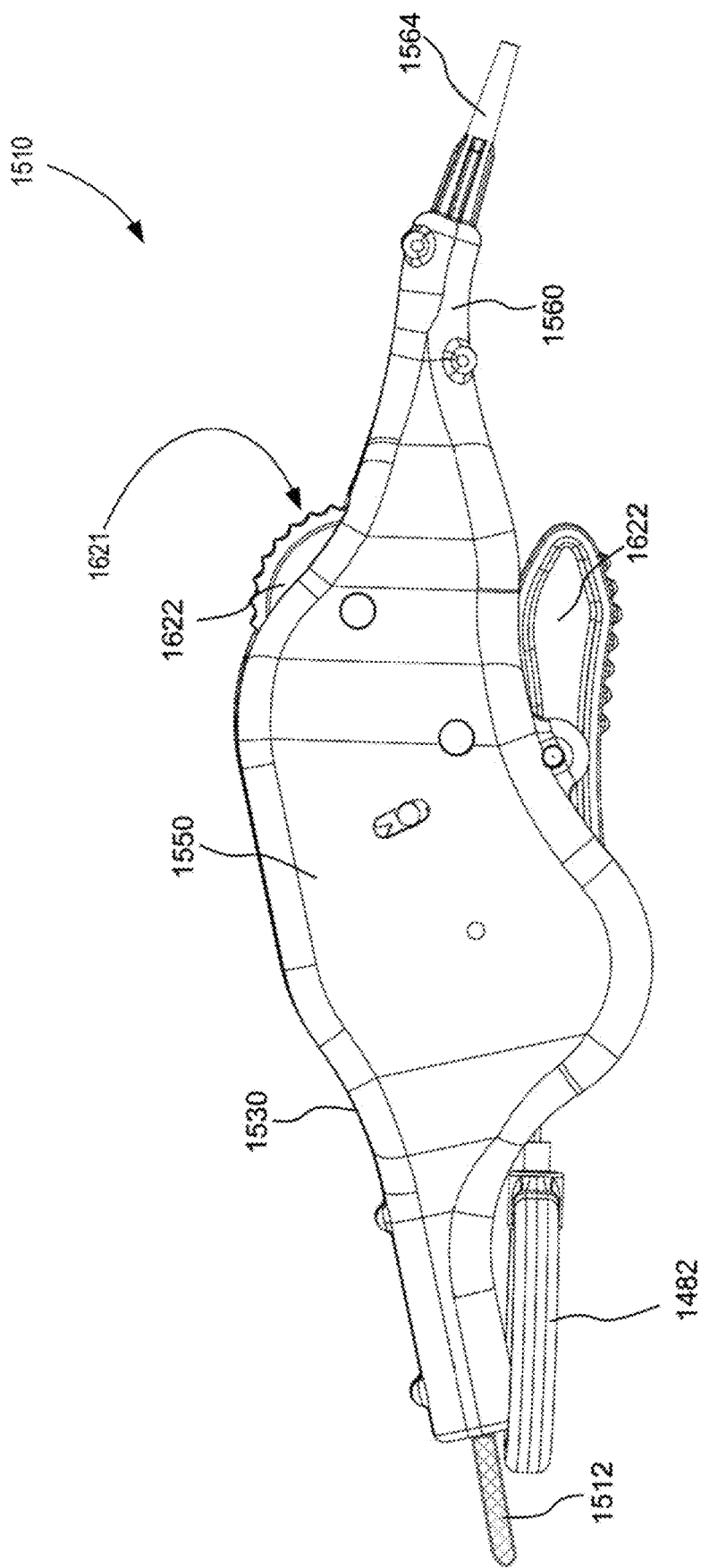
FIG. 46 is a right-side plan view of the elongate device advancer of FIG. 44A.
Figure 47:
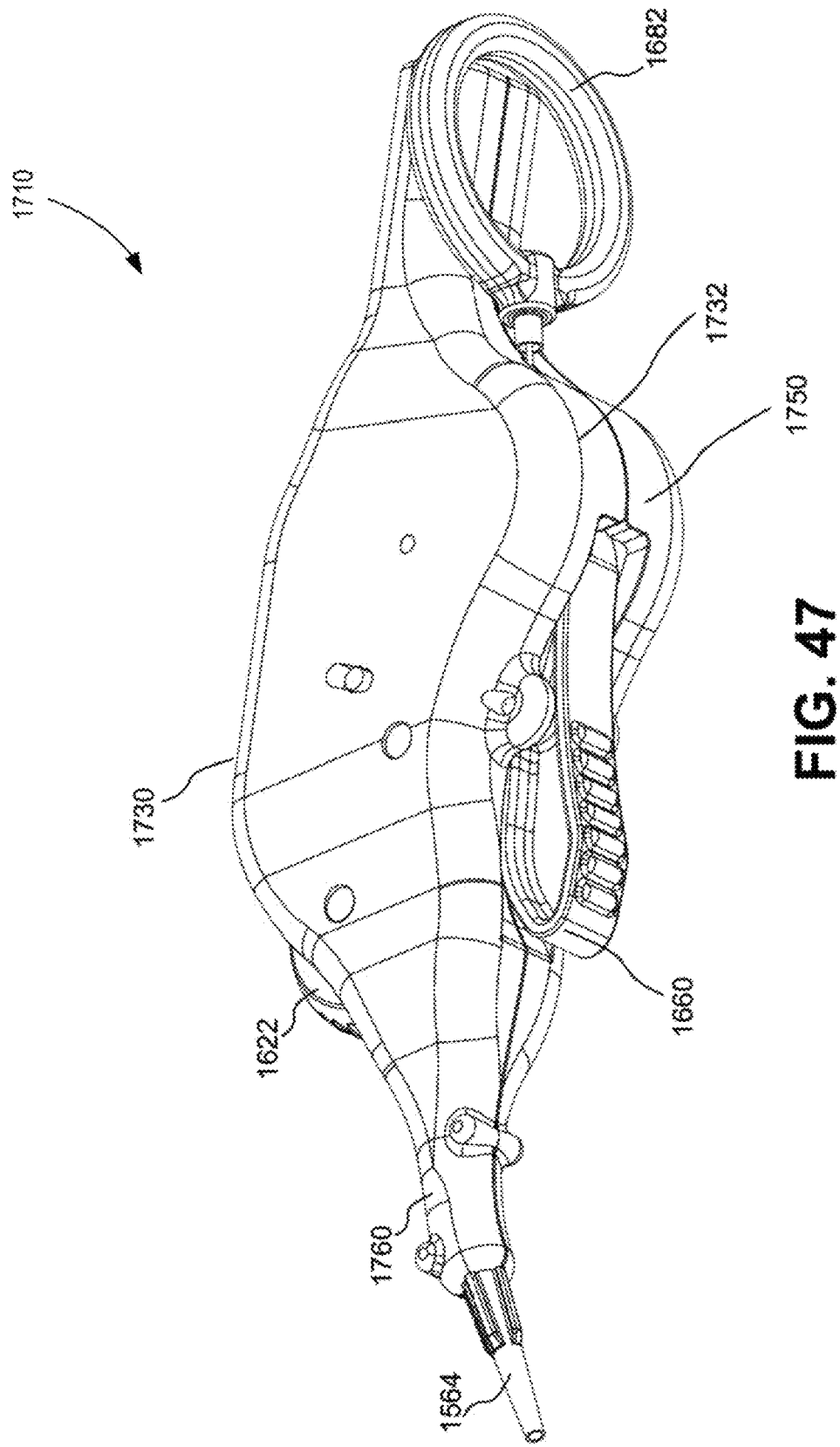
FIG. 47 is a bottom left perspective view of the elongate device advancer of FIG. 44A.
Figure 48:
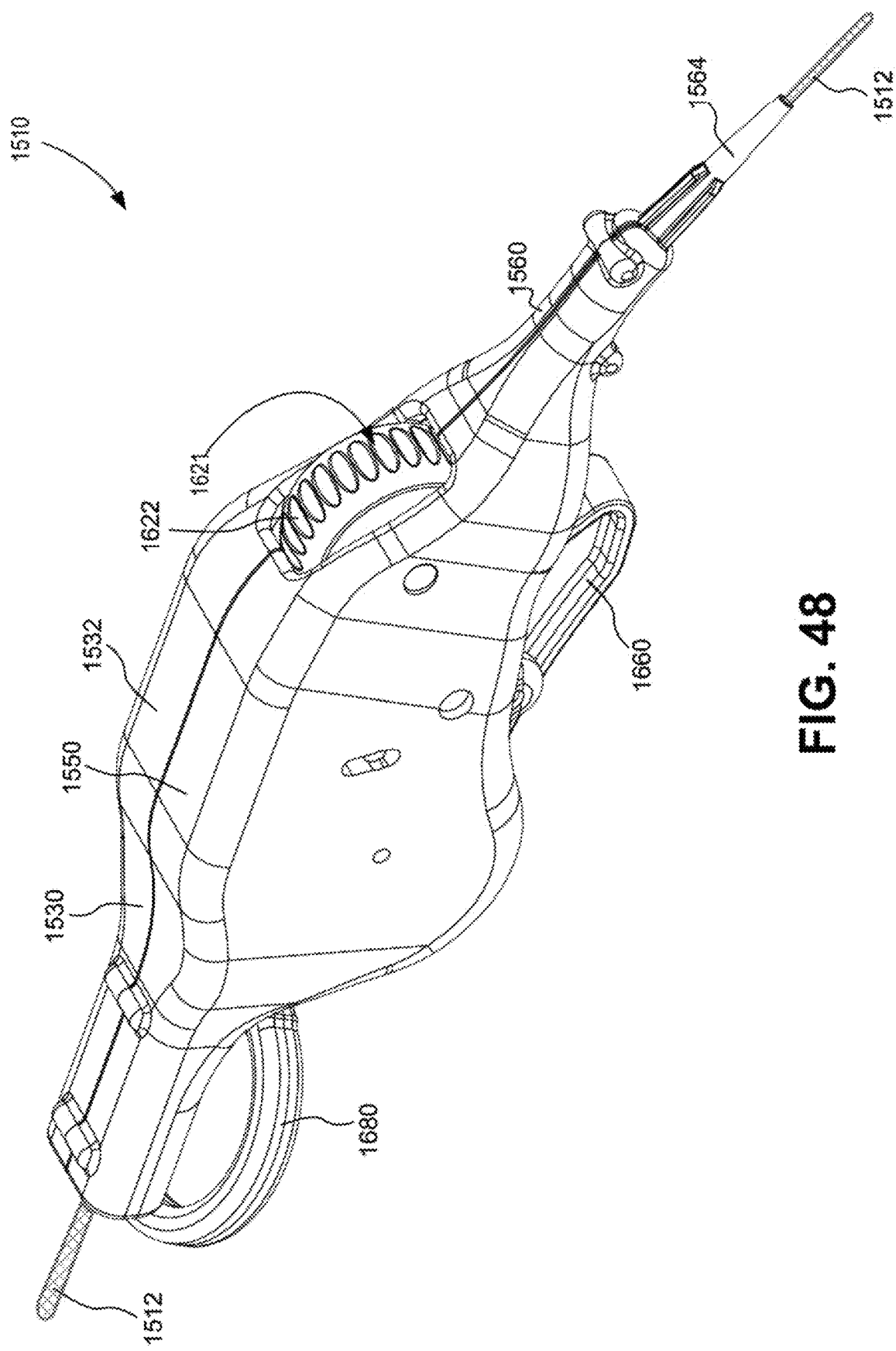
FIG. 48 is a front right perspective view of the elongate device advancer of FIG. 44A.
Figure 49:
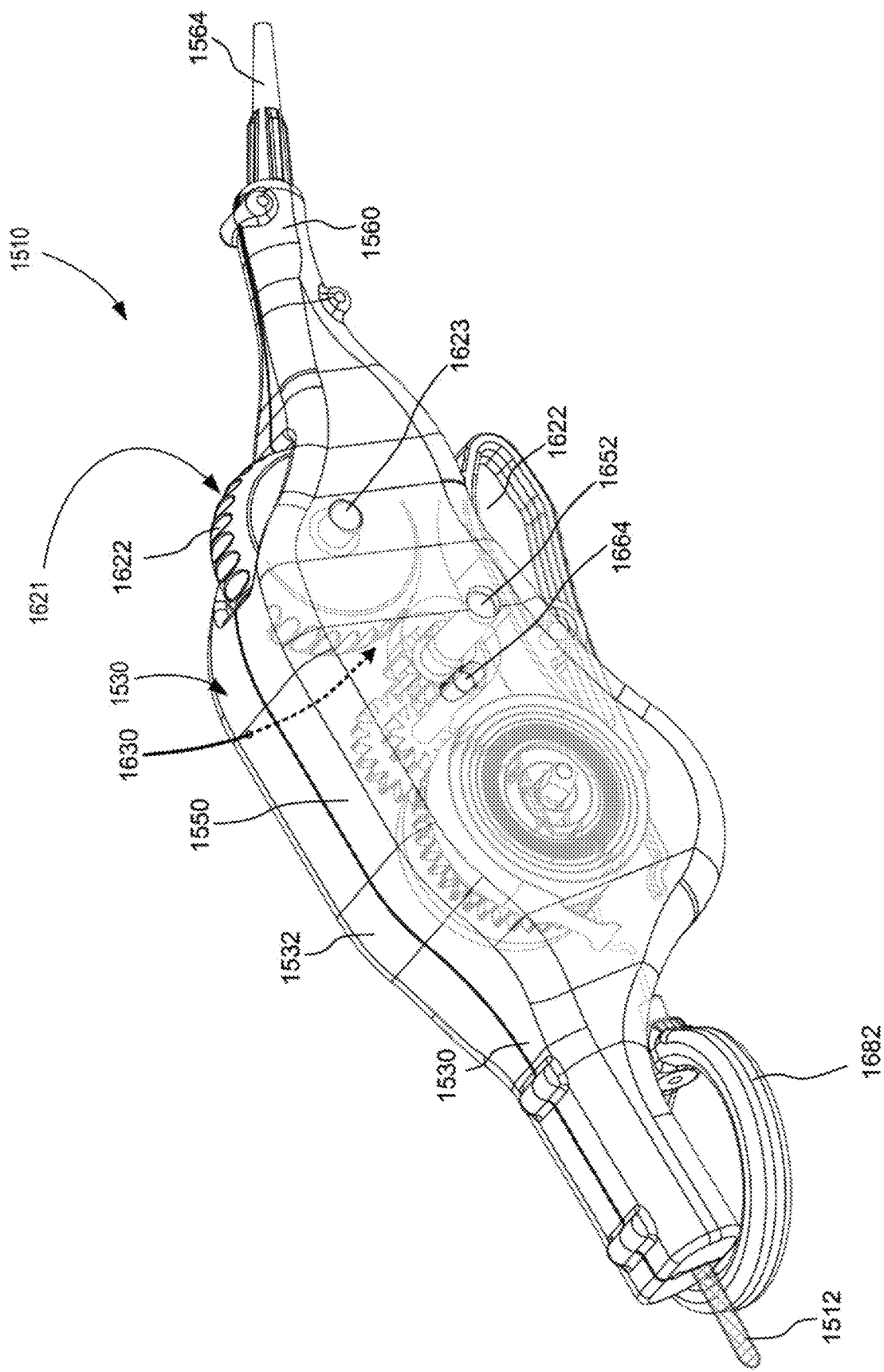
FIG. 49 is a right rear perspective view of the elongate device advancer of FIG. 44A with the right cover partially transparent to show an example arrangement of internal drive components.
Figure 50:
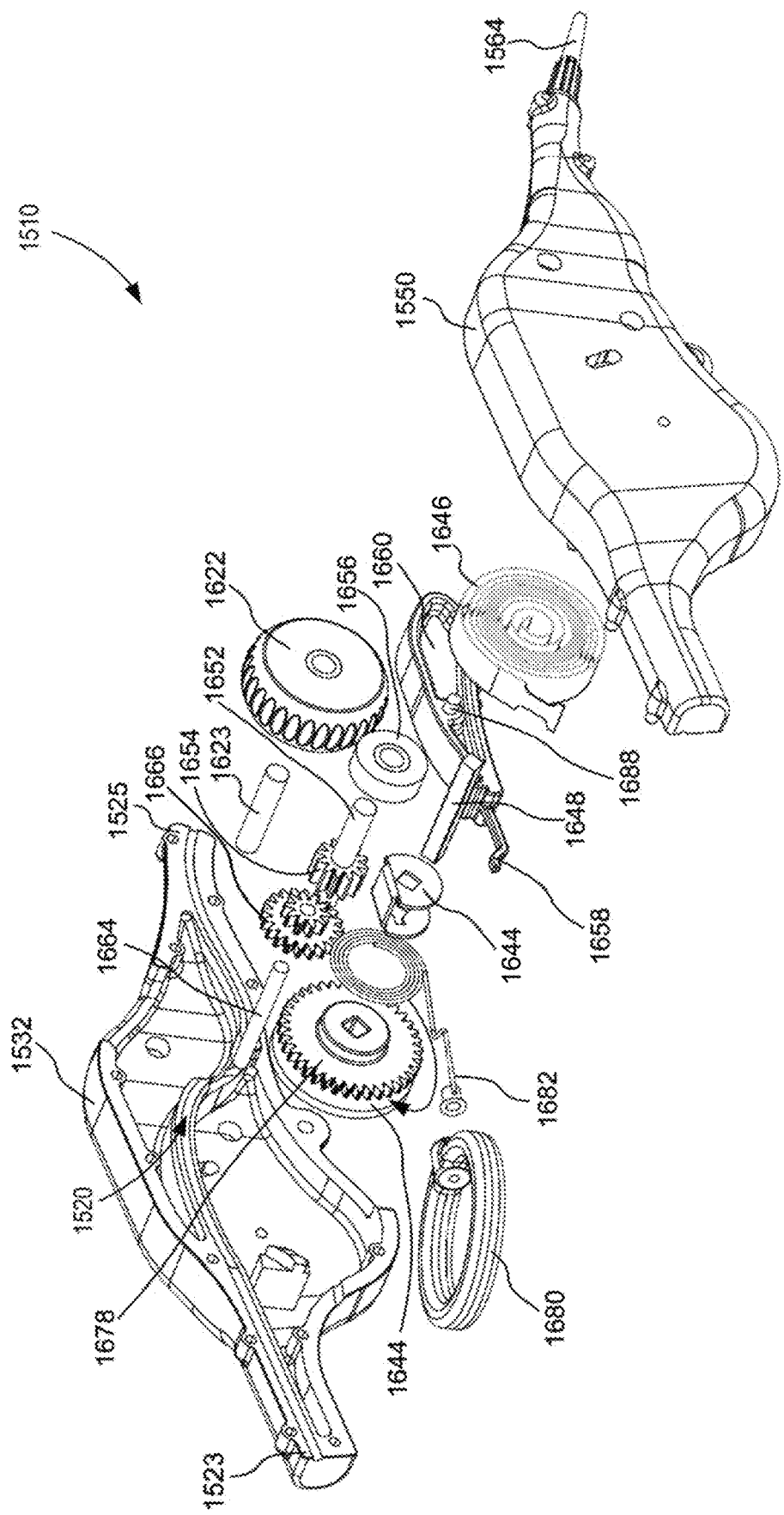
FIG. 50 is a right rear exploded perspective view of the elongate device advancer of FIG. 44A.
Figure 51:
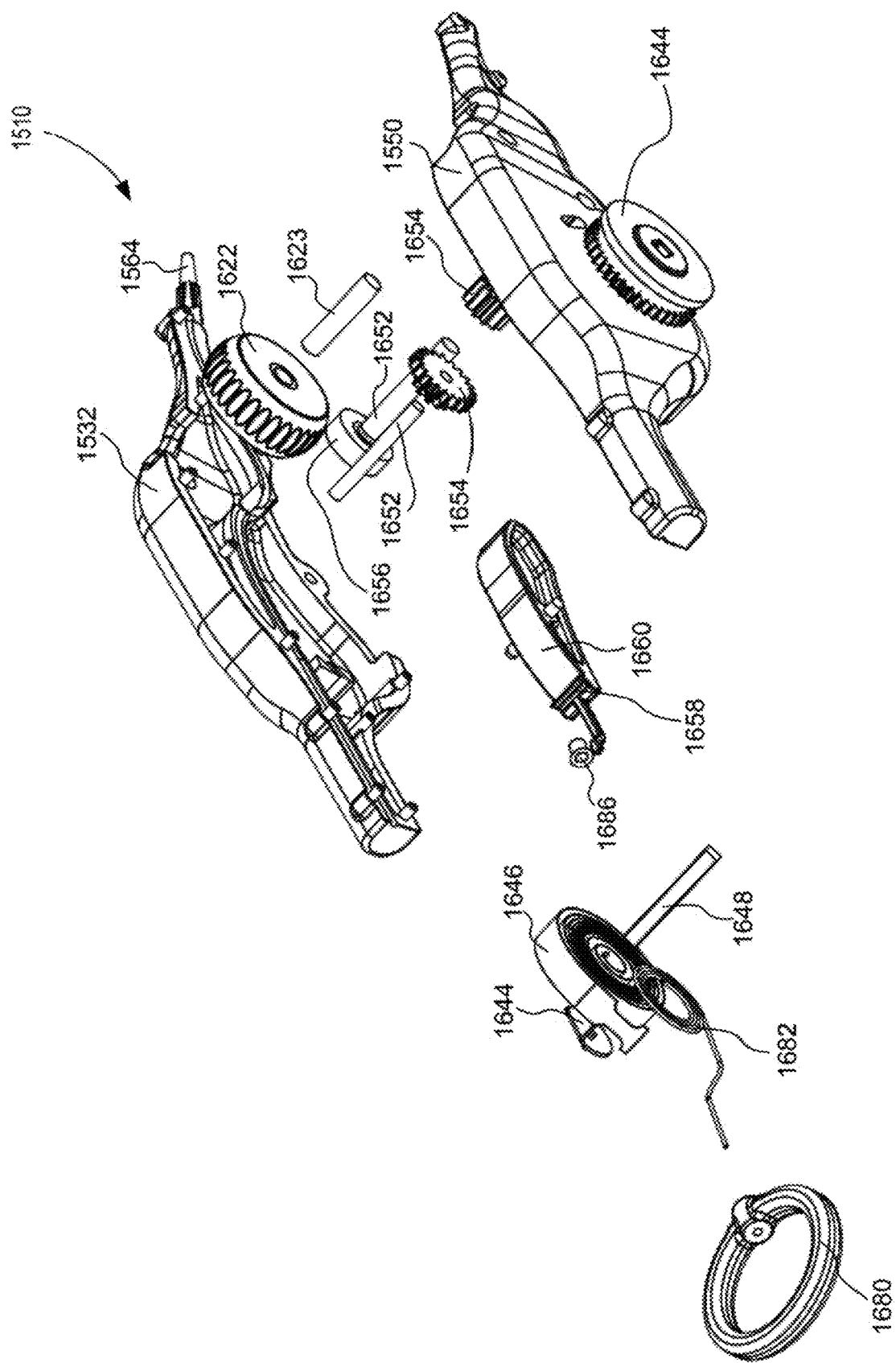
FIG. 51 is a rear bird's eye exploded perspective view of the elongate device advancer of FIG. 44A.
Figure 52:
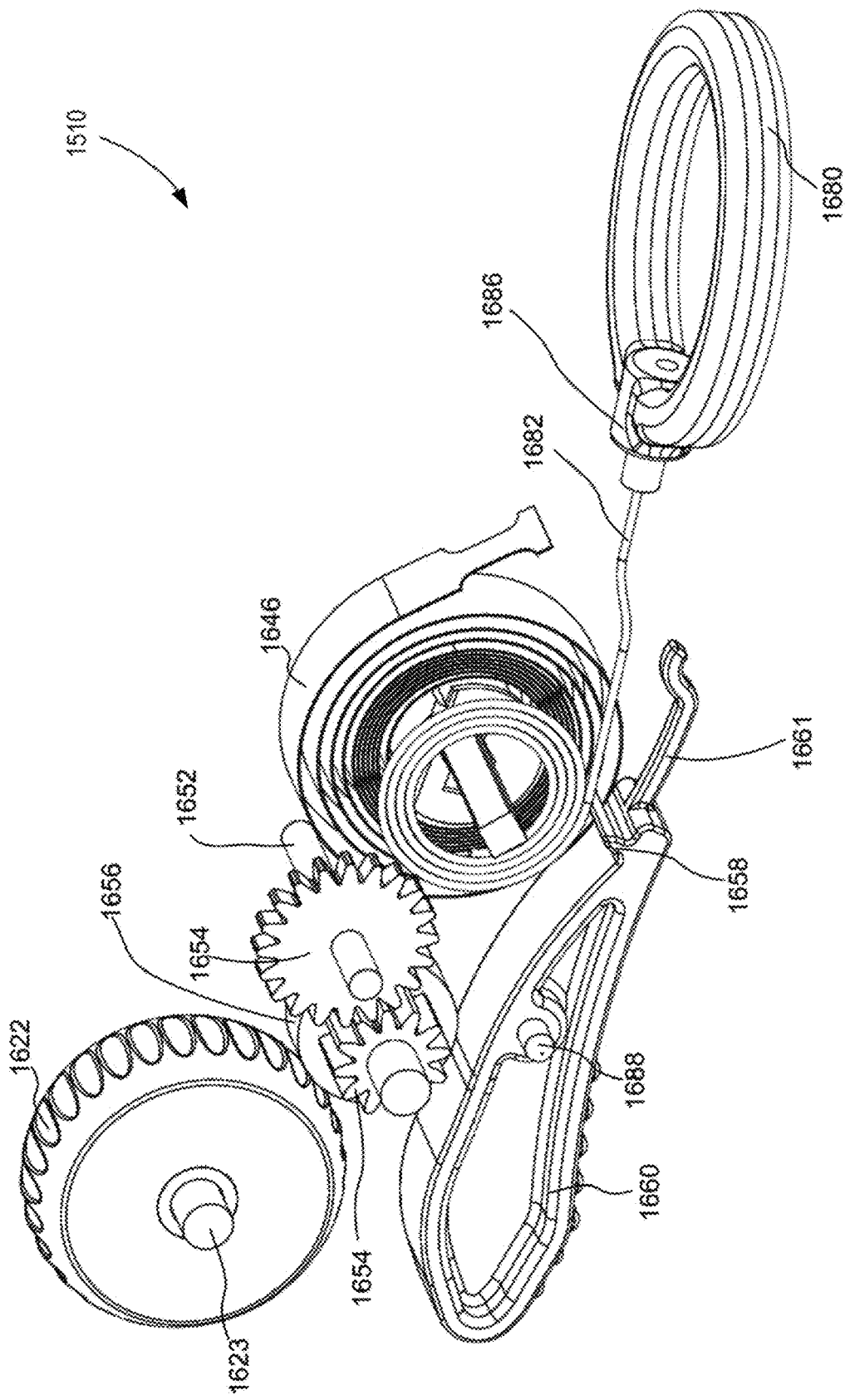
FIG. 52 is a left rear perspective view of internal components of the elongate device advancer of FIG. 44A shown with the housing removed.
Figures 53A, 53B:
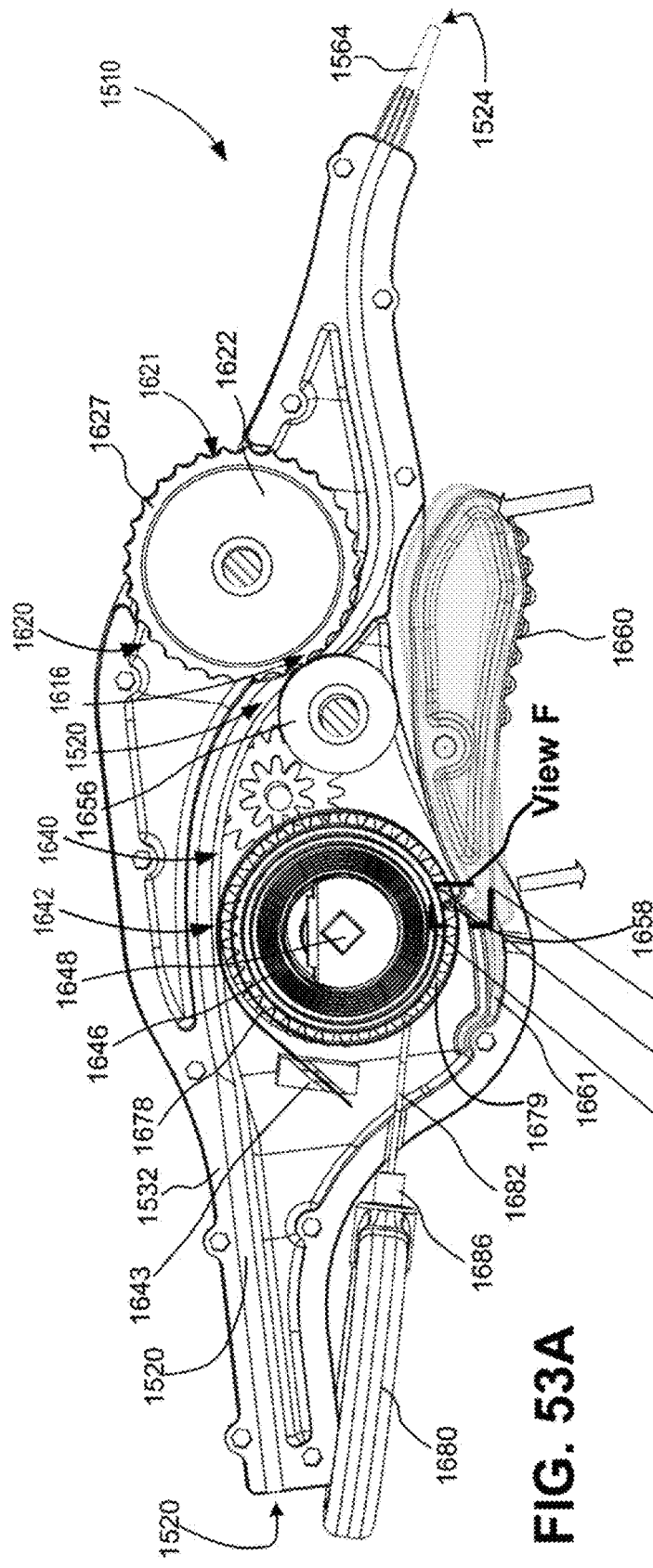
FIG. 53A is a right-side plan view of the elongate device advancer of FIG. 44A shown with the right housing removed to expose an example arrangement of internal components along with schematic representations pertaining to example operation of the actuator and automatic drive lock of the example configuration of FIG. 44A, which is shown without a guide wire arranged therewith.
FIG. 53B is a close view of a portion of the actuator and automatic drive lock as identified in FIG. 53A along with the schematic representations of FIG. 53B.
Figure 54:
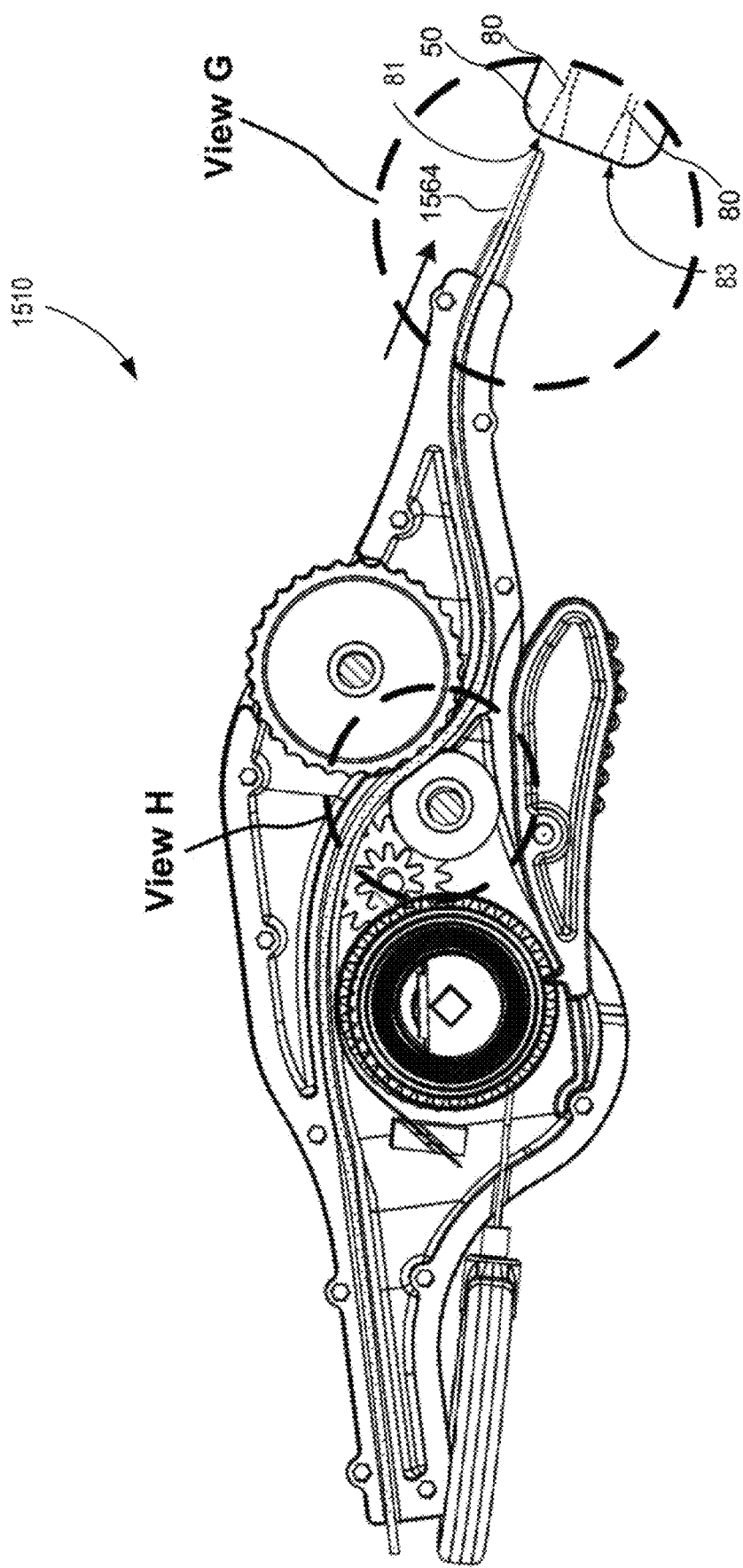
FIG. 54 is another right-side plan view of the elongate device advancer of FIG. 44A that is similar to FIG. 53B without including the schematic representations pertaining to the actuator and automatic drive lock, which includes schematic representations pertaining to routing and advancement of a guide wire along with identifying environmental information for close views (View G & View H) shown in more detail in FIGS. 55, 57 and 58.
Figure 56:
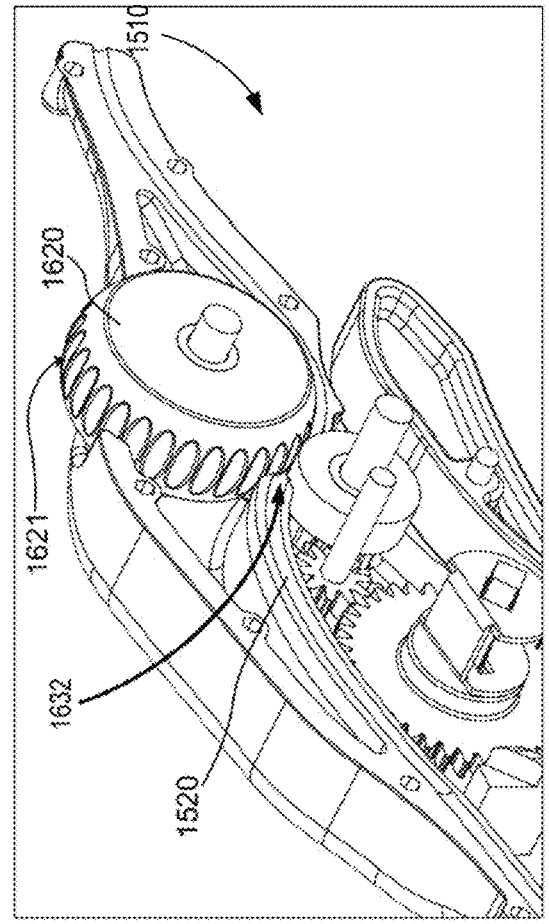
FIG. 56 is an upper right perspective of the elongate device advancer of FIG. 44A shown with the right cover removed providing a view of the nip portion of the drive mechanism.
Figure 55:
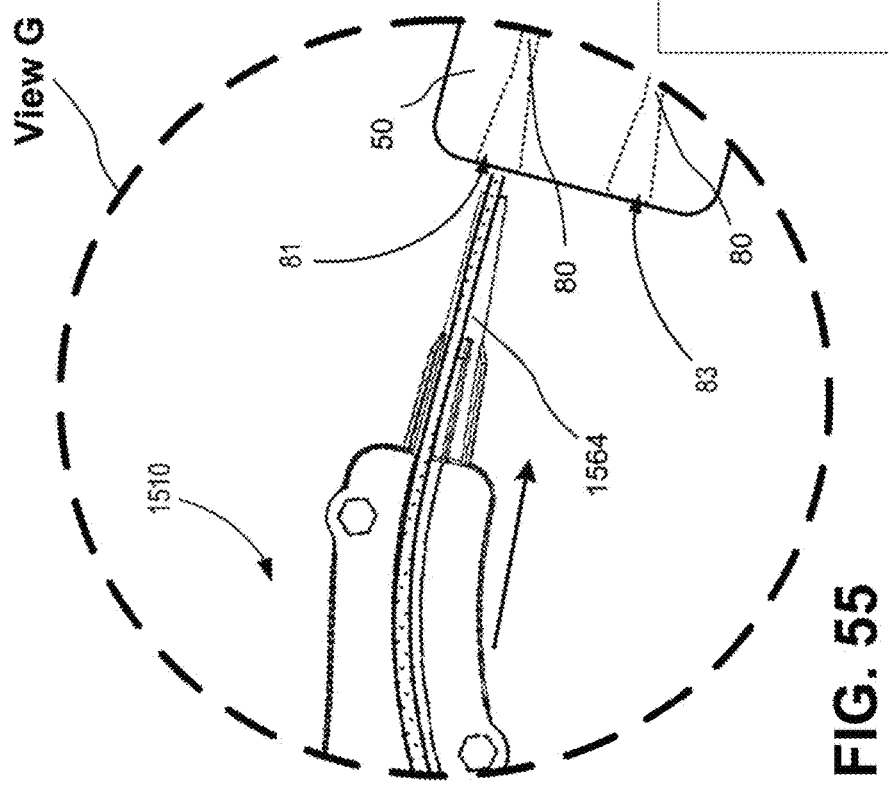
FIG. 55 is a close view of a tip portion of the elongate device advancer of FIG. 44A as identified in FIG. 54 (View G) showing a schematic representation for coupling with the example medical device shown configured as a suture placement device.
Figure 59:
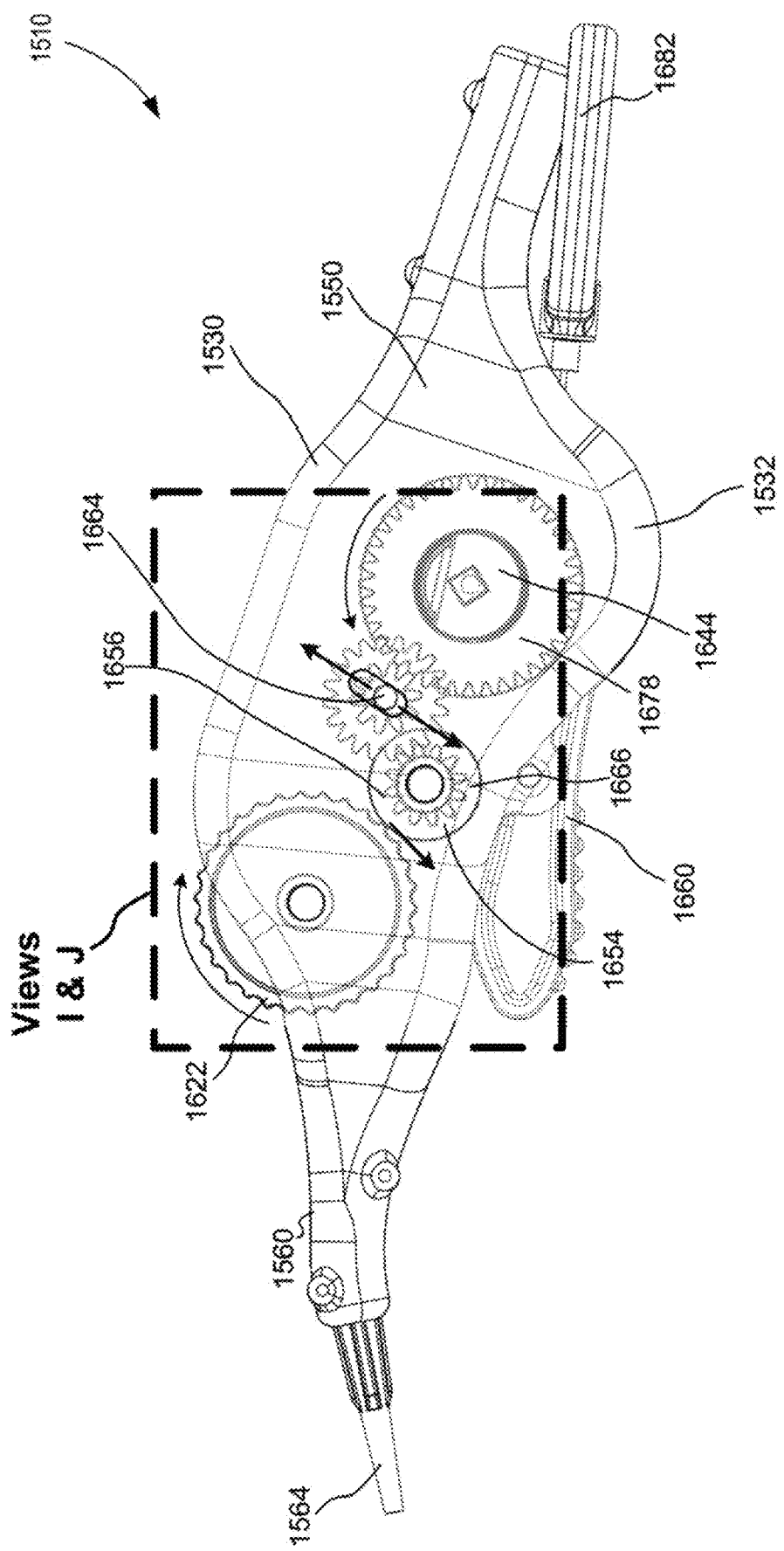
FIG. 59 is a left side plan view of the elongate device advancer of FIG. 44A with the left cover shown as partially transparent to expose the example arrangement of drive components and schematically represent aspects and features pertaining to the transmission switch feature including example movements of the float gear as indicated in subsequent Views I & J shown in FIGS. 60 and 61.
Figure 60:
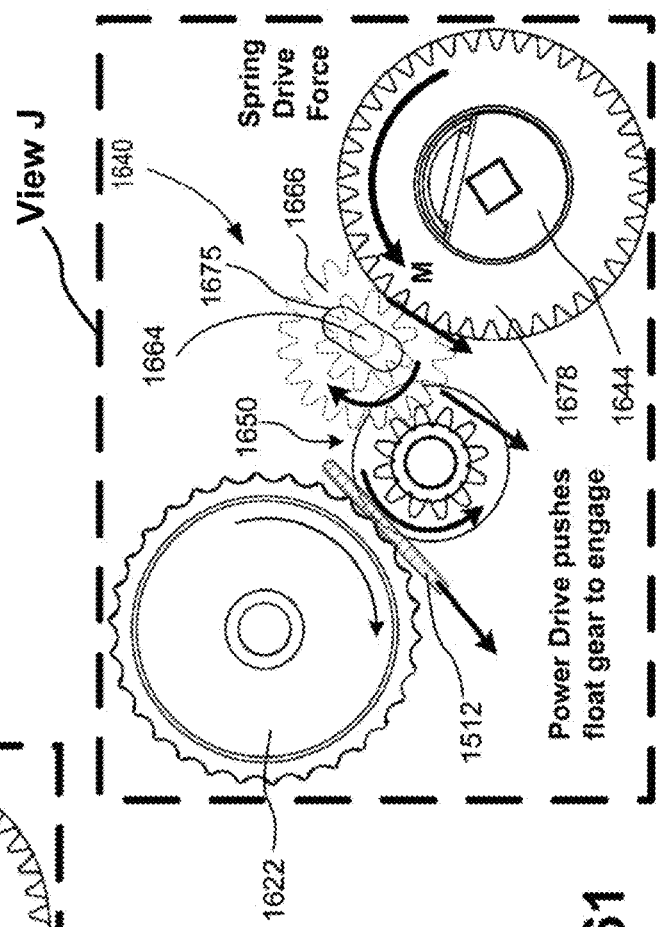
FIG. 60 shows View I identified in FIG. 59 and schematically represents additional potential options pertaining to automatic disengagement of the automatic drive in response to manual drive operations including movement aspects of the float gear and related transmission switch options.
Figure 61:
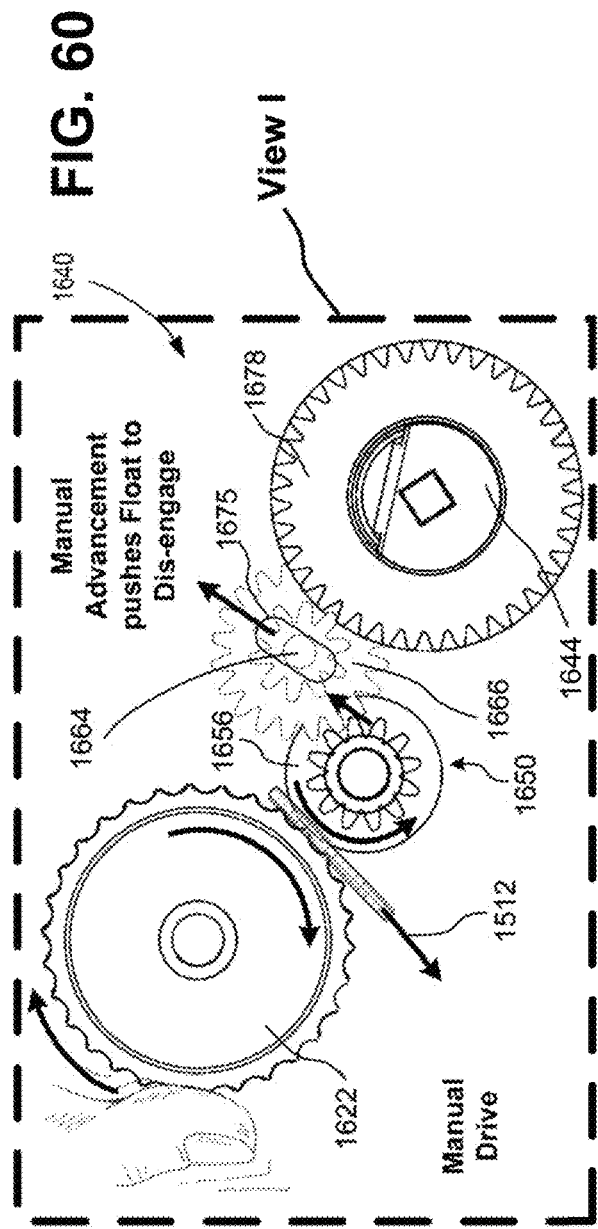
FIG. 61 shows View J identified in FIG. 59 and schematically represents additional potential options pertaining to automatic engagement of the automatic drive in response to actuation of the actuator to enable automatic drive operations selected by the user including movement aspects of the float gear and transmission switch options and features.

For example, in the configuration shown in FIGS. 38 and 39, pulley gear 1678 has a large pitch radius for its mesh teeth 1679 with respect to the comparatively small pitch radius of mesh teeth on floater gear 1666 engaged by mesh teeth 1679. As such, a single rotation of pulley gear 1678 drives multiple rotations of floater gear 1666 with a lesser force applied than if the pitch radius of mesh teeth 1679 were smaller. However, floater gear 1666 applies mechanical advantage benefits via transmitting moment applied to it by pulley gear 1678 to drive gear 1654 using an attached gear having a large pitch radius to mesh with the drive gear and increase the force applied to the gear teeth of drive gear 1654 by a corresponding mechanical advantage factor. In other words, the rate at which drive force can be applied via the flat coil spring for the amount of potential energy its stores and the force ultimately applied to the guide wire as a drive force can be modified and fine-tuned as appropriate for usage of the elongate device advancer 1510 with different types and configurations of surgical devices according to mechanical advantage, gear ratios and related drive train principles.

Figure 34:
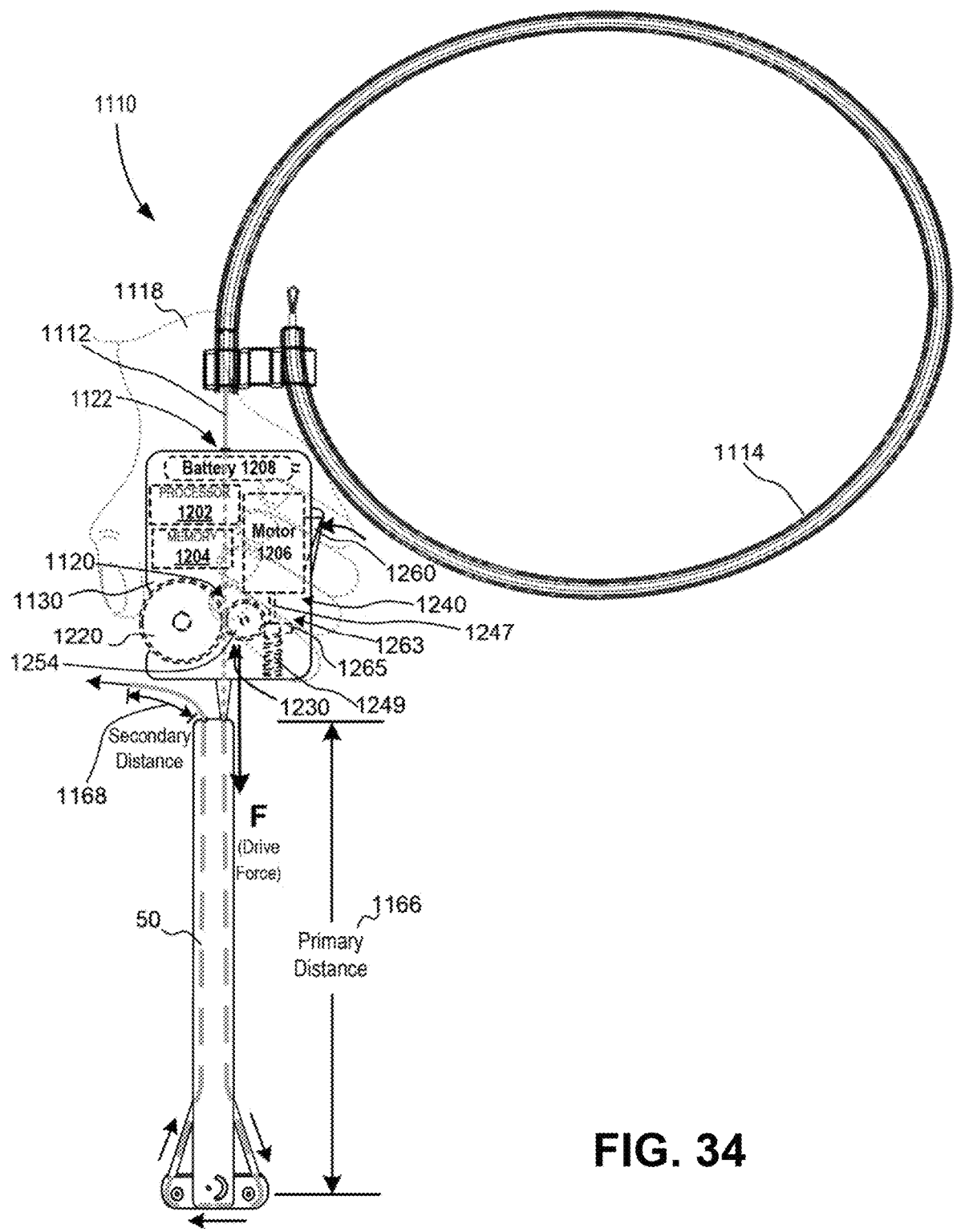
FIG. 34 is a diagrammatic plan view of another elongate device advancer representation according to aspects and features described herein illustrating advancement of a guide wire through the suture placement device of FIG. 3D.
Figure 35:
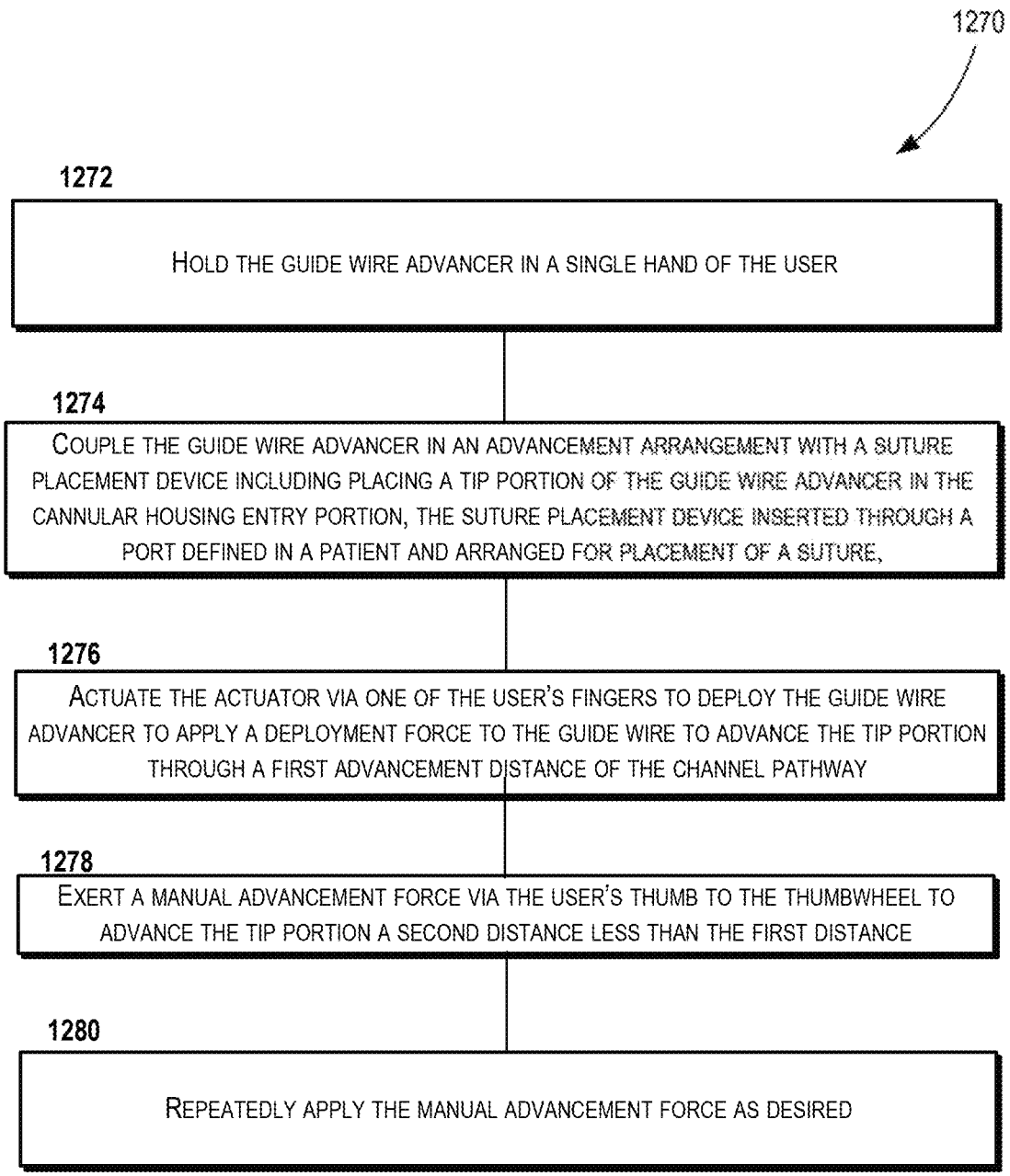
FIG. 35 is a schematic representation of a method for advancing a guide wire through the channel pathway of a medical device using the suture placement device of FIG. 3D as an illustrative example along with a diagrammatic representation or example configurations of an elongate device advancer discussed herein, such as the diagrammatic elongate device advancers of FIGS. 33A-34B and FIG. 34C.

Referring to FIGS. 31-35 and, in particular, to FIGS. 34 and 35, the integrated advancement driver 1630 generally includes a cooperative feed roller nip 1632 configured to advance the guide wire in response to transmission of an automated drive force from automated power drive 1640 or a manual drive force applied by the user via thumbwheel 1622 and manual drive 1620. In other words, the integrated advancement driver 1630 is configured as a multi-source advancement driver that can readily advance the guide wire according to the user's control movements including responsive to a user-exerted manual control or manual drive force on thumbwheel 1622, and in response to user-actuation of the automated driver 1640. As such, the cooperative feed roller nip 1632 includes a drive roller from both the manual drive 1620 and the automated drive 1640. Further, the cooperative feed roller nip 1632 is defined between the drive portion 1616 of the manual drive roller 1622 that extends into the guide wire pathway, which is configured in an opposed arrangement with the drive portion 1629 of the automated drive roller 1656 that likewise extends into the guide wire pathway. The opposing drive portions can be configured to engage opposite side regions of the guide wire and cooperate as a pair of feed rollers for advancing the guide wire 1512 along the pathway 1520 toward the second end portion 1525. Further, the opposing drive portions can each be configured to act as both a drive roller and a driven roller based on the drive roller that is acting as the operative drive providing drive force to the guide wire.

Figure 36A:
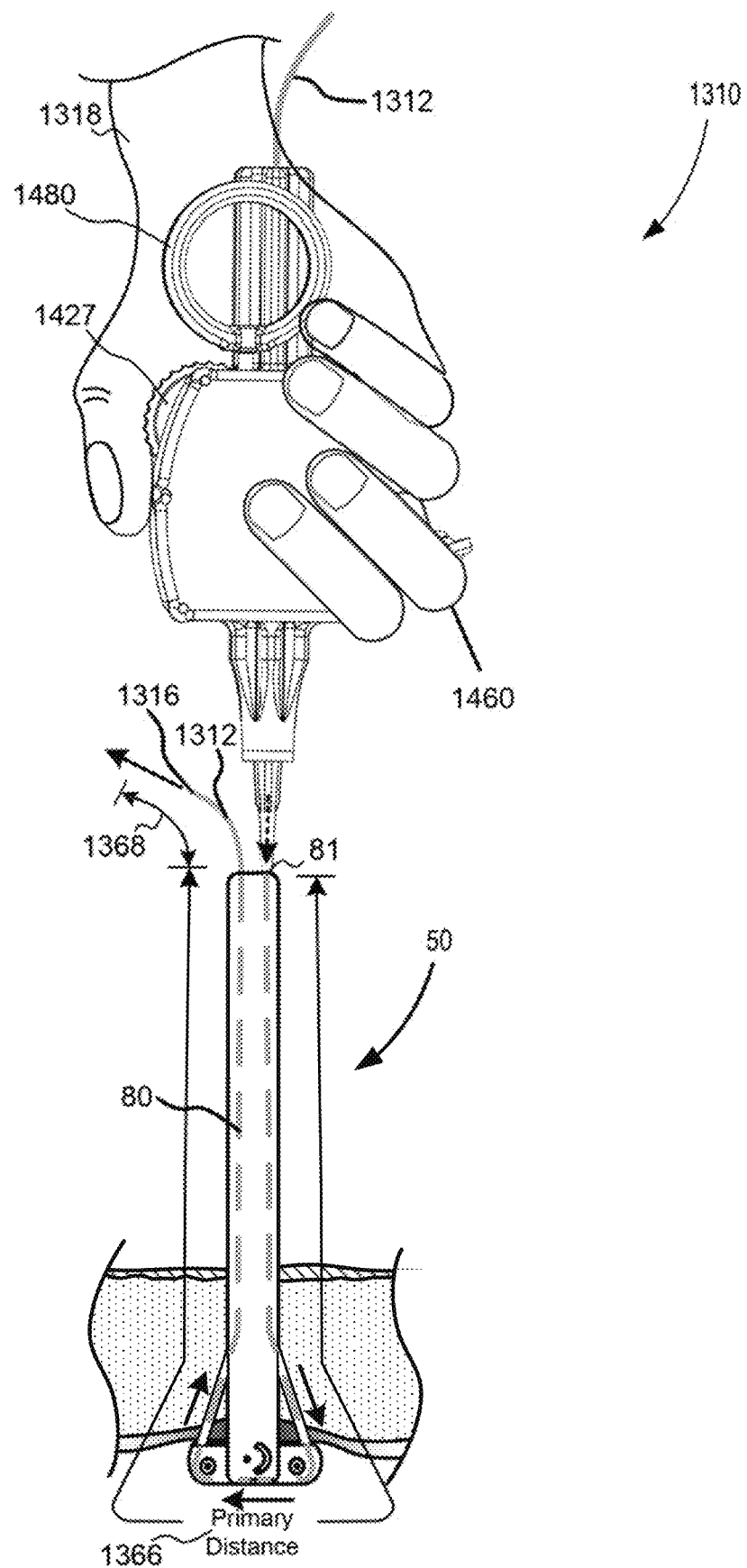
FIG. 36A is a plan view of an example elongate device advancer illustrating advancement of an elongate device, such as a guide wire, through the example suture placement device of FIG. 3D.
Figure 36B:
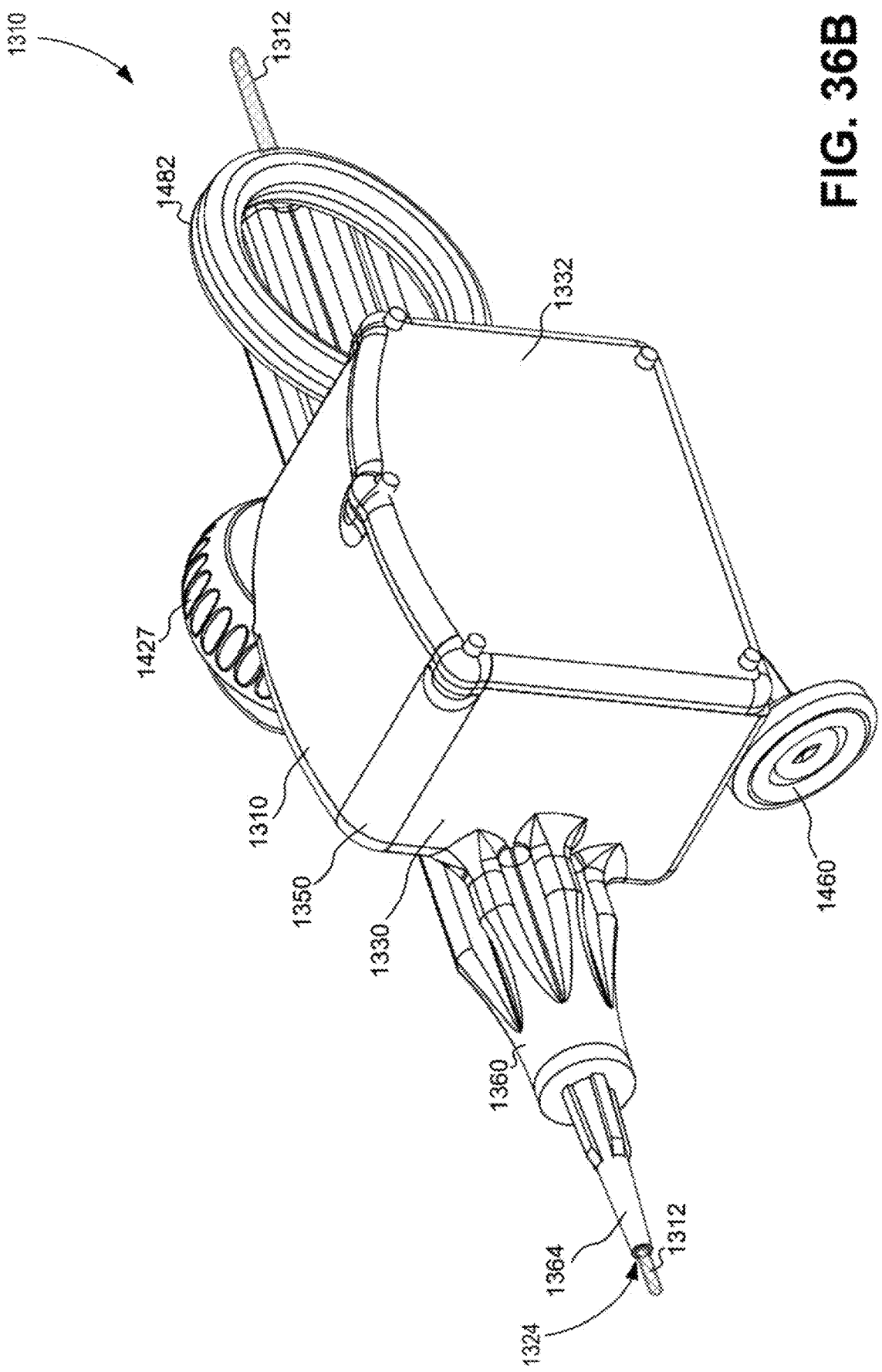
FIG. 36B is a left front perspective view of the elongate device advancer of FIG. 36A.
Figure 36C:
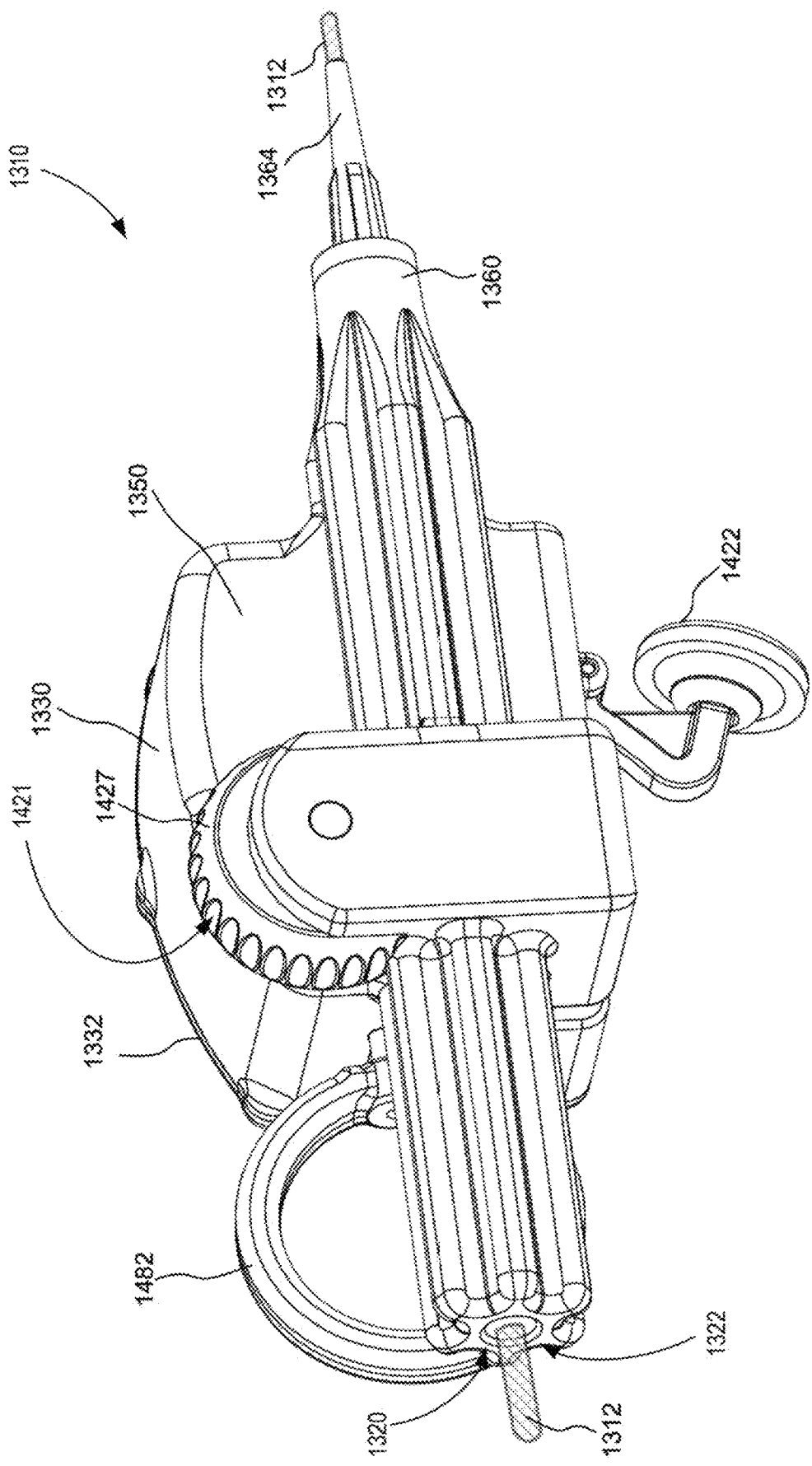
FIG. 36C is a right rear perspective view of the elongate device advancer of FIG. 36A.
Figure 37A:
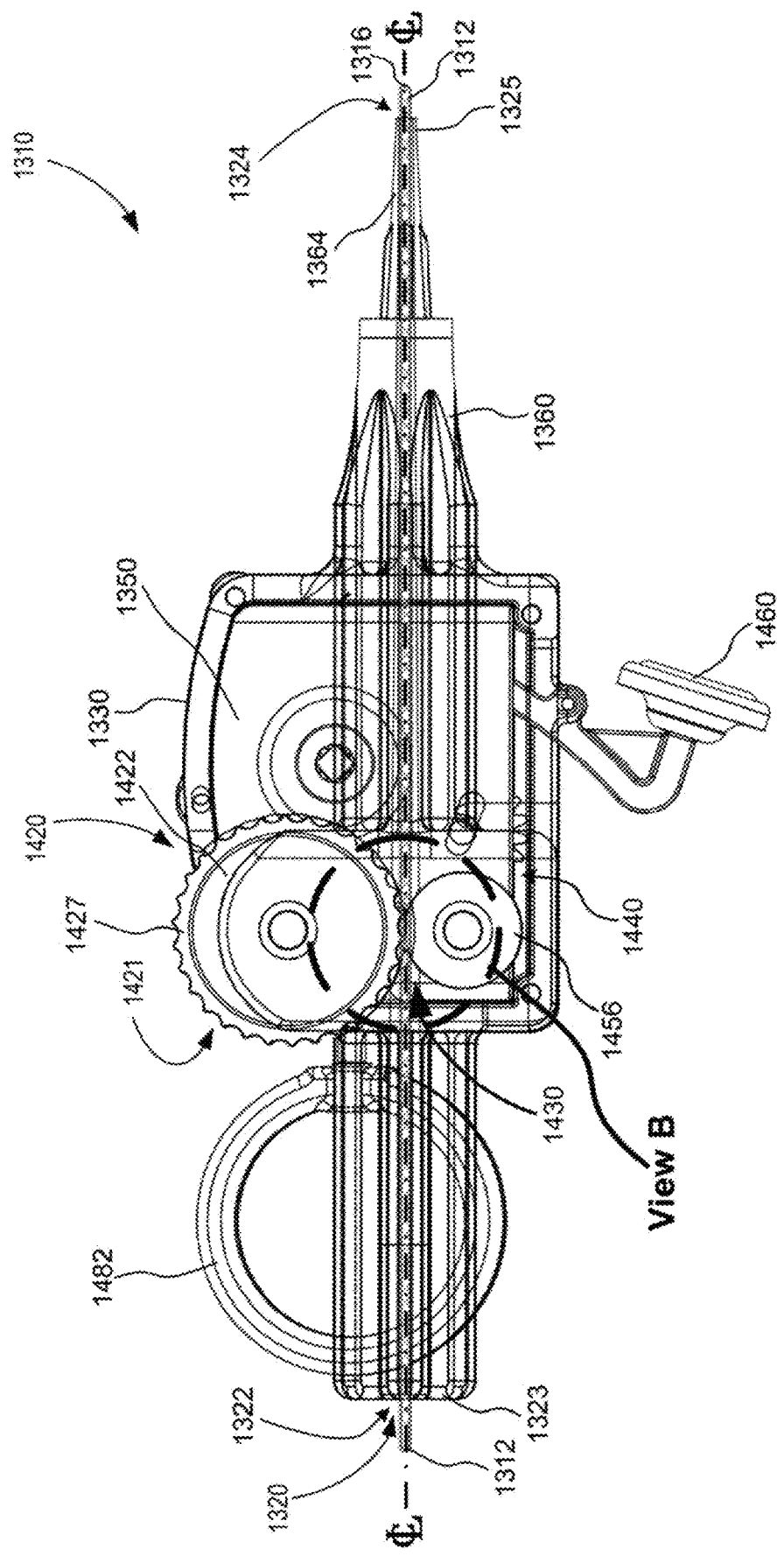
FIG. 37A is a right plan view of the elongate device advancer of FIG. 36A shown with the stylet body transparent to expose the guide wire pathway and portions of the drive system along with drive-related components viewable in the area identified as View B in FIG. 37B, which is shown in greater detail in FIG. 37C.
Figure 37C:
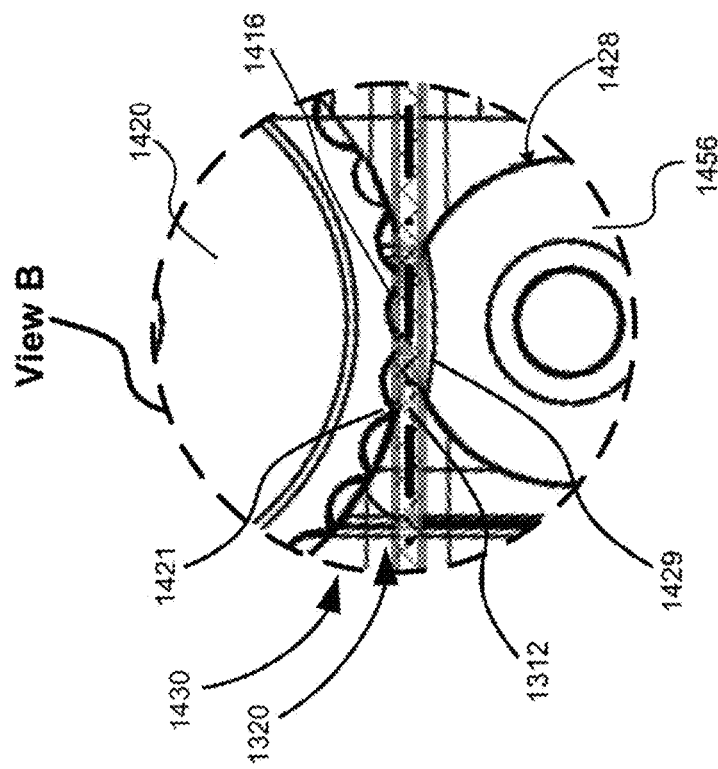
FIG. 37C is a close view of the portion labelled "View B" in FIG. 37B, which shows a plan view of the nip and a portion of the guide wire pathway for the elongate device advancer of FIG. 37A along with a portion of an example guide wire disposed in the pathway.
Figure 37B:
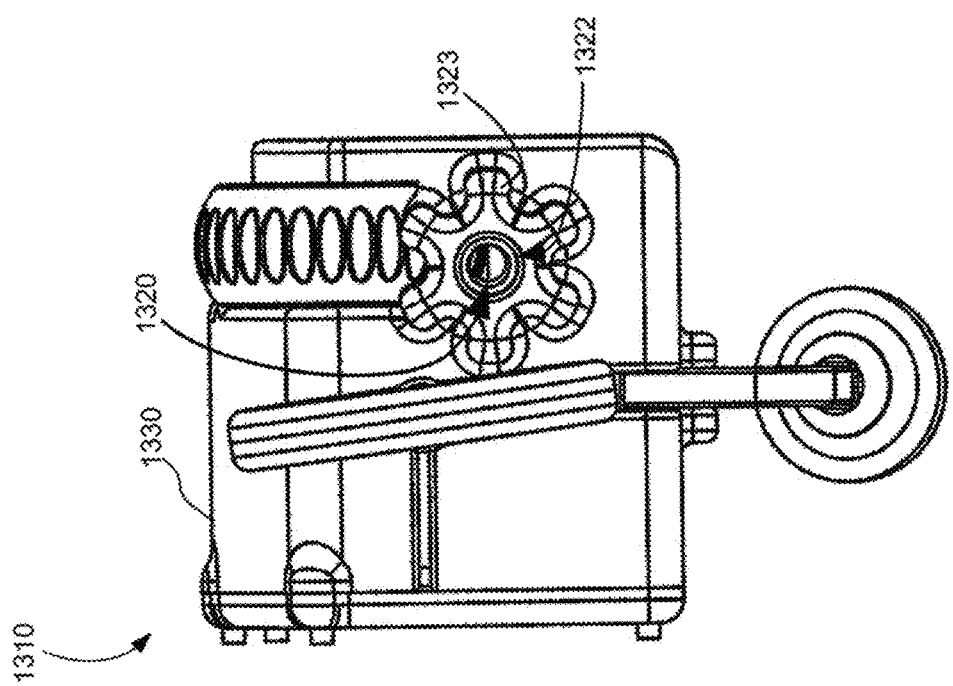
FIG. 37B is a rear plan view of the elongate device advancer of FIG. 37A.
Figure 38A:
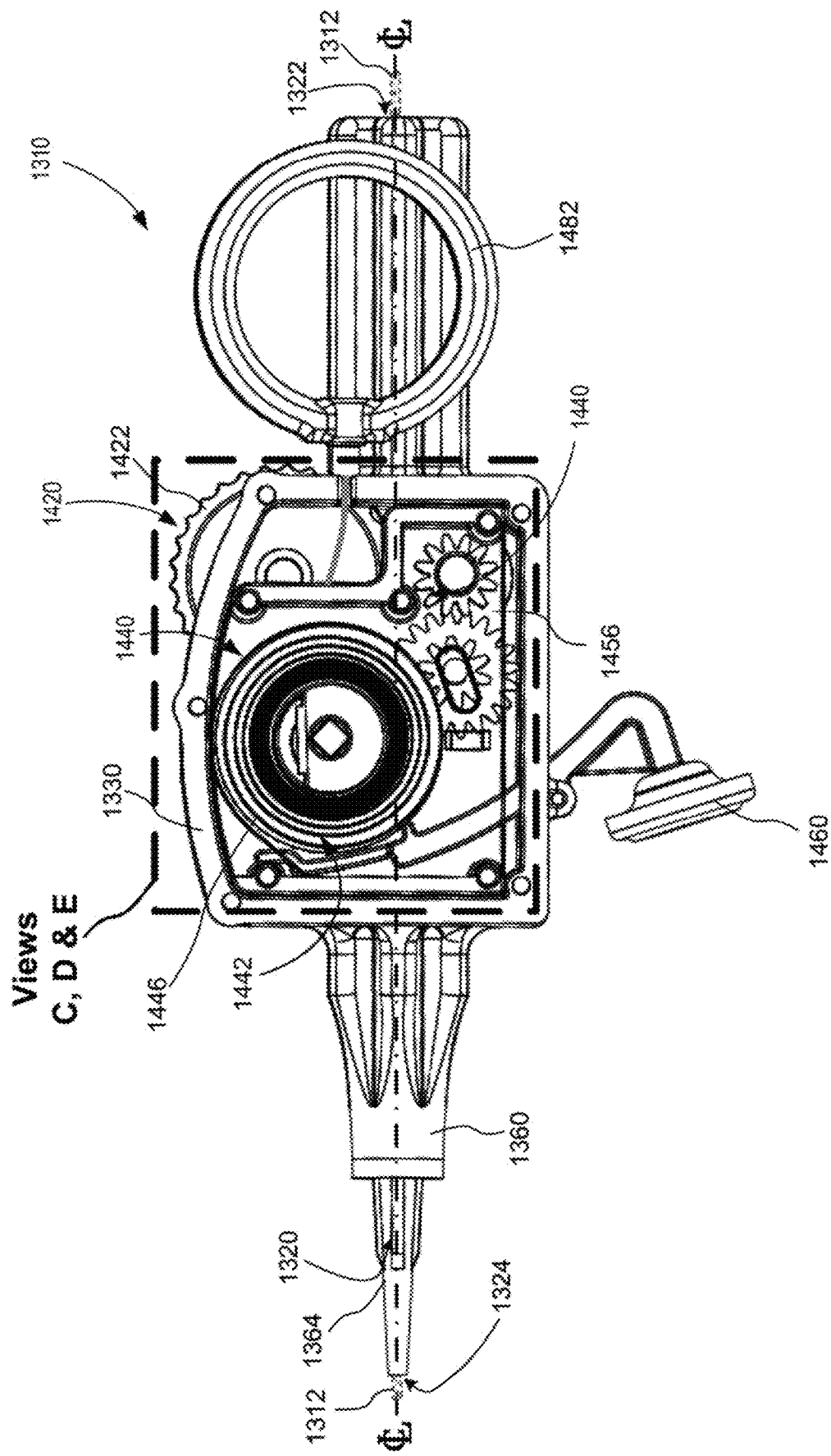
FIG. 38A is a left plan view of the elongate device advancer of FIG. 37A shown with the left side cover removed and the left side gearbox support plate transparent exposing some of the drive components of the elongate device advancer of FIG. 37A.
Figure 38B:
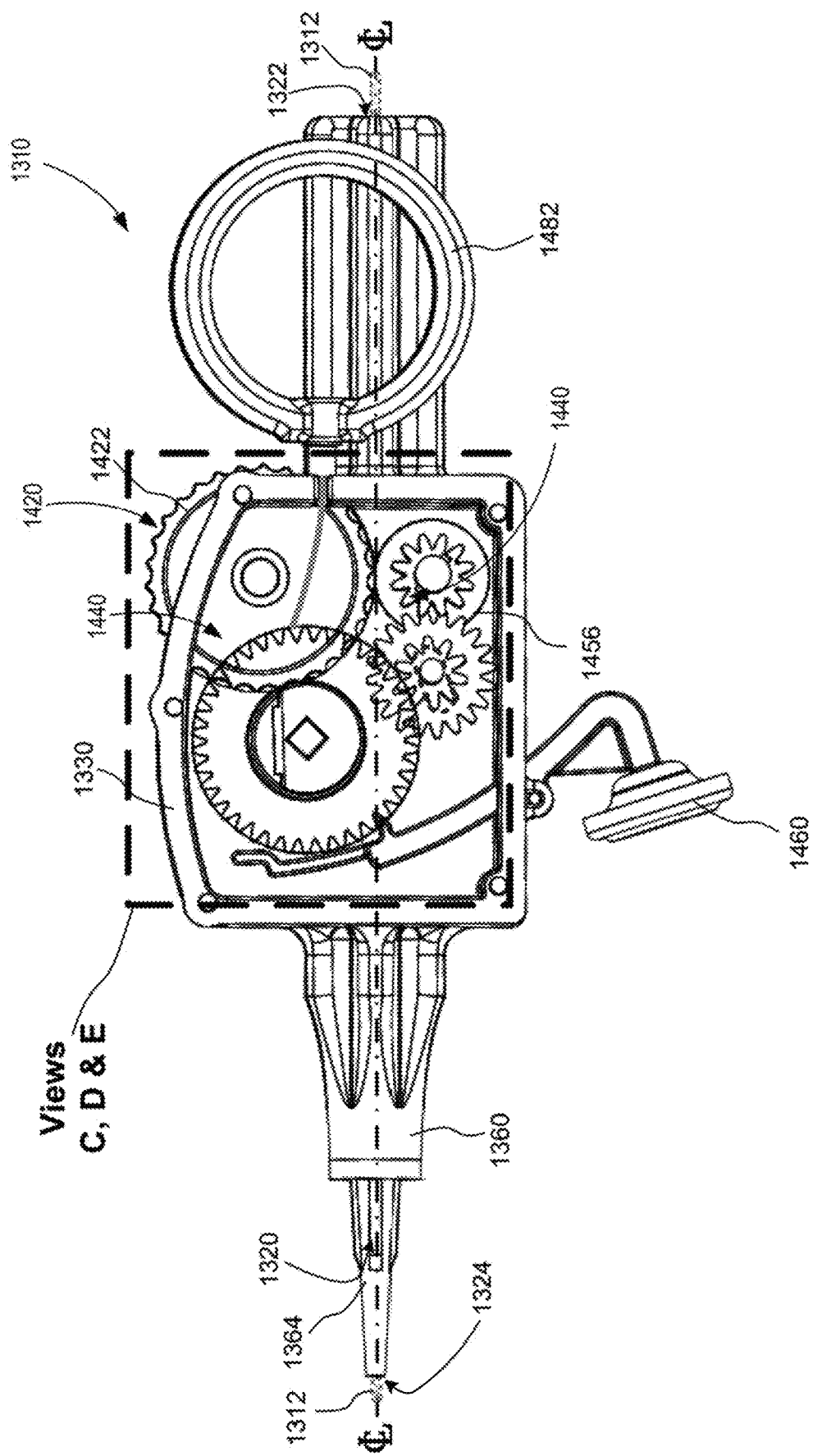
FIG. 38B is another left plan view of the elongate device advancer of FIG. 37A, but shown with the spring and the left side gearbox support plate removed, as well as the pulley gear transparent to expose components pertaining to the example arrangement of the transmission switch including a movable float gear.
Figure 38C:
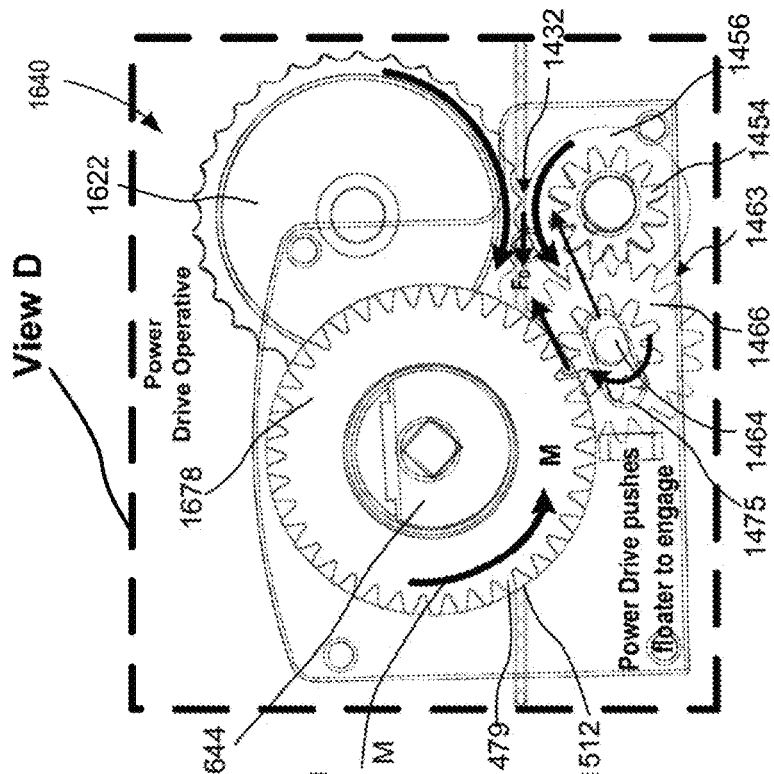
Figure 38D:
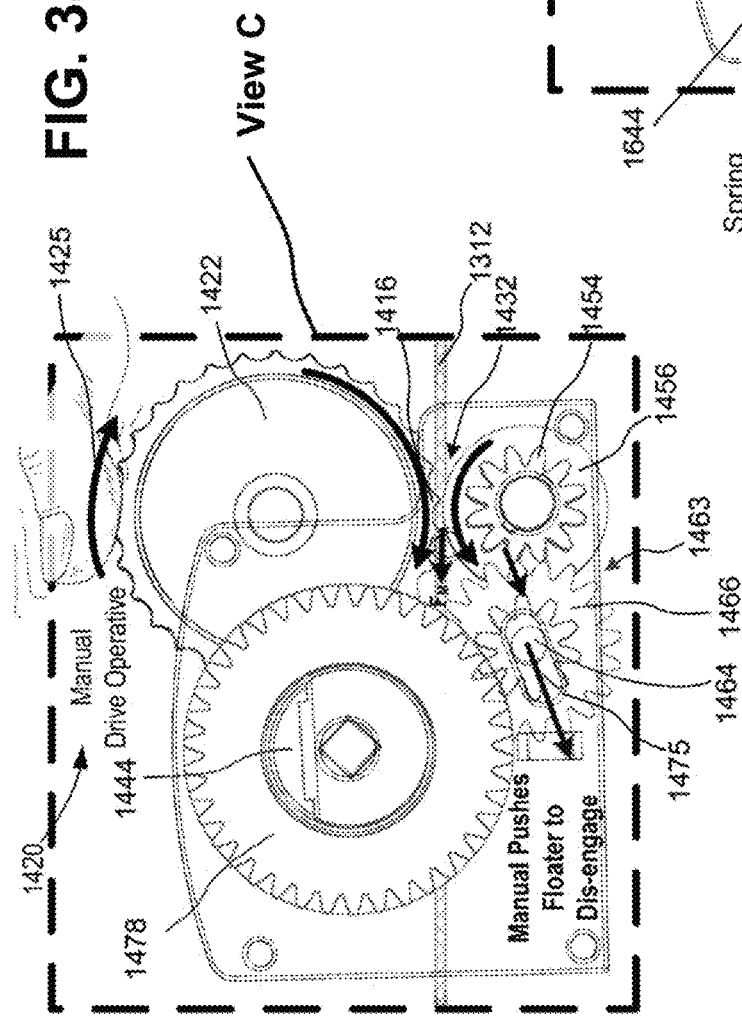

Referring now to FIGS. 36-38, further details of the manual drive 1620 and the power drive 1640 as drive components of the integrated advancement drive 1630 are shown, as well as aspects and features pertaining to a transmission switch 1663 configured to automatically move between a first position D and a second position E. The transmission switch is configured to automatically move to the first position D when the user exerts manual control via thumbwheel 1622. The first position D de-couples the power drive 1640 from its driving connection with the automated or powered drive roller 1654 to prevent drive force inadvertently being applied by the power drive 1640 on the guide wire 1512 while the user applying fine-tuning user-controlled advancement of the guide wire. The transmission switch is further configured to automatically engage or connect the power driver 1640 to the powered drive roller 1654 when the user actuates the actuator to transmit powered drive force to the guide wire 1512. The transmission switch 1663 generally includes a floater gear 1666, a floater gear shaft 1664, and a pair of guide slots 1675 configured to support opposite ends of the floater gear shaft. The pair of corresponding guide slots 1675 are formed through the left cover 1532 and right cover 1550. The opposing slots support opposite end portions of floater gear shaft 1664 such that the floater gear shaft extends laterally between left and right sides of the guide wire housing 1530 across the width of the elongate device advancer 1510. The floater gear shaft is supported within the opposing guide slots 1675 to allow rotation of floater gear shaft 1664 and sliding translation of the shaft along the slot.

Referring now to FIG. 37, operation of transmission switch 1663 is shown while the manual drive 1620 of the integrated combination drive 1618 is operative, as well as operations of the manual drive. Elongate device advancer 1510 is configured such that the user applies control movements to the manual control of the thumbwheel 1622 using the thumb of single hand 1518 via thumb movements rearward or in a proximal direction, which rotates the exposed control portion rearward or in a proximal direction. An outer surface portion 1621 of thumbwheel 1622 can be configured to have with a knurled, abrasive, tactile, contoured or other type of surface texture or features providing high frictional engagement, such as with the user's thumb of single hand 1518 and/or for driving engagement of the guide wire 1512. A manual drive portion 1616 of outer surface portion 1621 extends into the guide wire channel 1520 and drivingly engages a side portion of the guide wire 1512 disposed within the nip 1632 to transmit a manual drive force applied by the user to the guide wire. When the manual drive portion 1616 is applying a manual force to the guide wire, automated drive roller 1656 acts as a driven roller and correspondingly rotates in an opposite direction as thumbwheel 1622. Drive gear 1654 is attached to drive roller 1656 and, thus, correspondingly rotates along with the drive roller as shown in FIG. 15C. Mesh gear teeth disposed along drive gear 1654 engage corresponding mesh gear teeth of floater gear 1666 when the floater gear is proximate to or in engagement with the drive gear 1654 and push the floater gear 1666 along guide slots 1675 while rotating as shown responsive to application of a manual drive force. As such, floater gear 1666 automatically slides into the disengagement position D, which de-couples the pulley gear 1678 from engagement with drive gear 1654.

Referring now to FIG. 38, operation of transmission switch 1663 is shown while the power drive 1640 of the integrated combination drive 1618 is operative, as well as further operations of the power drive. Elongate device advancer 1510 is configured such that the user can actuate actuator 1660 as discussed above to release potential energy stored by flat coil spring 1646 such that a moment M applied to pulley gear 1678 rotates the pulley gear in the direction shown.

As discussed above along with FIGS. 34 and 35, gear teeth disposed along the pulley gear engage corresponding mesh teeth of floater gear 1666, which applies rotational force to rotate and translate the floater gear along guide slot 1675 into an engagement position E, in which the mesh gear teeth of the floater gear drivingly engage mesh gear teeth of drive gear 1654 to drive rotation of the drive gear in the drive direction shown. Rotation of drive gear 1654 as shown correspondingly rotates drive roller 1656 that is attached to the drive gear and exerts power drive force upon guide wire 1512 disposed within the nip as discussed above along with FIGS. 34 and 35. Thus, floater gear 1666 automatically slides into the engagement position E, which couples pulley gear 1678 into driving engagement with drive gear 1654 when the power drive is actuated. After potential energy stored in flat coil spring 1646 has been expended, the user can apply manual control via the thumbwheel and again disengage the floater as described above in FIG. 37.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An advancer for advancing an elongate medical device comprising:
   an advancer body arranged to be held in and controlled by a single hand, the advancer body defining a pathway between a proximal end portion and an opposite distal end portion for translating an elongate device therebetween, the advancer body comprising:
   an inlet having an inlet longitudinal axis defined at the proximal end portion for receiving the elongate device into the pathway; and
   an introducer tip at the distal end portion defining an exit for the longitudinal device to exit the pathway, the exit having an introducer longitudinal axis;
   a rotatable manual control partially embedded in the advancer body at the distal end portion arranged to receive a user-exerted manual control movement from a thumb of the hand including a torque applied by the thumb and a rotation arc distance rotated by the thumb as the torque is applied;
   a manual drive having a gripper-driver for concurrently engaging opposite outer surface regions of the elongate device at a drive location along the pathway within the advancer body, the gripper-driver comprising a pair of opposing rollers each having an outer engagement surface rotatable with the corresponding roller, the gripper-driver arranged to maintain a constant drive connection with the elongate device and apply a translation drive force for translating the elongate device an advancement distance in response to the user-exerted manual control movement, the manual drive converting the torque applied into the translation drive force and the rotation arc distance into the advancement distance, the translation drive force scaled by a force factor with respect to the torque applied by the thumb and the advancement distance scaled by a distance factor with respect to the rotation arc distance;

wherein the distance factor is 1 (one) or greater than 1 (one), and the elongate device is translated through the pathway an advancement distance equal to or greater than the rotation arc distance.

2. The advancer of claim 1, wherein the pair of opposing rollers form a nip, the pair of engagement surfaces engaging opposing radial perimeter portions of outer surface regions of the elongate device at the drive location, at least one engagement surface having a concave shape drivingly engaging a majority of a semi-circular radial perimeter portion of the corresponding radial portion.

3. The advancer of claim 2, the pair of opposing rollers comprising:
a first drive roller of the pair of opposing rollers rotatably coupled with the advancer body having a first outer engagement surface rotatable with the first drive roller, a first drive portion of the first drive roller extending into the pathway at the drive location, the first outer engagement surface of the first drive portion engaging a first radial portion of one of the outer surface regions at a contact region for the gripper-driver proximate the drive location; and
a second drive roller of the pair of opposing rollers rotatably coupled with the advancer having a second outer engagement surface rotatable with the second drive roller, the second drive portion opposing the first drive portion and extending into the pathway opposite the first drive portion at the drive location, the second outer engagement surface of the second drive portion engaging a second radial portion of another one of the outer surface regions at the contact region for the gripper-driver proximate drive location;
wherein:
the nip is defined between the drive portions of the first and second drive rollers extending into the pathway in an opposed arrangement, the opposing drive portions forming the gripper-driver and engaging the elongate device between the opposing drive portions; and
the manual rotatable control, the first and second drive rollers, and the nip are configured for manually translating the elongate medical device in accordance with the user-exerted manual control movement, the advancement distance of the elongate device being the same as or greater than the rotation arc length, the distance scale being 1 (one) or greater than one (1).

4. The advancer according to claim 3, wherein:
the first drive portion includes a compressible surface for engaging the elongate device;
the first drive portion is configured to engage the first radial portion in an interference relationship, wherein the compressible surface is compressed during engagement of the first drive roller with the elongate device; and
the compressible surface forms an elongate device contact surface, the elongate device contact surface having a concave curvature prior to engagement with the elongate device, the concave surface forming a continuous contact region with the corresponding outer surface region during engagement of the elongate device for gripping the elongate device.

5. The advancer according to claim 1, wherein:
the advancer body includes a first housing and a second housing, the first and second housings attached to each other in an opposed arrangement;
the pathway defined by mated opposite portions of the first and second housing;
the first housing including a wall extending from the first housing toward the second housing along a side portion of the pathway, the wall extending beyond pathway;
the second housing defining a recess along the side portion of the pathway corresponding to the wall, the recess extending inward away from the first housing and receiving the wall of the first housing; and
a tip portion of the wall and an interior end of the recess are laterally offset from the pathway and configured to block a portion of the elongate device from moving into a gap between the first housing and the second housing.

6. The advancer of claim 1, wherein the distance factor is greater than one, the advancer arranged to amplify translation of the elongate device through the pathway an amplified advancement distance greater than the rotation arc distance and the distance factor being greater than one (1).

7. The advancer of claim 1 arranged as an ergonomic advancer, the advancer body arranged for being held in and controlled by a single hand, the advancer body further comprising:
a precision-control edge region defined along a lower edge portion of the advancer body at the distal end portion inboard of the introducer tip when held in the hand, the precision-control edge region arranged to engage a middle phalanx and a PIP Joint of at least one of an index finger and a middle finger of the hand;
a power grip edge region defined at the proximal end portion along the lower edge portion inboard of the inlet when held in the hand, the power grip edge region arranged to engage a middle phalanx and a PIP Joint of at least one of a ring finger and pinky finger of the hand during use; and
an edge region bend defined between the precision-control edge region and the power grip edge region along the lower edge portion, the edge region bend extending an angular separation about the edge region bend along the lower edge portion between the precision-control edge region and the power grip edge region, the edge region bend separating the at least one of the index finger and the middle finger from the at least one of the ring finger and the pinky finger during use and orienting the at least one of the ring finger and the pinky finger greater than 180 degrees from the at least one of the index finger and the middle finger at an outboard angle and less than one-hundred eight (180) degrees from each other at an inboard angle;
wherein the thumb is located at the distal end portion proximate the rotatable manual control for providing the user-exerted manual control movement to the thumbwheel when the user desires.

8. The advancer of claim 7, the advancer body further comprising:
an upper edge portion opposite the lower edge portion extending from the proximal end portion to the distal end portion;
a grip contact surface defined at the proximal end portion along the upper edge portion opposite the power-grip edge region and outboard of the inlet during use, the grip contact surface arranged for engaging a surface region of a Thenar Eminence of the hand when the grip increases, the engagement with the Thenar Eminence cooperating with the engagement of the at least one the ring finger and the pinky finger with the power-grip edge region for enhancing the user's grip of the ergonomic advancer; and a thumbwheel access surface defined at the distal end portion along the upper edge portion opposite the precision-control edge region, at least a portion of the thumbwheel access surface extending between the thumbwheel and the grip contact surface and having an outboard angular orientation greater than one-eight degrees with respect to the grip contact surface corresponding with tensor rotation of a CMC joint of the thumb while the Thenar Eminence engages the grip contact surface;

wherein, opposing engagement of the concave shapes for the grip contact surface and the power grip region firmly retains the advancer in the hand, and the orientation of the thumbwheel access surface with respect to the grip contact surface concurrently enables freedom of movement for tensor rotation of the thumb at the CMC joint for providing the user-exerted manual control movements.

9. The ergonomic advance of claim 8, wherein:
the inlet longitudinal axis is angled away from the introducer longitudinal axis toward the user during use by a counter deviation angle for minimizing ulnar deviation of the wrist during use;
the precision-control edge region defines a concave shape for enhanced retention of the middle phalanx and the PIP Joint of at least one of the index finger and the middle finger of the hand;
the grip contact surface defines a concave shape for enhanced engagement of the surface region of a Thenar Eminence of the hand; and
the power grip edge region defines a concave shape opposing the grip contact surface concave shape for enhanced engagement of the middle phalanx and the PIP Joint of the least one of a ring finger and pinky finger of the hand during use and for enhanced grip.

10. The elongate device advancer according to claim 1, wherein:
the rotatable manual control includes a first thumbwheel and a second thumbwheel adjacent to and parallel with the first thumbwheel, the first thumbwheel lateral spaced apart from the first thumbwheel by a thumbwheel gap, the first and second thumbwheels partially disposed within an interior of the advancer body and each having an exposed external portion at an exterior of the advancer body for receiving the user-exerted manual control movement;
the rotatable manual control includes an input rotation axis affixed to the advancer body, each of the first and second thumbwheels rotatably attached to the input axis for rotation about the axis responsive to the user-exerted manual control movement;
a force applied by a thumb of the single hand for the user-exerted manual control movement is shared by the pair of thumbwheels;
the first thumbwheel has a first thickness; and
the thumbwheel gap is greater than the first thickness such that a portion of the engagement force applied to the first thumbwheel is concentrated according to the thickness of the first thumbwheel for increasing engagement with the thumb.

11. The elongate device advancer according to claim 10, wherein:
an edge portion of the first thumbwheel defines an alternating arrangement of peaks and valleys, the alternating arrangements of peaks and valleys further enhancing engagement with the thumb at contact points of the thumb with the one or more of the peaks, the arrangement of peaks and valleys defining gear teeth, the first thumbwheel forming a gear having a first drive radius;
the manual drive including a first drive roller, the first drive roller including a first driven gear attached at a first lateral portion and operatively engaging the first thumbwheel gear, the first driven gear having a first driven gear radius, the first driven gear and the first drive roller rotatably coupled with the advancer body at a first roller axis such that rotary movement applied to the first driven gear imparts rotation of the first driven gear with the first drive roller about the first roller axis;
the first drive roller having a first drive roller radius greater than the first driven gear radius;
the first drive roller radius being greater than the first driven gear radius such that rotation of the first thumbwheel gear for the rotation arc distance drives rotation of the first driven gear for the rotation arc distance manually applied by the thumb and imparts amplified rotation of the first drive roller a first drive roller arc length greater than the rotation arc distance manually applied by the thumb; and
the first drive roller is configured to impart amplified translation of the elongate device for the advancement distance equal to the first driver roller arc length responsive to the user-exerted manual control movement and corresponding rotation arc distance;
wherein the advancement distance is amplified with respect to the user-exerted manual control movement.

12. The elongate device advancer of claim 11, wherein:
an edge portion of the second thumbwheel defines an alternating arrangement of peaks and valleys defining gear teeth, the second thumbwheel forming a gear having a radius equal to the drive radius of the first thumbwheel;
the first drive roller including a second driven gear attached at an opposite second lateral portion from the first lateral portion and operatively engaging the second thumbwheel gear, the second driven gear having a second driven gear radius equal to the first driven gear radius, the second driven gear rotatably coupled with the first driven gear and the first drive roller to rotate with the first driven gear and the first drive roller about the first roller axis; wherein rotary movement applied to the second driven gear imparts rotation of the second driven gear with the first drive roller about the first roller axis;
the first thumbwheel and the second thumbwheel configured to engage the first drive roller at opposite sides of the first roller, the first and second thumbwheel together driving rotation of the first drive roller for the amplified rotation arc distance of the first drive roller greater than the rotation arc distance manually applied by the thumb;
wherein the advancement distance is amplified with respect to the user-exerted manual control movement applied to both the first thumbwheel and the second thumbwheel.

13. The elongate device advancer of claim 1, wherein:
the rotatable manual control includes a manual drive portion extending into the pathway configured to drivingly engage the elongate device at a distance factor of one (1), wherein the rotation arc distance and the torque applied by the thumb for the user-exerted manual control movement are configured to be equal to the translation drive force applied to the elongate device and the advancement distance;

the translation drive force and the advancement distance being a manual translation drive force and a manual advancement distance; and the manual drive includes a combination driver/driven roller rotatably coupled with the advancer body having an engagement surface rotatable with the combination driver/driven roller including a drive portion extending into the pathway;

the elongate device advancer further comprising:

an automated drive for translating the elongate device an automated primary distance when actuated that is greater than the manual advancement distance, the automated drive comprising:

a power driver configured to store potential energy for driving translation of the elongate device the automated primary distance and transmitting a corresponding automated linear drive force; and an actuator configured to be actuated by the single hand to activate the power driver for transmitting the automated linear drive force to the drive portion of the combination driver/driven roller;

wherein a cooperative feed roller nip is defined between the manual drive portion of the rotatable manual control extending into the pathway in an opposed arrangement with the drive portion of the combination driver/driven roller extending into the pathway, the opposing drive portions configured to engage opposite side regions of the elongate device and cooperate as a pair of feed rollers for translating the elongate device along the pathway toward the distal end portion responsive to one of the automated linear drive force or the manual translation drive force.

14. The elongate device advancer according to claim 13, wherein:

the actuator is configured to be actuated by at least one finger of the single hand when gripping the advancer;

the manual control is configured to receive the user-exerted manual control movement by movement of a thumb of the single hand of the user when gripping the elongate device advancer;

the automated drive roller is configured to rotate as a driven roller with the manual drive roller when the manual drive force is transmitted to the manual drive roller; and the manual drive roller is configured to rotate as a driven roller with the automated drive roller when the automated drive force is transmitted to the automated drive roller.

15. The elongate device advancer according to claim 13, wherein:

the advancer is configured for use with a suture placement device defining a return loop suture channel therein having a determined channel length;

the automated primary distance corresponds with the determined channel length; and the automated drive is configured to drive elongate device advancement substantially through the determined channel length when actuated.

16. The elongate device advancer according to claim 13, wherein the power driver includes a flat coil spring, the potential energy includes a mechanical spring force, and the potential energy is stored in the flat coil spring while in a wound condition, the elongate device advancer further comprising:

a transmission switch configured for automatic movement between a first position and a second position, the first position de-coupling the power driver from the automated drive roller when the manual control receives the user-exerted manual control movement, the second position drivingly connecting the power driver to the automated drive roller when the actuator is actuated; and a re-charger configured to receive a manual re-charge movement, the re-charger rewinding the flat coil to the wound condition to re-charge the potential energy.

17. The elongate device advancer according to claim 1, further comprising:

an elongate device lock attached to the advancer body for selectively locking movement of the elongate device extending through the pathway of the elongate device advancer, the elongate device lock comprising:

a first retainer extending into the pathway at the distal end portion proximate the introducer tip;

a second retainer extending into the pathway at the distal end portion proximate the introducer tip opposite the second retainer;

at least one of the first and the second retainer arranged for selective movement by the user from an unengaged position to an engaged position with the elongate device within the pathway, the engaged position applying force against opposite lateral side portions of the elongate device from both the first retainer and the second retainer gripping the elongate device therebetween;

wherein advancement of the elongate device along the pathway is restrained by engagement of the first and the second retainer proximate the introducer tip, and rotation of the elongate device is restrained proximate the introducer tip between the first and the second retainers.

18. An advancer for advancing an elongate medical device comprising:

an advancer body arranged to be held in and controlled by a single hand, the advancer body defining a pathway between a proximal end portion and an opposite distal end portion for translating an elongate device therebetween, the advancer body comprising:

an inlet having an inlet longitudinal axis defined at the proximal end portion for receiving the elongate device into the pathway; and an introducer tip at the distal end portion defining an exit for the longitudinal device to exit the pathway, the exit having an introducer longitudinal axis;

a rotatable manual control partially embedded in the advancer body at the distal end portion arranged to receive a user-exerted manual control movement from a thumb of the hand including a torque applied by the thumb and a rotation arc distance rotated by the thumb as the torque is applied;

a manual drive having a gripper-driver for concurrently engaging opposite outer surface regions of the elongate device at a drive location along the pathway within the advancer body, the gripper-driver arranged to maintain a constant drive connection with the elongate device and apply a translation drive force for translating the elongate device an advancement distance in response to the user-exerted manual control movement, the manual drive converting the torque applied into the translation drive force and the rotation arc distance into the advancement distance, the translation drive force scaled by a force factor with respect to the torque applied by the thumb and the advancement distance scaled by a distance factor with respect to the arc distance;

wherein:

the distance factor is 1 (one) or greater than 1 (one), and the elongate device is translated through the pathway an advancement distance equal to or greater than the rotation arc distance;

a nip longitudinal axis is defined along the pathway at the gripper-driver;

the nip longitudinal axis forms an acute angle with the inlet longitudinal axis; and the elongate device is configured to translate through the nip in a translation direction coaxial with the nip longitudinal axis at a transverse orientation from the inlet longitudinal axis; and wherein the orientation of the pathway and arrangement of the nip are arranged to provide the translation movement to the elongate device along within a compact ergonomic arrangement of the advancer body arrangement held in the single hand.

19. A method for rapid advancement of an elongate medical device responsive to manual user input, the method comprising:

defining an elongate device guided pathway through an advancer enclosure;

rotatably coupling a drive roller having a drive roller radius to the advancer enclosure in a drive arrangement with the guided pathway including projecting a rotary engagement surface of the drive roller into the pathway, the drive roller having a driven gear attached thereto such that the drive roller and the driven gear rotate together about a common axis, the driven gear having a driven gear radius less than the drive roller radius, the rotary engagement surface disposed at the drive roller radius;

rotatably coupling an idler roller to the advancer enclosure in a drive arrangement with the guided pathway opposite the drive roller including projecting an idler rotary engagement surface of the idler roller into the pathway opposing the drive roller engagement surface, the drive roller engagement surface and the idler roller engagement surface defining a nip for driving translation advancement of the elongate device along the guided pathway;

rotatably coupling a manual input wheel to the advancer enclosure in an operative rotating connection with the driven gear including locating a radial portion of the manual input wheel outside of the advancer disclosure configured to receive user-exerted rotary control movement applied to the manual input wheel and rotating the input wheel according to the rotatory inputs, the manual input wheel having an input radius, the manual input wheel engaging the driven gear at the input radius and driving rotation of the driven gear in response to receiving user-exerted movement applied to the manual input wheel; and arranging the elongate medical device advancer to amplify advancement of an elongate medical device responsive to manual advancement inputs of a user while an elongate medical device extends through the pathway;

wherein, in response to receiving a user-exerted movement applied to the manual input wheel for rotating the manual input wheel a first input arc, the elongate medical device advancer is arranged to perform actions comprising:

engaging the driven gear at the input radius including moving an engagement surface of the driven gear a first input arc length of the input wheel corresponding with the first input arc;

imparting rotation of the driven gear for an amplified arc based on movement of the engagement surface of the driven gear and the driven gear radius;

rotating the engagement surface of the drive roller for the amplified expanded arc, the engagement surface moving an amplified arc length based on the drive roller radius; and cooperatively driving translation of the elongate device disposed in the nip an amplified translation distance according to the amplified arc length, wherein the amplified translation distance is greater than the input arc length of the user-exerted first input arc.

20. The method according to claim 19, wherein:

rotatably coupling a drive roller having a drive roller radius to the advancer enclosure in a drive arrangement with the guided pathway including projecting a rotary engagement surface of the drive roller into the pathway comprises providing a compressible drive roller engagement surface having a concave shape;

rotatably coupling an idler roller to the advancer enclosure in a drive arrangement with the guided pathway opposite the drive roller including projecting an idler rotary engagement surface of the idler roller into the pathway opposing the drive roller engagement comprises providing a compressible idler rotary engagement surface having a concave shape; and the action of cooperatively driving translation of the elongate device disposed in the nip comprises gripping the elongate device in an interference fit between the compressible drive roller engagement surface having a concave shape and the idler rotary engagement surface having a concave shape, wherein a radial perimeter surface region of the elongate device within the nip along a circumference of the elongate device is engaged by nip the pair of engagement surfaces.

* * * * *